Figure 1A:
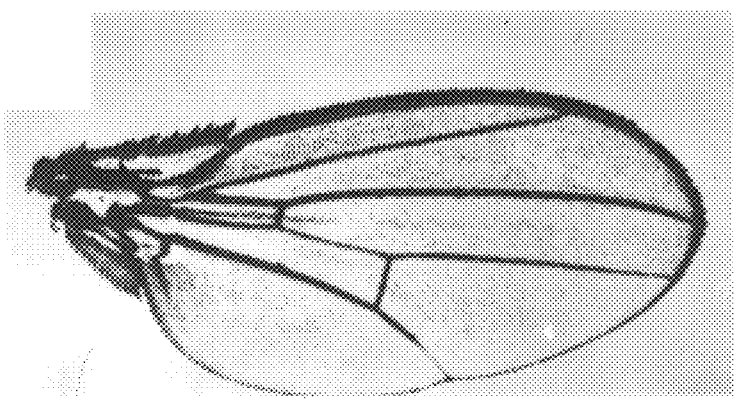
Figure 1B:
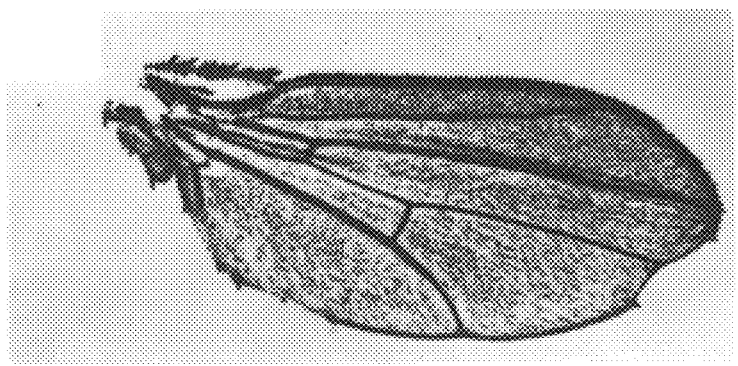
Figure 1C:
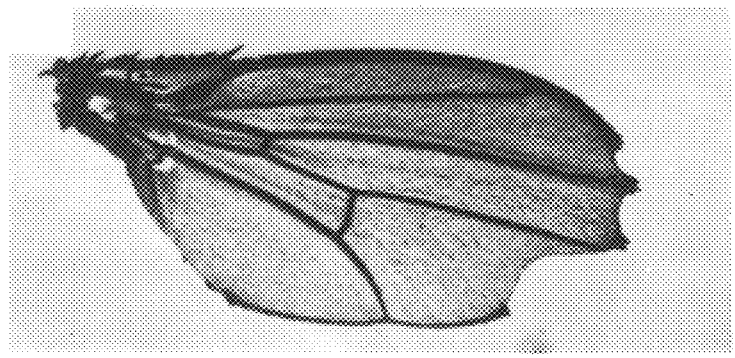

US006004924A

United States Patent [19]
Ish-Horowicz et al.

[11] Patent Number: 6,004,924
[45] Date of Patent: Dec. 21, 1999

[54] PROTEIN SEQUENCES OF SERRATE GENE PRODUCTS

[75] Inventors: David Ish-Horowicz; Domingos Manuel Pinto Henrique; Julian Hart Lewis; Anna Mary Myat, all of Oxford, United Kingdom; Robert J. Fleming, Rochester, N.Y.; Spyridon Artavanis-Tsakonas; Robert S. Mann, both of Hamden, Conn.; Grace E. Gray, New Haven, Conn.

[73] Assignees: Imperial Cancer Research Technology, Ltd., London, United Kingdom; Yale University, New Haven, Conn.

[21] Appl. No.: 08/611,729

[22] Filed: Mar. 6, 1996

Related U.S. Application Data

[63] Continuation-in-part of application No. 08/400,159, Mar. 7, 1995, which is a continuation-in-part of application No. 08/255,102, Jun. 7, 1994, abandoned, which is a continuation of application No. 08/121,979, Sep. 14, 1993, abandoned, which is a continuation of application No. 07/808,458, Dec. 11, 1991, abandoned.

[51] Int. Cl.$^6$ .......................... A01N 37/18; A61K 37/00; C07K 14/00
[52] U.S. Cl. .................. 514/2; 514/13; 514/15; 530/300; 530/326; 530/328; 530/350
[58] Field of Search .................... 530/300, 326, 530/328, 350; 514/15, 13, 2

[56] References Cited

U.S. PATENT DOCUMENTS 4,981,784   1/1991   Evans et al. .

FOREIGN PATENT DOCUMENTS

| WO 92/19734 | 11/1992 | WIPO . |
| WO 93/12141 | 6/1993 | WIPO . |
| WO 94/07474 | 4/1994 | WIPO . |
| WO 94/07522 | 4/1994 | WIPO . |
| WO 94/08037 | 4/1994 | WIPO . |
| WO 95/19779 | 7/1995 | WIPO . |

OTHER PUBLICATIONS

S. Artavanis–Tsakonas, 1997, "Alagille syndrome —a notch up for the Notch receptor ", *Nature Genetics* 16:212–213.

Coffman et al., 1990, "Xotch, the Xenopus homolog of Drosophila Notch", *Science* 249:1438–1441.

Knapp et al., 1989, "Molecular cloning, genomic structure and localization in a blood stage antigen of *Plasmodium falciparum* characterized by a serine stretch", *Mol. Biol. Parasit.* 32:73–84.

Li et al., 1997, "Alagille syndrome is caused by mutations in human Jagged1, which encodes a ligand for Notch 1", *Nature Genetics* 16:243–251.

Oda et al., 1997, "Mutations in the human Jagged1 gene are responsible for Alagille syndrome", *Nature Genetics* 16:235–242.

Thomas et al., 1991, "The Drosophila gene Serrate encodes an EGF–like transmembrane protein with a complex expression pattern in embryos and wing discs", *Development* 111:749–761.

Wosnick et al., 1987, "Rapid construction of large synthetic genes Total chemical synthesis of two different versions of the bovine prochymosin gene", *Gene* 60:115–127.

Thomas et al., 1991, "The Drosophila gene serrate encodes an EGF–like transmembrane protein with a complex expression pattern in embryos and wing discs," *Development* 111(3):749–761.

Anson et al., 1984, "The gene structure of human anti–haemophilic factor IX," *EMBO J.* 3:1053–1060.

Appella et al., 1987, "The receptor–binding sequence of Urokinase," *J. Biol. Chem.* 242:4437–4440.

Artavanis–Tsakonas, 1988, "The molecular biology of the Notch locus and the fine tuning of differentiation in Drosophila," *Trends Genet.* 4:95–100.

Artavanis–Tsakonas et al., 1991, "The Notch locus and the cell biology of neuroblast segregation," *Ann. Rev. Cell Biol.* 7:427–452.

Beachy et al., 1985, "Segmental distribution of bithorax complex proteins during Drosophila development," *Nature* 313:545–550.

Belt, 1971, Research notes, *Drosophila Inf. Serv.* 46:116.

Benton and Davis, 1977, Screening lambda gt10 recombinant clones by hybridizing to single plaques in situ, *Science* 196:180–182.

Cagan and Ready, 1989, "Notch is required for successive cell decisions in the developing *Drosophila retina*," *Genes Dev.* 3:1099–1112.

(List continued on next page.)

*Primary Examiner*—Karen Cochrane Carlson
*Attorney, Agent, or Firm*—Pennie & Edmonds LLP

[57] ABSTRACT

The present invention relates to nucleotide sequences of Serrate genes, and amino acid sequences of their encoded proteins, as well as derivatives (e.g., fragments) and analogs thereof. In a specific embodiment, the Serrate protein is a human protein. The invention further relates to fragments (and derivatives and analogs thereof) of Serrate which comprise one or more domains of the Serrate protein, including but not limited to the intracellular domain, extracellular domain, DSL domain, cysteine rich domain, transmembrane region, membrane-associated region, or one or more EGF-like repeats of a Serrate protein, or any combination of the foregoing. Antibodies to Serrate, its derivatives and analogs, are additionally provided. Methods of production of the Serrate proteins, derivatives and analogs, e.g., by recombinant means, are also provided. Therapeutic and diagnostic methods and pharmaceutical compositions are provided. In specific examples, isolated Serrate genes, from Drosophila, chick, mouse, Xenopus and human, are provided.

75 Claims, 38 Drawing Sheets

OTHER PUBLICATIONS

Campos–Ortega and Hartenstein, 1985, "The embryonic development of Drosophila melanogaster," Springer–Verlag, Berlin, pp. 1–8.

Carpenter, 1987, "Receptors for epidermal growth factor and other polypeptide mitogenes," Annu. Rev. Biochem. 56:881–914.

Cavaner, 1987, Comparison of the consensus sequence flanking translational start sites in Drosophila and vertebrates, Nucleic Acids Res. 15:1353–1361.

Clifford and Schüpbach, 1989, "Coordinately and differentially mutable activities of torpedo, the Drosophila melanogaster homolog of the vertebrate EGF receptor gene,"Genetics 123:771–787.

de la Concha et al., 1988, "Functional interactions of neurogenic genes in Drosophila melanogaster," Genetics 118:499–508.

Doe and Goodman, 1985, "Early events in insect neurogenesis. II. The role of cell interactions and cell lineage in the determination of neuronal precursor cells," Dev. Biol. 111:206–219.

Engel, 1989, "EGF–like domains in extracellular matrix proteins: Localized signals for growth and differentiation?" FEBS 251:1–7.

Fehon et al., 1990, Molecular interactions between the protein products of the neurogenic loci Notch and Delta, two EGF–homologous genes in Drosophila, Cell 61:523–534.

Fleming et al., 1990, "The gene Serrate encodes a putative EGF–like transmembrane protein essential for proper ectodermal development in Drosophila melanogaster," Genes Dev. 4:2188–2201.

Furie and Furie, 1988, "The molecular basis of blood coagulation," Cell 53:505–518.

Fryberg et al., 1983 "Transcripts of the six Drosophila genes accumulate in a stage– and tissue–specific manner," Cell 33:115–123.

Gottschewski, 1935, "New mutants: report of G. Gottschewski," Dros. Inf. Serv. 4:14, 16.

Gribshov et al., 1984, "The codon preference plot: Graphic analysis of protein coding sequences and prediction of gene expression," Nucleic Acids Res. 12:539–549.

Jan and Jan, 1982, "Antibodies to horseradish peroxidase as specific neuronal markers in Drosophila and in grasshopper embryos," Proc. Natl. Acad. Sci. USA 79:2700–2704.

Jürgens et al., 1984, "Mutations affecting the pattern of larval cuticle in Drosophila melanogaster. II. Zygotic loci on the third chromosome," Wilhelm Roux's Arch. Dev. Biol. 193:283–295.

Kidd et al., 1986, "Sequence of Notch locus of Drosophila melanogaster: relationship of the encoded protein to mammalian clotting and growth factors," Mol. Cell. Biol. 6:3094–3108.

King, 1988, "Cellular organization and peritrophic membrane formation in the cardia (proventriculus) of Drosophila melanogaster," J. Morphol. 196:253–282.

Kopczynski et al., 1988, Delta, a Drosophila neurogenic gene, is transcriptionally complex and encodes a protein related to blood coagulation factors and epidermal growth factor of vertebrates, Genes Dev. 2:1723–1735.

Lehmann et al., 1983, "On the phenotype and development of mutants of early neurogenesis in Drosophila melanogaster," Wilhelm Roux's Arch. Dev. Biol. 192:62–74.

Lindsley and Zimm, 1992, in The Genome of Drosophila melanogaster, Academic Press Inc.

Lindsley et al., 1972, "Segmental aneuploidy and the genetic gross structure of the Drosophila genome," Genetics 71:157–184.

Livneh et al., 1985, "The Drosophila EGF receptor gene homolog: conservation of both hormone binding and kinase domains," Cell 40:599–607.

Nüsslein–Volhard et al., 1984, "Mutations affecting the pattern of larval cuticle in Drosophila melanogaster. I. Zygotic loci on the second chromosome," Wilhelm Roux's Arch. Dev. Biol. 193:267–282.

Olson et al., 1990, "Glutactin, a novel Drosophila basement membrane–related glycoprotein with sequence similarity to serine esterases," EMBO J. 9:1219–1227.

Pirrotta et al., 1983, "Microdissection and cloning of the white locus and the 3B1–3C2 region of the Drosophila X chromosome," EMBO J. 2:927–934.

Poole et al., 1985, "The engrailed locus of Drosophila: structural analysis of an embryonic transcript," Cell 40:37–43.

Poulson, 1937, "Chromosomal deficiencies and embryonic development of Drosophila melangaster," Proc. Natl. Acad. Sci. USA 23:133–137.

Preiss et al., 1985, "Molecular genetics of Krüppel, a gene required for segmentation of the Drosophila embryo," Nature 313:27–32.

Price et al., 1989, "The maternal ventralizing locus torpedo is allelic to faint little ball, an embryonic lethal, and encodes the Drosophila EGF receptor homolog," Cell 56:1085–1092.

Ramos et al., 1989, "Physical and functional definition of the Drosophila Notch locus by P element transformation," Genetics 123:337–348.

Rebay et al., 1991, "Specific EGF repeats of Notch mediate interactions with Delta and Serrate: Implications for Notch as a multifunctional receptor," Cell 67:687–699.

Rothberg et al., 1988, "slit: an EGF–homologous locus in D. melanogaster involved in the development of the embryonic central nervous system," Cell 55:1047–1059.

Schejter and Shilo, 1989, "The Drosophila EGF receptor homolog (DER) gene is allelic to faint little ball, a locus essential for embryonic development," Cell 56:1093–1104.

Siegelman et al., 1990, "The mouse lymph node homing receptor is identical with the lymphocyte cell surface marker Ly–22: Role of the EGF domain in endothelial binding," Cell 61:611–622.

Tautz and Pfeifle, 1989, "A non–radioactive in situ hybridization method for the localization of specific RNAs in Drosophila embryos reveals translational control of the segmentation gene hunchback," Chromosoma 98:81–85.

Tepass et al., 1990, "crumbs encodes an EGF–like protein expressed on apical membranes of Drosophila epithelial cells and required for organization of epithelia," Cell 61:787–799.

Väet al., 1985, Genetic interactions in early neurogenesis of Drosophila melanogaster, J. Neurogenet. 2:291–308.

Vässin et al., 1987, "The neurogenic gene Delta of Drosophila melanogaster is expressed in neurogenic territories and encodes a putative transmembrane protein with EGF––like repeats," EMBO J. 6:3431–3440.

Wharton et al., 1985, "Nucleotide sequence from the neurogenic locus Notch implies a gene product that shares homology with proteins containing EGF–like repeats," Cell 43:567–581.

Wieschaus et al., 1984, "Mutations affecting the pattern of larval cuticle in *Drosophila melanogaster*. II. Zygotic loci on the X–chromosome and fourth chromosome," Wilhelm Roux's Arch. Dev. Biol. 193:296–307.

Xie et al., 1990, "Extracellular domain of lutropin/choriogonadotropin receptor expressed in transfected cells binds choriogonadotropin with high affinity," J. Biol. Chem. 265(35):21411–21414.

Xu et al., 1990, "The Notch locus and the genetic circuitry involved in early Drosophila neurogenesis," Genes Dev. 4:464–475.

Yochem et al., 1988, "The *Caenorhabditis elegans lin–12* gene encodes a transmembrane protein with overall similarity to Drosophila Notch," Nature 335:547–550.

Zak et al., 1990, "Localization of the DER/flb protein in embryos: Implications on the faint little ball lethal phenotype," Development 109:865–874.

Franco del Amo et al., 1992, "Expression pattern of Motch, a mouse homolog of Drosophila Notch, suggests an important role in early postimplantation mouse development", Development 115:737–744.

Gu et al., 1995, "Serrate expression can functionally replace Delta activity during neuroblast segregation in the Drosophila embryo", Development 121:855–865.

Hamburger and Hamilton, 1951, "A series of normal stages in the development of the chick embryo", J Exp Zool 88:49–92.

Kopan and Weintraub, 1993, "Mouse Notch: Expression in hair follicles correlates with cell fate determination", J Cell Biol 121:631–641.

Lardelli et al., 1994, "The novel Notch homologue mouse Notch 3 lacks specific epidermal growth factors–repeats and is expressed in proliferating neuroepithelium", Mech Dev 46:123–136.

Lindsell et al., 1995, "Jagged: A Mammalian ligand that activates Notch1", Cell 80:909–917.

Reaume et al., 1992, "Expression analysis of a Notch homologue in the mouse embryo", Dev Biol 154:377–387.

Speicher et al., 1994, "The Serrate locus of Drosophila and its role in morphogenesis of the wing imaginal discs: Control of cell proliferation", Development 120:535–544.

Weinmaster et al., 1992, "Notch2: A second mammalian Notch gene", Development 116:931–941.

Weinmaster et al., 1991, "A homolog of Drosophila Notch expressed during mammalian development", Development 113:199–205.

Chitnis et al., 1995, "Primary neurogenesis in Xenopus embryos regulated by a homologue of the Drosophila neurogenic gene Delta", Nature 375:761–766.

Gray et al., 1995, "Human ligands of the Notch receptor", Society for Neuroscience Abstracts 21(1–3):1524 (Abstr. 601.1).

Henrique et al., 1995, "Expression of a Delta homologue in prospective neurons in the chick", Nature 375:787–790.

Lindsell et al., 1995, "Jagged: a mammalian lignad that activates Notch1", Cell 80:909–917.

Lindsell et al., 1995, "Jagged–Notch interactions prevent muscle cell differentiation", Dev. Biol. 170:741.

Lindsell et al., 1995, "Expression and functional analysis of rat Jagged, a ligand for Notch", Dev. Biol. 170:752 (Abstr. 56).

Myat et al., 1996, "A chick homologue of Serrate and its relationship with Notch and Delta homologues during central neurogenesis", Dev. Biol. 174:233–247.

Zimrin et al., 1996, "An antisense oligonucleotide to the Notch ligand Jagged promotes angiogenesis in bovine microvascular endothelial cells", FASEB 10:A1094 (Abstr. 547).

FIG. 3A

FIG. 3B

1801 GGATTGGTGTCCCTAGTTCGCTGCAGCAGCAACTGCCCCTGACTTCACTTGCCACTGCCAGCAGCCGATGACGGACCGACATGCGAAATAAATATCGACGAGTGCGCCGGG
GlyLeuValSerLeuGlyGlySerLeuGlnLeuGlnGlnLeuAlaProAspPheThrCysAspCysAlaAlaGlyTrpThrCysAspCysGluIleAsnIleAspGluCysAlaGly 493

1921 GGTCCCTGCGAGCATGTGGCACTTGCATCGATCTAATCGGTTGGCTTTCGATGTGAATGTCCGCCGAGTGGCATGGGATGTCGTCAGGTGGATGGACCGAGTGCGAGGCGCCGCAT
GlyProCysGluHisGlyGlyThrCysIleAspLeuIleGlyGlyPheArgCysGluValCysGlnValAspValCysGlnValAsnGluCysGluAlaProHis 533

2041 TCCGCCGGAATCGCTGCGAACGATGCTGACCACCAGCCACCGCGATTATTGGTAGTAATCTGAGCAGTACTGTCTTCTTCGGCCGCTCTGACCAGTGCAGTGGCATCCACATCCTTG
SerAlaGlyIleAlaAlaAsnAlaLeuLeuThrThrAlaThrAlaIleIleIleGlySerAsnLeuSerSerThrAlaLeuLeuAlaAlaLeuThrSerAlaValAlaSerThrSerLeu 573

2161 GCCATCGGACCCTGCATCAATGCCAAGGAGTGTCGCAATCAGCCGGGTTCCTTTGCCTCGCAATCAGCCGGGAGCAGGAGGTGACCTGTGCCGAGAATCTAGATGACTGTGTGGGT
AlaIleGlyProCysIleAsnAlaLysGluProCysIleAsnAlaLysCysArgAsnGlnProGlySerPheAlaCysIleCysLysGluValThrCysAlaGluAsnLeuAspAspCysValGly 613

2281 CAGTGCCGGAATGGAGCCACTCGATTCATTGATCTGGTCAACGACTATAGGTGCCGCTGTCCCTGCTCTGGATTCAGGGTCGCAGTTGCGAGACGGACATAGACGAGTGCGCCACTTCCCGTGC
GlnCysArgAsnGlyAlaThrArgPheIleAspLeuValAsnAspTyrArgCysArgCysSerGlyPheThrGlyArgAspCysGluThrAspArgIleAspGluCysAlaThrSerProCys 653

2401 CGAAACGGAGGCGAATGTGTGGACATGTTGGGACAAATTCAATTGCATTTGCCCACTTGCCTACTCGGGTTCTCTGCGAGGAGGCCAAGGAGAACTGCACACCGTCGCCATGTTTGAG
ArgAsnGlyGlyCysValAspMetValGlyLysPheAsnCysIleCysProLeuGlyTyrSerGlyTyrSerGlyLeuCysGluAlaLysCysThrProSerProCysLeuGlu 693

```
SERRATE  TCATTAAAGTCTGCCTGCAACTTAATTGCTTTAATTTAATACTGTTAGTCCATAAG
DELTA    ATGCATTGGATTAAATGTTTATTAACAGCATTCATTTGCTTCACAGTCATCGTGCAG

SERRATE  ATATCCGGAGCTGTAACTTCGAGCTGGAAATATTAGAAATCTCAAATACCAACAGC
DELTA    GTTCACAGTTCCGGCAGCTTTGAGTTGGGCCCTGAAGTACTTCAGCAACGATCACGGG

SERRATE  CATCTACTCAACGGCTATTGCTGCCGCATGCCAGCGAACTTAGGGCCACCAAGACG
DELTA    CGGGACAACGAGGGTCGCTGCTGCAGCGGAGTCGGACGGAGCGACGGGCAAGTGC

SERRATE  ATAGGCTGCTCGCCATGCACGACGGCATTCCCGCTGCCTGAACGAGTACCAGACC
DELTA    CTGGGC------AGCTGCAAGACGCGGTTTCGCTCTGCCTAAAGCACTACCAGGCC
```

FIG. 8A

```
            10         20         30         40         50         60
      GAATTCCCCT CCCCCCTTTT TCCATGCAGC TGATCTAAAA GGGAATAAAA GGCTGCGCAT
            70         80         90        100        110        120
      AATCATAATA ATAAAAGAAG GGGAGCGCGA GAGAAGGAAA GAAAGCCGGG AGGTGGAAGA
           130        140        150        160        170        180
      GGAGGGGGAG CGTCTCAAAG AAGCGATCAG AATAATAAAA GGAGGCCGGG CTCTTTGCCT
           190        200        210        220        230        240
      TCTGGAAGGG GCCGCTCTTG AAAGGGCTTT TGAAAAGTGG TGTTGTTTTC CAGTCGTGCA
           250        260        270        280        290        300
      TGCTCCAATC GGCGGAGTAT ATTAGAGCCG GGACGCGGCC GCAGGGGCAG CGGCGACGGC
           310        320        330        340        350        360
      AGCACCGGCG GCAGCACCAG CGCGAACAGC AGCGGCGGCG TCCCGAGTGC CCGCGGCGGC
           370        380        390        400        410        420
      GCGCGCAGCG ATGCGTTCCC CACGGACACG CGGCCGGTCC GGGCGCCCCC TAAGCCTCCT
                  M   R   S   P   R   T   R   G   R   S   G   R   P   L   S   L   L>
           430        440        450        460        470        480
      GCTCGCCCTG CTCTGTGCCC TGCGAGCCAA GGTGTGTGGG GCCTCGGGTC AGTTCGAGTT
        L   A   L   L   C   A   L   R   A   K   V   C   G   A   S   G   Q   F   E   L>
           490        500        510        520        530        540
      GGAGATCCTG TCCATGCAGA ACGTGAACGG GGAGCTGCAG AACGGGAACT GCTGCGGCGG
        E   I   L   S   M   Q   N   V   N   G   E   L   Q   N   G   N   C   C   G   G>
           550        560        570        580        590        600
      CGCCCGGAAC CCGGGAGACC GCAAGTGCAC CCGCGACGAG TGTGACACAT ACTTCAAAGT
        A   R   N   P   G   D   R   K   C   T   R   D   E   C   D   T   Y   F   K   V>
           610        620        630        640        650        660
      GTGCCTCAAG GAGTATCAGT CCCGCGTCAC GGCCGGGGGG CCCTGCAGCT TCGGCTCAGG
        C   L   K   E   Y   Q   S   R   V   T   A   G   G   P   C   S   F   G   S   G>
           670        680        690        700        710        720
      GTCCACGCCT GTCATCGGGG GCAACACCTT CAACCTCAAG GCCAGCCGCG GCAACGACCC
        S   T   P   V   I   G   G   N   T   F   N   L   K   A   S   P   G   N   D   P>
           730        740        750        760        770        780
      GAACCGCATC GTGCTGCCTT TCAGTTTCGC CTGGCCGAGG TCCTATACGT TGCTTGTGGA
        N   R   I   V   L   P   F   S   F   A   W   P   R   S   Y   T   L   L   V   E>
           790        800        810        820        830        840
      GGCGTGGGAT TCCAGTAATG ACACCGTTCA ACCTGACAGT ATTATTGAAA AGGCTTCTCA
        A   W   D   S   S   N   D   T   V   Q   P   D   S   I   I   E   K   A   S   H>
           850        860        870        880        890        900
      CTCGGGCATG ATCAACCCCA GCCGGCAGTG GCAGACGCTG AAGCAGAACA CGGGCGTTGC
        S   G   M   I   N   P   S   R   Q   W   Q   T   L   K   Q   N   T   G   V   A>
```

FIG. 9A

```
     910        920        930        940        950        960
CCACTTTGAG TATCAGATCC GCGTGACCTG TGATGACTAC TACTATGGCT TTGGCTGTAA
 H  F  E    Y  Q  I    R  V  T  C  D  D  Y    Y  Y  G    F  G  C  N>
     970        980        990       1000       1010       1020
TAAGTTCTGC CGCCCCAGAG ATGACTTCTT TGGACACTAT GCCTGTGACC AGAATGGCAA
 K  F  C    R  P  R    D  D  F  F  G  H  Y    A  C  D    Q  N  G  N>
    1030       1040       1050       1060       1070       1080
CAAAACTTGC ATGGAAGGCT GGATGGGCCC CGAATGTAAC AGAGCTATTT GCCGACAAGG
 K  T  C    M  E  G    W  M  G  P  E  C  N    R  A  I    C  R  Q  G>
    1090       1100       1110       1120       1130       1140
CTGCAGTCCT AAGCATGGGT CTTGCAAACT CCCAGGTGAC TGCAGGTGCC AGTACGGCTG
 C  S  P    K  H  G    S  C  K  L  P  G  D    C  R  C    Q  Y  G  W>
    1150       1160       1170       1180       1190       1200
GCAAGGCCTG TACTGTGATA AGTGCATCCC ACACCCGGGA TGCGTCCACG GCATCTGTAA
 Q  G  L    Y  C  D    K  C  I  P  H  P  G    C  V  H    G  I  C  N>
    1210       1220       1230       1240       1250       1260
TGAGCCCTGG CAGTGCCTCT GTGAGACCAA CTGGGGCGGC CAGCTCTGTG ACAAAGATCT
 E  P  W    Q  C  L    C  E  T  N  W  G  G    Q  L  C    D  K  D  L>
    1270       1280       1290       1300       1310       1320
CAATTACTGT GGGACTCATC AGCCGTGTCT CAACGGGGGA ACTTGTAGCA ACACAGGCCC
 N  Y  C    G  T  H    Q  P  C  L  N  G  G    T  C  S    N  T  G  P>
    1330       1340       1350       1360       1370       1380
TGACAAATAT CAGTGTTCCT GCCCTGAGGG GTATTCAGGA CCCAACTGTG AAATTGCTGA
 D  K  Y    Q  C  S    C  P  E  G  Y  S  G    P  N  C    E  I  A  E>
    1390       1400       1410       1420       1430       1440
GCACGCCTGC CTCTCTGATC CCTGTCACAA CAGAGGCAGC TGTAAGGAGA CCTCCCTGGG
 H  A  C    L  S  D    P  C  H  N  R  G  S    C  K  E    T  S  L  G>
    1450       1460       1470       1480       1490       1500
CTTTGAGTGT GAGTGTTCCC CAGGCTGGAC CGGCCCCACA TGCTCTACAA ACATTGATGA
 F  E  C    E  C  S    P  G  W  T  G  P  T    C  S  T    N  I  D  D>
    1510       1520       1530       1540       1550       1560
CTGTTCTCCT AATAACTGTT CCCACGGGGG CACCTGCCAG GACCTGGTTA ACGGATTTAA
 C  S  P    N  N  C    S  H  G  G  T  C  Q    D  L  V    N  G  F  K>
    1570       1580       1590       1600       1610       1620
GTGTGTGTGC CCCCCACAGT GGACTGGGAA AACGTGCCAG TTAGATGCAA ATGAATGTGA
 C  V  C    P  P  Q    W  T  G  K  T  C  Q    L  D  A    N  E  C  E>
    1630       1640       1650       1660       1670       1680
GGCCAAACCT TGTGTAAACG CCAAATCCTG TAAGAATCTC ATTGCCAGCT ACTACTGCGA
 A  K  P    C  V  N    A  K  S  C  K  N  L    I  A  S    Y  Y  C  D>
```

FIG. 9B

```
            1690       1700       1710       1720       1730       1740
        CTGTCTTCCC GGCTGGATGG GTCAGAATTG TGACATAAAT ATTAATGACT GCCTTGGCCA
         C  L  P   G  W  M    G  Q  N   C  D  I  N  I  N  D   C  L  G  Q>
            1750       1760       1770       1780       1790       1800
        GTGTCAGAAT GACGCCTCCT GTCGGGATTT GGTTAATGGT TATCGCTGTA TCTGTCCACC
         C  Q  N   D  A  S    C  R  D   L  V  N  G  Y  R  C   I  C  P  P>
            1810       1820       1830       1840       1850       1860
        TGGCTATGCA GGCGATCACT GTGAGAGAGA CATCGATGAA TGTGCCAGCA ACCCCTGTTT
         G  Y  A   G  D  H    C  E  R   D  I  D  E  C  A  S   N  P  C  L>
            1870       1880       1890       1900       1910       1920
        GAATGGGGGT CACTGTCAGA ATGAAATCAA CAGATTCCAG TGTCTGTGTC CCACTGGTTT
         N  G  G   H  C  Q    N  E  I   N  R  F  Q  C  L  C   P  T  G  F>
            1930       1940       1950       1960       1970       1980
        CTCTGGAAAC CTCTGTCAGC TGGACATCGA TTATTGTGAG CCTAATCCCT GCCAGAACGG
         S  G  N   L  C  Q    L  D  I   D  Y  C  E  P  N  P   C  Q  N  G>
            1990       2000       2010       2020       2030       2040
        TGCCCAGTGC TACAACCGTG CCAGTGACTA TTTCTGCAAG TGCCCCGAGG ACTATGAGGG
         A  Q  C   Y  N  R    A  S  D   Y  F  C  K  C  P  E   D  Y  E  G>
            2050       2060       2070       2080       2090       2100
        CAAGAACTGC TCACACCTGA AAGACCACTG CCGCACGACC CCCTGTGAAG TGATTGACAG
         K  N  C   S  H  L    K  D  H   C  R  T  T  P  C  E   V  I  D  S>
            2110       2120       2130       2140       2150       2160
        CTGCACAGTG GCCATGGCTT CCAACGACAC ACCTGAAGGG GTGCGGTATA TTTCCTCCAA
         C  T  V   A  M  A    S  N  D   T  P  E  G  V  R  Y   I  S  S  N>
            2170       2180       2190       2200       2210       2220
        CGTCTGTGGT CCTCACGGGA AGTGCAAGAG TCAGTCGGGA GGCAAATTCA CCTGTGACTG
         V  C  G   P  H  G    K  C  K   S  Q  S  G  G  K  F   T  C  D  C>
            2230       2240       2250       2260       2270       2280
        TAACAAAGGC TTCACGGGAA CATACTGCCA TGAAAATATT AATGACTGTG AGAGCAACCC
         N  K  G   F  T  G    T  Y  C   H  E  N  I  N  D  C   E  S  N  P>
            2290       2300       2310       2320       2330       2340
        TTGTAGAAAC GGTGGCACTT GCATCGATGG TGTCAACTCC TACAAGTGCA TCTGTAGTGA
         C  R  N   G  G  T    C  I  D   G  V  N  S  Y  K  C   I  C  S  D>
            2350       2360       2370       2380       2390       2400
        CGGCTGGGAG GGGGCCTACT GTGAAACCAA TATTAATGAC TGCAGCCAGA ACCCCTGCCA
         G  W  E   G  A  Y    C  E  T   N  I  N  D  C  S  Q   N  P  C  H>
            2410       2420       2430       2440       2450       2460
        CAATGGGGGC ACGTGTCGCG ACCTGGTCAA TGACTTCTAC TGTGACTGTA AAAATGGGTG
         N  G  G   T  C  R    D  L  V   N  D  F  Y  C  D  C   K  N  G  W>
```

FIG. 9C

```
      2470        2480        2490        2500        2510        2520
GAAAGGAAAG  ACCTGCCACT  CACGTGACAG  TCAGTGTGAT  GAGGCCACGT  GCAACAACGG
  K G K       T C H       S R D S     Q C D       E A T       C N N G>
      2530        2540        2550        2560        2570        2580
TGGCACCTGC  TATGATGAGG  GGGATGCTTT  TAAGTGCATG  TGTCCTGGCG  GCTGGGAAGG
  G T C       Y D E       G D A F     K C M       C P G       G W E G>
      2590        2600        2610        2620        2630        2640
AACAACCTGT  AACATAGCCC  GAAACAGTAG  CTGCCTGCCC  AACCCCTGCC  ATAATGGGGG
  T T C       N I A       R N S S     C L P       N P C       H N G G>
      2650        2660        2670        2680        2690        2700
CACATGTGTG  GTCAACGGCG  AGTCCTTTAC  GTGCGTCTGC  AAGGAAGGCT  GGGAGGGGCC
  T C V       V N G       E S F T     C V C       K E G       W E G P>
      2710        2720        2730        2740        2750        2760
CATCTGTGCT  CAGAATACCA  ATGACTGCAG  CCCTCATCCC  TGTTACAACA  GCGGCACCTG
  I C A       Q N T       N D C S     P H P       C Y N       S G T C>
      2770        2780        2790        2800        2810        2820
TGTGGATGGA  GACAACTGGT  ACCGGTGCGA  ATGTGCCCCG  GGTTTTGCTG  GGCCCGACTG
  V D G       D N W       Y R C E     C A P       G F A       G P D C>
      2830        2840        2850        2860        2870        2880
CAGAATAAAC  ATCAATGAAT  GCCAGTCTTC  ACCTTGTGCC  TTTGGAGCGA  CCTGTGTGGA
  R I N       I N E       C Q S S     P C A       F G A       T C V D>
      2890        2900        2910        2920        2930        2940
TGAGATCAAT  GGCTACCGGT  GTGTCTGCCC  TCCAGGGCAC  AGTGGTGCCA  AGTGCCAGGA
  E I N       G Y R       C V C P     P G H       S G A       K C Q E>
      2950        2960        2970        2980        2990        3000
AGTTTCAGGG  AGACCTTGCA  TCACCATGGG  GAGTGTGATA  CCAGATGGGG  CCAAATGGGA
  V S G       R P C       I T M G     S V I       P D G       A K W D>
      3010        3020        3030         3040        3050        3060
TGATGACTGT  AATACCTGCC  AGTGCCTGAA  TGGACGGATC  GCCTGCTCAA  AGGTCTGGTG
  D D C       N T C       Q C L N     G R I       A C S       K V W C>
      3070        3080        3090        3100        3110        3120
TGGCCCTCGA  CCTTGCCTGC  TCCACAAAGG  GCACAGCGAG  TGCCCCAGCG  GGCAGAGCTG
  G P R       P C L       L H K G     H S E       C P S       G Q S C>
      3130        3140        3150        3160        3170        3180
CATCCCCATC  CTGGACGACC  AGTGCTTCGT  CCACCCCTGC  ACTGGTGTGG  GCGAGTGTCG
  I P I       L D D       Q C F V     H P C       T G V       G E C R>
      3190        3200        3210        3220        3230        3240
GTCTTCCAGT  CTCCAGCCGG  TGAAGACAAA  GTGCACCTCT  GACTCCTATT  ACCAGGATAA
  S S S       L Q P       V K T K     C T S       D S Y       Y Q D N>
      3250        3260        3270        3280        3290        3300
CTGTGCGAAC  ATCACATTTA  CCTTTAACAA  GGAGATGATG  TCACCAGGTC  TTACTACGGA
  C A N       I T F       T F N K     E M M       S P G       L T T E>
```

FIG. 9D

```
          3310       3320       3330       3340       3350       3360
     GCACATTTGC AGTGAATTGA GGAATTTGAA TATTTTGAAG AATGTTTCCG CTGAATATTC
      H  I  C   S  E  L   R  N  L   N  I  L  K  N  V  S   A  E  Y  S>
          3370       3380       3390       3400       3410       3420
     AATCTACATC GCTTGCGAGC CTTCCCCTTC AGCGAACAAT GAAATACATG TGGCCATTTC
      I  Y  I   A  C  E   P  S  P   S  A  N  N  E  I  H   V  A  I  S>
          3430       3440       3450       3460       3470       3480
     TGCTGAAGAT ATACGGGATG ATGGGAACCC GATCAAGGAA ATCACTGACA AAATAATCGA
      A  E  D   I  R  D   D  G  N   P  I  K  E  I  T  D   K  I  I  D>
          3490       3500       3510       3520       3530       3540
     TCTTGTTACT AAACGTGATG GAAACAGCTC GCTGATTGCT GCCGTTGAAG AAGTAAGAGT
      L  V  T   K  R  D   G  N  S   S  L  I  A  A  V  E   E  V  R  V>
          3550       3560       3570       3580       3590       3600
     TCAGAGGCGG CCTCTGAAGA ACAGAACAGA TTTCCTTGTT CCCTTGCTGA GCTCTGTCTT
      Q  R  R   P  L  K   N  R  T  D  F  L  V   P  L  L   S  S  V  L>
          3610       3620       3630       3640       3650       3660
     AACTGTGGCT TGGATCTGTT GCTTGGTGAC GGCCTTCTAC TGGTGCCTGC GGAAGCGGCG
      T  V  A   W  I  C   C  L  V   T  A  F  Y  W  C  L   R  K  R  R>
          3670       3680       3690       3700       3710       3720
     GAAGCCGGGC AGCCACACAC ACTCAGCCTC TGAGGACAAC ACCACCAACA ACGTGCGGGA
      K  P  G   S  H  T   H  S  A   S  E  D  N  T  T  N   N  V  R  E>
          3730       3740       3750       3760       3770       3780
     GCAGCTGAAC CAGATCAAAA ACCCCATTGA GAAACATGGG GCCAACACGG TCCCCATCAA
      Q  L  N   Q  I  K   N  P  I   E  K  H  G  A  N  T   V  P  I  K>
          3790       3800       3810       3820       3830       3840
     GGATTACGAG AACAAGAACT CCAAAATGTC TAAAATAAGG ACACACAATT CTGAAGTAGA
      D  Y  E   N  K  N   S  K  M   S  K  I  R  T  H  N   S  E  V  E>
          3850       3860       3870       3880       3890       3900
     AGAGGACGAC ATGGACAAAC ACCAGCAGAA AGCCCGGTTT GCCAAGCAGC CGGCGTACAC
      E  D  D   M  D  K   H  Q  Q   K  A  R  F  A  K  Q   P  A  Y  T>
          3910       3920       3930       3940       3950       3960
     GCTGGTAGAC AGAGAAGAGA AGCCCCCCAA CGGCACGCCG ACAAAACACC CAAACTGGAC
      L  V  D   R  E  E   K  P  P   N  G  T  P  T  K  H   P  N  W  T>
          3970       3980       3990       4000       4010       4020
     AAACAAACAG GACAACAGAG ACTTGGAAAG TGCCCAGAGC TTAAACCGAA TGGAGTACAT
      N  K  Q   D  N  R   D  L  E   S  A  Q  S  L  N  R   M  E  Y  I>
          4030       4040       4050       4060       4070       4080
     CGTATAGCAG ACCGCGGGCA CTGCCGCCGC TAGGTAGAGT CTGAGGGCTT GTAGTTCTTT
      V  >
```

FIG. 9E

```
      4090       4100       4110       4120       4130       4140
AAACTGTCGT GTCATACTCG AGTCTGAGGC CGTTGCTGAC TTAGAATCCC TGTGTTAATT
      4150       4160       4170       4180       4190       4200
TAGTTTGACA AGCTGGCTTA CACTGGCAAT GGTAGTTCTG TGGTTGGCTG GGAAATCGAG
      4210       4220       4230       4240       4250       4260
TGGCGCATCT CACAGCTATG CAAAAAGCTA GTCAACAGTA CCCCTGGTTG TGTGTCCCCT
      4270       4280       4290       4300       4310       4320
TGCAGCCGAC ACGGTCTCGG ATCAGGCTCC CAGGAGCTGC CCAGCCCCCT GGTACTTTGA
      4330       4340       4350       4360       4370       4380
GCTCCCACTT CTGCCAGATG TCTAATGGTG ATGCAGTCTT AGATCATAGT TTTATTTATA
      4390       4400       4410       4420       4430       4440
TTTATTGACT CTTGAGTTGT TTTTGTATAT TGGTTTTATG ATGACGTACA AGTAGTTCTG
      4450       4460       4470       4480       4490       4500
TATTTGAAAG TGCCTTTGCA GCTCAGAACC ACAGCAACGA TCACAAATGA CTTTATTATT
      4510       4520       4530       4540       4550       4560
TATTTTTTTT AATTGTATTT TTGTTGTTGG GGGAGGGGAG ACTTTGATGT CAGCAGTTGC
      4570       4580       4590       4600       4610       4620
TGGTAAAATG AAGAATTTAA AGAAAAAATG TCCAAAAGTA GAACTTTGTA TAGTTATGTA
      4630       4640       4650       4660       4670       4680
AATAATTCTT TTTTATTAAT CACTGTGTAT ATTTGATTTA TTAACTTAAT AATCAAGAGC
      4690       4700       4710       4720       4730       4740
CTTAAAACAT CATTCCTTTT TATTTATATG TATGTGTTTA GAATTGAAGG TTTTTGATAG
      4750       4760       4770       4780       4790       4800
CATTGTAAGC GTATGGCTTT ATTTTTTTGA ACTCTTCTCA TTACTTGTTG CCTATAAGCC
      4810       4820       4830       4840       4850       4860
AAAAAGGAAA GGGTGTTTTG AAAATAGTTT ATTTTAAAAC AATAGGATGG GCTACACGTA
      4870       4880       4890       4900       4910       4920
CATAGGTAAA TAATAGCACC GTACTGGTTA TGATGATGAA AATAACTGGA AACTTGAAAG
      4930       4940       4950       4960       4970       4980
CTTGTGGTAA TGGCAGATAA AGATGGTTCA CCTGGGAAAT TAAAACTTGA ATGGTTGTAC
      4990       5000       5010       5020       5030       5040
AGAAAAGCAC AGAGTGGAAT GCACATCAAT GACAGTAAGG GAGTTAGTTC TAGGAACAGC
      5050       5060       5070       5080       5090       5100
TCCTGAACAG TAAGATTCCC GCAATAGTCT CCGCCTCGTT CGTCTATGGT ATGCATCCCA
      5110       5120       5130       5140       5150       5160
TTCATTTTCT TCTTCTGATT ATTGTCATCT TTCCCTTTGC CAAATGGGCA GTTATTGTTT
      5170       5180       5190       5200       5210       5220
CAGGGAGAGA AGCTGCTCAT TGGCCAATCA TTCTGGTGTG CAGTGCTCCA TCGGATTCTA
      5230       5240       5250       5260       5270       5280
CATGTCCAAC AAGGCATGTC TGGATGATGC AATGTCTGTC TGACCCCCGG AATTCCGTGC
```

FIG. 9F

```
       5290       5300       5310       5320       5330       5340
  AGAGACAACA TTCTAGACAG ATATACACTT TTTATTATTA ACAAACTTTG GCCACAACCT
       5350       5360       5370       5380       5390       5400
  TTGATGTATA AATTGCCGGA TTTCCCCAGT CCTTTCATTG TGGCTTTGGA CAGGAGCAGG
       5410       5420       5430       5440       5450       5460
  CTCACTTGTC TGCTTCAGGC TGCCTTTCTC TTGGGTTGCA CCTCAGTTCT TACTTATTTA
       5470       5480       5490       5500       5510       5520
  TTTATTTTGA GTGGAGCATA GGGGCCTCTT CCAAAATGGG TAGAGCTCAG GGGCTTTCTT
       5530       5540       5550       5560       5570       5580
  ATTGAAATGG TCACATGATA AAAACGGGCT GAAAAGGAG AGTTCCAGGA GAAAAGCCCA
       5590       5600       5610       5620       5630       5640
  GAAAAGGCCC CTCCTCAGAA GACAGCCTTT AAGCCTCTTG CTTACTGAAG GAAGCCCCAC
       5650       5660       5670       5680       5690       5700
  CTTCTAGCAC TGAGGCCGGG TCTGATCTTC CAGAGGAGTT GGAGGAGTCC ATGAGAATGG
       5710       5720       5730       5740       5750       5760
  CCACCATTCT TGCTTGCTGC TGCTGATGTT GCAGTTTTGA GAGAACAGCG GGATCCTTGT
       5770       5780       5790       5800       5810       5820
  TGTCCTCTAG AGACTTGAGT CTGTCACTGA CATTTTTTCA GTTCCTTTGC TCATAGACCA
       5830       5840       5850       5860       5870       5880
  TACGAGGAAT TAGTGATGTG TCAGTTGAGA GTTCACAATC TCATTGTTCA TTTAATTCAC
       5890       5900       5910       5920       5930       5940
  TTTAAAGTTG TCAATTTCTG TGTGAGTAAC CTGTAAAAGA CACCTTTCCA GAAGAGTTTT
       5950       5960       5970       5980       5990       6000
  GCCGTCTGTT TGAAAAAAAA ATCTTTATAA ACTTTCCTAA GTATCTGGAT TTGGATTCCT
       6010       6020       6030       6040       6050       6060
  TATTTGGAGA GAAAATGTAC CCTGTCTCCA CCAAAAATAC AAAAATTAGC CAGGCTTGGT
       6070       6080       6090       6100       6110       6120
  GGTGCACACC GGTAATCCCA GCAACTCTGG AGACTAAGGC AGGAAGAATC GCTTGACCCA
       6130       6140       6150       6160       6170       6180
  GGAGGGTCGA GGCTACAATG AGTTGAAACC GCGCCACTGC ACTCCAGCCT GGGCGACAGT
       6190       6200       6210       6220       6230       6240
  GCGAGGCCCT GTCTCAAAAA TAAAATAAAA TAAATAAATA AATTAGCCAG ATACTGTGTG
       6250       6260       6270       6280       6290       6300
  CACGCCTGCA GTCCCAGCTA TTCTGGAAGC TGAGGTGGGA AGATGGTTAA GCCTGAGAGG
       6310       6320       6330       6340       6350       6360
  ACAAAGCTGC AGTGAGTCAT GTTTGCATCA CTGCACTCCA GCCTGGGTGA CAGAGCAAGA
       6370       6380       6390       6400       6410       6420
  CCCTGTCTAA AAAACAAAAA CAGGCCGGGT GTGGTGGCTC ATGCCTGCCA TCCCAGTGCT
       6430       6440       6450       6460
  TTGGGAGGCA GAGGTTGGCA TAATCCCAGC GCTCTGGGAA TTCC
```

FIG. 9G

```
GGCCGGGGCC GGGCGGGCGG GTCGCGGGGG CAATGCGGGC GCAGGGCCGG GGGCGCCTTC    60

CCCGGCGGCT GCTGCTGCTG CTGGCGCTCT GGGTGCAGGC GGCGCGGCCC ATGGGCTATT   120

TCGAGCTGCA GCTGAGCGCG CTGCGGAACG TGAACGGGGA GCTGCTGAGC GGCGCCTGCT   180

GTGACGGCGA CGGCCGGACA ACGCGCGCGG GGGGCTGCGG CCACGACGAG TGCGACACCG   240

CTCCTTTACC CTCATCGTGG AGGCCTGGGA CTGGGACAAC GATACCACCC CGAATGAGGA   300

GCTGCTGATC GAGCGAGTGT CGCATGCCGG C ATG ATC AAC CCG GAG GAC CGC       352
                                  Met Ile Asn Pro Glu Asp Arg
                                   1               5
TGG AAG AGC CTG CAC TTC AGC GGC CAC GTG GCG CAC CTG GAG CTG CAG     400
Trp Lys Ser Leu His Phe Ser Gly His Val Ala His Leu Glu Leu Gln
         10                  15                  20
ATC CGC GTG CGC TGC GAC GAG AAC TAC TAC AGC GCC ACT TGC AAC AAG     448
Ile Arg Val Arg Cys Asp Glu Asn Tyr Tyr Ser Ala Thr Cys Asn Lys
 25                  30                  35
TTC TGC CGG CCC CGC AAT GAC TTT TTC GGC CAC TAC ACC TGC GAC CAG     496
Phe Cys Arg Pro Arg Asn Asp Phe Phe Gly His Tyr Thr Cys Asp Gln
 40                  45                  50                  55
TAC GGC AAC AAG GCC TGC ATG GAC GGC TGG ATG GGC AAG GAG TGC AAG     544
Tyr Gly Asn Lys Ala Cys Met Asp Gly Trp Met Gly Lys Glu Cys Lys
                 60                  65                  70
GAA GCT GTG TGT AAA CAA GGG TGT AAT TTG CTC CAC GGG GGA TGC ACC     592
Glu Ala Val Cys Lys Gln Gly Cys Asn Leu Leu His Gly Gly Cys Thr
             75                  80                  85
GTG CCT GGG GAG TGC AGG TGC AGC TAC GGC TGG CAA GGG AGG TTC TGC     640
Val Pro Gly Glu Cys Arg Cys Ser Tyr Gly Trp Gln Gly Arg Phe Cys
         90                  95                 100
GAT GAG TGT GTC CCC TAC CCC GGC TGC GTG CAT GGC AGT TGT GTG GAG     688
Asp Glu Cys Val Pro Tyr Pro Gly Cys Val His Gly Ser Cys Val Glu
    105                 110                 115
CCC TGG CAG TGC AAC TGT GAG ACC AAC TGG GGC GGC CTG CTC TGT GAC     736
Pro Trp Gln Cys Asn Cys Glu Thr Asn Trp Gly Gly Leu Leu Cys Asp
120                 125                 130                 135
AAA GAC CTG AAC TAC TGT GGC AGC CAC CAC CCC TGC ACC AAC GGA GGC     784
Lys Asp Leu Asn Tyr Cys Gly Ser His His Pro Cys Thr Asn Gly Gly
             140                 145                 150
```

FIG. 10A

```
ACG TGC ATC AAC GCC GAG CCT GAC CAG TAC CGC TGC ACC TGC CCT GAC   832
Thr Cys Ile Asn Ala Glu Pro Asp Gln Tyr Arg Cys Thr Cys Pro Asp
            155                 160                 165
GGC TAC TCG GGC AGG AAC TGT GAG AAG GCT GAG CAC GCC TGC ACC TCC   880
Gly Tyr Ser Gly Arg Asn Cys Glu Lys Ala Glu His Ala Cys Thr Ser
            170                 175                 180
AAC CCG TGT GCC AAC GGG GGC TCT TGC CAT GAG GTG CCG TCC GGC TTC   928
Asn Pro Cys Ala Asn Gly Gly Ser Cys His Glu Val Pro Ser Gly Phe
            185                 190                 195
GAA TGC CAC TGC CCA TCG GGC TGG AGC GGG CCC ACC TGT GCC CTT GAC   976
Glu Cys His Cys Pro Ser Gly Trp Ser Gly Pro Thr Cys Ala Leu Asp
200                 205                 210                 215
ATC GAT GAG TGT GCT TCG AAC CCG TGT GCG GCC GGT GGC ACC TGT GTG  1024
Ile Asp Glu Cys Ala Ser Asn Pro Cys Ala Ala Gly Gly Thr Cys Val
                220                 225                 230
GAC CAG GTG GAC GGC TTT GAG TGC ATC TGC CCC GAG CAG TGG GTG GGG  1072
Asp Gln Val Asp Gly Phe Glu Cys Ile Cys Pro Glu Gln Trp Val Gly
                235                 240                 245
GCC ACC TGC CAG CTG GAC GCC AAT GAG TGT GAA GGG AAG CCA TGC CTT  1120
Ala Thr Cys Gln Leu Asp Ala Asn Glu Cys Glu Gly Lys Pro Cys Leu
            250                 255                 260
AAC GCT TTT TCT TGC AAA AAC CTG ATT GGC GGC TAT TAC TGT GAT TGC  1168
Asn Ala Phe Ser Cys Lys Asn Leu Ile Gly Gly Tyr Tyr Cys Asp Cys
            265                 270                 275
ATC CCG GGC TGG AAG GGC ATC AAC TGC CAT ATC AAC GTC AAC GAC TGT  1216
Ile Pro Gly Trp Lys Gly Ile Asn Cys His Ile Asn Val Asn Asp Cys
280                 285                 290                 295
CGC GGG CAG TGT CAG CAT GGG GGC ACC TGC AAG GAC CTG GTG AAC GGG  1264
Arg Gly Gln Cys Gln His Gly Gly Thr Cys Lys Asp Leu Val Asn Gly
                300                 305                 310
TAC CAG TGT GTG TGC CCA CGG GGC TTC GGA GGC CGG CAT TGC GAG CTG  1312
Tyr Gln Cys Val Cys Pro Arg Gly Phe Gly Gly Arg His Cys Glu Leu
                315                 320                 325
GAA CGA GAC AAG TGT GCC AGC AGC CCC TGC CAC AGC GGC GGC CTC TGC  1360
Glu Arg Asp Lys Cys Ala Ser Ser Pro Cys His Ser Gly Gly Leu Cys
            330                 335                 340
GAG GAC CTG GCC GAC GGC TTC CAC TGC CAC TGC CCC CAG GGC TTC TCC  1408
Glu Asp Leu Ala Asp Gly Phe His Cys His Cys Pro Gln Gly Phe Ser
            345                 350                 355
```

FIG. 10B

```
GGG CCT CTC TGT GAG GTG GAT GTC GAC CTT TGT GAG CCA AGC CCC TGC  1456
Gly Pro Leu Cys Glu Val Asp Val Asp Leu Cys Glu Pro Ser Pro Cys
360             365             370             375
CGG AAC GGC GCT CGC TGC TAT AAC CTG GAG GGT GAC TAT TAC TGC GCC  1504
Arg Asn Gly Ala Arg Cys Tyr Asn Leu Glu Gly Asp Tyr Tyr Cys Ala
                380             385             390
TGC CCT GAT GAC TTT GGT GGC AAG AAC TGC TCC GTG CCC CGC GAG CCG  1552
Cys Pro Asp Asp Phe Gly Gly Lys Asn Cys Ser Val Pro Arg Glu Pro
            395             400             405
TGC CCT GGC GGG GCC TGC AGA GTG ATC GAT GGC TGC GGG TCA GAC GCG  1600
Cys Pro Gly Gly Ala Cys Arg Val Ile Asp Gly Cys Gly Ser Asp Ala
        410             415             420
GGG CCT GGG ATG CCT GGC ACA GCA GCC TCC GGC GTG TGT GGC CCC CAT  1648
Gly Pro Gly Met Pro Gly Thr Ala Ala Ser Gly Val Cys Gly Pro His
    425             430             435
GGA CGC TGC GTC AGC CAG CCA GGG GGC AAC TTT TCC TGC ATC TGT GAC  1696
Gly Arg Cys Val Ser Gln Pro Gly Gly Asn Phe Ser Cys Ile Cys Asp
440             445             450             455
AGT GGC TTT ACT GGC ACC TAC TGC CAT GAG AAC ATT GAC GAC TGC CTG  1744
Ser Gly Phe Thr Gly Thr Tyr Cys His Glu Asn Ile Asp Asp Cys Leu
                460             465             470
GGC CAG CCC TGC CGC AAT GGG GGC ACA TGC ATC GAT GAG GTG GAC GCC  1792
Gly Gln Pro Cys Arg Asn Gly Gly Thr Cys Ile Asp Glu Val Asp Ala
            475             480             485
TTC CGC TGC TTC TGC CCC AGC GGT TGG GAG GGC GAG CTC TGC GAC ACC  1840
Phe Arg Cys Phe Cys Pro Ser Gly Trp Glu Gly Glu Leu Cys Asp Thr
        490             495             500
AAT CCC AAC GAC TGC CTT CCC GAT CCC TGC CAC AGC CGC GGC CGC TGC  1888
Asn Pro Asn Asp Cys Leu Pro Asp Pro Cys His Ser Arg Gly Arg Cys
    505             510             515
TAC GAC CTG GTC AAT GAC TTC TAC TGT GCG TGC GAC GAC GGC TGG AAG  1936
Tyr Asp Leu Val Asn Asp Phe Tyr Cys Ala Cys Asp Asp Gly Trp Lys
520             525             530             535
GGC AAG ACC TGC CAC TCA CGC GAG TTC CAG TGC GAT GCC TAC ACC TGC  1984
Gly Lys Thr Cys His Ser Arg Glu Phe Gln Cys Asp Ala Tyr Thr Cys
                540             545             550
AGC AAC GGT GGC ACC TGC TAC GAC AGC GGC GAC ACC TTC CGC TGC GCC  2032
Ser Asn Gly Gly Thr Cys Tyr Asp Ser Gly Asp Thr Phe Arg Cys Ala
            555             560             565
TGC CCC CCC GGC TGG AAG GGC AGC ACC TGC GCC GTC GCC AAG AAC AGC  2080
Cys Pro Pro Gly Trp Lys Gly Ser Thr Cys Ala Val Ala Lys Asn Ser
        570             575             580
```

FIG. 10C

```
AGC TGC CTG CCC AAC CCC TGT GTG AAT GGT GGC ACC TGC GTG GGC AGC    2128
Ser Cys Leu Pro Asn Pro Cys Val Asn Gly Gly Thr Cys Val Gly Ser
        585                 590                 595
GGG GCC TCC TTC TCC TGC ATC TGC CGG GAC GGC TGG GAG GGT CGT ACT    2176
Gly Ala Ser Phe Ser Cys Ile Cys Arg Asp Gly Trp Glu Gly Arg Thr
600                 605                 610                 615
TGC ACT CAC AAT ACC AAC GAC TGC AAC CCT CTG CCT TGC TAC AAT GGT    2224
Cys Thr His Asn Thr Asn Asp Cys Asn Pro Leu Pro Cys Tyr Asn Gly
                620                 625                 630
GGC ATC TGT GTT GAC GGC GTC AAC TGG TTC CGC TGC GAG TGT GCA CCT    2272
Gly Ile Cys Val Asp Gly Val Asn Trp Phe Arg Cys Glu Cys Ala Pro
            635                 640                 645
GGC TTC GCG GGG CCT GAC TGC CGC ATC AAC ATC GAC GAG TGC CAG TCC    2320
Gly Phe Ala Gly Pro Asp Cys Arg Ile Asn Ile Asp Glu Cys Gln Ser
            650                 655                 660
TCG CCC TGT GCC TAC GGG GCC ACG TGT GTG GAT GAG ATC AAC GGG TAT    2368
Ser Pro Cys Ala Tyr Gly Ala Thr Cys Val Asp Glu Ile Asn Gly Tyr
        665                 670                 675
CGC TGT AGC TGC CCA CCC GGC CGA GCC GGC CCC CGG TGC CAG GAA GTG    2416
Arg Cys Ser Cys Pro Pro Gly Arg Ala Gly Pro Arg Cys Gln Glu Val
680                 685                 690                 695
ATC GGG TTC GGG AGA TCC TGC TGG TCC CGG GGC ACT CCG TTC CCA CAC    2464
Ile Gly Phe Gly Arg Ser Cys Trp Ser Arg Gly Thr Pro Phe Pro His
                700                 705                 710
GGA AGC TCC TGG GTG GAA GAC TGC AAC AGC TGC CGC TGC CTG GAT GGC    2512
Gly Ser Ser Trp Val Glu Asp Cys Asn Ser Cys Arg Cys Leu Asp Gly
            715                 720                 725
CGC CGT GAC TGC AGC AAG GTG TGG TGC GGA TGG AAG CCT TGT CTG CTG    2560
Arg Arg Asp Cys Ser Lys Val Trp Cys Gly Trp Lys Pro Cys Leu Leu
            730                 735                 740
GCC GGC CAG CCC GAG GCC CTG AGC GCC CAG TGC CCA CTG GGG CAA AGG    2608
Ala Gly Gln Pro Glu Ala Leu Ser Ala Gln Cys Pro Leu Gly Gln Arg
        745                 750                 755
TGC CTG GAG AAG GCC CCA GGC CAG TGT CTG CGA CCA CCC TGT GAG GCC    2656
Cys Leu Glu Lys Ala Pro Gly Gln Cys Leu Arg Pro Pro Cys Glu Ala
760                 765                 770                 775
TGG GGG GAG TGC GGC GCA GAA GAG CCA CCG AGC ACC CCC TGC CTG CCA    2704
Trp Gly Glu Cys Gly Ala Glu Glu Pro Pro Ser Thr Pro Cys Leu Pro
                780                 785                 790
CGC TCC GGC CAC CTG GAC AAT AAC TGT GCC CGC CTC ACC TTG CAT TTC    2752
Arg Ser Gly His Leu Asp Asn Asn Cys Ala Arg Leu Thr Leu His Phe
            795                 800                 805
```

FIG. 10D

```
AAC CGT GAC CAC GTG CCC CAG GGC ACC ACG GTG GGC GCC ATT TGC TCC   2800
Asn Arg Asp His Val Pro Gln Gly Thr Thr Val Gly Ala Ile Cys Ser
            810                 815                 820
GGG ATC CGC TCC CTG CCA GCC ACA AGG GCT GTG GCA CGG GAC CGC CTG   2848
Gly Ile Arg Ser Leu Pro Ala Thr Arg Ala Val Ala Arg Asp Arg Leu
        825                 830                 835
CTG GTG TTG CTT TGC GAC CGG GCG TCC TCG GGG GCC AGT GCT GTG GAG   2896
Leu Val Leu Leu Cys Asp Arg Ala Ser Ser Gly Ala Ser Ala Val Glu
840                 845                 850                 855
GTG GCC GTG TCC TTC AGC CCT GCC AGG GAC CTG CCT GAC AGC AGC CTG   2944
Val Ala Val Ser Phe Ser Pro Ala Arg Asp Leu Pro Asp Ser Ser Leu
                860                 865                 870
ATC CAG GGC GCG GCC CAC GCC ATC GTG GCC GCC ATC ACC CAG CGG GGG   2992
Ile Gln Gly Ala Ala His Ala Ile Val Ala Ala Ile Thr Gln Arg Gly
            875                 880                 885
AAC AGC TCA CTG CTC CTG GCT GTC ACC GAG GTC AAG GTG GAG ACG GTT   3040
Asn Ser Ser Leu Leu Leu Ala Val Thr Glu Val Lys Val Glu Thr Val
        890                 895                 900
GTT ACG GGC GGC TCT TCC ACA GGT CTG CTG GTG CCT GTG CTG TGT GGT   3088
Val Thr Gly Gly Ser Ser Thr Gly Leu Leu Val Pro Val Leu Cys Gly
    905                 910                 915
GCC TTC AGC GTG CTG TGG CTG GCG TGC GTG GTC CTG TGC GTG TGG TGG   3136
Ala Phe Ser Val Leu Trp Leu Ala Cys Val Val Leu Cys Val Trp Trp
920                 925                 930                 935
ACA CGC AAG CGC AGG AAA GAG CGG GAG AGG AGC CGG CTG CCG CGG GAG   3184
Thr Arg Lys Arg Arg Lys Glu Arg Glu Arg Ser Arg Leu Pro Arg Glu
                940                 945                 950
GAG AGC GCC AAC AAC CAG TGG GCC CCG CTC AAC CCC ATC CGC AAC CCC   3232
Glu Ser Ala Asn Asn Gln Trp Ala Pro Leu Asn Pro Ile Arg Asn Pro
            955                 960                 965
ATT GAG CGG CCG GGG GGG CAC AAG GAC GTG CTC TAC CAG TGC AAG AAC   3280
Ile Glu Arg Pro Gly Gly His Lys Asp Val Leu Tyr Gln Cys Lys Asn
        970                 975                 980
TTC ACT CCA CCG CCG CGC AGG CGC TGC CCG GGC CGG CCG GCC ACG CGG   3328
Phe Thr Pro Pro Pro Arg Arg Arg Cys Pro Gly Arg Pro Ala Thr Arg
    985                 990                 995
CCG TCA GGG AGG ATG AGG AGG ACG AGG ATC TTG GCC GCG GTG AGG AGG   3376
Pro Ser Gly Arg Met Arg Arg Thr Arg Ile Leu Ala Ala Val Arg Arg
1000                1005                1010                1015
ACT CCC TGG AGG CGG AGA AGT TCC TCT CAC ACA AAT TCA CCA AAG ATC   3424
Thr Pro Trp Arg Arg Arg Ser Ser Ser His Thr Asn Ser Pro Lys Ile
                1020                1025                1030
```

FIG. 10E

```
CTG GCC GCT CGC CGG GGA GGC CGG CCC ACT GGG CCT CAG GCC CCA AAG    3472
Leu Ala Ala Arg Arg Gly Gly Arg Pro Thr Gly Pro Gln Ala Pro Lys
            1035                1040                1045
TGG ACA ACC GCG CGG TCA GGA GCA TCA ATG AGG CCC GCT ACG TCG GCA    3520
Trp Thr Thr Ala Arg Ser Gly Ala Ser Met Arg Pro Ala Thr Ser Ala
            1050                1055                1060
AGG GAA GTA GGG CGG CTG CAG CTG GGC CGG GAC CCA GGG CCC TCG GTG    3568
Arg Glu Val Gly Arg Leu Gln Leu Gly Arg Asp Pro Gly Pro Ser Val
            1065                1070                1075
GGA GCC ATG CCG TCT GCC GGA CCC GGA GGC CGA GGC CAT GTG CAT AGT    3616
Gly Ala Met Pro Ser Ala Gly Pro Gly Gly Arg Gly His Val His Ser
1080                1085                1090                1095
TTC TTT ATT TTG TGT AAA AAA ACC ACC AAA AAC AAA AAC CAA ATG TTT    3664
Phe Phe Ile Leu Cys Lys Lys Thr Thr Lys Asn Lys Asn Gln Met Phe
                    1100                1105                1110
ATT TTC TAC GTT TCT TTA ACC TTG TAT AAA TTA TTC AGT AAC TGT CAG    3712
Ile Phe Tyr Val Ser Leu Thr Leu Tyr Lys Leu Phe Ser Asn Cys Gln
            1115                1120                1125
GCT GAA AAC AAT GGA GTA TTC TCG GAT AGT TGC TAT TTT TGT AAA GTA    3760
Ala Glu Asn Asn Gly Val Phe Ser Asp Ser Cys Tyr Phe Cys Lys Val
            1130                1135                1140
GCC GTG CGT GGC ACT CGC TGT ATG AAA GGA GAG AGC AAA GGG TGT CTG    3808
Ala Val Arg Gly Thr Arg Cys Met Lys Gly Glu Ser Lys Gly Cys Leu
            1145                1150                1155
CGT CGT CAC CAA ATC GTC GCG TTT GTT ACC AGA GGT TGT GCA CTG TTT    3856
Arg Arg His Gln Ile Val Ala Phe Val Thr Arg Gly Cys Ala Leu Phe
1160                1165                1170                1175
ACA GAA TCT TCC TTT TAT TCC TCA CTC GGG TTT CTC TGT GCT CCA GGC    3904
Thr Glu Ser Ser Phe Tyr Ser Ser Leu Gly Phe Leu Cys Ala Pro Gly
                    1180                1185                1190
CAA AGT GCC GGT GAG ACC CAT GGC TGT GTT GGT GTG GCC CAT GGC TGT    3952
Gln Ser Ala Gly Glu Thr His Gly Cys Val Gly Val Ala His Gly Cys
            1195                1200                1205
TGG TGG GAC CCG TGG CTG ATG GTG TGG CCT GTG GCT GTC GGT GGG ACT    4000
Trp Trp Asp Pro Trp Leu Met Val Trp Pro Val Ala Val Gly Gly Thr
            1210                1215                1220
CGT GGC TGT CAA TGG GAC CTG TGG CTG TCG GTG GGA CCT ACG GTG GTC    4048
Arg Gly Cys Gln Trp Asp Leu Trp Leu Ser Val Gly Pro Thr Val Val
            1225                1230                1235
```

FIG. 10F

```
GGT GGG ACC CTG GTT ATT GAT GTG GCC CTG GCT GCC GGC ACG GCC CGT    4096
Gly Gly Thr Leu Val Ile Asp Val Ala Leu Ala Ala Gly Thr Ala Arg
1240            1245            1250            1255
GGC TGT TG ACGCACCTGT GGTTGTTAGT GGGGCCTGAG GTCATCGGCG TGGCCCAAGG  4154
Gly Cys
CCGGCAGGTC AACCTCGCGC TTGCTGGCCA GTCCACCCTG CCTGCCGTCT GTGCTTCCTC  4214

CTGCCCAGAA CGCCCGCTCC AGCGATCTCT CCACTGTGCT TTCAGAAGTG CCCTTCCTGC  4274

TGCGCAGTTC TCCCATCCTG GGACGGCGGC AGTATTGAAG CTCGTGACAA GTGCCTTCAC  4334

ACAGACCCCT CGCAACTGTC CACGCGTGCC GTGGCACCAG GCGCTGCCCA CCTGCCGGCC  4394

CCGGCCGCCC CTCCTCGTGA AAGTGCATTT TTGTAAATGT GTACATATTA AAGGAAGCAC  4454

TCTGTATAAA AAAAAAAAAC CGGAATTCC                                    4483
```

FIG. 10G

```
CAGGTGGCGTCAGCATCGGGACAGTTCGAGCTGGAGATCTTATCCGTGCAGAATGTGAACGGCGTGCT
GCAGAACGGGAACTGCTGCGACGGCACTCGAAACCCCGGAGATAAAAAGTGCACCAGAGATGAGTGTG
ACACCTACTTTAAAGTTTGCCTGAAGGAGTACCAGTCGCGGGTCACTGCTGGCGGCCCTTGCAGCTTC
GGATCCAAATCCACCCCTGTCATCGGCGGGAATACCTTCAATTTAAAGTACAGCCGGAATAATGAAAA
GAACCGGATTGTTATCCCTTTCACGTTCGCCTGGCCGAGATCCTACACGTTGCTTGTTGAGGCATGGG
ATTACAATGATAACTCTACTAATCCCGATCGCATAATTGAGAAGGCATCCCACTCTGGCATGATCAAT
CCAAGCCGTCAGTGGCAGACGTTGAAACATAACACAGGAGCTGCCCACTTTGAGTATCAAATCCGTGT
GACTTGCGCAGAACATTACTATGGCTTTGGATGCAACAAGTTTTGTCGACCGAGAGATGACTTCTTCA
CTCACCATACCTGTGACCAGAATGGCAACAAAACCTGCTTGGAAGGCTGGACGGGACCAGAATGCAAC
AAAGCTATTTGTCGTCAGGGATGTAGCCCCAAGCATGGTTCTTGCACAGTTCCAGGAGAGTGCAGGTG
TCAGTATGGATGGCAAGGCCAGTACTGTGATAAGTGCATTCCACACCCGGGATGTGTCCATGGCACTT
GCATTGAACCATGGCAGTGCCTCTGTGAAACCAACTGGGGTGGTCAGCTCTGTGACAAAGACCTGAAC
TACTGTGGAACCCACCCACCCTGTTTGAATGGTGGTACCTGCAGCAACACTGGCCCCGATAAATACCA
GTGTTCCTGCCCTGAGGGTTACTCAGGACAGAACTGTGAAATAGCGGAGCATGCGTGCCTCTCTGATC
CGTGCCACAACGGAGGAAGCTGCCTAGAAACGTCTACAGGATTTGAATGTGTGTGTGCACCTGGCTGG
GCTGGACCAACTTGCACTGATAATATTGATGATTGTTCTCCAAATCCCTGTGGTCATGGAGGAACTTG
CCAAGATCTAGTTGATGGATTTAAGTGTATTTGCCCACCTCAGTGGACTGGCAAAACATGCCAGCTAG
ATGCGAATGAATGTGAGGGCAAACCCTGTGTCAATGCCAACTCCTGCAGGAACTTGATTGGCAGCTAC
TATTGTGACTGCATTACTGGCTGGTCTGGCCACAACTGTGATATAAATATTAATGATTGTCGTGGACA
ATGTCAGAATGGAGGATCCTGTCGGGACTTGGTTAATGGTTATCGGTGCATCTGTTCACCTGGCTATG
CAGGAGATCACTGTGAGAAAGACATCAATGAATGTGCAAGTAACCCTTGCATGAATGGGGGTCACTGC
CAGGATGAAATCAATGGATTCCAATGTCTGTGTCCTGCTGGTTTCTCAGGAAACCTCTGTCAGCTGGA
TATAGACTACTGTGAGCCAAACCCTTGCCAGAACGGTGCCCAGTGCTTCAATCTTGCTATGGACTATT
TCTGTAACTGCCCTGAAGATTACGAAGGCAAGAACTGCTCCCACCTGAAAGATCACTGCCGCACAACT
CCTTGTGAAGTAATCGACAGCTGTACAGTGGCAGTGGCTTCTAACAGCACACCAGAAGGAGTTCGTTA
CATTTCTTCAAATGTCTGTGGTCCTCATGGAAAATGCAAGAGCCAAGCAGGTGGAAAATTCACCTGTG
AATGCAACAAAGGATTCACTGGCACCTACTGTCATGAGAATATCAATGACTGTGAGAGCAACCCCTGT
AAAAATGGTGGCACTTGTATTGACGGTGTAAACTCCTACAAATGTATTTGTAGTGATGGATGGGAAGG
AACATATTGTGAAACAAATATTAATGACTGCAGTAAAAACCCCTGCCACAATGGAGGAACTTGCCGAG
ACTTGGTCAATGACTTCTTCTGTGAATGTAAAAATGGGTGGAAAGGAAAAACTTGCCACTCTCGTGAC
AGCCAGTGTGATGAGGCAACATGCAATAATGGAGGAACATGTTATGATGAGGGGGACACTTTCAAGTG
CATGTGTCCTGCAGGATGGAAGGAGCCACTTGTAATATAGCAAGGAACAGCAGCTGCCTGCCAAACC
CCTGTCACAATGGTGGTACCTGTGTAGTTAGTGGGGATTCTTTCACTTGTGTCTGCAAGGAGGGCTGG
GAAGGACCGACATGTACTCAGAACACAAATGACTGCAGTCCTCATCCTTGTTACAACAGTGGTACTTG
TGTGGATGGAGACAACTGGTACCGCTGTGAGTGCGCTCCCGGCTTCGCAGGTCCCGACTGTAGGATCA
ACATCAATGAATGTCAGTCTTCACCCTGTGCCTTTGGGGCTACTTGTGTGGATGAAATTAATGGGTAC
CGTTGCATTTGTCCACCGGGTCGCAGTGGTCCAGGATGCCAGGAAGTTACAGGGAGGCCTTGCTTTAC
CAGTATTCGAGTAATGCCAGACGGTGCTAAGTGGGATGATGACTGTAATACTTGTCAGTGTTTGAATG
GAAAAGTCACCTGTTCTAAGGTTTGGTGTGGTCCTCGACCTTGTATAATACATGCCAAAGGTCATAAT
GAATGCCCAGCTGGACACGCTTGTGTTCCTGTTAAAGAAGACCATTGTTTCACTCATCCTTGTGCTGC
```

FIG. 11A

```
AGTGGGTGAATGCTGGCCTTCTAATCAGCAGCCTGTGAAGACCAAATGCAATTCTGATTCTTATTACC
AAGATAATTGTGCCAACATCACCTTCACCTTTAATAAGGAAATGATGGCACCAGGCCTTACCACGGAG
CACATTTGCAGTGAATTGAGGAATCTGAATATCCTGAAGAATGTTTCTGCTGAATATTCCATCTATAT
TACCTGTGAGCCTTCACACTTGGCAAATAATGAAATACATGTTGCTATTTCTGCTGAAGATATAGGAG
AAGATGAAAACCCAATCAAGGAAATCACAGATAAGATTATTGACCTTGTCAGTAAGCGTGATGGAAAC
AACACACTAATTGCTGCAGTCGCAGAAGTCAGAGTACAAAGGCGACCAGTTAAGAACAAAACAGATTT
CTTGGTGCCATTACTGAGCTCAGTCTTAACAGTAGCCTGGATCTGCTGTCTGGTAACTGTTTTCTATT
GGTGCATTCAAAAGCGCAGAAAGCAGAGCAGCCATACTCACACAGCATCTGATGACAACACCACCAAC
AACGTAAGGGAGCAGCTGAATCAGATTAAAAACCCCATAGAGAAACACGGAGCAAATACTGTTCCAAT
TAAAGACTATGAAAACAAAAACTCTAAAATCGCCAAAATAAGGACGCACAATTCAGAAGTGGAGGAAG
ATGACATGGACAAACACCAGCAAAAGGCCCGGTTTGCCAAGCAGCCAGCGTACACTTTGGTAGACAGA
GATGAAAAGCCACCCAACAGCACACCCACAAAACACCCAAACTGGACAAATAAACAGGACAACAGAGA
CTTGGAAAGTGCACAAAGTTTAAATAGAATGGAGTACATTGTATAG
```

FIG. 11B

```
QVASASGQFE LEILSVQNVN GVLQNGNCCD GTRNPGDKKC TRDECDTYFK    50
     ^
VCLKEYQSRV TAGGPCSFGS KSTPVIGGNT FNLKYSRNNE KNRIVIPFSF   100

AWPRSYTLLV EAWDYNDNST NPDRIIEKAS HSGMINPSRQ WQTLKHNTGA   150

AHFEYQIRVT CAEHYYGFGC NKFCRPRDDF FTEHTCDQNG NKTCLEGWTG   200
           *******************DSL DOMAIN***************
PECNKAICRQ GCSPKHGSCT VPGECRCQYG WQGQYCDKCI PHPGCVHGTC   250
***        <---------------EGF 1-------------><--------
IEPWQCLCET NWGGQLCDKD LNYCGTHPPC LNGGTCSNTG PDKYQCSCPE   300
-----EGF 2----------------><-------------------EGF 3----
GYSGQNCEIA EHACLSDPCH NGGSCLETST GFECVCAPGW AGPTCTDNID   350
-------------><-------------------EGF 4----------------
DCSPNPCGHG GTCQDLVDGF KCICPPQWTG KTCQLDANEC EGKPCVNANS   400
><--------------------EFG 5-----------------><---------
CRNLIGSYYC DCITGWSGHN CDININDCRG QCQNGGSCRD LVNGYRCICS   450
-------EFG 6-----------------><-----------------EFG 7---
PGYAGDHCEK DINECASNPC MNGGHCQDEI NGFQCLCPAG FSGNLCQLDI   500
--------------><-------------------EFG 8---------------
DYCEPNPCQN GAQCFNLAMD YFCNCPEDYE GKNCSHLKDH CRTTPCEVID   550
-><-------------------EFG 9----------------><----------
SCTVAVASNS TPEGVRYISS NVCGPHGKCK SQAGGKFTCE CNKGFTGTYC   600
-----------------------EFG 10--------------------------
HENINDCESN PCKNGGTCID GVNSYKCICS DGWEGTYCET NINDCSKNPC   650
------><-----------------EFG 11-----------------><-----
HNGGTCRDLV NDFFCECKNG WKGKTCHSRD SQCDEATCNN GGTCYDEGDT   700
-----------EFG 12-------------------><-----------------
FKCMCPAGWE GATCNIARNS SCLPNPCHNG GTCVVSGDSF TCVCKEGWEG   750
EGF 13------------------><------------------EGF 14------
PTCTQNTNDC SPHPCYNSGT CVDGDNWYRC ECAPGFAGPD CRININECQS   800
-------><-------------------EGF 15----------------><--
SPCAFGATCV DEINGYRCIC PPGRSGPGCQ EVTGRPCFTS IRVMPDGAKW   850
----------------EGF 16-----------------> 
DDDCNTCQCL NGKVTCSKVW CGPRPCIIHA KGHNECPAGH ACVPVKEDHC   900
    <-                       CYSTEINE-RICH REGION
FTHPCAAVGE CWPSNQQPVK TKCNSDSYYQ DNCANITFTF NKEMMAPGLT   950
            ->
TEHICSELRN LNILKNVSAE YSIYITCEPS HLANNEIHVA ISAEDIGEDE  1000
```

FIG. 12A

```
NPIKEITDKI  IDLVSKRDGN  NTLIAAVAEV  RVQRRPVKNK  TDFLVPLLSS  1050

VLTVAWICCL  VTVFYWCIQK  RRKQSSHTHT  ASDDNTTNNV  REQLNQIKNP  1100

IEKHGANTVP  IKDYENKNSK  IAKIRTHNSE  VEEDDMDKHQ  QKARFAKQPA  1150

YTLVDRDEKP  PNSTPTKHPN  WTNKQDNRDL  ESAQSLNRME  YIV         1193
```

FIG. 12B

```
DmDelta  SGSFELRLKY FSNDHGRDNE GRCCS-GESD GATGKCL-GS CKTRFRLCLK    48
CSer     SGQFELEILS VQNVNGVLQN GNCCD-GTRN PGDKKCTRDE CDTMFKVCLK    49
DmSer    AGNFELEILE ISNTNSHLLN GYCCGMPAEL RATKTIGCSP CTTAFRLCLK    50

DmDelta  HYQATIDTTS QCTYGDVITP ILGENSVNLT DAQRFQNKGF TNPIQFPFSP    98
CSer     EYQSRVTAGG PCSFGSKSTP VIGGNTFNL- --KYSRNNE KNRIVIPFSF    95
DmSer    EYQTTEQGAS ISTGCSFGNA TTKILGGSS- --FVLSDPG VGAIVLPFTF    96

DmDelta  SWPGTFSLIV EAWHDTNNSG NARTNKLLIQ RLLVQQVLEV SSEMKTNKSE   148
CSer     AWPRSYTLLV EAWDYNDNS- -TNPDR-IIE KASHSGMINP SRQWQTLKHN   142
DmSer    RWTKSFTLIL QALDMYNTS- YPDAER-LIE ETSYSGVILP SPEMKTLDHI   144

DmDelta  SQYTSLEYDF RVTCDLNYYG SGCAKFCRPR DDSFGHSTCS ETGEIICLTG   198
CSer     TGAAHFEYQI RVTCAEHYYG FGCNKFCRPR DDFFTHHTCD QNGNKTCLEG   192
DmSer    GRNARITYRV RVQCAVTYYN TTCTTFCRPR DDQFGHYACG SEGQKLCLNG   194
                                          ========= D S L DOMAIN ======

DmDelta  WQGDYC                                                  204
CSer     WTGPEC                                                  198
DmSer    WQGVNC                                                  200
         ======
```

FIG.13

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 5561 base pairs
      (B) TYPE: nucleic acid
      (C) STRANDEDNESS: double
      (D) TOPOLOGY: unknown (ii) MOLECULE TYPE: cDNA (ix) FEATURE:
      (A) NAME/KEY: CDS
      (B) LOCATION: 442..4653

(xi) SEQUENCE DESCRIPTION: SEQ ID NO:1:

```
CCGAGTCGAG CGCCGTGCTT CGAGCGGTGA TGAGCCCCTT TTCTGTCAAC GCTAAAGATC      60

TACAAAACAT CAGCGCCTAT CAAGTGGAAG TGTCAAGTGT GAACAAAACA AAACGAGAG      120

AAGCACATAC TAAGGTCCAT ATAAATAATA AATAATAATT GTGTGTGATA ACAACATTAT      180

CCAAACAAAA CCAAACAAAA CGAAGGCAAA GTGGAGAAAA TGATCAGCA TCCAGAGTAC       240

GGCCGTTATT CAGCTATCCA GAGCAAGTGT AGTGTGGCAA AATAGAAACA AACAAAGGCA     300

CCAAAATCTG CATACATGGG CTAATTAAGG CTGCCCAGCG AATTTACATT TGTGTGGTGC     360

CAATCCAGAG TGAATCCGAA ACAAACTCCA TCTAGATCGC CAACCAGCAT CACGCTCGCA     420

AACGCCCCCA GAATGTACAA A ATG TTT AGG AAA CAT TTT CGG CGA AAA CCA       471
                       Met Phe Arg Lys His Phe Arg Arg Lys Pro
                         1               5                  10

GCT ACG TCG TCG TCG TTG GAG TCA ACA ATA GAA TCA GCA GAC AGC CTG       519
Ala Thr Ser Ser Ser Leu Glu Ser Thr Ile Glu Ser Ala Asp Ser Leu
            15                  20                  25

GGA ATG TCC AAG AAG ACG GCG ACA AAA AGG CAG CGT CCG AGG CAT CGG       567
Gly Met Ser Lys Lys Thr Ala Thr Lys Arg Gln Arg Pro Arg His Arg
        30                  35                  40

GTA CCC AAA ATC GCG ACC CTG CCA TCG ACG ATC CGC GAT TGT CGA TCA       615
Val Pro Lys Ile Ala Thr Leu Pro Ser Thr Ile Arg Asp Cys Arg Ser
    45                  50                  55

TTA AAG TCT GCC TGC AAC TTA ATT GCT TTA ATT TTA ATA CTG TTA GTC       663
Leu Lys Ser Ala Cys Asn Leu Ile Ala Leu Ile Leu Ile Leu Leu Val
60                  65                  70

CAT AAG ATA TCC GCA GCT GGT AAC TTC GAG CTG GAA ATA TTA GAA ATC       711
His Lys Ile Ser Ala Ala Gly Asn Phe Glu Leu Glu Ile Leu Glu Ile
75                  80                  85                  90

TCA AAT ACC AAC AGC CAT CTA CTC AAC GGC TAT TGC TGC GGC ATG CCA       759
Ser Asn Thr Asn Ser His Leu Leu Asn Gly Tyr Cys Cys Gly Met Pro
            95                 100                 105

GCG GAA CTT AGG GCC ACC AAG ACG ATA GGC TGC TCG CCA TGC ACG ACG       807
Ala Glu Leu Arg Ala Thr Lys Thr Ile Gly Cys Ser Pro Cys Thr Thr
        110                 115                 120

GCA TTC CGG CTG TGC CTG AAG GAG TAC CAG ACC ACG GAG CAG GGT GCC       855
Ala Phe Arg Leu Cys Leu Lys Glu Tyr Gln Thr Thr Glu Gln Gly Ala
    125                 130                 135

AGC ATA TCC ACG GGC TGT TCG TTT GGC AAC GCC ACC ACC AAG ATA CTG       903
Ser Ile Ser Thr Gly Cys Ser Phe Gly Asn Ala Thr Thr Lys Ile Leu
140                 145                 150

GGT GGC TCC AGC TTT GTG CTC AGC GAT CCG GGT GTG GGA GCC ATT GTG       951
Gly Gly Ser Ser Phe Val Leu Ser Asp Pro Gly Val Gly Ala Ile Val
```

```
          155                 160                 165                 170
CTG CCC TTT ACG TTT CGT TGG ACG AAG TCG TTT ACG CTG ATA CTG CAG        999
Leu Pro Phe Thr Phe Arg Trp Thr Lys Ser Phe Thr Leu Ile Leu Gln
            175                 180                 185

GCG TTG GAT ATG TAC AAC ACA TCC TAT CCA GAT GCG GAG AGG TTA ATT       1047
Ala Leu Asp Met Tyr Asn Thr Ser Tyr Pro Asp Ala Glu Arg Leu Ile
            190                 195                 200

GAG GAA ACA TCA TAC TCG GGC GTG ATA CTG CCG TCG CCG GAG TGG AAG       1095
Glu Glu Thr Ser Tyr Ser Gly Val Ile Leu Pro Ser Pro Glu Trp Lys
            205                 210                 215

ACG CTG GAC CAC ATC GGG CGG AAC GCG CGG ATC ACC TAC CGT GTC CGG       1143
Thr Leu Asp His Ile Gly Arg Asn Ala Arg Ile Thr Tyr Arg Val Arg
            220                 225                 230

GTG CAA TGC GCC GTT ACC TAC TAC AAC ACG ACC TGC ACG ACC TTC TGC       1191
Val Gln Cys Ala Val Thr Tyr Tyr Asn Thr Thr Cys Thr Thr Phe Cys
235                 240                 245                 250

CGT CCG CGG GAC GAT CAG TTC GGT CAC TAC GCC TGC GGC TCC GAG GGT       1239
Arg Pro Arg Asp Asp Gln Phe Gly His Tyr Ala Cys Gly Ser Glu Gly
            255                 260                 265

CAG AAG CTC TGC CTG AAT GGC TGG CAG GGC GTC AAC TGC GAG GAG GCC       1287
Gln Lys Leu Cys Leu Asn Gly Trp Gln Gly Val Asn Cys Glu Glu Ala
            270                 275                 280

ATA TGC AAG GCG GGC TGC GAC CCC GTC CAC GGC AAG TGC GAT CGT CCG       1335
Ile Cys Lys Ala Gly Cys Asp Pro Val His Gly Lys Cys Asp Arg Pro
            285                 290                 295

GGG GAA TGC GAA TGC AGA CCC GGC TGG CGT GGT CCA TTG TGC AAC GAG       1383
Gly Glu Cys Glu Cys Arg Pro Gly Trp Arg Gly Pro Leu Cys Asn Glu
            300                 305                 310

TGC ATG GTC TAT CCC GGC TGC AAG CAT GGT TCC TGC AAC GGC AGC GCC       1431
Cys Met Val Tyr Pro Gly Cys Lys His Gly Ser Cys Asn Gly Ser Ala
315                 320                 325                 330

TGG AAA TGC GTG TGC GAC ACC AAC TGG GGT GGC ATA TTG TGC GAT CAA       1479
Trp Lys Cys Val Cys Asp Thr Asn Trp Gly Gly Ile Leu Cys Asp Gln
            335                 340                 345

GAT TTA AAT TTC TGC GGC ACC CAT GAA CCC TGC AAG CAC GGC GGC ACC       1527
Asp Leu Asn Phe Cys Gly Thr His Glu Pro Cys Lys His Gly Gly Thr
            350                 355                 360

TGC GAA AAT ACC GCT CCG GAC AAA TAT CGG TGC ACA TGC GCC GAG GGC       1575
Cys Glu Asn Thr Ala Pro Asp Lys Tyr Arg Cys Thr Cys Ala Glu Gly
            365                 370                 375

CTC TCG GGC GAG CAG TGC GAG ATC GTG GAG CAC CCA TGT GCC ACC AGG       1623
Leu Ser Gly Glu Gln Cys Glu Ile Val Glu His Pro Cys Ala Thr Arg
            380                 385                 390

CCA TGC CGC AAC GGC GGC ACA TGC ACA CTC AAG ACG AGT AAC CGA ACT       1671
Pro Cys Arg Asn Gly Gly Thr Cys Thr Leu Lys Thr Ser Asn Arg Thr
395                 400                 405                 410

CAA GCC CAA GTG TAT CGC ACA TCA CAT GGC AGG AGC AAC ATG GGC CGG       1719
Gln Ala Gln Val Tyr Arg Thr Ser His Gly Arg Ser Asn Met Gly Arg
            415                 420                 425

CCG GTA AGA CGC AGC AGT TCG ATG CGC AGC CTG GAT CAC CTG CGG CCG       1767
Pro Val Arg Arg Ser Ser Ser Met Arg Ser Leu Asp His Leu Arg Pro
            430                 435                 440

GAG GGG CAG GCG CTG AAT GGC AGC AGC TCC TCG GGA TTG GTG TCC CTA       1815
Glu Gly Gln Ala Leu Asn Gly Ser Ser Ser Ser Gly Leu Val Ser Leu
            445                 450                 455

GGT TCG CTG CAG CTG CAG CAG CAA CTG GCC CCC GAC TTC ACT TGC GAC       1863
Gly Ser Leu Gln Leu Gln Gln Gln Leu Ala Pro Asp Phe Thr Cys Asp
            460                 465                 470

TGC GCA GCC GGA TGG ACG GGA CCG ACA TGC GAA ATA AAT ATC GAC GAG       1911
Cys Ala Ala Gly Trp Thr Gly Pro Thr Cys Glu Ile Asn Ile Asp Glu
```

-continued

| | | | | |
|---|---|---|---|---|
| 475 | 480 | 485 | 490 | |

```
TGC GCC GGG GGT CCC TGC GAG CAT GGT GGC ACT TGC ATC GAT CTA ATC    1959
Cys Ala Gly Gly Pro Cys Glu His Gly Gly Thr Cys Ile Asp Leu Ile
                495                 500                 505

GGT GGC TTT CGA TGT GAA TGT CCG CCG GAG TGG CAT GGC GAT GTC TGT    2007
Gly Gly Phe Arg Cys Glu Cys Pro Pro Glu Trp His Gly Asp Val Cys
                510                 515                 520

CAG GTG GAT GTG AAC GAG TGC GAG GCG CCG CAT TCC GCC GGA ATC GCT    2055
Gln Val Asp Val Asn Glu Cys Glu Ala Pro His Ser Ala Gly Ile Ala
                525                 530                 535

GCG AAC GCA TTG CTG ACC ACC ACA GCC ACC GCG ATT ATT GGT AGT AAT    2103
Ala Asn Ala Leu Leu Thr Thr Thr Ala Thr Ala Ile Ile Gly Ser Asn
        540                 545                 550

CTG AGC AGT ACT GCT CTT CTG GCC GCT CTG ACC AGT GCA GTG GCA TCC    2151
Leu Ser Ser Thr Ala Leu Leu Ala Ala Leu Thr Ser Ala Val Ala Ser
555                 560                 565                 570

ACA TCC TTG GCC ATC GGA CCC TGC ATC AAT GCC AAG GAG TGT CGC AAT    2199
Thr Ser Leu Ala Ile Gly Pro Cys Ile Asn Ala Lys Glu Cys Arg Asn
                575                 580                 585

CAG CCG GGT TCC TTT GCC TGC ATC TGC AAG GAG GGC TGG GGC GGA GTG    2247
Gln Pro Gly Ser Phe Ala Cys Ile Cys Lys Glu Gly Trp Gly Gly Val
                590                 595                 600

ACC TGT GCC GAG AAT CTA GAT GAC TGT GTG GGT CAG TGC CGG AAT GGA    2295
Thr Cys Ala Glu Asn Leu Asp Asp Cys Val Gly Gln Cys Arg Asn Gly
                605                 610                 615

GCC ACC TGC ATT GAT CTG GTC AAC GAC TAT AGG TGC GCC TGT GCC TCT    2343
Ala Thr Cys Ile Asp Leu Val Asn Asp Tyr Arg Cys Ala Cys Ala Ser
        620                 625                 630

GGA TTC ACG GGT CGC GAT TGC GAG ACG GAC ATA GAC GAG TGC GCC ACT    2391
Gly Phe Thr Gly Arg Asp Cys Glu Thr Asp Ile Asp Glu Cys Ala Thr
635                 640                 645                 650

TCC CCG TGC CGA AAC GGA GGC GAA TGT GTG GAC ATG GTG GGC AAA TTC    2439
Ser Pro Cys Arg Asn Gly Gly Glu Cys Val Asp Met Val Gly Lys Phe
                655                 660                 665

AAT TGC ATT TGC CCA CTT GGC TAC TCG GGT TCT CTG TGC GAG GAG GCC    2487
Asn Cys Ile Cys Pro Leu Gly Tyr Ser Gly Ser Leu Cys Glu Glu Ala
                670                 675                 680

AAG GAG AAC TGC ACA CCG TCG CCA TGT TTG GAG GGT CAC TGC CTC AAC    2535
Lys Glu Asn Cys Thr Pro Ser Pro Cys Leu Glu Gly His Cys Leu Asn
                685                 690                 695

ACG CCC GAA GGA TAC TAC TGC CAT TGT CCA CCG GAT CGC GCC GGA AAG    2583
Thr Pro Glu Gly Tyr Tyr Cys His Cys Pro Pro Asp Arg Ala Gly Lys
        700                 705                 710

CAC TGC GAG CAA CTG CGT CCG CTC TGC TCC CAG CCG CCC TGC AAC GAG    2631
His Cys Glu Gln Leu Arg Pro Leu Cys Ser Gln Pro Pro Cys Asn Glu
715                 720                 725                 730

GGC TGC TTC GCC AAT GTC AGC CTA GCG ACG TCA GCG ACA ACG ACG ACG    2679
Gly Cys Phe Ala Asn Val Ser Leu Ala Thr Ser Ala Thr Thr Thr Thr
                735                 740                 745

ACA ACC ACC ACA ACG GCG ACA ACG ACA AGG AAG ATG GCC AAG CCA AGC    2727
Thr Thr Thr Thr Thr Ala Thr Thr Arg Lys Met Ala Lys Pro Ser
                750                 755                 760

GGA TTG CCC TGC AGC GGA CAC GGC AGC TGC GAG ATG AGC GAC GTG GGC    2775
Gly Leu Pro Cys Ser Gly His Gly Ser Cys Glu Met Ser Asp Val Gly
                765                 770                 775

ACC TTC TGC AAA TGC CAT GTG GGC CAC ACC GGC ACC TTC TGC GAG CAC    2823
Thr Phe Cys Lys Cys His Val Gly His Thr Gly Thr Phe Cys Glu His
                780                 785                 790

AAT CTC AAC GAA TGC TCG CCG AAT CCT TGT CGA AAT GGG GGA ATT TGC    2871
Asn Leu Asn Glu Cys Ser Pro Asn Pro Cys Arg Asn Gly Gly Ile Cys
```

-continued

| | | |
|---|---|---|
| 795 800 805 810 | | |
| CTT GAC GGC GAC GGC GAT TTT ACA TGC GAG TGC ATG TCG GGC TGG ACA<br>Leu Asp Gly Asp Gly Asp Phe Thr Cys Glu Cys Met Ser Gly Trp Thr<br>815 820 825 | | 2919 |
| GGT AAA CGC TGC TCG GAG CGC GCT ACA GGT TGT TAT GCC GGT CAG TGC<br>Gly Lys Arg Cys Ser Glu Arg Ala Thr Gly Cys Tyr Ala Gly Gln Cys<br>830 835 840 | | 2967 |
| CAG AAT GGT GGT ACC TGC ATG CCT GGA GCC CCG GAC AAG GCT CTG CAG<br>Gln Asn Gly Gly Thr Cys Met Pro Gly Ala Pro Asp Lys Ala Leu Gln<br>845 850 855 | | 3015 |
| CCG CAT TGC CGC TGT GCG CCA GGT TGG ACT GGT CTG TTT TGC GCC GAG<br>Pro His Cys Arg Cys Ala Pro Gly Trp Thr Gly Leu Phe Cys Ala Glu<br>860 865 870 | | 3063 |
| GCT ATT GAC CAG TGT CGC GGG CAG CCG TGC CAC AAT GGC GGA ACG TGC<br>Ala Ile Asp Gln Cys Arg Gly Gln Pro Cys His Asn Gly Gly Thr Cys<br>875 880 885 890 | | 3111 |
| GAG TCG GGA GCG GGC TGG TTC CGC TGC GTC TGC GCT CAG GGA TTC TCT<br>Glu Ser Gly Ala Gly Trp Phe Arg Cys Val Cys Ala Gln Gly Phe Ser<br>895 900 905 | | 3159 |
| GGT CCA GAC TGC CGC ATC AAT GTG AAC GAG TGC TCG CCA CAG CCT TGC<br>Gly Pro Asp Cys Arg Ile Asn Val Asn Glu Cys Ser Pro Gln Pro Cys<br>910 915 920 | | 3207 |
| CAG GGC GGT GCC ACC TGC ATC GAC GGA ATC GGT GGA TAC AGC TGC ATC<br>Gln Gly Gly Ala Thr Cys Ile Asp Gly Ile Gly Gly Tyr Ser Cys Ile<br>925 930 935 | | 3255 |
| TGC CCA CCA GGA AGG CAT GGA TTG CGG TGT GAA ATT TTG CTC TCC GAT<br>Cys Pro Pro Gly Arg His Gly Leu Arg Cys Glu Ile Leu Leu Ser Asp<br>940 945 950 | | 3303 |
| CCC AAG TCC GCC TGC CAG AAC GCA AGC AAC ACT ATC TCT CCG TAT ACA<br>Pro Lys Ser Ala Cys Gln Asn Ala Ser Asn Thr Ile Ser Pro Tyr Thr<br>955 960 965 970 | | 3351 |
| GCT CTA AAC CGA AGC CAA AAC TGG CTG GAT ATT GCT CTA ACC GGA AGA<br>Ala Leu Asn Arg Ser Gln Asn Trp Leu Asp Ile Ala Leu Thr Gly Arg<br>975 980 985 | | 3399 |
| ACA GAA GAC GAT GAG AAC TGC AAT GCG TGT GTC TGC GAA AAC GGC ACC<br>Thr Glu Asp Asp Glu Asn Cys Asn Ala Cys Val Cys Glu Asn Gly Thr<br>990 995 1000 | | 3447 |
| TCT CGG TGC ACG AAT CTC TGG TGT GGA TTG CCC AAT TGC TAT AAG GTG<br>Ser Arg Cys Thr Asn Leu Trp Cys Gly Leu Pro Asn Cys Tyr Lys Val<br>1005 1010 1015 | | 3495 |
| GAT CCG CTC TCC AAG TCC TCG AAT CTG TCC GGT GTT TGC AAA CAG CAC<br>Asp Pro Leu Ser Lys Ser Ser Asn Leu Ser Gly Val Cys Lys Gln His<br>1020 1025 1030 | | 3543 |
| GAG GTG TGC GTT CCG GCA CTG AGT GAG ACA TGC CTG TCA TCG CCT TGT<br>Glu Val Cys Val Pro Ala Leu Ser Glu Thr Cys Leu Ser Ser Pro Cys<br>1035 1040 1045 1050 | | 3591 |
| AAT GTT CGT GGA GAT TGC CGG GCA CTG GAA CCA TCG CGT CGG GTT GCT<br>Asn Val Arg Gly Asp Cys Arg Ala Leu Glu Pro Ser Arg Arg Val Ala<br>1055 1060 1065 | | 3639 |
| CCA CCC CGA CTG CCA GCC AAA TCT AGC TGC TGG CCC AAT CAG GCC GTG<br>Pro Pro Arg Leu Pro Ala Lys Ser Ser Cys Trp Pro Asn Gln Ala Val<br>1070 1075 1080 | | 3687 |
| GTC AAC GAG AAC TGC GCC CGA CTC ACC ATC CTT TTG GCC CTG GAG CGA<br>Val Asn Glu Asn Cys Ala Arg Leu Thr Ile Leu Leu Ala Leu Glu Arg<br>1085 1090 1095 | | 3735 |
| GTG GGC AAG GGA GCT TCG GTG GAG GGT CTC TGC TCC CTG GTA AGG GTG<br>Val Gly Lys Gly Ala Ser Val Glu Gly Leu Cys Ser Leu Val Arg Val<br>1100 1105 1110 | | 3783 |
| CTG CTG GCT GCC CAG TTG ATC AAG AAG CCG GCG AGT ACT TTT GGC CAG<br>Leu Leu Ala Ala Gln Leu Ile Lys Lys Pro Ala Ser Thr Phe Gly Gln | | 3831 |

-continued

| | | | |
|---|---|---|---|
| 1115 | 1120 | 1125 | 1130 |

```
GAT CCG GGA ATG CTT ATG GTG CTC TGC GAT CTC AAA ACG GGC ACC AAT        3879
Asp Pro Gly Met Leu Met Val Leu Cys Asp Leu Lys Thr Gly Thr Asn
                1135            1140            1145

GAT ACC GTT GAA CTA ACT GTG TCG TCC AGT AAA TTA AAT GAT CCC CAG        3927
Asp Thr Val Glu Leu Thr Val Ser Ser Ser Lys Leu Asn Asp Pro Gln
            1150            1155            1160

CTG CCA GTG GCG GTG GGT CTG CTG GGT GAA CTC CTG AGC TCC AGG CAG        3975
Leu Pro Val Ala Val Gly Leu Leu Gly Glu Leu Leu Ser Ser Arg Gln
            1165            1170            1175

TTG AAT GGC ATC CAG CGG CGC AAG GAA CTG GAG CTG CAG CAT GCA AAA        4023
Leu Asn Gly Ile Gln Arg Arg Lys Glu Leu Glu Leu Gln His Ala Lys
            1180            1185            1190

TTG GCT GCC CTC ACC TCC ATT GTG GAG GTC AAG TTG GAA ACG GCC CGC        4071
Leu Ala Ala Leu Thr Ser Ile Val Glu Val Lys Leu Glu Thr Ala Arg
    1195            1200            1205            1210

GTG GCC GAT GGA TCG GGT CAT AGT CTG CTG ATA GGA GTG CTA TGC GGT        4119
Val Ala Asp Gly Ser Gly His Ser Leu Leu Ile Gly Val Leu Cys Gly
                1215            1220            1225

GTC TTT ATA GTC CTG GTG GGA TTC TCG GTG TTC ATC AGT CTT TAC TGG        4167
Val Phe Ile Val Leu Val Gly Phe Ser Val Phe Ile Ser Leu Tyr Trp
            1230            1235            1240

AAA CAG CGT CTG GCT TAT CGC ACC AGT TCG GGA ATG AAC TTA ACT CCC        4215
Lys Gln Arg Leu Ala Tyr Arg Thr Ser Ser Gly Met Asn Leu Thr Pro
            1245            1250            1255

TCC CTG GAT GCA CTG CGT CAC GAG GAG GAG AAG TCG AAT AAT CTG CAG        4263
Ser Leu Asp Ala Leu Arg His Glu Glu Glu Lys Ser Asn Asn Leu Gln
            1260            1265            1270

AAC GAG GAG AAT CTG CGA AGG TAT ACA AAT CCG CTG AAG GGC AGC ACC        4311
Asn Glu Glu Asn Leu Arg Arg Tyr Thr Asn Pro Leu Lys Gly Ser Thr
1275            1280            1285            1290

AGT TCC CTA AGA GCG GCC ACC GGC ATG GAA CTA AGC CTC AAT CCC GCT        4359
Ser Ser Leu Arg Ala Ala Thr Gly Met Glu Leu Ser Leu Asn Pro Ala
                1295            1300            1305

CCG GAA TTA GCC GCC TCG GCG GCG AGT AGT TCC GCC TTG CAC AGA TCG        4407
Pro Glu Leu Ala Ala Ser Ala Ala Ser Ser Ala Leu His Arg Ser
            1310            1315            1320

CAG CCA CTA TTC CCG CCA TGC GAT TTC GAG CGT GAG CTG GAC TCC AGT        4455
Gln Pro Leu Phe Pro Pro Cys Asp Phe Glu Arg Glu Leu Asp Ser Ser
            1325            1330            1335

ACG GGC CTG AAG CAG GCG CAC AAG CGG AGC TCA CAG ATT CTG CTG CAC        4503
Thr Gly Leu Lys Gln Ala His Lys Arg Ser Ser Gln Ile Leu Leu His
    1340            1345            1350

AAA ACC CAA AAC TCG GAC ATG CGG AAG AAC ACT GTG GGC TCG CTG GAC        4551
Lys Thr Gln Asn Ser Asp Met Arg Lys Asn Thr Val Gly Ser Leu Asp
1355            1360            1365            1370

AGT CCG CGT AAG GAC TTT GGC AAG CGG TCG ATC AAC TGC AAG TCC ATG        4599
Ser Pro Arg Lys Asp Phe Gly Lys Arg Ser Ile Asn Cys Lys Ser Met
                1375            1380            1385

CCA CCC TCT TCG GGC GAC GAG GGC TCC GAT GTC CTT GCC ACC ACT GTG        4647
Pro Pro Ser Ser Gly Asp Glu Gly Ser Asp Val Leu Ala Thr Thr Val
                1390            1395            1400

ATG GTT TAGCCGTGAT CTCACCAACC AACCAATCAA GAAACCAACC AGCCGCCCAC         4703
Met Val

AGCCAGCTCA AAGTTCCAAT TGCCACAGCA CGGGCGCTAT TTCCAAGTGC ATTAGTAGCG      4763

TAATTAAAAC TAGGATATTG TTAAGGATAC CAAGGTAGGC CACAACGGAG TGGCTCTGTT      4823

GAAAACGTAA AGTTCTAAAA ATCCAGGTCT CTCAGACAAA GATGAGGTAC ACAAATAAAT      4883

TGGCTAGTTA ATCAAGCATG TTATGGCCAC GGGATGGGCA AATTTATTTG TATACCTGAT      4943
```

-continued

```
CTTATCTTAA TACTAAACCA GTTTTCTACT ATTTTTTTTT TGTGGATCAA GCTTAAAAGT    5003

TCAGCTAGGC AGGCGTTTTC CGCAGTGCCA TGTCGATGTG GAAGCCCAAA ATATTTAGGT    5063

TAGATAGTGT AATTTCGAAC TCTTCTCTTC GCTAAGCAAC ATCCTACACA GTGTGATATT    5123

TAGTGTAACC CAGGCGCGCA TTTACATTCA ATTAAAGACA ATGATATATA AATATAAACG    5183

AAATCAACTC CTTGGCTAGC ACAAGCTGTA TGTATATAGT TCTCATTTAG GATCGTCGCG    5243

CTCTATATTG TGTATAAGCT GTAAATACTG TAAATTAGCA GTTACCGTTA TTGTATTTTG    5303

TCTATAGTTA GATTGGTACT ATTAAACTAA GAACCAGCCG CAACGCGTTA GACTTTAAAA    5363

GTTGTTTGCA ATTGTACGCA ATAATATAGT TTTATGCTCG TAGTTAGGTA GCTGTGTAAC    5423

CGGGTAAGAT TCAAACGATT TTGTACTGTA TTATATACCT ATCTGTGTAG TAATATTTAT    5483

TTATTATATT AAATTTGATC TAGACGCAAT AAAGTAATAT CAATAAAGAT AGTAAAAGAC    5543

ATAAAAAAAA AAAAAAAA                                                  5561
```

(2) INFORMATION FOR SEQ ID NO:2:

(i) SEQUENCE CHARACTERISTICS:
        (A) LENGTH: 1404 amino acids
        (B) TYPE: amino acid
        (D) TOPOLOGY: unknown (ii) MOLECULE TYPE: protein (xi) SEQUENCE DESCRIPTION: SEQ ID NO:2:

```
Met Phe Arg Lys His Phe Arg Arg Lys Pro Ala Thr Ser Ser Ser Leu
 1               5                  10                  15

Glu Ser Thr Ile Glu Ser Ala Asp Ser Leu Gly Met Ser Lys Lys Thr
            20                  25                  30

Ala Thr Lys Arg Gln Arg Pro Arg His Arg Val Pro Lys Ile Ala Thr
        35                  40                  45

Leu Pro Ser Thr Ile Arg Asp Cys Arg Ser Leu Lys Ser Ala Cys Asn
    50                  55                  60

Leu Ile Ala Leu Ile Leu Ile Leu Leu Val His Lys Ile Ser Ala Ala
65                  70                  75                  80

Gly Asn Phe Glu Leu Glu Ile Leu Glu Ile Ser Asn Thr Asn Ser His
                85                  90                  95

Leu Leu Asn Gly Tyr Cys Cys Gly Met Pro Ala Glu Leu Arg Ala Thr
           100                 105                 110

Lys Thr Ile Gly Cys Ser Pro Cys Thr Thr Ala Phe Arg Leu Cys Leu
       115                 120                 125

Lys Glu Tyr Gln Thr Thr Glu Gln Gly Ala Ser Ile Ser Thr Gly Cys
   130                 135                 140

Ser Phe Gly Asn Ala Thr Thr Lys Ile Leu Gly Gly Ser Ser Phe Val
145                 150                 155                 160

Leu Ser Asp Pro Gly Val Gly Ala Ile Val Leu Pro Phe Thr Phe Arg
               165                 170                 175

Trp Thr Lys Ser Phe Thr Leu Ile Leu Gln Ala Leu Asp Met Tyr Asn
           180                 185                 190

Thr Ser Tyr Pro Asp Ala Glu Arg Leu Ile Glu Glu Thr Ser Tyr Ser
       195                 200                 205

Gly Val Ile Leu Pro Ser Pro Glu Trp Lys Thr Leu Asp His Ile Gly
   210                 215                 220

Arg Asn Ala Arg Ile Thr Tyr Arg Val Arg Val Gln Cys Ala Val Thr
225                 230                 235                 240
```

-continued

```
Tyr Tyr Asn Thr Thr Cys Thr Thr Phe Cys Arg Pro Arg Asp Asp Gln
            245                 250                 255

Phe Gly His Tyr Ala Cys Gly Ser Glu Gly Gln Lys Leu Cys Leu Asn
            260                 265                 270

Gly Trp Gln Gly Val Asn Cys Glu Ala Ile Cys Lys Ala Gly Cys
            275                 280                 285

Asp Pro Val His Gly Lys Cys Asp Arg Pro Gly Glu Cys Glu Cys Arg
290                 295                 300

Pro Gly Trp Arg Gly Pro Leu Cys Asn Glu Cys Met Val Tyr Pro Gly
305                 310                 315                 320

Cys Lys His Gly Ser Cys Asn Gly Ser Ala Trp Lys Cys Val Cys Asp
            325                 330                 335

Thr Asn Trp Gly Gly Ile Leu Cys Asp Gln Asp Leu Asn Phe Cys Gly
            340                 345                 350

Thr His Glu Pro Cys Lys His Gly Gly Thr Cys Glu Asn Thr Ala Pro
            355                 360                 365

Asp Lys Tyr Arg Cys Thr Cys Ala Glu Gly Leu Ser Gly Glu Gln Cys
            370                 375                 380

Glu Ile Val Glu His Pro Cys Ala Thr Arg Pro Cys Arg Asn Gly Gly
385                 390                 395                 400

Thr Cys Thr Leu Lys Thr Ser Asn Arg Thr Gln Ala Gln Val Tyr Arg
            405                 410                 415

Thr Ser His Gly Arg Ser Asn Met Gly Arg Pro Val Arg Arg Ser Ser
            420                 425                 430

Ser Met Arg Ser Leu Asp His Leu Arg Pro Glu Gly Gln Ala Leu Asn
            435                 440                 445

Gly Ser Ser Ser Gly Leu Val Ser Leu Gly Ser Leu Gln Leu Gln
450                 455                 460

Gln Gln Leu Ala Pro Asp Phe Thr Cys Asp Cys Ala Ala Gly Trp Thr
465                 470                 475                 480

Gly Pro Thr Cys Glu Ile Asn Ile Asp Glu Cys Ala Gly Gly Pro Cys
            485                 490                 495

Glu His Gly Gly Thr Cys Ile Asp Leu Ile Gly Gly Phe Arg Cys Glu
            500                 505                 510

Cys Pro Pro Glu Trp His Gly Asp Val Cys Gln Val Asp Val Asn Glu
            515                 520                 525

Cys Glu Ala Pro His Ser Ala Gly Ile Ala Ala Asn Ala Leu Leu Thr
            530                 535                 540

Thr Thr Ala Thr Ala Ile Ile Gly Ser Asn Leu Ser Ser Thr Ala Leu
545                 550                 555                 560

Leu Ala Ala Leu Thr Ser Ala Val Ala Ser Thr Ser Leu Ala Ile Gly
            565                 570                 575

Pro Cys Ile Asn Ala Lys Glu Cys Arg Asn Gln Pro Gly Ser Phe Ala
            580                 585                 590

Cys Ile Cys Lys Glu Gly Trp Gly Gly Val Thr Cys Ala Glu Asn Leu
            595                 600                 605

Asp Asp Cys Val Gly Gln Cys Arg Asn Gly Ala Thr Cys Ile Asp Leu
            610                 615                 620

Val Asn Asp Tyr Arg Cys Ala Cys Ala Ser Gly Phe Thr Gly Arg Asp
625                 630                 635                 640

Cys Glu Thr Asp Ile Asp Glu Cys Ala Thr Ser Pro Cys Arg Asn Gly
            645                 650                 655

Gly Glu Cys Val Asp Met Val Gly Lys Phe Asn Cys Ile Cys Pro Leu
            660                 665                 670
```

-continued

```
Gly Tyr Ser Gly Ser Leu Cys Glu Ala Lys Glu Asn Cys Thr Pro
            675                 680                 685

Ser Pro Cys Leu Glu Gly His Cys Leu Asn Thr Pro Glu Gly Tyr Tyr
    690                 695                 700

Cys His Cys Pro Pro Asp Arg Ala Gly Lys His Cys Glu Gln Leu Arg
705                 710                 715                 720

Pro Leu Cys Ser Gln Pro Pro Cys Asn Glu Gly Cys Phe Ala Asn Val
                725                 730                 735

Ser Leu Ala Thr Ser Ala Thr Thr Thr Thr Thr Thr Thr Thr Thr Ala
            740                 745                 750

Thr Thr Thr Arg Lys Met Ala Lys Pro Ser Gly Leu Pro Cys Ser Gly
            755                 760                 765

His Gly Ser Cys Glu Met Ser Asp Val Gly Thr Phe Cys Lys Cys His
    770                 775                 780

Val Gly His Thr Gly Thr Phe Cys Glu His Asn Leu Asn Glu Cys Ser
785                 790                 795                 800

Pro Asn Pro Cys Arg Asn Gly Gly Ile Cys Leu Asp Gly Asp Gly Asp
                805                 810                 815

Phe Thr Cys Glu Cys Met Ser Gly Trp Thr Gly Lys Arg Cys Ser Glu
            820                 825                 830

Arg Ala Thr Gly Cys Tyr Ala Gly Gln Cys Gln Asn Gly Gly Thr Cys
            835                 840                 845

Met Pro Gly Ala Pro Asp Lys Ala Leu Gln Pro His Cys Arg Cys Ala
    850                 855                 860

Pro Gly Trp Thr Gly Leu Phe Cys Ala Glu Ala Ile Asp Gln Cys Arg
865                 870                 875                 880

Gly Gln Pro Cys His Asn Gly Gly Thr Cys Glu Ser Gly Ala Gly Trp
                885                 890                 895

Phe Arg Cys Val Cys Ala Gln Gly Phe Ser Gly Pro Asp Cys Arg Ile
            900                 905                 910

Asn Val Asn Glu Cys Ser Pro Gln Pro Cys Gln Gly Gly Ala Thr Cys
            915                 920                 925

Ile Asp Gly Ile Gly Gly Tyr Ser Cys Ile Cys Pro Pro Gly Arg His
    930                 935                 940

Gly Leu Arg Cys Glu Ile Leu Leu Ser Asp Pro Lys Ser Ala Cys Gln
945                 950                 955                 960

Asn Ala Ser Asn Thr Ile Ser Pro Tyr Thr Ala Leu Asn Arg Ser Gln
                965                 970                 975

Asn Trp Leu Asp Ile Ala Leu Thr Gly Arg Thr Glu Asp Glu Asn
            980                 985                 990

Cys Asn Ala Cys Val Cys Glu Asn Gly Thr Ser Arg Cys Thr Asn Leu
    995                 1000                1005

Trp Cys Gly Leu Pro Asn Cys Tyr Lys Val Asp Pro Leu Ser Lys Ser
    1010                1015                1020

Ser Asn Leu Ser Gly Val Cys Lys Gln His Glu Val Cys Val Pro Ala
1025                1030                1035                1040

Leu Ser Glu Thr Cys Leu Ser Ser Pro Cys Asn Val Arg Gly Asp Cys
                1045                1050                1055

Arg Ala Leu Glu Pro Ser Arg Arg Val Ala Pro Arg Leu Pro Ala
            1060                1065                1070

Lys Ser Ser Cys Trp Pro Asn Gln Ala Val Val Asn Glu Asn Cys Ala
    1075                1080                1085

Arg Leu Thr Ile Leu Leu Ala Leu Glu Arg Val Gly Lys Gly Ala Ser
```

-continued

```
          1090                1095                1100

Val Glu Gly Leu Cys Ser Leu Val Arg Val Leu Leu Ala Ala Gln Leu
1105                1110                1115                1120

Ile Lys Lys Pro Ala Ser Thr Phe Gly Gln Asp Pro Gly Met Leu Met
                1125                1130                1135

Val Leu Cys Asp Leu Lys Thr Gly Thr Asn Asp Thr Val Glu Leu Thr
            1140                1145                1150

Val Ser Ser Ser Lys Leu Asn Asp Pro Gln Leu Pro Val Ala Val Gly
        1155                1160                1165

Leu Leu Gly Glu Leu Leu Ser Ser Arg Gln Leu Asn Gly Ile Gln Arg
    1170                1175                1180

Arg Lys Glu Leu Glu Leu Gln His Ala Lys Leu Ala Ala Leu Thr Ser
1185                1190                1195                1200

Ile Val Glu Val Lys Leu Glu Thr Ala Arg Val Ala Asp Gly Ser Gly
                1205                1210                1215

His Ser Leu Leu Ile Gly Val Leu Cys Gly Val Phe Ile Val Leu Val
            1220                1225                1230

Gly Phe Ser Val Phe Ile Ser Leu Tyr Trp Lys Gln Arg Leu Ala Tyr
        1235                1240                1245

Arg Thr Ser Ser Gly Met Asn Leu Thr Pro Ser Leu Asp Ala Leu Arg
    1250                1255                1260

His Glu Glu Glu Lys Ser Asn Asn Leu Gln Asn Glu Asn Leu Arg
1265                1270                1275                1280

Arg Tyr Thr Asn Pro Leu Lys Gly Ser Thr Ser Leu Arg Ala Ala
                1285                1290                1295

Thr Gly Met Glu Leu Ser Leu Asn Pro Ala Pro Glu Leu Ala Ala Ser
            1300                1305                1310

Ala Ala Ser Ser Ser Ala Leu His Arg Ser Gln Pro Leu Phe Pro Pro
        1315                1320                1325

Cys Asp Phe Glu Arg Glu Leu Asp Ser Ser Thr Gly Leu Lys Gln Ala
    1330                1335                1340

His Lys Arg Ser Ser Gln Ile Leu Leu His Lys Thr Gln Asn Ser Asp
1345                1350                1355                1360

Met Arg Lys Asn Thr Val Gly Ser Leu Asp Ser Pro Arg Lys Asp Phe
                1365                1370                1375

Gly Lys Arg Ser Ile Asn Cys Lys Ser Met Pro Pro Ser Gly Asp
            1380                1385                1390

Glu Gly Ser Asp Val Leu Ala Thr Thr Val Met Val
        1395                1400
```

(2) INFORMATION FOR SEQ ID NO:3:

(i) SEQUENCE CHARACTERISTICS:
       (A) LENGTH: 708 base pairs
       (B) TYPE: nucleic acid
       (C) STRANDEDNESS: double
       (D) TOPOLOGY: unknown (ii) MOLECULE TYPE: cDNA (ix) FEATURE:
       (A) NAME/KEY: CDS
       (B) LOCATION: 1..708

(xi) SEQUENCE DESCRIPTION: SEQ ID NO:3:

```
ATG CAT TGG ATT AAA TGT TTA TTA ACA GCA TTC ATT TGC TTC ACA GTC      48
Met His Trp Ile Lys Cys Leu Leu Thr Ala Phe Ile Cys Phe Thr Val
  1               5                  10                  15
```

-continued

| | |
|---|---|
| ATC GTG CAG GTT CAC AGT TCC GGC AGC TTT GAG TTG CGC CTG AAG TAC<br>Ile Val Gln Val His Ser Ser Gly Ser Phe Glu Leu Arg Leu Lys Tyr<br>　　　　　20　　　　　　　　　　25　　　　　　　　　30 | 96 |
| TTC AGC AAC GAT CAC GGG CGG GAC AAC GAG GGT CGC TGC TGC AGC GGG<br>Phe Ser Asn Asp His Gly Arg Asp Asn Glu Gly Arg Cys Cys Ser Gly<br>　　　　35　　　　　　　　　　40　　　　　　　　　45 | 144 |
| GAG TCG GAC GGA GCG ACG GGC AAG TGC CTG GGC AGC TGC AAG ACG CGG<br>Glu Ser Asp Gly Ala Thr Gly Lys Cys Leu Gly Ser Cys Lys Thr Arg<br>50　　　　　　　　　　55　　　　　　　　　60 | 192 |
| TTT CGC GTC TGC CTA AAG CAC TAC CAG GCC ACC ATC GAC ACC ACC TCC<br>Phe Arg Val Cys Leu Lys His Tyr Gln Ala Thr Ile Asp Thr Thr Ser<br>65　　　　　　　　　70　　　　　　　　　75　　　　　　　　　80 | 240 |
| CAG TGC ACC TAC GGG GAC GTG ATC ACG CCC ATT CTC GGC GAG AAC TCG<br>Gln Cys Thr Tyr Gly Asp Val Ile Thr Pro Ile Leu Gly Glu Asn Ser<br>　　　　　　　　85　　　　　　　　　　90　　　　　　　　　95 | 288 |
| GTC AAT CTG ACC GAC GCC CAG CGC TTC CAG AAC AAG GGC TTC ACG AAT<br>Val Asn Leu Thr Asp Ala Gln Arg Phe Gln Asn Lys Gly Phe Thr Asn<br>　　　　　100　　　　　　　　　105　　　　　　　　　110 | 336 |
| CCC ATC CAG TTC CCC TTC TCG TTC TCA TGG CCG GGT ACC TTC TCG CTG<br>Pro Ile Gln Phe Pro Phe Ser Phe Ser Trp Pro Gly Thr Phe Ser Leu<br>　　　　115　　　　　　　　　120　　　　　　　　　125 | 384 |
| ATC GTC GAG GCC TGG CAT GAT ACG AAC AAT AGC GGC AAT GCG CGA ACC<br>Ile Val Glu Ala Trp His Asp Thr Asn Asn Ser Gly Asn Ala Arg Thr<br>130　　　　　　　　　135　　　　　　　　　140 | 432 |
| AAC AAG CTC CTC ATC CAG CGA CTC TTG GTG CAG CAG GTA CTG GAG GTG<br>Asn Lys Leu Leu Ile Gln Arg Leu Leu Val Gln Gln Val Leu Glu Val<br>145　　　　　　　　　150　　　　　　　　　155　　　　　　　　　160 | 480 |
| TCC TCC GAA TGG AAG ACG AAC AAG TCG GAA TCG CAG TAC ACG TCG CTG<br>Ser Ser Glu Trp Lys Thr Asn Lys Ser Glu Ser Gln Tyr Thr Ser Leu<br>　　　　　　　　165　　　　　　　　　170　　　　　　　　　175 | 528 |
| GAG TAC GAT TTC CGT GTC ACC TGC GAT CTC AAC TAC TAC GGA TCC GGC<br>Glu Tyr Asp Phe Arg Val Thr Cys Asp Leu Asn Tyr Tyr Gly Ser Gly<br>　　　　　180　　　　　　　　　185　　　　　　　　　190 | 576 |
| TGT GCC AAG TTC TGC CGG CCC CGC GAC GAT TCA TTT GGA CAC TCG ACT<br>Cys Ala Lys Phe Cys Arg Pro Arg Asp Asp Ser Phe Gly His Ser Thr<br>　　　　195　　　　　　　　　200　　　　　　　　　205 | 624 |
| TGC TCG GAG ACG GGC GAA ATT ATC TGT TTG ACC GGA TGG CAG GGC GAT<br>Cys Ser Glu Thr Gly Glu Ile Ile Cys Leu Thr Gly Trp Gln Gly Asp<br>210　　　　　　　　　215　　　　　　　　　220 | 672 |
| TAC TGT CAC ATA CCC AAA TGC GCC AAA GGC TGT GAA<br>Tyr Cys His Ile Pro Lys Cys Ala Lys Gly Cys Glu<br>225　　　　　　　　　230　　　　　　　　　235 | 708 |

(2) INFORMATION FOR SEQ ID NO:4:

(i) SEQUENCE CHARACTERISTICS:
        (A) LENGTH: 236 amino acids
        (B) TYPE: amino acid
        (D) TOPOLOGY: unknown (ii) MOLECULE TYPE: protein (xi) SEQUENCE DESCRIPTION: SEQ ID NO:4:

Met His Trp Ile Lys Cys Leu Leu Thr Ala Phe Ile Cys Phe Thr Val
 1               5                  10                  15

Ile Val Gln Val His Ser Ser Gly Ser Phe Glu Leu Arg Leu Lys Tyr
                20                  25                  30

Phe Ser Asn Asp His Gly Arg Asp Asn Glu Gly Arg Cys Cys Ser Gly
            35                  40                  45

Glu Ser Asp Gly Ala Thr Gly Lys Cys Leu Gly Ser Cys Lys Thr Arg
        50                  55                  60

```
Phe Arg Val Cys Leu Lys His Tyr Gln Ala Thr Ile Asp Thr Thr Ser
 65                  70                  75                  80

Gln Cys Thr Tyr Gly Asp Val Ile Thr Pro Ile Leu Gly Glu Asn Ser
                 85                  90                  95

Val Asn Leu Thr Asp Ala Gln Arg Phe Gln Asn Lys Gly Phe Thr Asn
            100                 105                 110

Pro Ile Gln Phe Pro Phe Ser Phe Ser Trp Pro Gly Thr Phe Ser Leu
        115                 120                 125

Ile Val Glu Ala Trp His Asp Thr Asn Asn Ser Gly Asn Ala Arg Thr
130                 135                 140

Asn Lys Leu Leu Ile Gln Arg Leu Leu Val Gln Val Leu Glu Val
145                 150                 155                 160

Ser Ser Glu Trp Lys Thr Asn Lys Ser Glu Ser Gln Tyr Thr Ser Leu
                165                 170                 175

Glu Tyr Asp Phe Arg Val Thr Cys Asp Leu Asn Tyr Tyr Gly Ser Gly
            180                 185                 190

Cys Ala Lys Phe Cys Arg Pro Arg Asp Asp Ser Phe Gly His Ser Thr
        195                 200                 205

Cys Ser Glu Thr Gly Glu Ile Ile Cys Leu Thr Gly Trp Gln Gly Asp
210                 215                 220

Tyr Cys His Ile Pro Lys Cys Ala Lys Gly Cys Glu
225                 230                 235

(2) INFORMATION FOR SEQ ID NO:5:

(i) SEQUENCE CHARACTERISTICS:
        (A) LENGTH: 6464 base pairs
        (B) TYPE: nucleic acid
        (C) STRANDEDNESS: double
        (D) TOPOLOGY: unknown (ii) MOLECULE TYPE: cDNA (ix) FEATURE:
         (A) NAME/KEY: CDS
         (B) LOCATION: 371..4024

(xi) SEQUENCE DESCRIPTION: SEQ ID NO:5:

GAATTCCCCT CCCCCCTTTT TCCATGCAGC TGATCTAAAA GGGAATAAAA GGCTGCGCAT      60

AATCATAATA ATAAAAGAAG GGGAGCGCGA GAGAAGGAAA GAAAGCCGGG AGGTGGAAGA     120

GGAGGGGGAG CGTCTCAAAG AAGCGATCAG AATAATAAAA GGAGGCCGGG CTCTTTGCCT     180

TCTGGAACGG GCCGCTCTTG AAAGGGCTTT TGAAAAGTGG TGTTGTTTTC CAGTCGTGCA     240

TGCTCCAATC GGCGGAGTAT ATTAGAGCCG GGACGCGGCC GCAGGGGCAG CGGCGACGGC     300

AGCACCGGCG GCAGCACCAG CGCGAACAGC AGCGGCGGCG TCCCGAGTGC CCGCGGCGGC     360

GCGCGCAGCG ATG CGT TCC CCA CGG ACA CGC GGC CGG TCC GGG CGC CCC      409
           Met Arg Ser Pro Arg Thr Arg Gly Arg Ser Gly Arg Pro
             1               5                  10

CTA AGC CTC CTG CTC GCC CTG CTC TGT GCC CTG CGA GCC AAG GTG TGT      457
Leu Ser Leu Leu Leu Ala Leu Leu Cys Ala Leu Arg Ala Lys Val Cys
         15                  20                  25

GGG GCC TCG GGT CAG TTC GAG TTG GAG ATC CTG TCC ATG CAG AAC GTG      505
Gly Ala Ser Gly Gln Phe Glu Leu Glu Ile Leu Ser Met Gln Asn Val
 30                  35                  40                  45

AAC GGG GAG CTG CAG AAC GGG AAC TGC TGC GGC GGC GCC CGG AAC CCG      553
Asn Gly Glu Leu Gln Asn Gly Asn Cys Cys Gly Gly Ala Arg Asn Pro
                 50                  55                  60

GGA GAC CGC AAG TGC ACC CGC GAC GAG TGT GAC ACA TAC TTC AAA GTG      601
Gly Asp Arg Lys Cys Thr Arg Asp Glu Cys Asp Thr Tyr Phe Lys Val
```

|  |  |  |  |  |  |  |  |  |  |  |  |  |  |  |  |
|---|---|---|---|---|---|---|---|---|---|---|---|---|---|---|---|
|  |  | 65 |  |  |  |  | 70 |  |  |  |  | 75 |  |  |  |

```
TGC CTC AAG GAG TAT CAG TCC CGC GTC ACG GCC GGG GGG CCC TGC AGC     649
Cys Leu Lys Glu Tyr Gln Ser Arg Val Thr Ala Gly Gly Pro Cys Ser
        80                  85                  90

TTC GGC TCA GGG TCC ACG CCT GTC ATC GGG GGC AAC ACC TTC AAC CTC     697
Phe Gly Ser Gly Ser Thr Pro Val Ile Gly Gly Asn Thr Phe Asn Leu
    95                 100                 105

AAG GCC AGC CGC GGC AAC GAC CCG AAC CGC ATC GTG CTG CCT TTC AGT     745
Lys Ala Ser Arg Gly Asn Asp Pro Asn Arg Ile Val Leu Pro Phe Ser
110                 115                 120                 125

TTC GCC TGG CCG AGG TCC TAT ACG TTG CTT GTG GAG GCG TGG GAT TCC     793
Phe Ala Trp Pro Arg Ser Tyr Thr Leu Leu Val Glu Ala Trp Asp Ser
            130                 135                 140

AGT AAT GAC ACC GTT CAA CCT GAC AGT ATT ATT GAA AAG GCT TCT CAC     841
Ser Asn Asp Thr Val Gln Pro Asp Ser Ile Ile Glu Lys Ala Ser His
                145                 150                 155

TCG GGC ATG ATC AAC CCC AGC CGG CAG TGG CAG ACG CTG AAG CAG AAC     889
Ser Gly Met Ile Asn Pro Ser Arg Gln Trp Gln Thr Leu Lys Gln Asn
                    160                 165                 170

ACG GGC GTT GCC CAC TTT GAG TAT CAG ATC CGC GTG ACC TGT GAT GAC     937
Thr Gly Val Ala His Phe Glu Tyr Gln Ile Arg Val Thr Cys Asp Asp
175                 180                 185

TAC TAC TAT GGC TTT GGC TGT AAT AAG TTC TGC CGC CCC AGA GAT GAC     985
Tyr Tyr Tyr Gly Phe Gly Cys Asn Lys Phe Cys Arg Pro Arg Asp Asp
190                 195                 200                 205

TTC TTT GGA CAC TAT GCC TGT GAC CAG AAT GGC AAC AAA ACT TGC ATG    1033
Phe Phe Gly His Tyr Ala Cys Asp Gln Asn Gly Asn Lys Thr Cys Met
                210                 215                 220

GAA GGC TGG ATG GGC CCC GAA TGT AAC AGA GCT ATT TGC CGA CAA GGC    1081
Glu Gly Trp Met Gly Pro Glu Cys Asn Arg Ala Ile Cys Arg Gln Gly
                225                 230                 235

TGC AGT CCT AAG CAT GGG TCT TGC AAA CTC CCA GGT GAC TGC AGG TGC    1129
Cys Ser Pro Lys His Gly Ser Cys Lys Leu Pro Gly Asp Cys Arg Cys
            240                 245                 250

CAG TAC GGC TGG CAA GGC CTG TAC TGT GAT AAG TGC ATC CCA CAC CCG    1177
Gln Tyr Gly Trp Gln Gly Leu Tyr Cys Asp Lys Cys Ile Pro His Pro
        255                 260                 265

GGA TGC GTC CAC GGC ATC TGT AAT GAG CCC TGG CAG TGC CTC TGT GAG    1225
Gly Cys Val His Gly Ile Cys Asn Glu Pro Trp Gln Cys Leu Cys Glu
270                 275                 280                 285

ACC AAC TGG GGC GGC CAG CTC TGT GAC AAA GAT CTC AAT TAC TGT GGG    1273
Thr Asn Trp Gly Gly Gln Leu Cys Asp Lys Asp Leu Asn Tyr Cys Gly
                290                 295                 300

ACT CAT CAG CCG TGT CTC AAC GGG GGA ACT TGT AGC AAC ACA GGC CCT    1321
Thr His Gln Pro Cys Leu Asn Gly Gly Thr Cys Ser Asn Thr Gly Pro
                305                 310                 315

GAC AAA TAT CAG TGT TCC TGC CCT GAG GGG TAT TCA GGA CCC AAC TGT    1369
Asp Lys Tyr Gln Cys Ser Cys Pro Glu Gly Tyr Ser Gly Pro Asn Cys
                    320                 325                 330

GAA ATT GCT GAG CAC GCC TGC CTC TCT GAT CCC TGT CAC AAC AGA GGC    1417
Glu Ile Ala Glu His Ala Cys Leu Ser Asp Pro Cys His Asn Arg Gly
335                 340                 345

AGC TGT AAG GAG ACC TCC CTG GGC TTT GAG TGT GAG TGT TCC CCA GGC    1465
Ser Cys Lys Glu Thr Ser Leu Gly Phe Glu Cys Glu Cys Ser Pro Gly
350                 355                 360                 365

TGG ACC GGC CCC ACA TGC TCT ACA AAC ATT GAT GAC TGT TCT CCT AAT    1513
Trp Thr Gly Pro Thr Cys Ser Thr Asn Ile Asp Asp Cys Ser Pro Asn
                370                 375                 380

AAC TGT TCC CAC GGG GGC ACC TGC CAG GAC CTG GTT AAC GGA TTT AAG    1561
Asn Cys Ser His Gly Gly Thr Cys Gln Asp Leu Val Asn Gly Phe Lys
```

-continued

|  |  | 385 |  |  |  | 390 |  |  |  | 395 |  |  |  |  |
|---|---|---|---|---|---|---|---|---|---|---|---|---|---|---|
| TGT | GTG | TGC | CCC | CCA | CAG | TGG | ACT | GGG | AAA | ACG | TGC | CAG | TTA | GAT | GCA | 1609 |
| Cys | Val | Cys | Pro | Pro | Gln | Trp | Thr | Gly | Lys | Thr | Cys | Gln | Leu | Asp | Ala |
|  |  | 400 |  |  |  | 405 |  |  |  | 410 |  |  |  |  |

```
TGT GTG TGC CCC CCA CAG TGG ACT GGG AAA ACG TGC CAG TTA GAT GCA    1609
Cys Val Cys Pro Pro Gln Trp Thr Gly Lys Thr Cys Gln Leu Asp Ala
        400             405             410

AAT GAA TGT GAG GCC AAA CCT TGT GTA AAC GCC AAA TCC TGT AAG AAT    1657
Asn Glu Cys Glu Ala Lys Pro Cys Val Asn Ala Lys Ser Cys Lys Asn
        415             420             425

CTC ATT GCC AGC TAC TAC TGC GAC TGT CTT CCC GGC TGG ATG GGT CAG    1705
Leu Ile Ala Ser Tyr Tyr Cys Asp Cys Leu Pro Gly Trp Met Gly Gln
430             435             440                     445

AAT TGT GAC ATA AAT ATT AAT GAC TGC CTT GGC CAG TGT CAG AAT GAC    1753
Asn Cys Asp Ile Asn Ile Asn Asp Cys Leu Gly Gln Cys Gln Asn Asp
            450             455             460

GCC TCC TGT CGG GAT TTG GTT AAT GGT TAT CGC TGT ATC TGT CCA CCT    1801
Ala Ser Cys Arg Asp Leu Val Asn Gly Tyr Arg Cys Ile Cys Pro Pro
        465             470             475

GGC TAT GCA GGC GAT CAC TGT GAG AGA GAC ATC GAT GAA TGT GCC AGC    1849
Gly Tyr Ala Gly Asp His Cys Glu Arg Asp Ile Asp Glu Cys Ala Ser
            480             485             490

AAC CCC TGT TTG AAT GGG GGT CAC TGT CAG AAT GAA ATC AAC AGA TTC    1897
Asn Pro Cys Leu Asn Gly Gly His Cys Gln Asn Glu Ile Asn Arg Phe
495             500             505

CAG TGT CTG TGT CCC ACT GGT TTC TCT GGA AAC CTC TGT CAG CTG GAC    1945
Gln Cys Leu Cys Pro Thr Gly Phe Ser Gly Asn Leu Cys Gln Leu Asp
510             515             520                     525

ATC GAT TAT TGT GAG CCT AAT CCC TGC CAG AAC GGT GCC CAG TGC TAC    1993
Ile Asp Tyr Cys Glu Pro Asn Pro Cys Gln Asn Gly Ala Gln Cys Tyr
            530             535             540

AAC CGT GCC AGT GAC TAT TTC TGC AAG TGC CCC GAG GAC TAT GAG GGC    2041
Asn Arg Ala Ser Asp Tyr Phe Cys Lys Cys Pro Glu Asp Tyr Glu Gly
        545             550             555

AAG AAC TGC TCA CAC CTG AAA GAC CAC TGC CGC ACG ACC CCC TGT GAA    2089
Lys Asn Cys Ser His Leu Lys Asp His Cys Arg Thr Thr Pro Cys Glu
        560             565             570

GTG ATT GAC AGC TGC ACA GTG GCC ATG GCT TCC AAC GAC ACA CCT GAA    2137
Val Ile Asp Ser Cys Thr Val Ala Met Ala Ser Asn Asp Thr Pro Glu
575             580             585

GGG GTG CGG TAT ATT TCC TCC AAC GTC TGT GGT CCT CAC GGG AAG TGC    2185
Gly Val Arg Tyr Ile Ser Ser Asn Val Cys Gly Pro His Gly Lys Cys
590             595             600             605

AAG AGT CAG TCG GGA GGC AAA TTC ACC TGT GAC TGT AAC AAA GGC TTC    2233
Lys Ser Gln Ser Gly Gly Lys Phe Thr Cys Asp Cys Asn Lys Gly Phe
            610             615             620

ACG GGA ACA TAC TGC CAT GAA AAT ATT AAT GAC TGT GAG AGC AAC CCT    2281
Thr Gly Thr Tyr Cys His Glu Asn Ile Asn Asp Cys Glu Ser Asn Pro
            625             630             635

TGT AGA AAC GGT GGC ACT TGC ATC GAT GGT GTC AAC TCC TAC AAG TGC    2329
Cys Arg Asn Gly Gly Thr Cys Ile Asp Gly Val Asn Ser Tyr Lys Cys
        640             645             650

ATC TGT AGT GAC GGC TGG GAG GGG GCC TAC TGT GAA ACC AAT ATT AAT    2377
Ile Cys Ser Asp Gly Trp Glu Gly Ala Tyr Cys Glu Thr Asn Ile Asn
        655             660             665

GAC TGC AGC CAG AAC CCC TGC CAC AAT GGG GGC ACG TGT CGC GAC CTG    2425
Asp Cys Ser Gln Asn Pro Cys His Asn Gly Gly Thr Cys Arg Asp Leu
670             675             680             685

GTC AAT GAC TTC TAC TGT GAC TGT AAA AAT GGG TGG AAA GGA AAG ACC    2473
Val Asn Asp Phe Tyr Cys Asp Cys Lys Asn Gly Trp Lys Gly Lys Thr
            690             695             700

TGC CAC TCA CGT GAC AGT CAG TGT GAT GAG GCC ACG TGC AAC AAC GGT    2521
Cys His Ser Arg Asp Ser Gln Cys Asp Glu Ala Thr Cys Asn Asn Gly
```

-continued

```
                705                  710                  715
GGC ACC TGC TAT GAT GAG GGG GAT GCT TTT AAG TGC ATG TGT CCT GGC    2569
Gly Thr Cys Tyr Asp Glu Gly Asp Ala Phe Lys Cys Met Cys Pro Gly
        720                  725                  730

GGC TGG GAA GGA ACA ACC TGT AAC ATA GCC CGA AAC AGT AGC TGC CTG    2617
Gly Trp Glu Gly Thr Thr Cys Asn Ile Ala Arg Asn Ser Ser Cys Leu
735                  740                  745

CCC AAC CCC TGC CAT AAT GGG GGC ACA TGT GTG GTC AAC GGC GAG TCC    2665
Pro Asn Pro Cys His Asn Gly Gly Thr Cys Val Val Asn Gly Glu Ser
750                  755                  760                  765

TTT ACG TGC GTC TGC AAG GAA GGC TGG GAG GGG CCC ATC TGT GCT CAG    2713
Phe Thr Cys Val Cys Lys Glu Gly Trp Glu Gly Pro Ile Cys Ala Gln
                770                  775                  780

AAT ACC AAT GAC TGC AGC CCT CAT CCC TGT TAC AAC AGC GGC ACC TGT    2761
Asn Thr Asn Asp Cys Ser Pro His Pro Cys Tyr Asn Ser Gly Thr Cys
            785                  790                  795

GTG GAT GGA GAC AAC TGG TAC CGG TGC GAA TGT GCC CCG GGT TTT GCT    2809
Val Asp Gly Asp Asn Trp Tyr Arg Cys Glu Cys Ala Pro Gly Phe Ala
        800                  805                  810

GGG CCC GAC TGC AGA ATA AAC ATC AAT GAA TGC CAG TCT TCA CCT TGT    2857
Gly Pro Asp Cys Arg Ile Asn Ile Asn Glu Cys Gln Ser Ser Pro Cys
815                  820                  825

GCC TTT GGA GCG ACC TGT GTG GAT GAG ATC AAT GGC TAC CGG TGT GTC    2905
Ala Phe Gly Ala Thr Cys Val Asp Glu Ile Asn Gly Tyr Arg Cys Val
830                  835                  840                  845

TGC CCT CCA GGG CAC AGT GGT GCC AAG TGC CAG GAA GTT TCA GGG AGA    2953
Cys Pro Pro Gly His Ser Gly Ala Lys Cys Gln Glu Val Ser Gly Arg
                850                  855                  860

CCT TGC ATC ACC ATG GGG AGT GTG ATA CCA GAT GGG GCC AAA TGG GAT    3001
Pro Cys Ile Thr Met Gly Ser Val Ile Pro Asp Gly Ala Lys Trp Asp
            865                  870                  875

GAT GAC TGT AAT ACC TGC CAG TGC CTG AAT GGA CGG ATC GCC TGC TCA    3049
Asp Asp Cys Asn Thr Cys Gln Cys Leu Asn Gly Arg Ile Ala Cys Ser
        880                  885                  890

AAG GTC TGG TGT GGC CCT CGA CCT TGC CTG CTC CAC AAA GGG CAC AGC    3097
Lys Val Trp Cys Gly Pro Arg Pro Cys Leu Leu His Lys Gly His Ser
895                  900                  905

GAG TGC CCC AGC GGG CAG AGC TGC ATC CCC ATC CTG GAC GAC CAG TGC    3145
Glu Cys Pro Ser Gly Gln Ser Cys Ile Pro Ile Leu Asp Asp Gln Cys
910                  915                  920                  925

TTC GTC CAC CCC TGC ACT GGT GTG GGC GAG TGT CGG TCT TCC AGT CTC    3193
Phe Val His Pro Cys Thr Gly Val Gly Glu Cys Arg Ser Ser Ser Leu
                930                  935                  940

CAG CCG GTG AAG ACA AAG TGC ACC TCT GAC TCC TAT TAC CAG GAT AAC    3241
Gln Pro Val Lys Thr Lys Cys Thr Ser Asp Ser Tyr Tyr Gln Asp Asn
            945                  950                  955

TGT GCG AAC ATC ACA TTT ACC TTT AAC AAG GAG ATG ATG TCA CCA GGT    3289
Cys Ala Asn Ile Thr Phe Thr Phe Asn Lys Glu Met Met Ser Pro Gly
        960                  965                  970

CTT ACT ACG GAG CAC ATT TGC AGT GAA TTG AGG AAT TTG AAT ATT TTG    3337
Leu Thr Thr Glu His Ile Cys Ser Glu Leu Arg Asn Leu Asn Ile Leu
975                  980                  985

AAG AAT GTT TCC GCT GAA TAT TCA ATC TAC ATC GCT TGC GAG CCT TCC    3385
Lys Asn Val Ser Ala Glu Tyr Ser Ile Tyr Ile Ala Cys Glu Pro Ser
990                  995                  1000                 1005

CCT TCA GCG AAC AAT GAA ATA CAT GTG GCC ATT TCT GCT GAA GAT ATA    3433
Pro Ser Ala Asn Asn Glu Ile His Val Ala Ile Ser Ala Glu Asp Ile
                1010                 1015                 1020

CGG GAT GAT GGG AAC CCG ATC AAG GAA ATC ACT GAC AAA ATA ATC GAT    3481
Arg Asp Asp Gly Asn Pro Ile Lys Glu Ile Thr Asp Lys Ile Ile Asp
```

```
                        1025             1030              1035
CTT GTT ACT AAA CGT GAT GGA AAC AGC TCG CTG ATT GCT GCC GTT GAA      3529
Leu Val Thr Lys Arg Asp Gly Asn Ser Ser Leu Ile Ala Ala Val Glu
            1040             1045             1050

GAA GTA AGA GTT CAG AGG CGG CCT CTG AAG AAC AGA ACA GAT TTC CTT      3577
Glu Val Arg Val Gln Arg Arg Pro Leu Lys Asn Arg Thr Asp Phe Leu
        1055             1060             1065

GTT CCC TTG CTG AGC TCT GTC TTA ACT GTG GCT TGG ATC TGT TGC TTG      3625
Val Pro Leu Leu Ser Ser Val Leu Thr Val Ala Trp Ile Cys Cys Leu
1070             1075             1080             1085

GTG ACG GCC TTC TAC TGG TGC CTG CGG AAG CGG CGG AAG CCG GGC AGC      3673
Val Thr Ala Phe Tyr Trp Cys Leu Arg Lys Arg Arg Lys Pro Gly Ser
            1090             1095             1100

CAC ACA CAC TCA GCC TCT GAG GAC AAC ACC ACC AAC AAC GTG CGG GAG      3721
His Thr His Ser Ala Ser Glu Asp Asn Thr Thr Asn Asn Val Arg Glu
        1105             1110             1115

CAG CTG AAC CAG ATC AAA AAC CCC ATT GAG AAA CAT GGG GCC AAC ACG      3769
Gln Leu Asn Gln Ile Lys Asn Pro Ile Glu Lys His Gly Ala Asn Thr
        1120             1125             1130

GTC CCC ATC AAG GAT TAC GAG AAC AAG AAC TCC AAA ATG TCT AAA ATA      3817
Val Pro Ile Lys Asp Tyr Glu Asn Lys Asn Ser Lys Met Ser Lys Ile
1135             1140             1145

AGG ACA CAC AAT TCT GAA GTA GAA GAG GAC GAC ATG GAC AAA CAC CAG      3865
Arg Thr His Asn Ser Glu Val Glu Glu Asp Asp Met Asp Lys His Gln
1150             1155             1160             1165

CAG AAA GCC CGG TTT GCC AAG CAG CCG GCG TAC ACG CTG GTA GAC AGA      3913
Gln Lys Ala Arg Phe Ala Lys Gln Pro Ala Tyr Thr Leu Val Asp Arg
            1170             1175             1180

GAA GAG AAG CCC CCC AAC GGC ACG CCG ACA AAA CAC CCA AAC TGG ACA      3961
Glu Glu Lys Pro Pro Asn Gly Thr Pro Thr Lys His Pro Asn Trp Thr
            1185             1190             1195

AAC AAA CAG GAC AAC AGA GAC TTG GAA AGT GCC CAG AGC TTA AAC CGA      4009
Asn Lys Gln Asp Asn Arg Asp Leu Glu Ser Ala Gln Ser Leu Asn Arg
            1200             1205             1210

ATG GAG TAC ATC GTA TAGCAGACCG CGGGCACTGC CGCCGCTAGG TAGAGTCTGA      4064
Met Glu Tyr Ile Val
    1215

GGGCTTGTAG TTCTTTAAAC TGTCGTGTCA TACTCGAGTC TGAGGCCGTT GCTGACTTAG    4124

AATCCCTGTG TTAATTTAGT TTGACAAGCT GGCTTACACT GGCAATGGTA GTTCTGTGGT    4184

TGGCTGGGAA ATCGAGTGGC GCATCTCACA GCTATGCAAA AAGCTAGTCA ACAGTACCCC    4244

TGGTTGTGTG TCCCCTTGCA GCCGACACGG TCTCGGATCA GGCTCCCAGG AGCTGCCCAG    4304

CCCCCTGGTA CTTTGAGCTC CCACTTCTGC CAGATGTCTA ATGGTGATGC AGTCTTAGAT    4364

CATAGTTTTA TTTATATTTA TTGACTCTTG AGTTGTTTTT GTATATTGGT TTTATGATGA    4424

CGTACAAGTA GTTCTGTATT TGAAAGTGCC TTTGCAGCTC AGAACCACAG CAACGATCAC    4484

AAATGACTTT ATTATTTATT TTTTTAATT GTATTTTTGT TGTTGGGGGA GGGGAGACTT    4544

TGATGTCAGC AGTTGCTGGT AAAATGAAGA ATTTAAAGAA AAAATGTCCA AAAGTAGAAC    4604

TTTGTATAGT TATGTAAATA ATTCTTTTTT ATTAATCACT GTGTATATTT GATTTATTAA    4664

CTTAATAATC AAGAGCCTTA AAACATCATT CCTTTTTATT TATATGTATG TGTTTAGAAT    4724

TGAAGGTTTT TGATAGCATT GTAAGCGTAT GGCTTTATTT TTTTGAACTC TTCTCATTAC    4784

TTGTTGCCTA TAAGCCAAAA AGGAAAGGGT GTTTTGAAAA TAGTTTATTT TAAAACAATA    4844

GGATGGGCTA CACGTACATA GGTAAATAAT AGCACCGTAC TGGTTATGAT GATGAAAATA    4904

ACTGGAAACT TGAAAGCTTG TGGTAATGGC AGATAAAGAT GGTTCACCTG GAAATTAAA     4964
```

-continued

```
ACTTGAATGG TTGTACAGAA AAGCACAGAG TGGAATGCAC ATCAATGACA GTAAGGGAGT      5024

TAGTTCTAGG AACAGCTCCT GAACAGTAAG ATTCCCGCAA TAGTCTCCGC CTCGTTCGTC      5084

TATGGTATGC ATCCCATTCA TTTTCTTCTT CTGATTATTG TCATCTTTCC CTTTGCCAAA      5144

TGGGCAGTTA TTGTTTCAGG GAGAGAAGCT GCTCATTGGC CAATCATTCT GGTGTGCAGT      5204

GCTCCATCGG ATTCTACATG TCCAACAAGG CATGTCTGGA TGATGCAATG TCTGTCTGAC      5264

CCCCGGAATT CCGTGCAGAG ACAACATTCT AGACAGATAT ACACTTTTTA TTATTAACAA      5324

ACTTTGGCCA CAACCTTTGA TGTATAAATT GCCGGATTTC CCCAGTCCTT TCATTGTGGC      5384

TTTGGACAGG AGCAGGCTCA CTTGTCTGCT TCAGGCTGCC TTTCTCTTGG GTTGCACCTC      5444

AGTTCTTACT TATTTATTTA TTTTGAGTGG AGCATAGGGG CCTCTTCCAA AATGGGTAGA      5504

GCTCAGGGGC TTTCTTATTG AAATGGTCAC ATGATAAAAA CGGGCTGAAA AAGGAGAGTT      5564

CCAGGAGAAA AGCCCAGAAA AGGCCCCTCC TCAGAAGACA GCCTTTAAGC CTCTTGCTTA      5624

CTGAAGGAAG CCCCACCTTC TAGCACTGAG GCCGGGTCTG ATCTTCCAGA GGAGTTGGAG      5684

GAGTCCATGA GAATGGCCAC CATTCTTGCT TGCTGCTGCT GATGTTGCAG TTTTGAGAGA      5744

ACAGCGGGAT CCTTGTTGTC CTCTAGAGAC TTGAGTCTGT CACTGACATT TTTTCAGTTC      5804

CTTTGCTCAT AGACCATACG AGGAATTAGT GATGTGTCAG TTGAGAGTTC ACAATCTCAT      5864

TGTTCATTTA ATTCACTTTA AAGTTGTCAA TTTCTGTGTG AGTAACCTGT AAAAGACACC      5924

TTTCCAGAAG AGTTTTGCCG TCTGTTTGAA AAAAAAATCT TTATAAACTT TCCTAAGTAT      5984

CTGGATTTGG ATTCCTTATT TGGAGAGAAA ATGTACCCTG TCTCCACCAA AAATACAAAA      6044

ATTAGCCAGG CTTGGTGGTG CACACCGGTA ATCCCAGCAA CTCTGGAGAC TAAGGCAGGA      6104

AGAATCGCTT GACCCAGGAG GGTCGAGGCT ACAATGAGTT GAAACCGCGC CACTGCACTC      6164

CAGCCTGGGC GACAGTGCGA GGCCCTGTCT CAAAAATAAA ATAAAATAAA TAAATAAATT      6224

AGCCAGATAC TGTGTGCACG CCTGCAGTCC CAGCTATTCT GGAAGCTGAG GTGGGAAGAT      6284

GGTTAAGCCT GAGAGGACAA AGCTGCAGTG AGTCATGTTT GCATCACTGC ACTCCAGCCT      6344

GGGTGACAGA GCAAGACCCT GTCTAAAAAA CAAAAACAGG CCGGGTGTGG TGGCTCATGC      6404

CTGCCATCCC AGTGCTTTGG GAGGCAGAGG TTGGCATAAT CCCAGCGCTC TGGGAATTCC      6464
```

(2) INFORMATION FOR SEQ ID NO:6:

(i) SEQUENCE CHARACTERISTICS:
        (A) LENGTH: 1218 amino acids
        (B) TYPE: amino acid
        (D) TOPOLOGY: unknown (ii) MOLECULE TYPE: protein (xi) SEQUENCE DESCRIPTION: SEQ ID NO:6:

```
Met Arg Ser Pro Arg Thr Arg Gly Arg Ser Gly Arg Pro Leu Ser Leu
 1               5                  10                  15

Leu Leu Ala Leu Leu Cys Ala Leu Arg Ala Lys Val Cys Gly Ala Ser
             20                  25                  30

Gly Gln Phe Glu Leu Glu Ile Leu Ser Met Gln Asn Val Asn Gly Glu
         35                  40                  45

Leu Gln Asn Gly Asn Cys Cys Gly Gly Ala Arg Asn Pro Gly Asp Arg
     50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                 85                  90                  95
```

-continued

```
Gly Ser Thr Pro Val Ile Gly Gly Asn Thr Phe Asn Leu Lys Ala Ser
            100                 105                 110

Arg Gly Asn Asp Pro Asn Arg Ile Val Leu Pro Phe Ser Phe Ala Trp
            115                 120                 125

Pro Arg Ser Tyr Thr Leu Leu Val Glu Ala Trp Asp Ser Ser Asn Asp
130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
            195                 200                 205

His Tyr Ala Cys Asp Gln Asn Gly Asn Lys Thr Cys Met Glu Gly Trp
        210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525
```

```
Cys Glu Pro Asn Pro Cys Gln Asn Gly Ala Gln Cys Tyr Asn Arg Ala
        530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
        580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
            645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
            725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
            805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
            885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
```

```
                    945                 950                 955                 960
Ile Thr Phe Thr Phe Asn Lys Glu Met Met Ser Pro Gly Leu Thr Thr
                        965                 970                 975
Glu His Ile Cys Ser Glu Leu Arg Asn Leu Asn Ile Leu Lys Asn Val
                    980                 985                 990
Ser Ala Glu Tyr Ser Ile Tyr Ile Ala Cys Glu Pro Ser Pro Ser Ala
                995                 1000                1005
Asn Asn Glu Ile His Val Ala Ile Ser Ala Glu Asp Ile Arg Asp Asp
            1010                1015                1020
Gly Asn Pro Ile Lys Glu Ile Thr Asp Lys Ile Ile Asp Leu Val Thr
1025                1030                1035                1040
Lys Arg Asp Gly Asn Ser Ser Leu Ile Ala Ala Val Glu Glu Val Arg
                1045                1050                1055
Val Gln Arg Arg Pro Leu Lys Asn Arg Thr Asp Phe Leu Val Pro Leu
                    1060                1065                1070
Leu Ser Ser Val Leu Thr Val Ala Trp Ile Cys Cys Leu Val Thr Ala
                        1075                1080                1085
Phe Tyr Trp Cys Leu Arg Lys Arg Arg Lys Pro Gly Ser His Thr His
                            1090                1095                1100
Ser Ala Ser Glu Asp Asn Thr Thr Asn Val Arg Glu Gln Leu Asn
1105                1110                1115                1120
Gln Ile Lys Asn Pro Ile Glu Lys His Gly Ala Asn Thr Val Pro Ile
                    1125                1130                1135
Lys Asp Tyr Glu Asn Lys Asn Ser Lys Met Ser Lys Ile Arg Thr His
                        1140                1145                1150
Asn Ser Glu Val Glu Glu Asp Asp Met Asp Lys His Gln Gln Lys Ala
                            1155                1160                1165
Arg Phe Ala Lys Gln Pro Ala Tyr Thr Leu Val Asp Arg Glu Glu Lys
                1170                1175                1180
Pro Pro Asn Gly Thr Pro Thr Lys His Pro Asn Trp Thr Asn Lys Gln
1185                1190                1195                1200
Asp Asn Arg Asp Leu Glu Ser Ala Gln Ser Leu Asn Arg Met Glu Tyr
                    1205                1210                1215
Ile Val (2) INFORMATION FOR SEQ ID NO:7:

(i) SEQUENCE CHARACTERISTICS:
        (A) LENGTH: 4483 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 332..4102

(xi) SEQUENCE DESCRIPTION: SEQ ID NO:7:

GGCCGGGGCC GGGCGGGCGG GTCGCGGGGG CAATGCGGGC GCAGGGCCGG GGGCGCCTTC      60

CCCGGCGGCT GCTGCTGCTG CTGGCGCTCT GGGTGCAGGC GGCGCGGCCC ATGGGCTATT     120

TCGAGCTGCA GCTGAGCGCG CTGCGGAACG TGAACGGGGA GCTGCTGAGC GGCGCCTGCT     180

GTGACGGCGA CGGCCGGACA ACGCGCGCGG GGGCTGCGG CCACGACGAG TGCGACACCG     240

CTCCTTTACC CTCATCGTGG AGGCCTGGGA CTGGACAAC GATACCACCC CGAATGAGGA     300

GCTGCTGATC GAGCGAGTGT CGCATGCCGG C ATG ATC AAC CCG GAG GAC CGC        352
```

```
                    Met Ile Asn Pro Glu Asp Arg
                     1               5
TGG AAG AGC CTG CAC TTC AGC GGC CAC GTG GCG CAC CTG GAG CTG CAG    400
Trp Lys Ser Leu His Phe Ser Gly His Val Ala His Leu Glu Leu Gln
         10              15              20

ATC CGC GTG CGC TGC GAC GAG AAC TAC TAC AGC GCC ACT TGC AAC AAG    448
Ile Arg Val Arg Cys Asp Glu Asn Tyr Tyr Ser Ala Thr Cys Asn Lys
         25              30              35

TTC TGC CGG CCC CGC AAT GAC TTT TTC GGC CAC TAC ACC TGC GAC CAG    496
Phe Cys Arg Pro Arg Asn Asp Phe Phe Gly His Tyr Thr Cys Asp Gln
 40              45              50              55

TAC GGC AAC AAG GCC TGC ATG GAC GGC TGG ATG GGC AAG GAG TGC AAG    544
Tyr Gly Asn Lys Ala Cys Met Asp Gly Trp Met Gly Lys Glu Cys Lys
             60              65              70

GAA GCT GTG TGT AAA CAA GGG TGT AAT TTG CTC CAC GGG GGA TGC ACC    592
Glu Ala Val Cys Lys Gln Gly Cys Asn Leu Leu His Gly Gly Cys Thr
                 75              80              85

GTG CCT GGG GAG TGC AGG TGC AGC TAC GGC TGG CAA GGG AGG TTC TGC    640
Val Pro Gly Glu Cys Arg Cys Ser Tyr Gly Trp Gln Gly Arg Phe Cys
             90              95             100

GAT GAG TGT GTC CCC TAC CCC GGC TGC GTG CAT GGC AGT TGT GTG GAG    688
Asp Glu Cys Val Pro Tyr Pro Gly Cys Val His Gly Ser Cys Val Glu
        105             110             115

CCC TGG CAG TGC AAC TGT GAG ACC AAC TGG GGC GGC CTG CTC TGT GAC    736
Pro Trp Gln Cys Asn Cys Glu Thr Asn Trp Gly Gly Leu Leu Cys Asp
120             125             130             135

AAA GAC CTG AAC TAC TGT GGC AGC CAC CAC CCC TGC ACC AAC GGA GGC    784
Lys Asp Leu Asn Tyr Cys Gly Ser His His Pro Cys Thr Asn Gly Gly
                140             145             150

ACG TGC ATC AAC GCC GAG CCT GAC CAG TAC CGC TGC ACC TGC CCT GAC    832
Thr Cys Ile Asn Ala Glu Pro Asp Gln Tyr Arg Cys Thr Cys Pro Asp
            155             160             165

GGC TAC TCG GGC AGG AAC TGT GAG AAG GCT GAG CAC GCC TGC ACC TCC    880
Gly Tyr Ser Gly Arg Asn Cys Glu Lys Ala Glu His Ala Cys Thr Ser
        170             175             180

AAC CCG TGT GCC AAC GGG GGC TCT TGC CAT GAG GTG CCG TCC GGC TTC    928
Asn Pro Cys Ala Asn Gly Gly Ser Cys His Glu Val Pro Ser Gly Phe
185             190             195

GAA TGC CAC TGC CCA TCG GGC TGG AGC GGG CCC ACC TGT GCC CTT GAC    976
Glu Cys His Cys Pro Ser Gly Trp Ser Gly Pro Thr Cys Ala Leu Asp
200             205             210             215

ATC GAT GAG TGT GCT TCG AAC CCG TGT GCG GCC GGT GGC ACC TGT GTG    1024
Ile Asp Glu Cys Ala Ser Asn Pro Cys Ala Ala Gly Gly Thr Cys Val
                220             225             230

GAC CAG GTG GAC GGC TTT GAG TGC ATC TGC CCC GAG CAG TGG GTG GGG    1072
Asp Gln Val Asp Gly Phe Glu Cys Ile Cys Pro Glu Gln Trp Val Gly
            235             240             245

GCC ACC TGC CAG CTG GAC GCC AAT GAG TGT GAA GGG AAG CCA TGC CTT    1120
Ala Thr Cys Gln Leu Asp Ala Asn Glu Cys Glu Gly Lys Pro Cys Leu
        250             255             260

AAC GCT TTT TCT TGC AAA AAC CTG ATT GGC GGC TAT TAC TGT GAT TGC    1168
Asn Ala Phe Ser Cys Lys Asn Leu Ile Gly Gly Tyr Tyr Cys Asp Cys
    265             270             275

ATC CCG GGC TGG AAG GGC ATC AAC TGC CAT ATC AAC GTC AAC GAC TGT    1216
Ile Pro Gly Trp Lys Gly Ile Asn Cys His Ile Asn Val Asn Asp Cys
280             285             290             295

CGC GGG CAG TGT CAG CAT GGG GGC ACC TGC AAG GAC CTG GTG AAC GGG    1264
Arg Gly Gln Cys Gln His Gly Gly Thr Cys Lys Asp Leu Val Asn Gly
            300             305             310

TAC CAG TGT GTG TGC CCA CGG GGC TTC GGA GGC CGG CAT TGC GAG CTG    1312
```

-continued

| | | | | | | | | | | | | |
|---|---|---|---|---|---|---|---|---|---|---|---|---|
| Tyr | Gln | Cys | Val | Cys | Pro | Arg | Gly | Phe | Gly | Arg | His | Cys | Glu | Leu |
| | | 315 | | | | | 320 | | | | 325 | | | |

| GAA | CGA | GAC | AAG | TGT | GCC | AGC | AGC | CCC | TGC | CAC | AGC | GGC | GGC | CTC | TGC | 1360 |
|---|---|---|---|---|---|---|---|---|---|---|---|---|---|---|---|---|
| Glu | Arg | Asp | Lys | Cys | Ala | Ser | Ser | Pro | Cys | His | Ser | Gly | Gly | Leu | Cys | |
| | | 330 | | | | 335 | | | | 340 | | | | | | |

| GAG | GAC | CTG | GCC | GAC | GGC | TTC | CAC | TGC | CAC | TGC | CCC | CAG | GGC | TTC | TCC | 1408 |
| Glu | Asp | Leu | Ala | Asp | Gly | Phe | His | Cys | His | Cys | Pro | Gln | Gly | Phe | Ser | |
| 345 | | | | | 350 | | | | 355 | | | | | | | |

| GGG | CCT | CTC | TGT | GAG | GTG | GAT | GTC | GAC | CTT | TGT | GAG | CCA | AGC | CCC | TGC | 1456 |
| Gly | Pro | Leu | Cys | Glu | Val | Asp | Val | Asp | Leu | Cys | Glu | Pro | Ser | Pro | Cys | |
| 360 | | | | 365 | | | | | 370 | | | | | 375 | | |

| CGG | AAC | GGC | GCT | CGC | TGC | TAT | AAC | CTG | GAG | GGT | GAC | TAT | TAC | TGC | GCC | 1504 |
| Arg | Asn | Gly | Ala | Arg | Cys | Tyr | Asn | Leu | Glu | Gly | Asp | Tyr | Tyr | Cys | Ala | |
| | | | 380 | | | | | 385 | | | | | 390 | | | |

| TGC | CCT | GAT | GAC | TTT | GGT | GGC | AAG | AAC | TGC | TCC | GTG | CCC | CGC | GAG | CCG | 1552 |
| Cys | Pro | Asp | Asp | Phe | Gly | Gly | Lys | Asn | Cys | Ser | Val | Pro | Arg | Glu | Pro | |
| | | | 395 | | | | 400 | | | | | 405 | | | | |

| TGC | CCT | GGC | GGG | GCC | TGC | AGA | GTG | ATC | GAT | GGC | TGC | GGG | TCA | GAC | GCG | 1600 |
| Cys | Pro | Gly | Gly | Ala | Cys | Arg | Val | Ile | Asp | Gly | Cys | Gly | Ser | Asp | Ala | |
| | | 410 | | | | | 415 | | | | | 420 | | | | |

| GGG | CCT | GGG | ATG | CCT | GGC | ACA | GCA | GCC | TCC | GGC | GTG | TGT | GGC | CCC | CAT | 1648 |
| Gly | Pro | Gly | Met | Pro | Gly | Thr | Ala | Ala | Ser | Gly | Val | Cys | Gly | Pro | His | |
| 425 | | | | | 430 | | | | | 435 | | | | | | |

| GGA | CGC | TGC | GTC | AGC | CAG | CCA | GGG | GGC | AAC | TTT | TCC | TGC | ATC | TGT | GAC | 1696 |
| Gly | Arg | Cys | Val | Ser | Gln | Pro | Gly | Gly | Asn | Phe | Ser | Cys | Ile | Cys | Asp | |
| 440 | | | | | 445 | | | | | 450 | | | | | 455 | |

| AGT | GGC | TTT | ACT | GGC | ACC | TAC | TGC | CAT | GAG | AAC | ATT | GAC | GAC | TGC | CTG | 1744 |
| Ser | Gly | Phe | Thr | Gly | Thr | Tyr | Cys | His | Glu | Asn | Ile | Asp | Asp | Cys | Leu | |
| | | | | 460 | | | | | 465 | | | | | 470 | | |

| GGC | CAG | CCC | TGC | CGC | AAT | GGG | GGC | ACA | TGC | ATC | GAT | GAG | GTG | GAC | GCC | 1792 |
| Gly | Gln | Pro | Cys | Arg | Asn | Gly | Gly | Thr | Cys | Ile | Asp | Glu | Val | Asp | Ala | |
| | | | 475 | | | | | 480 | | | | | 485 | | | |

| TTC | CGC | TGC | TTC | TGC | CCC | AGC | GGT | TGG | GAG | GGC | GAG | CTC | TGC | GAC | ACC | 1840 |
| Phe | Arg | Cys | Phe | Cys | Pro | Ser | Gly | Trp | Glu | Gly | Glu | Leu | Cys | Asp | Thr | |
| | | 490 | | | | | 495 | | | | | 500 | | | | |

| AAT | CCC | AAC | GAC | TGC | CTT | CCC | GAT | CCC | TGC | CAC | AGC | CGC | GGC | CGC | TGC | 1888 |
| Asn | Pro | Asn | Asp | Cys | Leu | Pro | Asp | Pro | Cys | His | Ser | Arg | Gly | Arg | Cys | |
| 505 | | | | | 510 | | | | | 515 | | | | | | |

| TAC | GAC | CTG | GTC | AAT | GAC | TTC | TAC | TGT | GCG | TGC | GAC | GAC | GGC | TGG | AAG | 1936 |
| Tyr | Asp | Leu | Val | Asn | Asp | Phe | Tyr | Cys | Ala | Cys | Asp | Asp | Gly | Trp | Lys | |
| 520 | | | | | 525 | | | | | 530 | | | | | 535 | |

| GGC | AAG | ACC | TGC | CAC | TCA | CGC | GAG | TTC | CAG | TGC | GAT | GCC | TAC | ACC | TGC | 1984 |
| Gly | Lys | Thr | Cys | His | Ser | Arg | Glu | Phe | Gln | Cys | Asp | Ala | Tyr | Thr | Cys | |
| | | | | 540 | | | | | 545 | | | | | 550 | | |

| AGC | AAC | GGT | GGC | ACC | TGC | TAC | GAC | AGC | GGC | GAC | ACC | TTC | CGC | TGC | GCC | 2032 |
| Ser | Asn | Gly | Gly | Thr | Cys | Tyr | Asp | Ser | Gly | Asp | Thr | Phe | Arg | Cys | Ala | |
| | | | 555 | | | | | 560 | | | | | 565 | | | |

| TGC | CCC | CCC | GGC | TGG | AAG | GGC | AGC | ACC | TGC | GCC | GTC | GCC | AAG | AAC | AGC | 2080 |
| Cys | Pro | Pro | Gly | Trp | Lys | Gly | Ser | Thr | Cys | Ala | Val | Ala | Lys | Asn | Ser | |
| | | 570 | | | | | 575 | | | | | 580 | | | | |

| AGC | TGC | CTG | CCC | AAC | CCC | TGT | GTG | AAT | GGT | GGC | ACC | TGC | GTG | GGC | AGC | 2128 |
| Ser | Cys | Leu | Pro | Asn | Pro | Cys | Val | Asn | Gly | Gly | Thr | Cys | Val | Gly | Ser | |
| 585 | | | | | 590 | | | | | 595 | | | | | | |

| GGG | GCC | TCC | TTC | TCC | TGC | ATC | TGC | CGG | GAC | GGC | TGG | GAG | GGT | CGT | ACT | 2176 |
| Gly | Ala | Ser | Phe | Ser | Cys | Ile | Cys | Arg | Asp | Gly | Trp | Glu | Gly | Arg | Thr | |
| 600 | | | | | 605 | | | | | 610 | | | | | 615 | |

| TGC | ACT | CAC | AAT | ACC | AAC | GAC | TGC | AAC | CCT | CTG | CCT | TGC | TAC | AAT | GGT | 2224 |
| Cys | Thr | His | Asn | Thr | Asn | Asp | Cys | Asn | Pro | Leu | Pro | Cys | Tyr | Asn | Gly | |
| | | | | 620 | | | | | 625 | | | | | 630 | | |

| GGC | ATC | TGT | GTT | GAC | GGC | GTC | AAC | TGG | TTC | CGC | TGC | GAG | TGT | GCA | CCT | 2272 |

```
            Gly Ile Cys Val Asp Gly Val Asn Trp Phe Arg Cys Glu Cys Ala Pro
                        635                 640                 645

GGC TTC GCG GGG CCT GAC TGC CGC ATC AAC ATC GAC GAG TGC CAG TCC            2320
Gly Phe Ala Gly Pro Asp Cys Arg Ile Asn Ile Asp Glu Cys Gln Ser
            650                 655                 660

TCG CCC TGT GCC TAC GGG GCC ACG TGT GTG GAT GAG ATC AAC GGG TAT            2368
Ser Pro Cys Ala Tyr Gly Ala Thr Cys Val Asp Glu Ile Asn Gly Tyr
            665                 670                 675

CGC TGT AGC TGC CCA CCC GGC CGA GCC GGC CCC CGG TGC CAG GAA GTG            2416
Arg Cys Ser Cys Pro Pro Gly Arg Ala Gly Pro Arg Cys Gln Glu Val
680                 685                 690                 695

ATC GGG TTC GGG AGA TCC TGC TGG TCC CGG GGC ACT CCG TTC CCA CAC            2464
Ile Gly Phe Gly Arg Ser Cys Trp Ser Arg Gly Thr Pro Phe Pro His
                    700                 705                 710

GGA AGC TCC TGG GTG GAA GAC TGC AAC AGC TGC CGC TGC CTG GAT GGC            2512
Gly Ser Ser Trp Val Glu Asp Cys Asn Ser Cys Arg Cys Leu Asp Gly
                715                 720                 725

CGC CGT GAC TGC AGC AAG GTG TGG TGC GGA TGG AAG CCT TGT CTG CTG            2560
Arg Arg Asp Cys Ser Lys Val Trp Cys Gly Trp Lys Pro Cys Leu Leu
            730                 735                 740

GCC GGC CAG CCC GAG GCC CTG AGC GCC CAG TGC CCA CTG GGG CAA AGG            2608
Ala Gly Gln Pro Glu Ala Leu Ser Ala Gln Cys Pro Leu Gly Gln Arg
            745                 750                 755

TGC CTG GAG AAG GCC CCA GGC CAG TGT CTG CGA CCA CCC TGT GAG GCC            2656
Cys Leu Glu Lys Ala Pro Gly Gln Cys Leu Arg Pro Pro Cys Glu Ala
760                 765                 770                 775

TGG GGG GAG TGC GGC GCA GAA GAG CCA CCG AGC ACC CCC TGC CTG CCA            2704
Trp Gly Glu Cys Gly Ala Glu Glu Pro Pro Ser Thr Pro Cys Leu Pro
                    780                 785                 790

CGC TCC GGC CAC CTG GAC AAT AAC TGT GCC CGC CTC ACC TTG CAT TTC            2752
Arg Ser Gly His Leu Asp Asn Asn Cys Ala Arg Leu Thr Leu His Phe
                795                 800                 805

AAC CGT GAC CAC GTG CCC CAG GGC ACC ACG GTG GGC GCC ATT TGC TCC            2800
Asn Arg Asp His Val Pro Gln Gly Thr Thr Val Gly Ala Ile Cys Ser
            810                 815                 820

GGG ATC CGC TCC CTG CCA GCC ACA AGG GCT GTG GCA CGG GAC CGC CTG            2848
Gly Ile Arg Ser Leu Pro Ala Thr Arg Ala Val Ala Arg Asp Arg Leu
825                 830                 835

CTG GTG TTG CTT TGC GAC CGG GCG TCC TCG GGG GCC AGT GCT GTG GAG            2896
Leu Val Leu Leu Cys Asp Arg Ala Ser Ser Gly Ala Ser Ala Val Glu
840                 845                 850                 855

GTG GCC GTG TCC TTC AGC CCT GCC AGG GAC CTG CCT GAC AGC AGC CTG            2944
Val Ala Val Ser Phe Ser Pro Ala Arg Asp Leu Pro Asp Ser Ser Leu
                    860                 865                 870

ATC CAG GGC GCG GCC CAC GCC ATC GTG GCC GCC ATC ACC CAG CGG GGG            2992
Ile Gln Gly Ala Ala His Ala Ile Val Ala Ala Ile Thr Gln Arg Gly
                875                 880                 885

AAC AGC TCA CTG CTC CTG GCT GTC ACC GAG GTC AAG GTG GAG ACG GTT            3040
Asn Ser Ser Leu Leu Leu Ala Val Thr Glu Val Lys Val Glu Thr Val
            890                 895                 900

GTT ACG GGC GGC TCT TCC ACA GGT CTG CTG GTG CCT GTG CTG TGT GGT            3088
Val Thr Gly Gly Ser Ser Thr Gly Leu Leu Val Pro Val Leu Cys Gly
            905                 910                 915

GCC TTC AGC GTG CTG TGG CTG GCG TGC GTG GTC CTG TGC GTG TGG TGG            3136
Ala Phe Ser Val Leu Trp Leu Ala Cys Val Val Leu Cys Val Trp Trp
920                 925                 930                 935

ACA CGC AAG CGC AGG AAA GAG CGG GAG AGG AGC CGG CTG CCG CGG GAG            3184
Thr Arg Lys Arg Arg Lys Glu Arg Glu Arg Ser Arg Leu Pro Arg Glu
                    940                 945                 950

GAG AGC GCC AAC AAC CAG TGG GCC CCG CTC AAC CCC ATC CGC AAC CCC            3232
```

-continued

```
            Glu Ser Ala Asn Asn Gln Trp Ala Pro Leu Asn Pro Ile Arg Asn Pro
                        955                 960                 965

ATT GAG CGG CCG GGG GGG CAC AAG GAC GTG CTC TAC CAG TGC AAG AAC            3280
Ile Glu Arg Pro Gly Gly His Lys Asp Val Leu Tyr Gln Cys Lys Asn
            970                 975                 980

TTC ACT CCA CCG CGC AGG CGC TGC CCG GGC CGG CCG GCC ACG CGG                3328
Phe Thr Pro Pro Pro Arg Arg Arg Cys Pro Gly Arg Pro Ala Thr Arg
985                 990                 995

CCG TCA GGG AGG ATG AGG AGG ACG AGG ATC TTG GCC GCG GTG AGG AGG            3376
Pro Ser Gly Arg Met Arg Arg Thr Arg Ile Leu Ala Ala Val Arg Arg
1000                1005                1010                1015

ACT CCC TGG AGG CGG AGA AGT TCC TCT CAC ACA AAT TCA CCA AAG ATC            3424
Thr Pro Trp Arg Arg Arg Ser Ser Ser His Thr Asn Ser Pro Lys Ile
            1020                1025                1030

CTG GCC GCT CGC CGG GGA GGC CGG CCC ACT GGG CCT CAG GCC CCA AAG            3472
Leu Ala Ala Arg Arg Gly Gly Arg Pro Thr Gly Pro Gln Ala Pro Lys
            1035                1040                1045

TGG ACA ACC GCG CGG TCA GGA GCA TCA ATG AGG CCC GCT ACG TCG GCA            3520
Trp Thr Thr Ala Arg Ser Gly Ala Ser Met Arg Pro Ala Thr Ser Ala
            1050                1055                1060

AGG GAA GTA GGG CGG CTG CAG CTG GGC CGG GAC CCA GGG CCC TCG GTG            3568
Arg Glu Val Gly Arg Leu Gln Leu Gly Arg Asp Pro Gly Pro Ser Val
            1065                1070                1075

GGA GCC ATG CCG TCT GCC GGA CCC GGA GGC CGA GGC CAT GTG CAT AGT            3616
Gly Ala Met Pro Ser Ala Gly Pro Gly Gly Arg Gly His Val His Ser
1080                1085                1090                1095

TTC TTT ATT TTG TGT AAA AAA ACC ACC AAA AAC AAA AAC CAA ATG TTT            3664
Phe Phe Ile Leu Cys Lys Lys Thr Thr Lys Asn Lys Asn Gln Met Phe
            1100                1105                1110

ATT TTC TAC GTT TCT TTA ACC TTG TAT AAA TTA TTC AGT AAC TGT CAG            3712
Ile Phe Tyr Val Ser Leu Thr Leu Tyr Lys Leu Phe Ser Asn Cys Gln
            1115                1120                1125

GCT GAA AAC AAT GGA GTA TTC TCG GAT AGT TGC TAT TTT TGT AAA GTA            3760
Ala Glu Asn Asn Gly Val Phe Ser Asp Ser Cys Tyr Phe Cys Lys Val
            1130                1135                1140

GCC GTG CGT GGC ACT CGC TGT ATG AAA GGA GAG AGC AAA GGG TGT CTG            3808
Ala Val Arg Gly Thr Arg Cys Met Lys Gly Glu Ser Lys Gly Cys Leu
1145                1150                1155

CGT CGT CAC CAA ATC GTC GCG TTT GTT ACC AGA GGT TGT GCA CTG TTT            3856
Arg Arg His Gln Ile Val Ala Phe Val Thr Arg Gly Cys Ala Leu Phe
1160                1165                1170                1175

ACA GAA TCT TCC TTT TAT TCC TCA CTC GGG TTT CTC TGT GCT CCA GGC            3904
Thr Glu Ser Ser Phe Tyr Ser Ser Leu Gly Phe Leu Cys Ala Pro Gly
                    1180                1185                1190

CAA AGT GCC GGT GAG ACC CAT GGC TGT GTT GGT GTG GCC CAT GGC TGT            3952
Gln Ser Ala Gly Glu Thr His Gly Cys Val Gly Val Ala His Gly Cys
            1195                1200                1205

TGG TGG GAC CCG TGG CTG ATG GTG TGG CCT GTG GCT GTC GGT GGG ACT            4000
Trp Trp Asp Pro Trp Leu Met Val Trp Pro Val Ala Val Gly Gly Thr
            1210                1215                1220

CGT GGC TGT CAA TGG GAC CTG TGG CTG TCG GTG GGA CCT ACG GTG GTC            4048
Arg Gly Cys Gln Trp Asp Leu Trp Leu Ser Val Gly Pro Thr Val Val
1225                1230                1235

GGT GGG ACC CTG GTT ATT GAT GTG GCC CTG GCT GCC GGC ACG GCC CGT            4096
Gly Gly Thr Leu Val Ile Asp Val Ala Leu Ala Ala Gly Thr Ala Arg
1240                1245                1250                1255

GGC TGT TGACGCACCT GTGGTTGTTA GTGGGGCCTG AGGTCATCGG CGTGGCCCAA             4152
Gly Cys

GGCCGGCAGG TCAACCTCGC GCTTGCTGGC CAGTCCACCC TGCCTGCCGT CTGTGCTTCC          4212
```

```
TCCTGCCCAG AACGCCCGCT CCAGCGATCT CTCCACTGTG CTTTCAGAAG TGCCCTTCCT      4272

GCTGCGCAGT TCTCCCATCC TGGGACGGCG GCAGTATTGA AGCTCGTGAC AAGTGCCTTC      4332

ACACAGACCC CTCGCAACTG TCCACGCGTG CCGTGGCACC AGGCGCTGCC CACCTGCCGG      4392

CCCCGGCCGC CCCTCCTCGT GAAAGTGCAT TTTTGTAAAT GTGTACATAT TAAAGGAAGC      4452

ACTCTGTATA AAAAAAAAA ACCGGAATTC C                                     4483
```

(2) INFORMATION FOR SEQ ID NO:8:

(i) SEQUENCE CHARACTERISTICS:
        (A) LENGTH: 1257 amino acids
        (B) TYPE: amino acid
        (D) TOPOLOGY: unknown (ii) MOLECULE TYPE: protein (xi) SEQUENCE DESCRIPTION: SEQ ID NO:8:

```
Met Ile Asn Pro Glu Asp Arg Trp Lys Ser Leu His Phe Ser Gly His
 1               5                  10                  15

Val Ala His Leu Glu Leu Gln Ile Arg Val Arg Cys Asp Glu Asn Tyr
            20                  25                  30

Tyr Ser Ala Thr Cys Asn Lys Phe Cys Arg Pro Arg Asn Asp Phe Phe
        35                  40                  45

Gly His Tyr Thr Cys Asp Gln Tyr Gly Asn Lys Ala Cys Met Asp Gly
    50                  55                  60

Trp Met Gly Lys Glu Cys Lys Glu Ala Val Cys Lys Gln Gly Cys Asn
65                  70                  75                  80

Leu Leu His Gly Gly Cys Thr Val Pro Gly Glu Cys Arg Cys Ser Tyr
                85                  90                  95

Gly Trp Gln Gly Arg Phe Cys Asp Glu Cys Val Pro Tyr Pro Gly Cys
            100                 105                 110

Val His Gly Ser Cys Val Glu Pro Trp Gln Cys Asn Cys Glu Thr Asn
        115                 120                 125

Trp Gly Gly Leu Leu Cys Asp Lys Asp Leu Asn Tyr Cys Gly Ser His
    130                 135                 140

His Pro Cys Thr Asn Gly Gly Thr Cys Ile Asn Ala Glu Pro Asp Gln
145                 150                 155                 160

Tyr Arg Cys Thr Cys Pro Asp Gly Tyr Ser Gly Arg Asn Cys Glu Lys
                165                 170                 175

Ala Glu His Ala Cys Thr Ser Asn Pro Cys Ala Asn Gly Gly Ser Cys
            180                 185                 190

His Glu Val Pro Ser Gly Phe Glu Cys His Cys Pro Ser Gly Trp Ser
        195                 200                 205

Gly Pro Thr Cys Ala Leu Asp Ile Asp Glu Cys Ala Ser Asn Pro Cys
    210                 215                 220

Ala Ala Gly Gly Thr Cys Val Asp Gln Val Asp Gly Phe Glu Cys Ile
225                 230                 235                 240

Cys Pro Glu Gln Trp Val Gly Ala Thr Cys Gln Leu Asp Ala Asn Glu
                245                 250                 255

Cys Glu Gly Lys Pro Cys Leu Asn Ala Phe Ser Cys Lys Asn Leu Ile
            260                 265                 270

Gly Gly Tyr Tyr Cys Asp Cys Ile Pro Gly Trp Lys Gly Ile Asn Cys
        275                 280                 285

His Ile Asn Val Asn Asp Cys Arg Gly Gln Cys Gln His Gly Gly Thr
    290                 295                 300

Cys Lys Asp Leu Val Asn Gly Tyr Gln Cys Val Cys Pro Arg Gly Phe
```

```
                305                 310                 315                 320
Gly Gly Arg His Cys Glu Leu Glu Arg Asp Lys Cys Ala Ser Ser Pro
                    325                 330                 335

Cys His Ser Gly Gly Leu Cys Glu Asp Leu Ala Asp Gly Phe His Cys
                340                 345                 350

His Cys Pro Gln Gly Phe Ser Gly Pro Leu Cys Glu Val Asp Val Asp
            355                 360                 365

Leu Cys Glu Pro Ser Pro Cys Arg Asn Gly Ala Arg Cys Tyr Asn Leu
    370                 375                 380

Glu Gly Asp Tyr Tyr Cys Ala Cys Pro Asp Asp Phe Gly Gly Lys Asn
385                 390                 395                 400

Cys Ser Val Pro Arg Glu Pro Cys Pro Gly Gly Ala Cys Arg Val Ile
                405                 410                 415

Asp Gly Cys Gly Ser Asp Ala Gly Pro Gly Met Pro Gly Thr Ala Ala
                420                 425                 430

Ser Gly Val Cys Gly Pro His Gly Arg Cys Val Ser Gln Pro Gly Gly
                435                 440                 445

Asn Phe Ser Cys Ile Cys Asp Ser Gly Phe Thr Gly Thr Tyr Cys His
    450                 455                 460

Glu Asn Ile Asp Asp Cys Leu Gly Gln Pro Cys Arg Asn Gly Gly Thr
465                 470                 475                 480

Cys Ile Asp Glu Val Asp Ala Phe Arg Cys Phe Cys Pro Ser Gly Trp
                485                 490                 495

Glu Gly Glu Leu Cys Asp Thr Asn Pro Asn Asp Cys Leu Pro Asp Pro
                500                 505                 510

Cys His Ser Arg Gly Arg Cys Tyr Asp Leu Val Asn Asp Phe Tyr Cys
            515                 520                 525

Ala Cys Asp Asp Gly Trp Lys Gly Lys Thr Cys His Ser Arg Glu Phe
    530                 535                 540

Gln Cys Asp Ala Tyr Thr Cys Ser Asn Gly Gly Thr Cys Tyr Asp Ser
545                 550                 555                 560

Gly Asp Thr Phe Arg Cys Ala Cys Pro Pro Gly Trp Lys Gly Ser Thr
                565                 570                 575

Cys Ala Val Ala Lys Asn Ser Ser Cys Leu Pro Asn Pro Cys Val Asn
                580                 585                 590

Gly Gly Thr Cys Val Gly Ser Gly Ala Ser Phe Ser Cys Ile Cys Arg
                595                 600                 605

Asp Gly Trp Glu Gly Arg Thr Cys Thr His Asn Thr Asn Asp Cys Asn
            610                 615                 620

Pro Leu Pro Cys Tyr Asn Gly Ile Cys Val Asp Gly Val Asn Trp
625                 630                 635                 640

Phe Arg Cys Glu Cys Ala Pro Gly Phe Ala Gly Pro Asp Cys Arg Ile
                645                 650                 655

Asn Ile Asp Glu Cys Gln Ser Ser Pro Cys Ala Tyr Gly Ala Thr Cys
                660                 665                 670

Val Asp Glu Ile Asn Gly Tyr Arg Cys Ser Cys Pro Pro Gly Arg Ala
            675                 680                 685

Gly Pro Arg Cys Gln Glu Val Ile Gly Phe Gly Arg Ser Cys Trp Ser
    690                 695                 700

Arg Gly Thr Pro Phe Pro His Gly Ser Ser Trp Val Glu Asp Cys Asn
705                 710                 715                 720

Ser Cys Arg Cys Leu Asp Gly Arg Arg Asp Cys Ser Lys Val Trp Cys
                725                 730                 735
```

```
Gly Trp Lys Pro Cys Leu Leu Ala Gly Gln Pro Glu Ala Leu Ser Ala
            740                 745                 750

Gln Cys Pro Leu Gly Gln Arg Cys Leu Glu Lys Ala Pro Gly Gln Cys
        755                 760                 765

Leu Arg Pro Pro Cys Glu Ala Trp Gly Glu Cys Gly Ala Glu Glu Pro
    770                 775                 780

Pro Ser Thr Pro Cys Leu Pro Arg Ser Gly His Leu Asp Asn Asn Cys
785                 790                 795                 800

Ala Arg Leu Thr Leu His Phe Asn Arg Asp His Val Pro Gln Gly Thr
                805                 810                 815

Thr Val Gly Ala Ile Cys Ser Gly Ile Arg Ser Leu Pro Ala Thr Arg
            820                 825                 830

Ala Val Ala Arg Asp Arg Leu Leu Val Leu Leu Cys Asp Arg Ala Ser
        835                 840                 845

Ser Gly Ala Ser Ala Val Glu Val Ala Val Ser Phe Ser Pro Ala Arg
    850                 855                 860

Asp Leu Pro Asp Ser Ser Leu Ile Gln Gly Ala Ala His Ala Ile Val
865                 870                 875                 880

Ala Ala Ile Thr Gln Arg Gly Asn Ser Ser Leu Leu Ala Val Thr
                885                 890                 895

Glu Val Lys Val Glu Thr Val Val Thr Gly Gly Ser Ser Thr Gly Leu
            900                 905                 910

Leu Val Pro Val Leu Cys Gly Ala Phe Ser Val Leu Trp Leu Ala Cys
        915                 920                 925

Val Val Leu Cys Val Trp Trp Thr Arg Lys Arg Lys Glu Arg Glu
    930                 935                 940

Arg Ser Arg Leu Pro Arg Glu Glu Ser Ala Asn Asn Gln Trp Ala Pro
945                 950                 955                 960

Leu Asn Pro Ile Arg Asn Pro Ile Glu Arg Pro Gly Gly His Lys Asp
                965                 970                 975

Val Leu Tyr Gln Cys Lys Asn Phe Thr Pro Pro Arg Arg Arg Cys
            980                 985                 990

Pro Gly Arg Pro Ala Thr Arg Pro Ser Gly Arg Met Arg Arg Thr Arg
        995                 1000                1005

Ile Leu Ala Ala Val Arg Arg Thr Pro Trp Arg Arg Ser Ser Ser
    1010                1015                1020

His Thr Asn Ser Pro Lys Ile Leu Ala Ala Arg Arg Gly Gly Arg Pro
1025                1030                1035                1040

Thr Gly Pro Gln Ala Pro Lys Trp Thr Thr Ala Arg Ser Gly Ala Ser
                1045                1050                1055

Met Arg Pro Ala Thr Ser Ala Arg Glu Val Gly Arg Leu Gln Leu Gly
            1060                1065                1070

Arg Asp Pro Gly Pro Ser Val Gly Ala Met Pro Ser Ala Gly Pro Gly
        1075                1080                1085

Gly Arg Gly His Val His Ser Phe Phe Ile Leu Cys Lys Lys Thr Thr
    1090                1095                1100

Lys Asn Lys Asn Gln Met Phe Ile Phe Tyr Val Ser Leu Thr Leu Tyr
1105                1110                1115                1120

Lys Leu Phe Ser Asn Cys Gln Ala Glu Asn Asn Gly Val Phe Ser Asp
                1125                1130                1135

Ser Cys Tyr Phe Cys Lys Val Ala Val Arg Gly Thr Arg Cys Met Lys
            1140                1145                1150

Gly Glu Ser Lys Gly Cys Leu Arg Arg His Gln Ile Val Ala Phe Val
        1155                1160                1165
```

```
Thr Arg Gly Cys Ala Leu Phe Thr Glu Ser Ser Phe Tyr Ser Ser Leu
    1170                1175                1180

Gly Phe Leu Cys Ala Pro Gly Gln Ser Ala Gly Glu Thr His Gly Cys
1185                1190                1195                1200

Val Gly Val Ala His Gly Cys Trp Trp Asp Pro Trp Leu Met Val Trp
            1205                1210                1215

Pro Val Ala Val Gly Gly Thr Arg Gly Cys Gln Trp Asp Leu Trp Leu
            1220                1225                1230

Ser Val Gly Pro Thr Val Val Gly Gly Thr Leu Val Ile Asp Val Ala
                1235                1240                1245

Leu Ala Ala Gly Thr Ala Arg Gly Cys
        1250                1255

(2) INFORMATION FOR SEQ ID NO:9:

(i) SEQUENCE CHARACTERISTICS:
         (A) LENGTH: 3582 base pairs
         (B) TYPE: nucleic acid
         (C) STRANDEDNESS: double
         (D) TOPOLOGY: unknown (ii) MOLECULE TYPE: cDNA (ix) FEATURE:
         (A) NAME/KEY: CDS
         (B) LOCATION: 1..3579

(xi) SEQUENCE DESCRIPTION: SEQ ID NO:9:

CAG GTG GCG TCA GCA TCG GGA CAG TTC GAG CTG GAG ATC TTA TCC GTG          48
Gln Val Ala Ser Ala Ser Gly Gln Phe Glu Leu Glu Ile Leu Ser Val
  1               5                  10                  15

CAG AAT GTG AAC GGC GTG CTG CAG AAC GGG AAC TGC TGC GAC GGC ACT          96
Gln Asn Val Asn Gly Val Leu Gln Asn Gly Asn Cys Cys Asp Gly Thr
             20                  25                  30

CGA AAC CCC GGA GAT AAA AAG TGC ACC AGA GAT GAG TGT GAC ACC TAC         144
Arg Asn Pro Gly Asp Lys Lys Cys Thr Arg Asp Glu Cys Asp Thr Tyr
         35                  40                  45

TTT AAA GTT TGC CTG AAG GAG TAC CAG TCG CGG GTC ACT GCT GGC GGC         192
Phe Lys Val Cys Leu Lys Glu Tyr Gln Ser Arg Val Thr Ala Gly Gly
     50                  55                  60

CCT TGC AGC TTC GGA TCC AAA TCC ACC CCT GTC ATC GGC GGG AAT ACC         240
Pro Cys Ser Phe Gly Ser Lys Ser Thr Pro Val Ile Gly Gly Asn Thr
 65                  70                  75                  80

TTC AAT TTA AAG TAC AGC CGG AAT AAT GAA AAG AAC CGG ATT GTT ATC         288
Phe Asn Leu Lys Tyr Ser Arg Asn Asn Glu Lys Asn Arg Ile Val Ile
                 85                  90                  95

CCT TTC ACG TTC GCC TGG CCG AGA TCC TAC ACG TTG CTT GTT GAG GCA         336
Pro Phe Thr Phe Ala Trp Pro Arg Ser Tyr Thr Leu Leu Val Glu Ala
            100                 105                 110

TGG GAT TAC AAT GAT AAC TCT ACT AAT CCC GAT CGC ATA ATT GAG AAG         384
Trp Asp Tyr Asn Asp Asn Ser Thr Asn Pro Asp Arg Ile Ile Glu Lys
        115                 120                 125

GCA TCC CAC TCT GGC ATG ATC AAT CCA AGC CGT CAG TGG CAG ACG TTG         432
Ala Ser His Ser Gly Met Ile Asn Pro Ser Arg Gln Trp Gln Thr Leu
    130                 135                 140

AAA CAT AAC ACA GGA GCT GCC CAC TTT GAG TAT CAA ATC CGT GTG ACT         480
Lys His Asn Thr Gly Ala Ala His Phe Glu Tyr Gln Ile Arg Val Thr
145                 150                 155                 160

TGC GCA GAA CAT TAC TAT GGC TTT GGA TGC AAC AAG TTT TGT CGA CCG         528
Cys Ala Glu His Tyr Tyr Gly Phe Gly Cys Asn Lys Phe Cys Arg Pro
                165                 170                 175
```

| | | |
|---|---|---|
| AGA GAT GAC TTC TTC ACT CAC CAT ACC TGT GAC CAG AAT GGC AAC AAA | 576 | |
| Arg Asp Asp Phe Phe Thr His His Thr Cys Asp Gln Asn Gly Asn Lys | | |
| 180 185 190 | | |
| ACC TGC TTG GAA GGC TGG ACG GGA CCA GAA TGC AAC AAA GCT ATT TGT | 624 | |
| Thr Cys Leu Glu Gly Trp Thr Gly Pro Glu Cys Asn Lys Ala Ile Cys | | |
| 195 200 205 | | |
| CGT CAG GGA TGT AGC CCC AAG CAT GGT TCT TGC ACA GTT CCA GGA GAG | 672 | |
| Arg Gln Gly Cys Ser Pro Lys His Gly Ser Cys Thr Val Pro Gly Glu | | |
| 210 215 220 | | |
| TGC AGG TGT CAG TAT GGA TGG CAA GGC CAG TAC TGT GAT AAG TGC ATT | 720 | |
| Cys Arg Cys Gln Tyr Gly Trp Gln Gly Gln Tyr Cys Asp Lys Cys Ile | | |
| 225 230 235 240 | | |
| CCA CAC CCG GGA TGT GTC CAT GGC ACT TGC ATT GAA CCA TGG CAG TGC | 768 | |
| Pro His Pro Gly Cys Val His Gly Thr Cys Ile Glu Pro Trp Gln Cys | | |
| 245 250 255 | | |
| CTC TGT GAA ACC AAC TGG GGT GGT CAG CTC TGT GAC AAA GAC CTG AAC | 816 | |
| Leu Cys Glu Thr Asn Trp Gly Gly Gln Leu Cys Asp Lys Asp Leu Asn | | |
| 260 265 270 | | |
| TAC TGT GGA ACC CAC CCA CCC TGT TTG AAT GGT GGT ACC TGC AGC AAC | 864 | |
| Tyr Cys Gly Thr His Pro Pro Cys Leu Asn Gly Gly Thr Cys Ser Asn | | |
| 275 280 285 | | |
| ACT GGC CCC GAT AAA TAC CAG TGT TCC TGC CCT GAG GGT TAC TCA GGA | 912 | |
| Thr Gly Pro Asp Lys Tyr Gln Cys Ser Cys Pro Glu Gly Tyr Ser Gly | | |
| 290 295 300 | | |
| CAG AAC TGT GAA ATA GCG GAG CAT GCG TGC CTC TCT GAT CCG TGC CAC | 960 | |
| Gln Asn Cys Glu Ile Ala Glu His Ala Cys Leu Ser Asp Pro Cys His | | |
| 305 310 315 320 | | |
| AAC GGA GGA AGC TGC CTA GAA ACG TCT ACA GGA TTT GAA TGT GTG TGT | 1008 | |
| Asn Gly Gly Ser Cys Leu Glu Thr Ser Thr Gly Phe Glu Cys Val Cys | | |
| 325 330 335 | | |
| GCA CCT GGC TGG GCT GGA CCA ACT TGC ACT GAT AAT ATT GAT GAT TGT | 1056 | |
| Ala Pro Gly Trp Ala Gly Pro Thr Cys Thr Asp Asn Ile Asp Asp Cys | | |
| 340 345 350 | | |
| TCT CCA AAT CCC TGT GGT CAT GGA GGA ACT TGC CAA GAT CTA GTT GAT | 1104 | |
| Ser Pro Asn Pro Cys Gly His Gly Gly Thr Cys Gln Asp Leu Val Asp | | |
| 355 360 365 | | |
| GGA TTT AAG TGT ATT TGC CCA CCT CAG TGG ACT GGC AAA ACA TGC CAG | 1152 | |
| Gly Phe Lys Cys Ile Cys Pro Pro Gln Trp Thr Gly Lys Thr Cys Gln | | |
| 370 375 380 | | |
| CTA GAT GCG AAT GAA TGT GAG GGC AAA CCC TGT GTC AAT GCC AAC TCC | 1200 | |
| Leu Asp Ala Asn Glu Cys Glu Gly Lys Pro Cys Val Asn Ala Asn Ser | | |
| 385 390 395 400 | | |
| TGC AGG AAC TTG ATT GGC AGC TAC TAT TGT GAC TGC ATT ACT GGC TGG | 1248 | |
| Cys Arg Asn Leu Ile Gly Ser Tyr Tyr Cys Asp Cys Ile Thr Gly Trp | | |
| 405 410 415 | | |
| TCT GGC CAC AAC TGT GAT ATA AAT ATT AAT GAT TGT CGT GGA CAA TGT | 1296 | |
| Ser Gly His Asn Cys Asp Ile Asn Ile Asn Asp Cys Arg Gly Gln Cys | | |
| 420 425 430 | | |
| CAG AAT GGA GGA TCC TGT CGG GAC TTG GTT AAT GGT TAT CGG TGC ATC | 1344 | |
| Gln Asn Gly Gly Ser Cys Arg Asp Leu Val Asn Gly Tyr Arg Cys Ile | | |
| 435 440 445 | | |
| TGT TCA CCT GGC TAT GCA GGA GAT CAC TGT GAG AAA GAC ATC AAT GAA | 1392 | |
| Cys Ser Pro Gly Tyr Ala Gly Asp His Cys Glu Lys Asp Ile Asn Glu | | |
| 450 455 460 | | |
| TGT GCA AGT AAC CCT TGC ATG AAT GGG GGT CAC TGC CAG GAT GAA ATC | 1440 | |
| Cys Ala Ser Asn Pro Cys Met Asn Gly Gly His Cys Gln Asp Glu Ile | | |
| 465 470 475 480 | | |
| AAT GGA TTC CAA TGT CTG TGT CCT GCT GGT TTC TCA GGA AAC CTC TGT | 1488 | |
| Asn Gly Phe Gln Cys Leu Cys Pro Ala Gly Phe Ser Gly Asn Leu Cys | | |
| 485 490 495 | | |

```
CAG CTG GAT ATA GAC TAC TGT GAG CCA AAC CCT TGC CAG AAC GGT GCC      1536
Gln Leu Asp Ile Asp Tyr Cys Glu Pro Asn Pro Cys Gln Asn Gly Ala
            500                 505                 510

CAG TGC TTC AAT CTT GCT ATG GAC TAT TTC TGT AAC TGC CCT GAA GAT      1584
Gln Cys Phe Asn Leu Ala Met Asp Tyr Phe Cys Asn Cys Pro Glu Asp
        515                 520                 525

TAC GAA GGC AAG AAC TGC TCC CAC CTG AAA GAT CAC TGC CGC ACA ACT      1632
Tyr Glu Gly Lys Asn Cys Ser His Leu Lys Asp His Cys Arg Thr Thr
530                 535                 540

CCT TGT GAA GTA ATC GAC AGC TGT ACA GTG GCA GTG GCT TCT AAC AGC      1680
Pro Cys Glu Val Ile Asp Ser Cys Thr Val Ala Val Ala Ser Asn Ser
545                 550                 555                 560

ACA CCA GAA GGA GTT CGT TAC ATT TCT TCA AAT GTC TGT GGT CCT CAT      1728
Thr Pro Glu Gly Val Arg Tyr Ile Ser Ser Asn Val Cys Gly Pro His
                565                 570                 575

GGA AAA TGC AAG AGC CAA GCA GGT GGA AAA TTC ACC TGT GAA TGC AAC      1776
Gly Lys Cys Lys Ser Gln Ala Gly Gly Lys Phe Thr Cys Glu Cys Asn
            580                 585                 590

AAA GGA TTC ACT GGC ACC TAC TGT CAT GAG AAT ATC AAT GAC TGT GAG      1824
Lys Gly Phe Thr Gly Thr Tyr Cys His Glu Asn Ile Asn Asp Cys Glu
        595                 600                 605

AGC AAC CCC TGT AAA AAT GGT GGC ACT TGT ATT GAC GGT GTA AAC TCC      1872
Ser Asn Pro Cys Lys Asn Gly Gly Thr Cys Ile Asp Gly Val Asn Ser
610                 615                 620

TAC AAA TGT ATT TGT AGT GAT GGA TGG GAA GGA ACA TAT TGT GAA ACA      1920
Tyr Lys Cys Ile Cys Ser Asp Gly Trp Glu Gly Thr Tyr Cys Glu Thr
625                 630                 635                 640

AAT ATT AAT GAC TGC AGT AAA AAC CCC TGC CAC AAT GGA GGA ACT TGC      1968
Asn Ile Asn Asp Cys Ser Lys Asn Pro Cys His Asn Gly Gly Thr Cys
                645                 650                 655

CGA GAC TTG GTC AAT GAC TTC TTC TGT GAA TGT AAA AAT GGG TGG AAA      2016
Arg Asp Leu Val Asn Asp Phe Phe Cys Glu Cys Lys Asn Gly Trp Lys
            660                 665                 670

GGA AAA ACT TGC CAC TCT CGT GAC AGC CAG TGT GAT GAG GCA ACA TGC      2064
Gly Lys Thr Cys His Ser Arg Asp Ser Gln Cys Asp Glu Ala Thr Cys
        675                 680                 685

AAT AAT GGA GGA ACA TGT TAT GAT GAG GGG GAC ACT TTC AAG TGC ATG      2112
Asn Asn Gly Gly Thr Cys Tyr Asp Glu Gly Asp Thr Phe Lys Cys Met
690                 695                 700

TGT CCT GCA GGA TGG GAA GGA GCC ACT TGT AAT ATA GCA AGG AAC AGC      2160
Cys Pro Ala Gly Trp Glu Gly Ala Thr Cys Asn Ile Ala Arg Asn Ser
705                 710                 715                 720

AGC TGC CTG CCA AAC CCC TGT CAC AAT GGT GGT ACC TGT GTA GTT AGT      2208
Ser Cys Leu Pro Asn Pro Cys His Asn Gly Gly Thr Cys Val Val Ser
                725                 730                 735

GGG GAT TCT TTC ACT TGT GTC TGC AAG GAG GGC TGG GAA GGA CCG ACA      2256
Gly Asp Ser Phe Thr Cys Val Cys Lys Glu Gly Trp Glu Gly Pro Thr
            740                 745                 750

TGT ACT CAG AAC ACA AAT GAC TGC AGT CCT CAT CCT TGT TAC AAC AGT      2304
Cys Thr Gln Asn Thr Asn Asp Cys Ser Pro His Pro Cys Tyr Asn Ser
        755                 760                 765

GGT ACT TGT GTG GAT GGA GAC AAC TGG TAC CGC TGT GAG TGC GCT CCC      2352
Gly Thr Cys Val Asp Gly Asp Asn Trp Tyr Arg Cys Glu Cys Ala Pro
770                 775                 780

GGC TTC GCA GGT CCC GAC TGT AGG ATC AAC ATC AAT GAA TGT CAG TCT      2400
Gly Phe Ala Gly Pro Asp Cys Arg Ile Asn Ile Asn Glu Cys Gln Ser
785                 790                 795                 800

TCA CCC TGT GCC TTT GGG GCT ACT TGT GTG GAT GAA ATT AAT GGG TAC      2448
Ser Pro Cys Ala Phe Gly Ala Thr Cys Val Asp Glu Ile Asn Gly Tyr
                805                 810                 815
```

| | |
|---|---|
| CGT TGC ATT TGT CCA CCG GGT CGC AGT GGT CCA GGA TGC CAG GAA GTT<br>Arg Cys Ile Cys Pro Pro Gly Arg Ser Gly Pro Gly Cys Gln Glu Val<br>                  820                        825                      830 | 2496 |
| ACA GGG AGG CCT TGC TTT ACC AGT ATT CGA GTA ATG CCA GAC GGT GCT<br>Thr Gly Arg Pro Cys Phe Thr Ser Ile Arg Val Met Pro Asp Gly Ala<br>              835                        840                        845 | 2544 |
| AAG TGG GAT GAT GAC TGT AAT ACT TGT CAG TGT TTG AAT GGA AAA GTC<br>Lys Trp Asp Asp Asp Cys Asn Thr Cys Gln Cys Leu Asn Gly Lys Val<br>850                          855                        860 | 2592 |
| ACC TGT TCT AAG GTT TGG TGT GGT CCT CGA CCT TGT ATA ATA CAT GCC<br>Thr Cys Ser Lys Val Trp Cys Gly Pro Arg Pro Cys Ile Ile His Ala<br>865                      870                        875                        880 | 2640 |
| AAA GGT CAT AAT GAA TGC CCA GCT GGA CAC GCT TGT GTT CCT GTT AAA<br>Lys Gly His Asn Glu Cys Pro Ala Gly His Ala Cys Val Pro Val Lys<br>                        885                        890                        895 | 2688 |
| GAA GAC CAT TGT TTC ACT CAT CCT TGT GCT GCA GTG GGT GAA TGC TGG<br>Glu Asp His Cys Phe Thr His Pro Cys Ala Ala Val Gly Glu Cys Trp<br>              900                        905                        910 | 2736 |
| CCT TCT AAT CAG CAG CCT GTG AAG ACC AAA TGC AAT TCT GAT TCT TAT<br>Pro Ser Asn Gln Gln Pro Val Lys Thr Lys Cys Asn Ser Asp Ser Tyr<br>              915                        920                        925 | 2784 |
| TAC CAA GAT AAT TGT GCC AAC ATC ACC TTC ACC TTT AAT AAG GAA ATG<br>Tyr Gln Asp Asn Cys Ala Asn Ile Thr Phe Thr Phe Asn Lys Glu Met<br>930                          935                        940 | 2832 |
| ATG GCA CCA GGC CTT ACC ACG GAG CAC ATT TGC AGT GAA TTG AGG AAT<br>Met Ala Pro Gly Leu Thr Thr Glu His Ile Cys Ser Glu Leu Arg Asn<br>945                        950                        955                        960 | 2880 |
| CTG AAT ATC CTG AAG AAT GTT TCT GCT GAA TAT TCC ATC TAT ATT ACC<br>Leu Asn Ile Leu Lys Asn Val Ser Ala Glu Tyr Ser Ile Tyr Ile Thr<br>                        965                        970                        975 | 2928 |
| TGT GAG CCT TCA CAC TTG GCA AAT AAT GAA ATA CAT GTT GCT ATT TCT<br>Cys Glu Pro Ser His Leu Ala Asn Asn Glu Ile His Val Ala Ile Ser<br>              980                        985                        990 | 2976 |
| GCT GAA GAT ATA GGA GAA GAT GAA AAC CCA ATC AAG GAA ATC ACA GAT<br>Ala Glu Asp Ile Gly Glu Asp Glu Asn Pro Ile Lys Glu Ile Thr Asp<br>              995                        1000                    1005 | 3024 |
| AAG ATT ATT GAC CTT GTC AGT AAG CGT GAT GGA AAC AAC ACA CTA ATT<br>Lys Ile Ile Asp Leu Val Ser Lys Arg Asp Gly Asn Asn Thr Leu Ile<br>1010                        1015                        1020 | 3072 |
| GCT GCA GTC GCA GAA GTC AGA GTA CAA AGG CGA CCA GTT AAG AAC AAA<br>Ala Ala Val Ala Glu Val Arg Val Gln Arg Arg Pro Val Lys Asn Lys<br>1025                        1030                        1035                    1040 | 3120 |
| ACA GAT TTC TTG GTG CCA TTA CTG AGC TCA GTC TTA ACA GTA GCC TGG<br>Thr Asp Phe Leu Val Pro Leu Leu Ser Ser Val Leu Thr Val Ala Trp<br>                        1045                        1050                    1055 | 3168 |
| ATC TGC TGT CTG GTA ACT GTT TTC TAT TGG TGC ATT CAA AAG CGC AGA<br>Ile Cys Cys Leu Val Thr Val Phe Tyr Trp Cys Ile Gln Lys Arg Arg<br>                        1060                        1065                    1070 | 3216 |
| AAG CAG AGC AGC CAT ACT CAC ACA GCA TCT GAT GAC AAC ACC ACC AAC<br>Lys Gln Ser Ser His Thr His Thr Ala Ser Asp Asp Asn Thr Thr Asn<br>1075                        1080                        1085 | 3264 |
| AAC GTA AGG GAG CAG CTG AAT CAG ATT AAA AAC CCC ATA GAG AAA CAC<br>Asn Val Arg Glu Gln Leu Asn Gln Ile Lys Asn Pro Ile Glu Lys His<br>1090                        1095                        1100 | 3312 |
| GGA GCA AAT ACT GTT CCA ATT AAA GAC TAT GAA AAC AAA AAC TCT AAA<br>Gly Ala Asn Thr Val Pro Ile Lys Asp Tyr Glu Asn Lys Asn Ser Lys<br>1105                        1110                        1115                    1120 | 3360 |
| ATC GCC AAA ATA AGG ACG CAC AAT TCA GAA GTG GAG GAA GAT GAC ATG<br>Ile Ala Lys Ile Arg Thr His Asn Ser Glu Val Glu Glu Asp Asp Met<br>                        1125                        1130                    1135 | 3408 |

-continued

```
GAC AAA CAC CAG CAA AAG GCC CGG TTT GCC AAG CAG CCA GCG TAC ACT    3456
Asp Lys His Gln Gln Lys Ala Arg Phe Ala Lys Gln Pro Ala Tyr Thr
        1140                1145                1150

TTG GTA GAC AGA GAT GAA AAG CCA CCC AAC AGC ACA CCC ACA AAA CAC    3504
Leu Val Asp Arg Asp Glu Lys Pro Pro Asn Ser Thr Pro Thr Lys His
            1155                1160                1165

CCA AAC TGG ACA AAT AAA CAG GAC AAC AGA GAC TTG GAA AGT GCA CAA    3552
Pro Asn Trp Thr Asn Lys Gln Asp Asn Arg Asp Leu Glu Ser Ala Gln
        1170                1175                1180

AGT TTA AAT AGA ATG GAG TAC ATT GTA TAG                            3582
Ser Leu Asn Arg Met Glu Tyr Ile Val
1185                1190
```

(2) INFORMATION FOR SEQ ID NO:10:

(i) SEQUENCE CHARACTERISTICS:
        (A) LENGTH: 1193 amino acids
        (B) TYPE: amino acid
        (D) TOPOLOGY: unknown (ii) MOLECULE TYPE: protein (xi) SEQUENCE DESCRIPTION: SEQ ID NO:10:

```
Gln Val Ala Ser Ala Ser Gly Gln Phe Glu Leu Glu Ile Leu Ser Val
 1               5                  10                  15

Gln Asn Val Asn Gly Val Leu Gln Asn Gly Asn Cys Cys Asp Gly Thr
            20                  25                  30

Arg Asn Pro Gly Asp Lys Lys Cys Thr Arg Asp Glu Cys Asp Thr Tyr
        35                  40                  45

Phe Lys Val Cys Leu Lys Glu Tyr Gln Ser Arg Val Thr Ala Gly Gly
    50                  55                  60

Pro Cys Ser Phe Gly Ser Lys Ser Thr Pro Val Ile Gly Gly Asn Thr
65                  70                  75                  80

Phe Asn Leu Lys Tyr Ser Arg Asn Asn Glu Lys Asn Arg Ile Val Ile
                85                  90                  95

Pro Phe Thr Phe Ala Trp Pro Arg Ser Tyr Thr Leu Leu Val Glu Ala
            100                 105                 110

Trp Asp Tyr Asn Asp Asn Ser Thr Asn Pro Asp Arg Ile Ile Glu Lys
        115                 120                 125

Ala Ser His Ser Gly Met Ile Asn Pro Ser Arg Gln Trp Gln Thr Leu
    130                 135                 140

Lys His Asn Thr Gly Ala Ala His Phe Glu Tyr Gln Ile Arg Val Thr
145                 150                 155                 160

Cys Ala Glu His Tyr Tyr Gly Phe Gly Cys Asn Lys Phe Cys Arg Pro
                165                 170                 175

Arg Asp Asp Phe Phe Thr His Thr Cys Asp Gln Asn Gly Asn Lys
            180                 185                 190

Thr Cys Leu Glu Gly Trp Thr Gly Pro Glu Cys Asn Lys Ala Ile Cys
        195                 200                 205

Arg Gln Gly Cys Ser Pro Lys His Gly Ser Cys Thr Val Pro Gly Glu
    210                 215                 220

Cys Arg Cys Gln Tyr Gly Trp Gln Gly Tyr Cys Asp Lys Cys Ile
225                 230                 235                 240

Pro His Pro Gly Cys Val His Gly Thr Cys Ile Glu Pro Trp Gln Cys
                245                 250                 255

Leu Cys Glu Thr Asn Trp Gly Gly Gln Leu Cys Asp Lys Asp Leu Asn
            260                 265                 270

Tyr Cys Gly Thr His Pro Pro Cys Leu Asn Gly Gly Thr Cys Ser Asn
```

-continued

```
            275                 280                 285
Thr Gly Pro Asp Lys Tyr Gln Cys Ser Cys Pro Glu Gly Tyr Ser Gly
    290                 295                 300
Gln Asn Cys Glu Ile Ala Glu His Ala Cys Leu Ser Asp Pro Cys His
305                 310                 315                 320
Asn Gly Gly Ser Cys Leu Glu Thr Ser Thr Gly Phe Glu Cys Val Cys
                325                 330                 335
Ala Pro Gly Trp Ala Gly Pro Thr Cys Thr Asp Asn Ile Asp Asp Cys
                340                 345                 350
Ser Pro Asn Pro Cys Gly His Gly Gly Thr Cys Gln Asp Leu Val Asp
355                 360                 365
Gly Phe Lys Cys Ile Cys Pro Pro Gln Trp Thr Gly Lys Thr Cys Gln
    370                 375                 380
Leu Asp Ala Asn Glu Cys Glu Gly Lys Pro Cys Val Asn Ala Asn Ser
385                 390                 395                 400
Cys Arg Asn Leu Ile Gly Ser Tyr Tyr Cys Asp Cys Ile Thr Gly Trp
                405                 410                 415
Ser Gly His Asn Cys Asp Ile Asn Ile Asn Asp Cys Arg Gly Gln Cys
                420                 425                 430
Gln Asn Gly Gly Ser Cys Arg Asp Leu Val Asn Gly Tyr Arg Cys Ile
            435                 440                 445
Cys Ser Pro Gly Tyr Ala Gly Asp His Cys Glu Lys Asp Ile Asn Glu
    450                 455                 460
Cys Ala Ser Asn Pro Cys Met Asn Gly His Cys Gln Asp Glu Ile
465                 470                 475                 480
Asn Gly Phe Gln Cys Leu Cys Pro Ala Gly Phe Ser Gly Asn Leu Cys
                485                 490                 495
Gln Leu Asp Ile Asp Tyr Cys Glu Pro Asn Pro Cys Gln Asn Gly Ala
                500                 505                 510
Gln Cys Phe Asn Leu Ala Met Asp Tyr Phe Cys Asn Cys Pro Glu Asp
            515                 520                 525
Tyr Glu Gly Lys Asn Cys Ser His Leu Lys Asp His Cys Arg Thr Thr
    530                 535                 540
Pro Cys Glu Val Ile Asp Ser Cys Thr Val Ala Val Ala Ser Asn Ser
545                 550                 555                 560
Thr Pro Glu Gly Val Arg Tyr Ile Ser Ser Asn Val Cys Gly Pro His
                565                 570                 575
Gly Lys Cys Lys Ser Gln Ala Gly Gly Lys Phe Thr Cys Glu Cys Asn
            580                 585                 590
Lys Gly Phe Thr Gly Thr Tyr Cys His Glu Asn Ile Asn Asp Cys Glu
            595                 600                 605
Ser Asn Pro Cys Lys Asn Gly Gly Thr Cys Ile Asp Gly Val Asn Ser
610                 615                 620
Tyr Lys Cys Ile Cys Ser Asp Gly Trp Glu Gly Thr Tyr Cys Glu Thr
625                 630                 635                 640
Asn Ile Asn Asp Cys Ser Lys Asn Pro Cys His Asn Gly Gly Thr Cys
                645                 650                 655
Arg Asp Leu Val Asn Asp Phe Phe Cys Glu Cys Lys Asn Gly Trp Lys
                660                 665                 670
Gly Lys Thr Cys His Ser Arg Asp Ser Gln Cys Asp Glu Ala Thr Cys
            675                 680                 685
Asn Asn Gly Gly Thr Cys Tyr Asp Glu Gly Asp Thr Phe Lys Cys Met
            690                 695                 700
```

-continued

```
Cys Pro Ala Gly Trp Glu Gly Ala Thr Cys Asn Ile Ala Arg Asn Ser
705                 710                 715                 720

Ser Cys Leu Pro Asn Pro Cys His Asn Gly Thr Cys Val Val Ser
            725                 730                 735

Gly Asp Ser Phe Thr Cys Val Cys Lys Glu Gly Trp Glu Gly Pro Thr
            740                 745                 750

Cys Thr Gln Asn Thr Asn Asp Cys Ser Pro His Pro Cys Tyr Asn Ser
            755                 760                 765

Gly Thr Cys Val Asp Gly Asp Asn Trp Tyr Arg Cys Glu Cys Ala Pro
770                 775                 780

Gly Phe Ala Gly Pro Asp Cys Arg Ile Asn Ile Asn Glu Cys Gln Ser
785                 790                 795                 800

Ser Pro Cys Ala Phe Gly Ala Thr Cys Val Asp Glu Ile Asn Gly Tyr
                805                 810                 815

Arg Cys Ile Cys Pro Pro Gly Arg Ser Gly Pro Gly Cys Gln Glu Val
                820                 825                 830

Thr Gly Arg Pro Cys Phe Thr Ser Ile Arg Val Met Pro Asp Gly Ala
            835                 840                 845

Lys Trp Asp Asp Asp Cys Asn Thr Cys Gln Cys Leu Asn Gly Lys Val
            850                 855                 860

Thr Cys Ser Lys Val Trp Cys Gly Pro Arg Pro Cys Ile Ile His Ala
865                 870                 875                 880

Lys Gly His Asn Glu Cys Pro Ala Gly His Ala Cys Val Pro Val Lys
                885                 890                 895

Glu Asp His Cys Phe Thr His Pro Cys Ala Ala Val Gly Glu Cys Trp
                900                 905                 910

Pro Ser Asn Gln Gln Pro Val Lys Thr Lys Cys Asn Ser Asp Ser Tyr
            915                 920                 925

Tyr Gln Asp Asn Cys Ala Asn Ile Thr Phe Thr Phe Asn Lys Glu Met
            930                 935                 940

Met Ala Pro Gly Leu Thr Thr Glu His Ile Cys Ser Glu Leu Arg Asn
945                 950                 955                 960

Leu Asn Ile Leu Lys Asn Val Ser Ala Glu Tyr Ser Ile Tyr Ile Thr
                965                 970                 975

Cys Glu Pro Ser His Leu Ala Asn Asn Glu Ile His Val Ala Ile Ser
                980                 985                 990

Ala Glu Asp Ile Gly Glu Asp Glu Asn Pro Ile Lys Glu Ile Thr Asp
            995                 1000                1005

Lys Ile Ile Asp Leu Val Ser Lys Arg Asp Gly Asn Asn Thr Leu Ile
    1010                1015                1020

Ala Ala Val Ala Glu Val Arg Val Gln Arg Arg Pro Leu Lys Asn Lys
1025                1030                1035                1040

Thr Asp Phe Leu Val Pro Leu Leu Ser Ser Val Leu Thr Val Ala Trp
                1045                1050                1055

Ile Cys Cys Leu Val Thr Val Phe Tyr Trp Cys Ile Gln Lys Arg Arg
                1060                1065                1070

Lys Gln Ser Ser His Thr His Thr Ala Ser Asp Asp Asn Thr Thr Asn
            1075                1080                1085

Asn Val Arg Glu Gln Leu Asn Gln Ile Lys Asn Pro Ile Glu Lys His
        1090                1095                1100

Gly Ala Asn Thr Val Pro Ile Lys Asp Tyr Glu Asn Lys Asn Ser Lys
1105                1110                1115                1120

Ile Ala Lys Ile Arg Thr His Asn Ser Glu Val Glu Glu Asp Asp Met
                1125                1130                1135
```

```
Asp Lys His Gln Gln Lys Ala Arg Phe Ala Lys Gln Pro Ala Tyr Thr
        1140                1145                1150
Leu Val Asp Arg Asp Glu Lys Pro Pro Asn Ser Thr Pro Thr Lys His
        1155                1160                1165
Pro Asn Trp Thr Asn Lys Gln Asp Asn Arg Asp Leu Glu Ser Ala Gln
        1170                1175                1180
Ser Leu Asn Arg Met Glu Tyr Ile Val
1185                1190
```

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:11:

```
CGNYTTTGCY TNAARSANTA YCA                                          23
```

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /note= "Xaa = histidine or glutamic
            acid"

(xi) SEQUENCE DESCRIPTION: SEQ ID NO:12:

```
Arg Leu Cys Cys Lys Xaa Tyr Gln
1               5
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 3
        (D) OTHER INFORMATION: /mod_base= i -continued

```
        (ix) FEATURE:
              (A) NAME/KEY: modified_base
              (B) LOCATION: 9
              (D) OTHER INFORMATION: /mod_base= i (ix) FEATURE:
              (A) NAME/KEY: modified_base
              (B) LOCATION: 12
              (D) OTHER INFORMATION: /mod_base= i (ix) FEATURE:
              (A) NAME/KEY: modified_base
              (B) LOCATION: 15
              (D) OTHER INFORMATION: /mod_base= i (xi) SEQUENCE DESCRIPTION: SEQ ID NO:13:

TCNATGCANG TNCCNCCRTT                                                20

(2) INFORMATION FOR SEQ ID NO:14:

(i) SEQUENCE CHARACTERISTICS:
              (A) LENGTH: 7 amino acids
              (B) TYPE: amino acid
              (D) TOPOLOGY: linear (ii) MOLECULE TYPE: peptide (xi) SEQUENCE DESCRIPTION: SEQ ID NO:14:

Asn Gly Gly Thr Cys Ile Asp
1               5

(2) INFORMATION FOR SEQ ID NO:15:

(i) SEQUENCE CHARACTERISTICS:
              (A) LENGTH: 163 base pairs
              (B) TYPE: nucleic acid
              (C) STRANDEDNESS: unknown
              (D) TOPOLOGY: unknown (ii) MOLECULE TYPE: cDNA (ix) FEATURE:
              (A) NAME/KEY: CDS
              (B) LOCATION: 2..163

(xi) SEQUENCE DESCRIPTION: SEQ ID NO:15:

G TCC CGC GTC ACT GCC GGG GGA CCC TGC AGC TTC GGC TCA GGG TCT         46
  Ser Arg Val Thr Ala Gly Gly Pro Cys Ser Phe Gly Ser Gly Ser
   1               5                  10                  15

ACG CCT GTC ATC GGG GGT AAC ACC TTC AAT CTC AAG GCC AGC CGT GGC       94
Thr Pro Val Ile Gly Gly Asn Thr Phe Asn Leu Lys Ala Ser Arg Gly
                 20                  25                  30

AAC GAC CGT AAT CGC ATC GTA CTG CCT TTC AGT TTC ACC TGG CCG AGG      142
Asn Asp Arg Asn Arg Ile Val Leu Pro Phe Ser Phe Thr Trp Pro Arg
                 35                  40                  45

TCC TAC ACT TTG CTG GTG GAG                                          163
Ser Tyr Thr Leu Leu Val Glu
        50

(2) INFORMATION FOR SEQ ID NO:16:

(i) SEQUENCE CHARACTERISTICS:
              (A) LENGTH: 54 amino acids
              (B) TYPE: amino acid
              (D) TOPOLOGY: unknown (ii) MOLECULE TYPE: protein (xi) SEQUENCE DESCRIPTION: SEQ ID NO:16:

Ser Arg Val Thr Ala Gly Gly Pro Cys Ser Phe Gly Ser Gly Ser Thr
```

6,004,924

137                                                                138

-continued

```
                 1               5                  10                 15
Pro Val Ile Gly Gly Asn Thr Phe Asn Leu Lys Ala Ser Arg Gly Asn
                        20                   25                  30

Asp Arg Asn Arg Ile Val Leu Pro Phe Ser Phe Thr Trp Pro Arg Ser
                  35                  40                  45

Tyr Thr Leu Leu Val Glu
        50
```

(2) INFORMATION FOR SEQ ID NO:17:

(i) SEQUENCE CHARACTERISTICS:
        (A) LENGTH: 135 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: CDS
        (B) LOCATION: 1..135

(xi) SEQUENCE DESCRIPTION: SEQ ID NO:17:

```
TCT TCT AAC GTC TGT GGT CCC CAT GGC AAG TGC AAG AGC CAG TCG GCA        48
Ser Ser Asn Val Cys Gly Pro His Gly Lys Cys Lys Ser Gln Ser Ala
 1               5                  10                  15

GGC AAA TTC ACC TGT GAC TGT AAC AAA GGC TTC ACC GGC ACC TAC TGC        96
Gly Lys Phe Thr Cys Asp Cys Asn Lys Gly Phe Thr Gly Thr Tyr Cys
              20                  25                  30

CAT GAA AAT ATC AAC GAC TGC GAG AGC AAC CCC TGT AAA                   135
His Glu Asn Ile Asn Asp Cys Glu Ser Asn Pro Cys Lys
              35                  40                  45
```

(2) INFORMATION FOR SEQ ID NO:18:

(i) SEQUENCE CHARACTERISTICS:
        (A) LENGTH: 45 amino acids
        (B) TYPE: amino acid
        (D) TOPOLOGY: unknown (ii) MOLECULE TYPE: protein (xi) SEQUENCE DESCRIPTION: SEQ ID NO:18:

```
Ser Ser Asn Val Cys Gly Pro His Gly Lys Cys Lys Ser Gln Ser Ala
 1               5                  10                  15

Gly Lys Phe Thr Cys Asp Cys Asn Lys Gly Phe Thr Gly Thr Tyr Cys
              20                  25                  30

His Glu Asn Ile Asn Asp Cys Glu Ser Asn Pro Cys Lys
              35                  40                  45
```

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 6

```
            (D) OTHER INFORMATION: /mod_base= i (ix) FEATURE:
            (A) NAME/KEY: modified_base
            (B) LOCATION: 12
            (D) OTHER INFORMATION: /mod_base= i (ix) FEATURE:
            (A) NAME/KEY: modified_base
            (B) LOCATION: 18
            (D) OTHER INFORMATION: /mod_base= i (xi) SEQUENCE DESCRIPTION: SEQ ID NO:19:

CGNYTNTGCY TNAARSANTA YCA                                              23

(2) INFORMATION FOR SEQ ID NO:20:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 6
            (D) OTHER INFORMATION: /note= "Xaa = glutamic acid or
                histidine"

(xi) SEQUENCE DESCRIPTION: SEQ ID NO:20:

Arg Leu Cys Leu Lys Xaa Tyr Gln
1               5
```

PROTEIN SEQUENCES OF SERRATE GENE PRODUCTS

This application is a continuation-in-part of copending application Ser. No. 08/400,159 filed Mar. 7, 1995, which is a continuation-in-part of application Ser. No. 08/255,102 filed Jun. 7, 1994, now abandoned, which is a continuation of application Ser. No. 08/121,979 filed Sep. 14, 1993, now abandoned, which is a continuation of Ser. No. 07/808,458 filed Dec. 11, 1991, now abandoned, each of which is incorporated by reference herein in its entirety.

This invention was made in part with government support under Grant numbers GM 29093 and NS 26084 awarded by the Department of Health and Human Services. The government has certain rights in the invention.

TABLE OF CONTENTS
1. INTRODUCTION
2. BACKGROUND OF THE INVENTION
3. SUMMARY OF THE INVENTION
   3.1. DEFINITIONS
4. DESCRIPTION OF THE FIGURES
5. DETAILED DESCRIPTION OF THE INVENTION
   5.1. ISOLATION OF THE SERRATE GENES
   5.2. EXPRESSION OF THE SERRATE GENES
   5.3. IDENTIFICATION AND PURIFICATION OF THE SERRATE GENE PRODUCTS
   5.4. STRUCTURE OF THE SERRATE GENES AND PROTEIN
      5.4.1. GENETIC ANALYSIS
      5.4.2. PROTEIN ANALYSIS
   5.5. GENERATION OF ANTIBODIES TO SERRATE PROTEINS AND DERIVATIVES THEREOF
   5.6. SERRATE PROTEINS, DERIVATIVES AND ANALOGS
      5.6.1. DERIVATIVES OF SERRATE CONTAINING ONE OR MORE DOMAINS OF THE PROTEIN
      5.6.2. DERIVATIVES OF SERRATE THAT MEDIATE BINDING TO TOPORYTHMIC PROTEIN DOMAINS
   5.7. ASSAYS OF SERRATE PROTEINS, DERIVATIVES AND ANALOGS
   5.8. THERAPEUTIC USES
      5.8.1. MALIGNANCIES
      5.8.2. NERVOUS SYSTEM DISORDERS
      5.8.3. TISSUE REPAIR AND REGENERATION
   5.9. PROPHYLACTIC USES
      5.9.1. MALIGNANCIES
      5.9.2. OTHER DISORDERS
   5.10. DEMONSTRATION OF THERAPEUTIC OR PROPHYLACTIC UTILITY
   5.11. ANTISENSE REGULATION OF SERRATE EXPRESSION
      5.11.1. SERRATE ANTISENSE NUCLEIC ACIDS
      5.11.2. THERAPEUTIC UTILITY OF SERRATE ANTISENSE NUCLEIC ACIDS
   5.12. THERAPEUTIC/PROPHYLACTIC ADMINISTRATION AND COMPOSITIONS
   5.13. DIAGNOSTIC UTILITY
6. THE GENE SERRATE ENCODES A PUTATIVE EGF-LIKE TRANSMEMBRANE PROTEIN ESSENTIAL FOR PROPER ECTODERMAL DEVELOPMENT IN DROSOPHILA MELANOGASTER
   6.1. RESULTS
      6.1.1. THE SERRATE AND NOTCH GENES INTERACT PHENOTYPICALLY
      6.1.2. GENETIC CHARACTERIZATION OF SERRATE
      6.1.3. CHARACTERIZATION OF SERRATE MUTANT PHENOTYPES
      6.1.4. MOLECULAR CHARACTERIZATION OF SERRATE DNA
      6.1.5. SERRATE ENCODES A PUTATIVE TRANSMEMBRANE PROTEIN WITH 14 EGF-LIKE REPEATS
      6.1.6. EXPRESSION OF SERRATE RNA
   6.2. DISCUSSION
   6.3. MATERIALS AND METHODS
      6.3.1. DROSOPHILA CULTURES AND STRAINS
      6.3.2. MUTAGENESIS
      6.3.3. EMBRYONIC PHENOTYPE ANALYSIS
      6.3.4. ISOLATION OF NUCLEIC ACIDS
      6.3.5. SEQUENCING AND ANALYSIS
      6.3.6. WHOLE MOUNT IN SITU PROCEDURE
7. EXPRESSION OF A SERRATE FRAGMENT AS A FUSION PROTEIN AND PRODUCTION OF ANTIBODIES THERETO
8. EXPRESSION OF SERRATE AND A FRAGMENT AND A CHIMERIC DERIVATIVE THEREOF; IDENTIFICATION OF A NOTCH-BINDING DOMAIN
   8.1. EXPRESSION OF SERRATE AND OF DERIVATIVES THEREOF
   8.2. AGGREGATION ASSAYS FOR BINDING TO NOTCH
      8.2.1. METHODS
      8.2.2. RESULTS
9. ISOLATION AND CHARACTERIZATION OF A MOUSE SERRATE HOMOLOG
10. ISOLATION AND CHARACTERIZATION OF A XENOPUS SERRATE HOMOLOG
11. ISOLATION AND CHARACTERIZATION OF A CHICK SERRATE HOMOLOG
12. ISOLATION AND CHARACTERIZATION OF HUMAN SERRATE HOMOLOGS
13. DEPOSIT OF MICROORGANISMS

1. INTRODUCTION

The present invention relates to Serrate genes and their encoded protein products, as well as derivatives and analogs thereof. Production of Serrate proteins, derivatives, and antibodies is also provided. The invention further relates to therapeutic compositions and methods of diagnosis and therapy.

2. BACKGROUND OF THE INVENTION

Genetic analyses in Drosophila have been extremely useful in dissecting the complexity of developmental pathways and identifying interacting loci. However, understanding the precise nature of the processes that underlie genetic interactions requires a knowledge of the protein products of the genes in question.

Embryological, genetic and molecular evidence indicates that the early steps of ectodermal differentiation in Drosophila depend on cell interactions (Doe and Goodman, 1985, Dev. Biol. 111:206–219; Technau and Campos-Ortega, 1986, Dev. Biol. 195:445–454; Vassin et al., 1985, J. Neurogenet. 2:291–308; de la Concha et al., 1988, Genetics 118:499–508; Xu et al., 1990, Genes Dev. 4:464–475; Artavanis-Tsakonas, 1988, Trends Genet. 4:95–100). Mutational analyses reveal a small group of zygotically-acting genes, the so called neurogenic loci, which affect the choice of ectodermal cells between epidermal and neural pathways (Poulson, 1937, Proc. Natl. Acad. Sci. 23:133–137; Lehmann et al., 1983, Wilhelm Roux's Arch. Dev. Biol. 192:62–74; Jurgens et al., 1984, Wilhelm Roux's Arch. Dev. Biol. 10 193:283–295; Wieschaus et al., 1984, Wilhelm Roux's Arch. Dev. Biol. 193:296–307; Nüsslein-Volhard et al., 1984, Wilhelm Roux's Arch. Dev. Biol. 193:267–282). Null mutations in any one of the zygotic neurogenic loci—Notch (N), Delta (Dl), mastermind (mam), Enhancer of Split (E(spl), neuralized (neu), and big brain (bib)—result in hypertrophy of the nervous system at the expense of ventral and lateral epidermal structures. This effect is due to the misrouting of epidermal precursor cells into a neuronal pathway, and implies that neurogenic gene function is necessary to divert cells within the neurogenic region from a neuronal fate to an epithelial fate. Serrate has been identified as a genetic unit capable of interacting with the Notch locus (Xu et al., 1990, Genes Dev. 4:464–475). These genetic and developmental observations have led to the hypothesis that the protein products of the neurogenic loci function as components of a cellular interaction mechanism necessary for proper epidermal development (Artavanis-Tsakonas, S., 1988, Trends Genet. 4:95–100).

Mutational analyses also reveal that the action of the neurogenic genes is pleiotropic and is not limited solely to embryogenesis. For example, ommatidial, bristle and wing formation, which are known also to depend upon cell interactions, are affected by neurogenic mutations (Morgan et al., 1925, Bibliogr. Genet. 2:1–226; Welshons, 1956, Dros. Inf. Serv. 30:157–158; Preiss et al., 1988, EMBO J. 7:3917–3927; Shellenbarger and Mohler, 1978, Dev. Biol. 62:432–446; Technau and Campos-Ortega, 1986, Wilhelm Roux's Dev. Biol. 195:445–454; Tomlison and Ready, 1987, Dev. Biol. 120:366–376; Cagan and Ready, 1989, Genes Dev. 3:1099–1112).

Sequence analyses (Wharton et al., 1985, Cell 43:567–581; Kidd and Young, 1986, Mol. Cell. Biol. 6:3094–3108; Vässin, et al., 1987, EMBO J. 6:3431–3440; Kopczynski, et al., 1988, Genes Dev. 2:1723–1735) have shown that two of the neurogenic loci, Notch and Delta, appear to encode transmembrane proteins that span the membrane a single time. The Notch gene encodes a ~300 kd protein (we use "Notch" to denote this protein) with a large N-terminal extracellular domain that includes 36 epidermal growth factor (EGF)-like tandem repeats followed by three other cysteine-rich repeats, designated Notch/1in-12 repeats (Wharton, et al., 1985, Cell 43:567–581; Kidd and Young, 1986, Mol. Cell. Biol. 6:3094–3108; Yochem, et al., 1988, Nature 335:547–550). Delta encodes a ~100 kd protein (we use "Delta" to denote DLZM, the protein product of the predominant zygotic and maternal transcripts; Kopczynski, et al., 1988, Genes Dev. 2:1723–1735) that has nine EGF-like repeats within its extracellular domain (Vässin, et al., 1987, EMBO J. 6:3431–3440; Kopczynski, et al., 1988, Genes Dev. 2:1723–1735). Molecular studies have lead to the suggestion that Notch and Delta constitute biochemically interacting elements of a cell communication mechanism involved in early developmental decisions (Fehon et al., 1990, Cell 61:523–534).

The EGF-like motif has been found in a variety of proteins, including those involved in the blood clotting cascade (Furie and Furie, 1988, Cell 53: 505–518). In particular, this motif has been found in extracellular proteins such as the blood clotting factors IX and X (Rees et al., 1988, EMBO J. 7:2053–2061; Furie and Furie, 1988, Cell 53: 505–518), in other Drosophila genes (Knust et al., 1987 EMBO J. 761–766; Rothberg et al., 1988, Cell 55:1047–1059), and in some cell-surface receptor proteins, such as thrombomodulin (Suzuki et al., 1987, EMBO J. 6:1891–1897) and LDL receptor (Sudhof et al., 1985, Science 228:815–822). A protein binding site has been mapped to the EGF repeat domain in thrombomodulin and urokinase (Kurosawa et al., 1988, J. Biol. Chem 263:5993–5996; Appella et al., 1987, J. Biol. Chem. 262:4437–4440).

Citation of references hereinabove shall not be construed as an admission that such references are prior art to the present invention.

3. SUMMARY OF THE INVENTION

The present invention relates to nucleotide sequences of Serrate genes (Drosophila Serrate and related genes of other species), and amino acid sequences of their encoded proteins, as well as derivatives (e.g., fragments) and analogs thereof. Nucleic acids hybridizable to or complementary to the foregoing nucleotide sequences are also provided. In a specific embodiment, the Serrate protein is a human protein.

The invention relates to Serrate derivatives and analogs of the invention which are functionally active, i.e., they are capable of displaying one or more known functional activities associated with a full-length (wild-type) Serrate protein. Such functional activities include but are not limited to antigenicity [ability to bind (or compete with Serrate for binding) to an anti-Serrate antibody], immunogenicity (ability to generate antibody which binds to Serrate), ability to bind (or compete with Serrate for binding) to Notch or other toporythmic proteins or fragments thereof ("adhesiveness"), ability to bind (or compete with Serrate for binding) to a receptor for Serrate. "Toporythmic proteins" as used herein, refers to the protein products of Notch, Delta, Serrate, Enhancer of split, and Deltex, as well as other members of this interacting gene family which may be identified, e.g., by virtue of the ability of their gene sequences to hybridize, or their homology to Delta, Serrate, or Notch, or the ability of their genes to display phenotypic interactions.

The invention further relates to fragments (and derivatives and analogs thereof) of Serrate which comprise one or more domains of the Serrate protein, including but not limited to the intracellular domain, extracellular domain, transmembrane domain, membrane-associated region, or one or more EGF-like (homologous) repeats of a Serrate protein, or any combination of the foregoing.

Antibodies to Serrate, its derivatives and analogs, are additionally provided.

Methods of production of the Serrate proteins, derivatives and analogs, e.g., by recombinant means, are also provided.

The present invention also relates to therapeutic and diagnostic methods and compositions based on Serrate proteins and nucleic acids. The invention provides for treatment of disorders of cell fate or differentiation by administration of a therapeutic compound of the invention. Such therapeutic compounds (termed herein "Therapeutics") include: Serrate proteins and analogs and derivatives (including fragments) thereof; antibodies thereto; nucleic acids encoding the Serrate proteins, analogs, or derivatives; and Serrate antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, therapeutics which antagonize, or inhibit, Notch and/or Serrate function (hereinafter "antagonist therapeutics") are administered for therapeutic effect. In another embodiment, therapeutics which promote Notch and/or Serrate function (hereinafter "agonist therapeutics") are administered for therapeutic effect.

Disorders of cell fate, in particular hyperproliferative (e.g., cancer) or hypoproliferative disorders, involving aberrant or undesirable levels of expression or activity or localization of Notch and/or Serrate protein can be diagnosed by detecting such levels, as described more fully infra.

In a preferred aspect, a therapeutic of the invention is a protein consisting of at least a fragment (termed herein "adhesive fragment") of Serrate which mediates binding to a Notch protein or a fragment thereof.

3.1. DEFINITIONS

As used herein, underscoring or italicizing the name of a gene shall indicate the gene, in contrast to its encoded protein product which is indicated by the name of the gene in the absence of any underscoring. For example, "Serrate" shall mean the Serrate gene, whereas "Serrate" shall indicate the protein product of the Serrate gene.

4. DESCRIPTION OF THE FIGURES

FIG. 1. Phenotypic interactions between Notch and Serrate. (a) $w^a$wspl wing blade showing characteristic wild-type symmetry, venation, and marginal wing bristles and hairs. (b) nd/Y male. Distal wing notches and loss of posterior hairs are evident. (c) $Ser^D$/+heterozygote. Note similarity to nd/Y wing blade in FIG. 1b. (d) nd/Y; $Ser^D$/+ transheterozygote wing blade. Mutant wing shows typical "fig leaf" shape, distorted wing veins, and loss of the majority of marginal bristles and hairs, with the exception of the anterodistal wing margin. (e) +/Y; $Ser^D$Dp(3R) CosP479BE (N$^+$) male. The extra N$^+$ copy suppresses the heterozygous $Ser^D$ dominant phenotype (compare to FIG. 1c). Also note suppression of the Confluens phenotype (see text). (f) $Ser^D$/$Ser^D$ homozygote. Note the increased severity of the phenotype relative to $Ser^D$/+ (compare to FIG. 1c).

Figure 2:
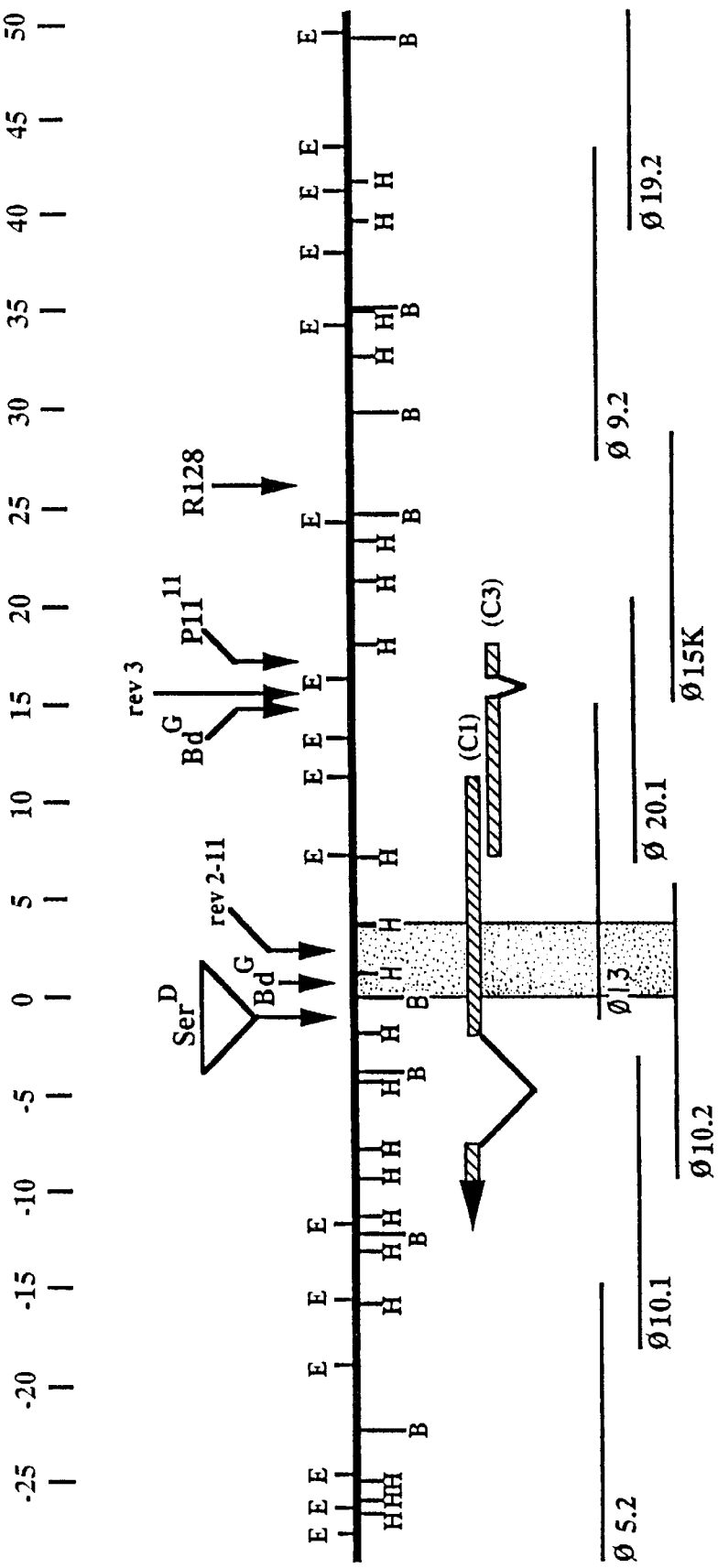

FIG. 2. Molecular map of the Serrate-encoding region. Approximately 85 kb of cloned genomic DNA from the 97F chromosomal region are presented along with the restriction sites of three enzymes [(B) BamHI; (E) EcoRI; (H) HindIII]. The locations of individual DNA alterations associated with Serrate allelic breakpoints are displayed above the genomic DNA (for descriptions of mutant alleles, see Section 6, infra; (rev 3 and rev 2–11) $Ser^{rev\ 3}$ and $Ser^{rev\ 2-11}$, respectively; (R128) T(Y:3)R128. The shaded box from coordinates 0 to +3 represents the region of EGF homology detectable by Southern hybridization. The BamHI site adjacent to the EGF homology was arbitrarily chosen as position 0. map orientation is with the centromere to the left. At the bottom of the figure are shown the individual recombinant phage isolates. The C1 and C3 cDNAs together constitute the larger of the two Serrate messages (~5.6 kb). Intron positions and coding capacities have been approximated solely upon cross hybridization of the cDNAs with the genomic DNA regions.

Figure 3A:
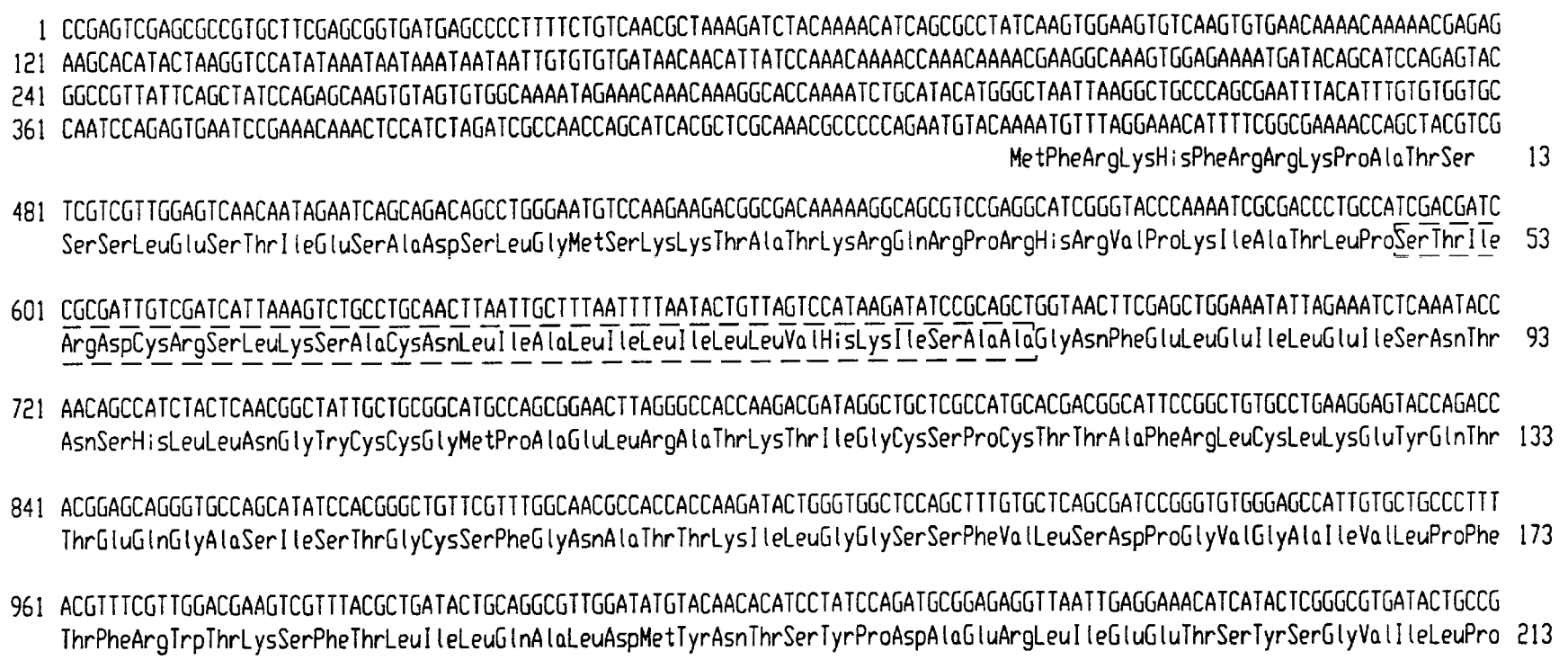
Figure 3B:
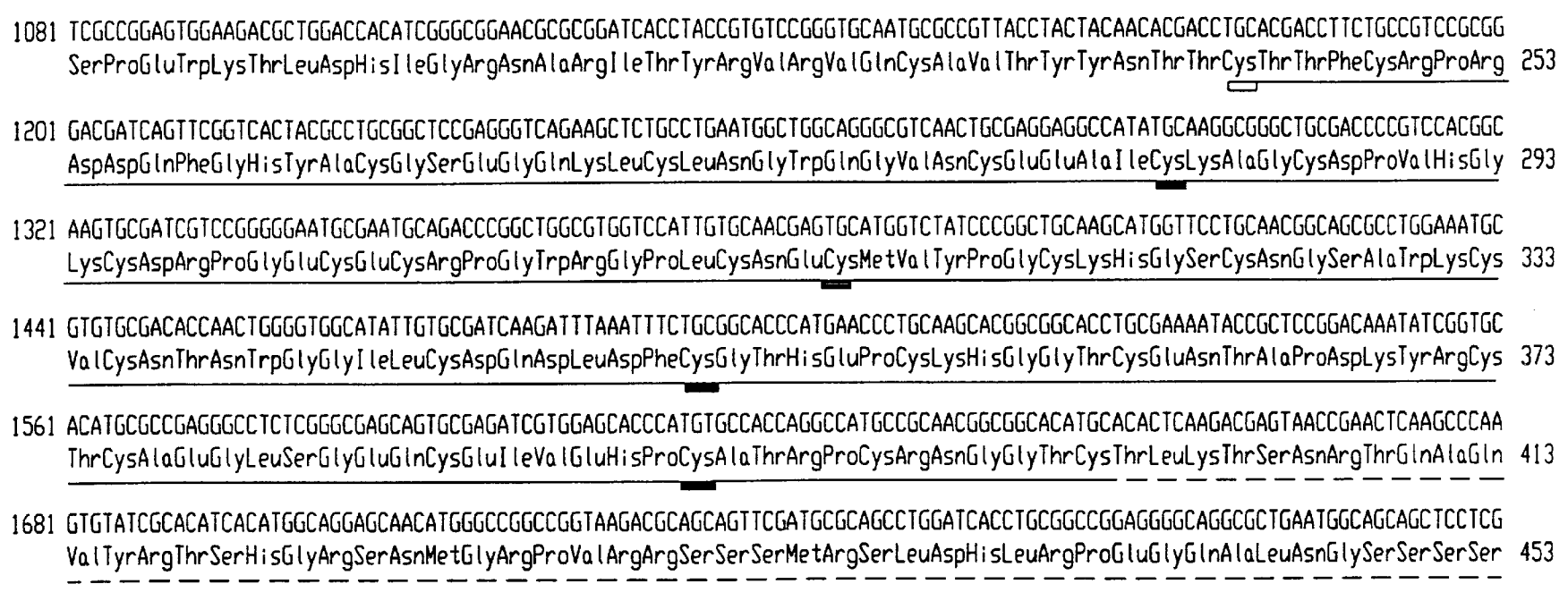
Figure 3D:
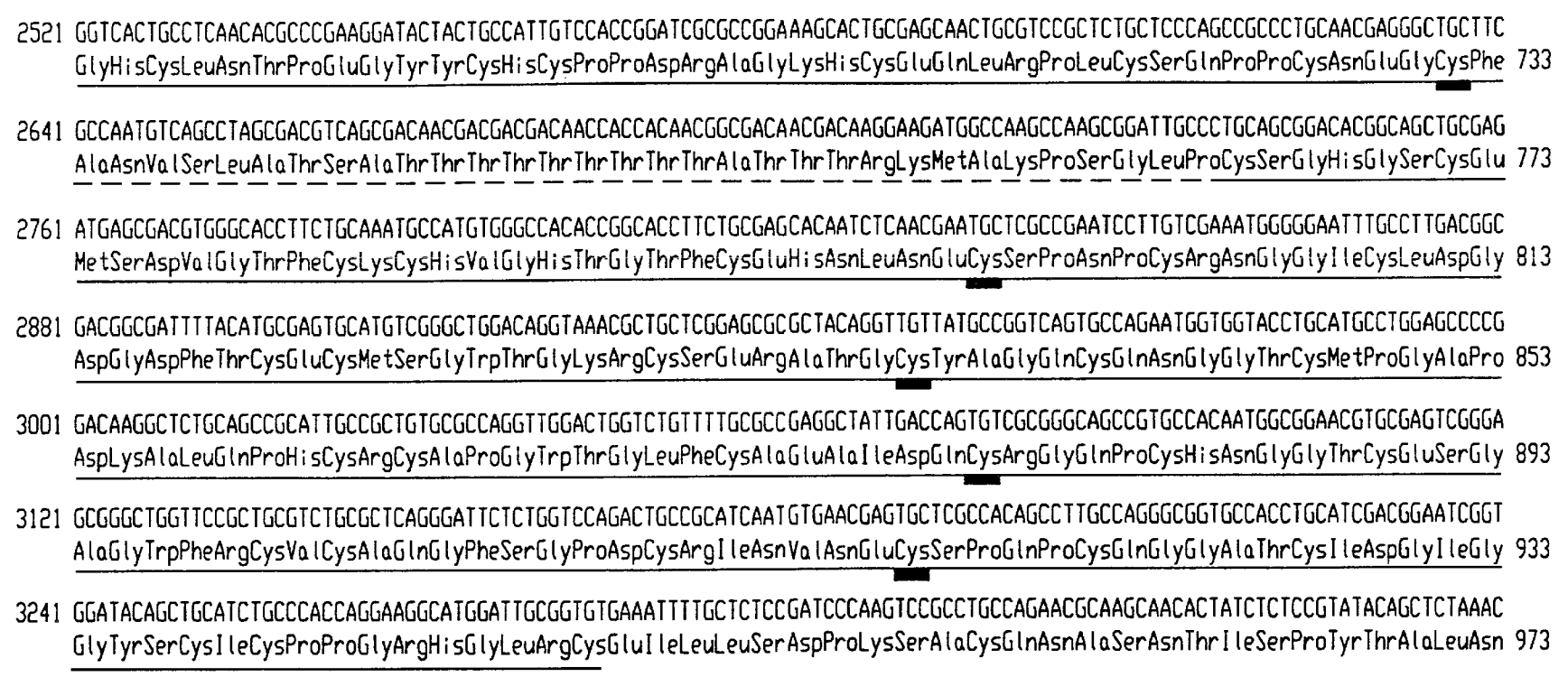
Figure 3E:
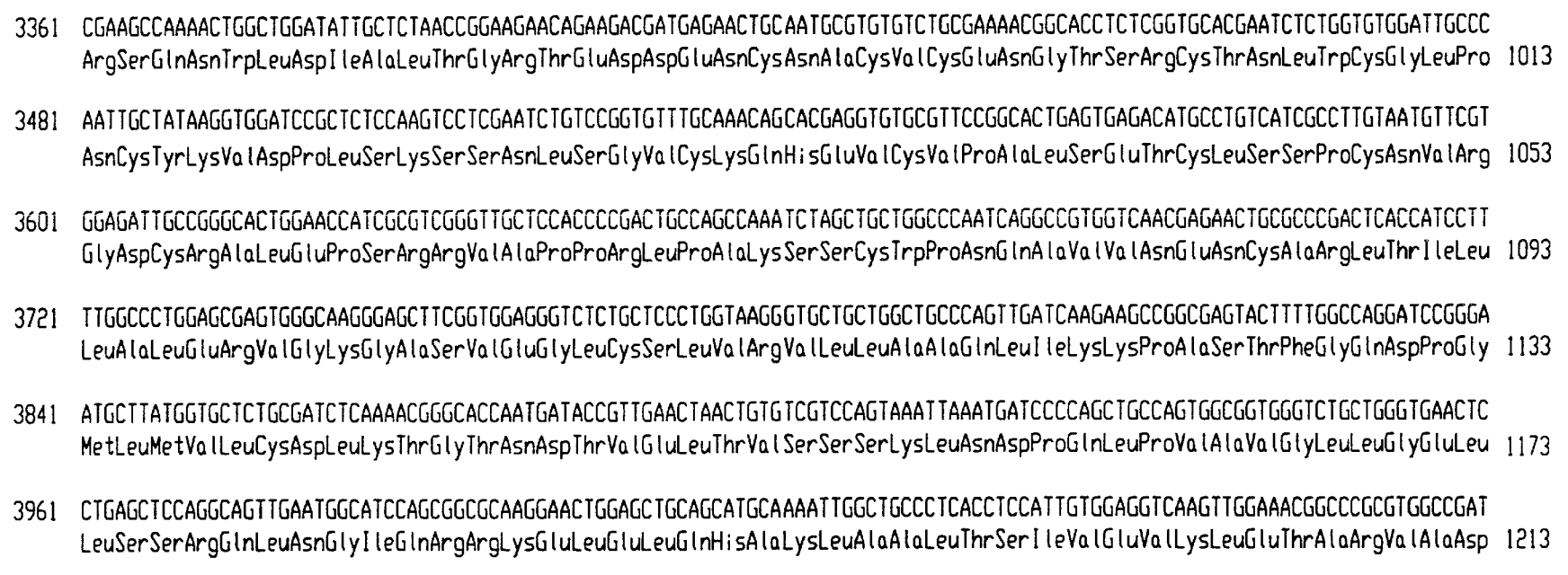
Figure 3F:
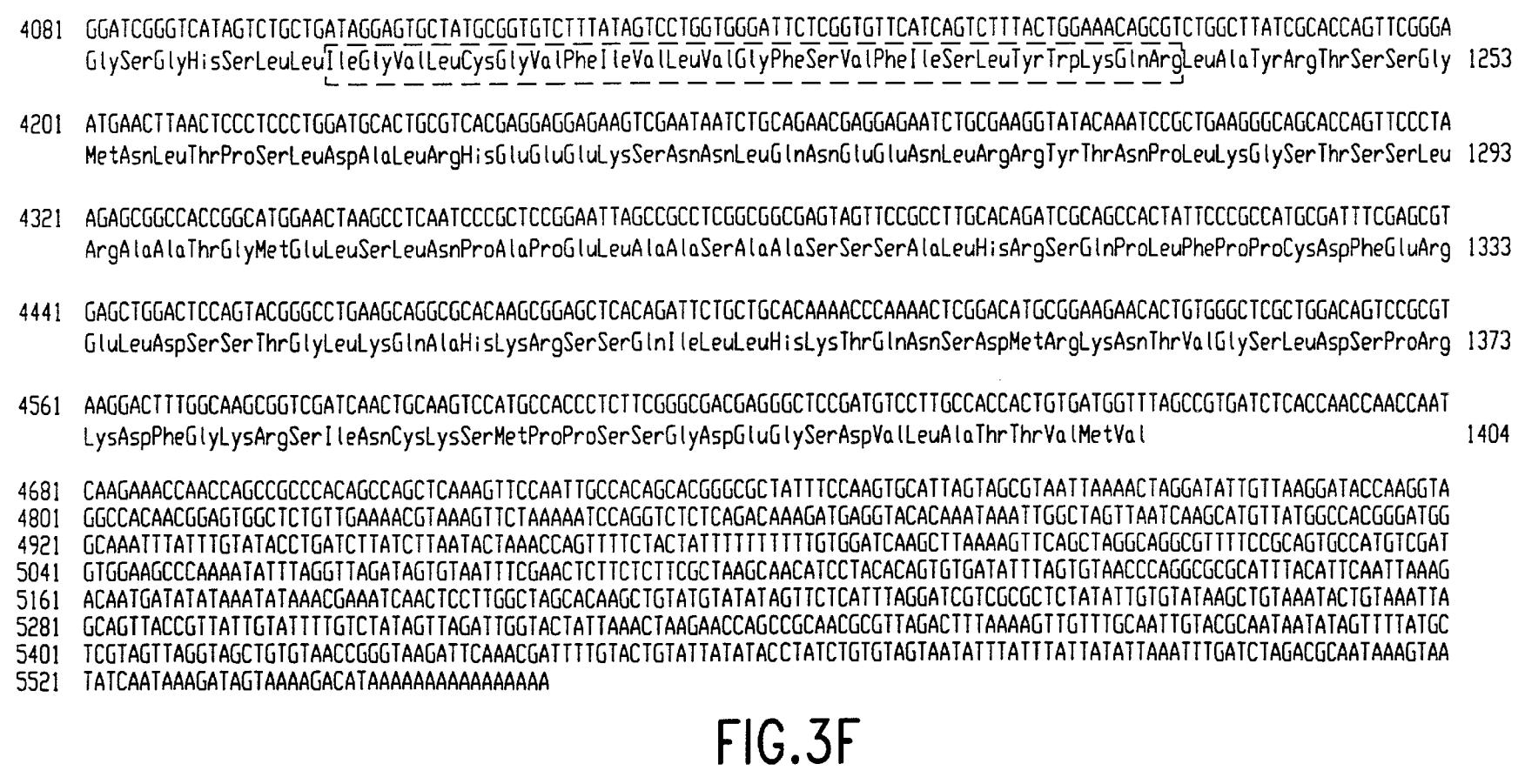

FIG. 3. Serrate sequence analysis. The complete 5561 bp sequence (SEQ ID NO:1) derived from cDNAs C1 and C3 is shown. Nucleotide numbering is at left, amino acid numbering of the predicted open reading frame (ORF) is at right. The deduced protein product appears to be a transmembrane protein of 1404 amino acids (SEQ ID NO:2). Hydrophobic regions are denoted inside dashed boxes; amino acids 51 to 80 represent the likely signal peptide; amino acids 542 to 564 represent the potential membrane associated region; amino acids 1221 to 1245 represent the putative transmembrane domain. The first cysteine of each of the fourteen EGF-like repeats is denoted with a solid black box, and each repeat is underlined. The partial EGF-like repeat is considered "degenerate," since the fourth cysteine residue of this repeat has been changed to lysine (shown in boldface type at amino acid position 268). The initial cysteine of his repeat is denoted with an open box (amino acid 284), and the repeat is underlined. Amino acid insertions occur in the fourth, sixth, and tenth EGF-like repeats and are denoted by hatched underlines.

FIG. 4. The Serrate transcript and deduced rotein product. (a) The composite transcript shown was onstructed from the C1 and C3 cDNAs, which overlap by 109 bp. Selected restriction enzyme cleavage sites are shown. The hatched box represents the 4212 bp ORF. Open boxes represent the 442 bp 5'-untranslated leader and 900 bp 3'-trailer sequence. (b) Kyte-Doolittle hydropathy plot of the deduced 1404 amino acid protein. (SP) Putative signal peptide; (MA) potential membrane associated region; (TM) likely transmembrane domain. (c) Cartoon representation of the gross structural features of the predicted Serrate protein. The darkly shaded region, including the partial EGF-like repeat (PR) is ~250 amino acids in length and homologous to the Delta protein. Bracketed EGF-like repeats labeled (A, B, and C) contain insertions of amino acids and thus differ from the canonical EGF-like structure. Other features of the protein include the signal peptide (SP), a cysteine rich region, a transmembrane domain (TM), and an intracellular region of ~160 amino acids.

Figure 5:
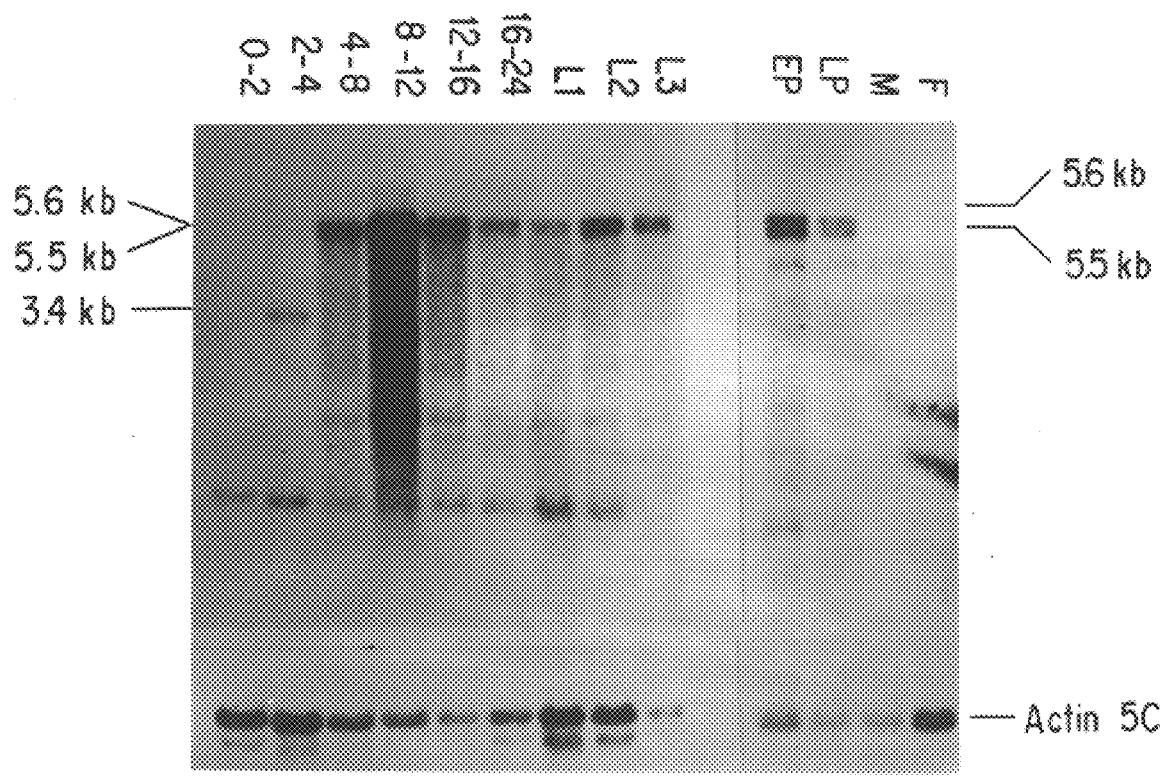

FIG. 5. Temporal profile of Serrate transcript accumulation. Each lane contains five μg of poly(A)$^+$ RNA. The stage of the embryonic RNAs is denoted in hours after egg laying; (L1, L2, and L3) RNA from the first, second and third larval instar periods; (EP and LP) early and late pupal stages; (M and F) adult male and female RNAs, respectively. A composite cDNA subclone (constructed from C1 and C3) was used as a hybridization probe. Serrate transcription is represented primarily as a 5.5 kb and 5.6 kb doublet beginning at 4–8 hours of embryogenesis. A transient 3.4 kb transcript is observed only during 2–4 hr of embryogenesis. The pupal and adult RNAs were fractionated on a separate gel for a longer period of time for better resolution. Equivalent loadings of RNA were noted by ethidium bromide staining of the RNA gels and confirmed by subsequent probing with an actin 5C probe shown at bottom; Fyrberg et al., 1983, Cell 33:115–123). Minor bands were not consistently observed in other blots and may reflect other EGF-homologous transcripts.

FIG. 6. Whole-mount in situ Serrate transcripts. Embryos are oriented with anterior to the left and dorsal side up unless otherwise noted. (a) Dorsal view of an early stage 10 embryo (mid-dorsal focal plane). Earliest expression occurs in the ectoderm of the foregut (FG) and presumptive clypeolabrum (CL). (b) Dorsal view of a germ band-extended embryo (late stage 10). Additional expression occurs near the proctodeum (PR), within the eighth (A8) and ninth (A9) abdominal segments, and in the labial and maxillary primordia (arrow). (c) Lateral view of an early stage 11 embryo. The lateral (LE) and ventral (VE) expression patterns are out of register and do not include the tracheal pits (TP). (d) Germ band-extended embryo (mid stage 11) dissected and flattened such that the dorsal surfaces are at the lateral edges. Extensive expression is observed between the labial (LB), maxillary (MX), and mandibular (MN) lobes, and within the hypopharynx (HP) and clypeolabrum (CL). Expression is also apparent in the salivary gland placodes (SP) that have moved to the ventral midline. Note relationship between lateral and ventral patterns and elaboration of expression in the tail region [presumptive telson (TL)]. (e) Germ band-retracting embryo (stage 12; lateral view). Lateral expression (LE) is beginning to coalesce. (f) Lateral view of a germ band-retracted embryo (stage 13). The lateral expression is beginning to extend both dorsally and ventrally in each thoracic and abdominal segment and is most pronounced in the first thoracic segment (T1). A portion of the lateral expression now appears to include the presumptive trachea (T). Ventrally, note different expression (VE) patterns in the thoracic versus abdominal segments. (g) Lateral view of an early stage 14 embryo. Outline of the presumptive trachea (T) is distinct from the overlying epidermal expression. Arrows denote the zigzag pattern of lateral expression. (h) Dissected embryo (stage 14) opened along the dorsal midline and laid flat. Two areas of hindgut expression (HG1 and HG2) are apparent; HG1 occurs near the origin of the Malpighian tubules. (i) Ventral view of a stage-16 embryo focusing on the ventral nerve cord (VNC). Earlier expression in the salivary gland placodes (SP in panel d) now constitutes the SD. Expression in the proventriculus (PV) and the maxillary/mandibular region (MX/MN) is slightly out of focus. (j) Dorsomedial focal plane of same embryo as in (i); head involution is nearly complete. The in-pocketings of expression in the thoracic segments (T1, T2, and T3) may represent imaginal disc primordia. Pharyngeal expression (PH) is a combination of clypeolabrum and hypopharyngeal expression noted earlier. (k) Dorsal view of the same embryo as in (i) and (j). Note individual expressing cells in the brain lobes (BC). Expression in the fully differentiated trachea (T) and hindgut (H1) is evident. (1) Flattened preparation of early stage 16 embryo. Expression within the telson (TL) now constitutes a ring around the presumptive anal pads.

Figure 7:
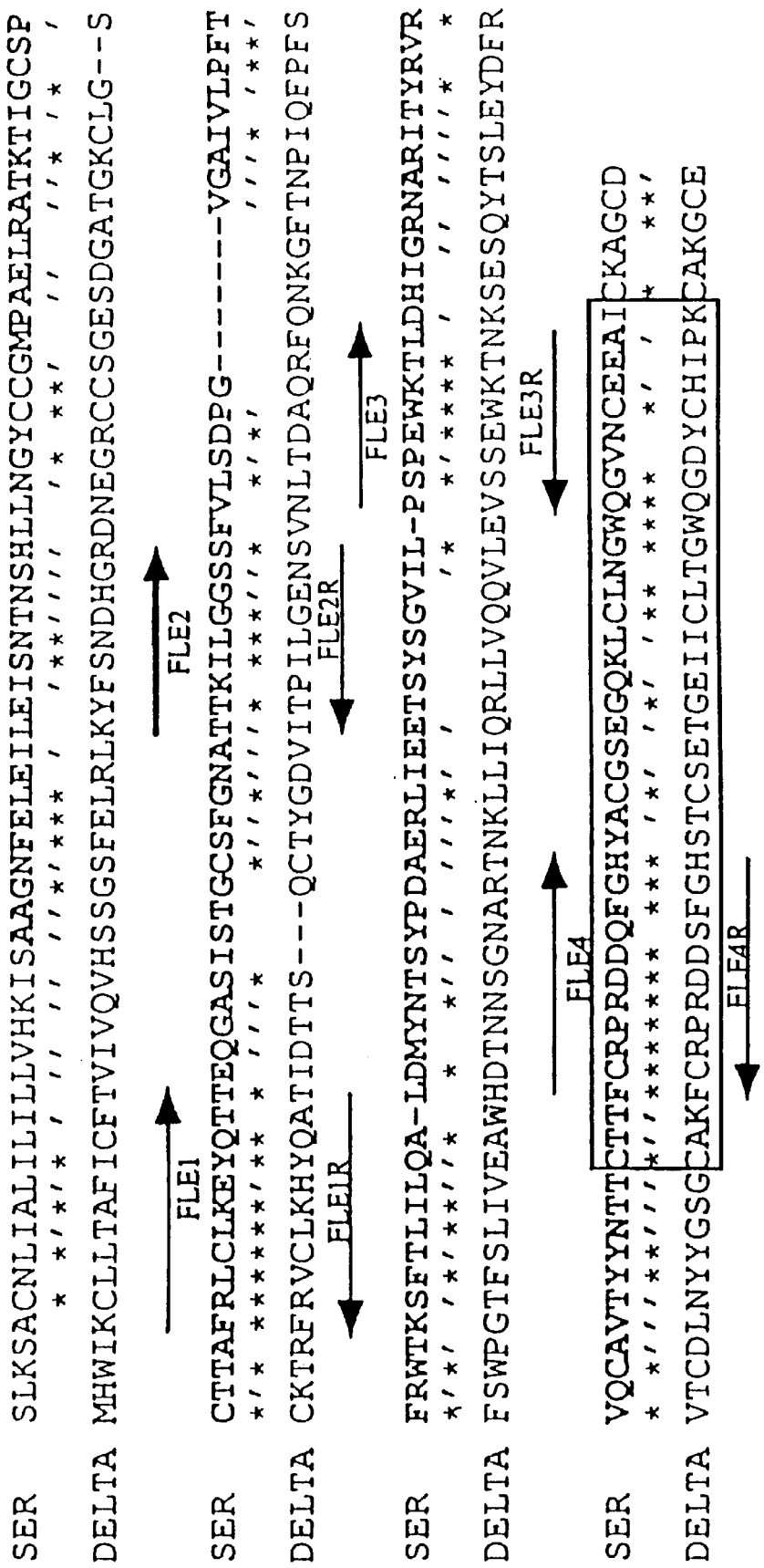

FIG. 7. Amino acid comparison of amino-terminal Serrate-Delta homology. Conserved regions are indicated at the top of the figure (*=identical amino acids; '=conservative changes in sequence). Serrate (see SEQ ID NO:2) is shown above line, Delta (SEQ ID NO:4) below. The sequence begins at Serrate amino acid position 59; the partial EGF-like repeat of both Serrate and Delta is boxed. The Serrate amino acid sequence (amino acids 79–282 of FIG. 3) placed into the chimeric AEGF Notch construct and determined to be sufficient for Notch binding is presented in boldface type. The positions of the synthetic degenerate primers (designated FLE1 through FLE4R) are shown; refer to FIG. 8 for nucleotide composition.

Figure 8B:
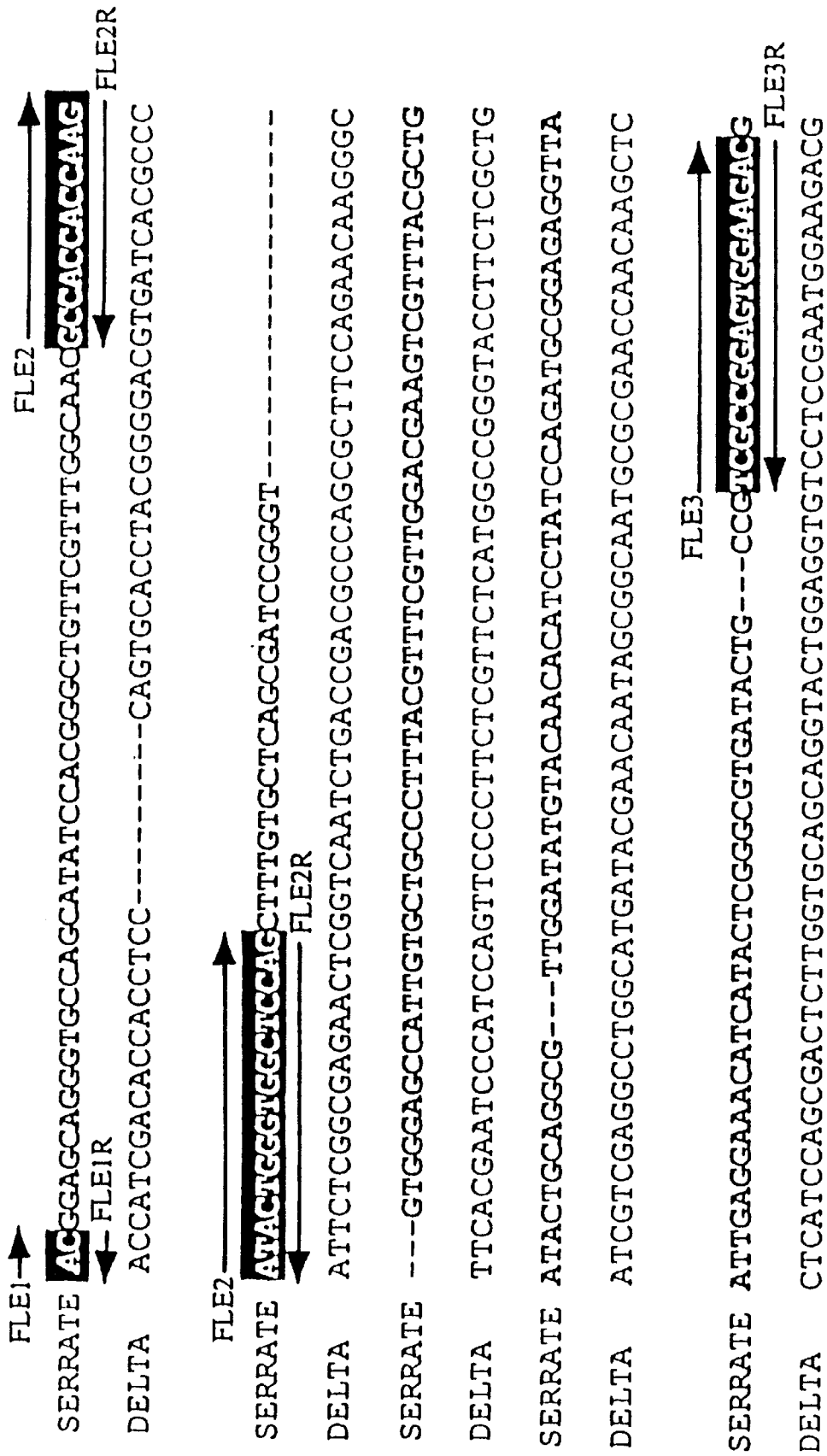
Figure 8C:
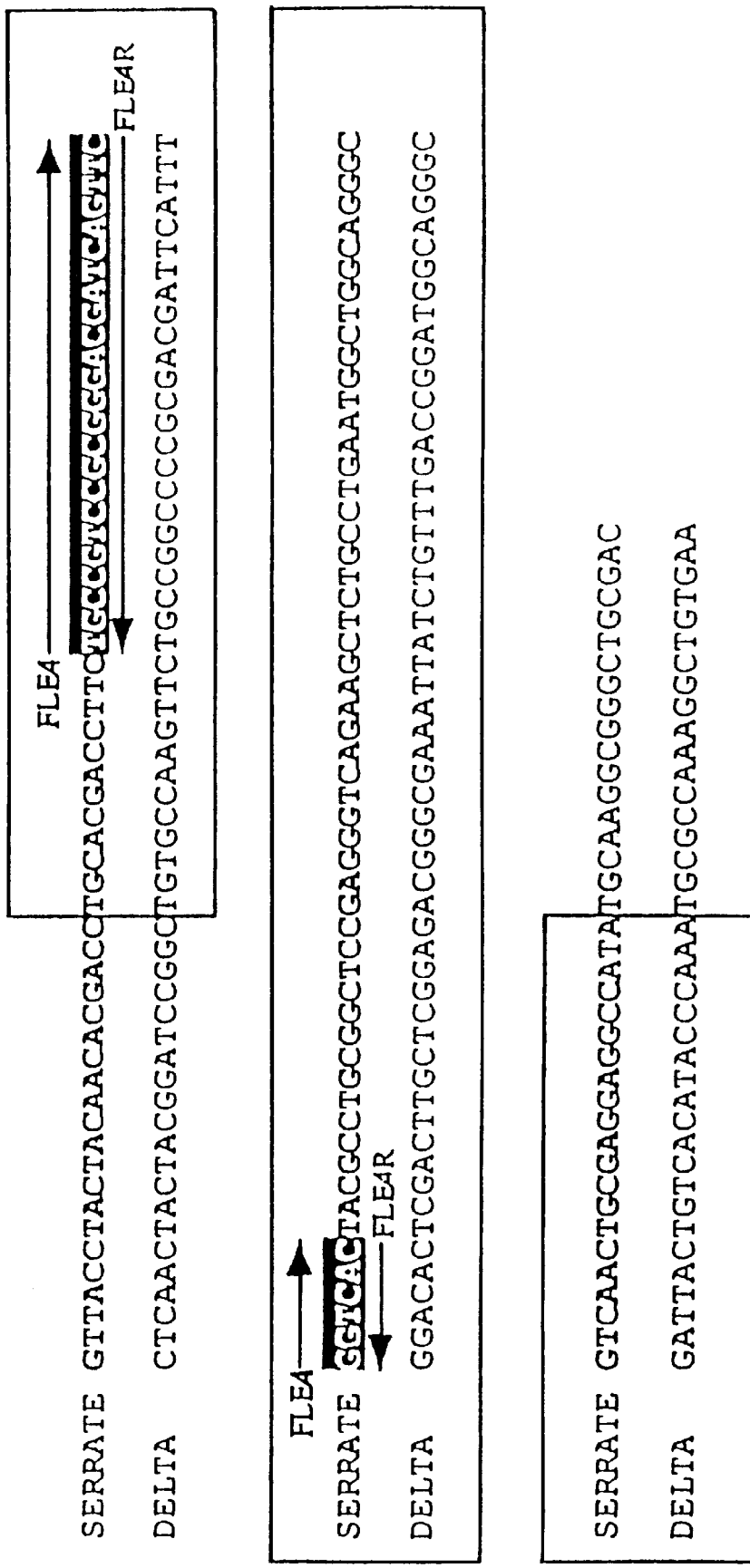

FIG. 8. Nucleotide comparison of amino-terminal Serrate-Delta homology. The nucleotide sequence corresponding to the amino acid sequence in FIG. 7 is shown (Serrate sequence: see SEQ ID NO:1; Delta sequence: SEQ ID NO:3). The DNA encoding the partial EGF-repeat is boxed. The Serrate nucleotide sequence (nucleotides 676–1287 of FIG. 3) placed into the chimeric AEGF Notch construct determined to be sufficient for Notch binding is presented in boldface type.

FIG. 9. Nucleotide sequence (SEQ ID NO:5) and protein sequence (SEQ ID NO:6) of Human Serrate-1 (also known as Human Jagged-1 (HJ1)).

FIG. 10. "Complete" nucleotide sequence (SEQ ID NO:7) and amino acid sequence (SEQ ID NO:8) of Human Serrate-2 (also known as Human Jagged-2 (HJ2) generated on the computer by combining the sequence of clones pBS15 and pBS3-2 isolated from human fetal brain cDNA libraries. There is a deletion of approximately 120 nucleotides in the region of this sequence which encodes the portion of Human Serrate-2 between the signal sequence and the beginning of the DSL domain.

FIG. 11. Nucleotide sequence (SEQ ID NO:9) of chick Serrate (C-Serrate) cDNA.

FIG. 12. Amino acid sequence (SEQ ID NO:10) of C-Serrate (lacking the amino-terminus of the signal sequence). The putative cleavage site following the signal sequence (marking the predicted amino-terminus of the mature protein) is marked with an arrowhead; the DSL domain is indicated by asterisks; the EGF-like repeats (ELRs) are underlined with dashed lines; the cysteine rich region between the ELRs and the transmembrane domain is marked between arrows, and the single transmembrane domain (between amino acids 1042 and 1066) is shown in bold.

FIG. 13. Alignment of the amino terminal sequences of *Drosophila melanogaster* Delta (SEQ ID NO:4) and Serrate (SEQ ID NO:2) with C-Serrate (SEQ ID NO:10). The region shown extends from the end of the signal sequence to the end of the DSL domain. The DSL domain is indicated. Identical amino acids in all three proteins are boxed.

Figure 14:
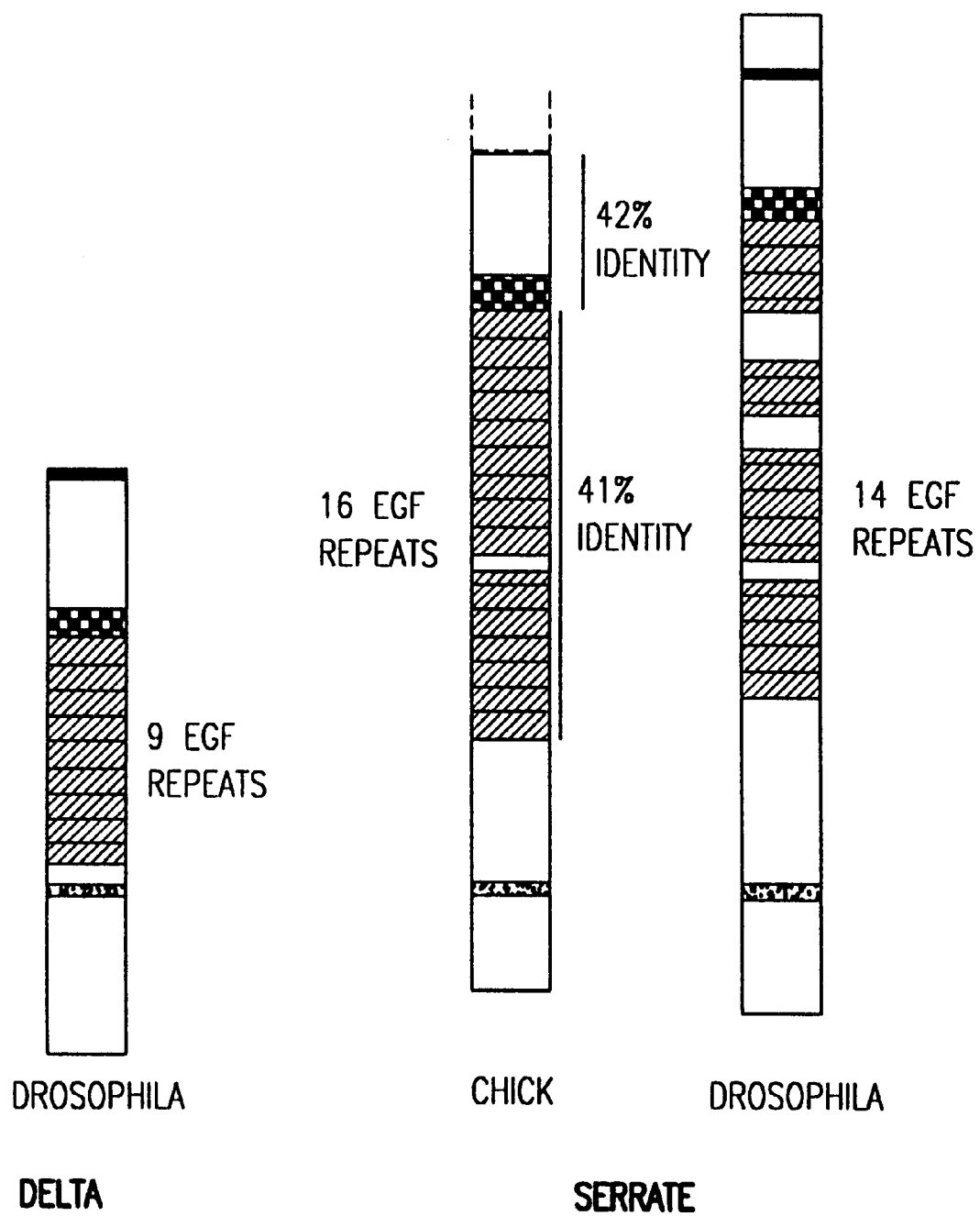

FIG. 14. Diagram showing the domain structures of Drosophila Delta and Drosophila Serrate compared with C-Serrate. The second cysteine-rich region just downstream of the EGF repeats, present only in C-Serrate and Drosophila Serrate, is not shown. Hydrophobic regions are shown in black; DSL domains are checkered and EGF-like repeats are hatched.

5. DETAILED DESCRIPTION OF THE INVENTION

The present invention relates to nucleotide sequences of Serrate genes, and amino acid sequences of their encoded proteins. The invention further relates to fragments and other derivatives, and analogs, of Serrate proteins. Nucleic acids encoding such fragments or derivatives are also within the scope of the invention. The invention provides Serrate genes and their encoded proteins of many different species. The Serrate genes of the invention include Drosophila Serrate and related genes (homologs) in species other than Drosophila. In specific embodiments, the Serrate genes and proteins are from vertebrates, or more particularly, mammals. In a preferred embodiment of the invention, the Serrate protein is a human protein. In most preferred embodiments, the Serrate protein is Human Serrate-1 or Human Serrate-2. Production of the foregoing proteins and derivatives, e.g., by recombinant methods, is provided.

The invention relates to Serrate derivatives and analogs of the invention which are functionally active, i.e., they are capable of displaying one or more known functional activities associated with a full-length (wild-type) Serrate protein. Such functional activities include but are not limited to antigenicity [ability to bind (or compete with Serrate for binding) to an anti-Serrate antibody], immunogenicity (ability to generate antibody which binds to Serrate), ability to bind (or compete with Serrate for binding) to Notch or other toporythmic proteins or fragments thereof ("adhesiveness"), ability to bind (or compete with Serrate for binding) to a receptor for Serrate. "Toporythmic proteins" as used herein, refers to the protein products of Notch, Delta, Serrate, Enhancer of split, and Deltex, as well as other members of this interacting gene family which may be identified, e.g., by virtue of the ability of their gene sequences to hybridize, or their homology to Delta, Serrate, or Notch, or the ability of their genes to display phenotypic interactions.

The invention further relates to fragments (and derivatives and analogs thereof) of Serrate which comprise one or more domains of the Serrate protein, including but not limited to the intracellular domain, extracellular domain, transmembrane domain, membrane-associated region, or one or more EGF-like (homologous) repeats of a Serrate protein, or any combination of the foregoing.

Antibodies to Serrate, its derivatives and analogs, are additionally provided.

As demonstrated infra, Serrate plays a critical role in development and other physiological processes, in particular, as a ligand to Notch, which is involved in cell fate (differentiation) determination. In particular, Serrate is believed to play a major role in determining cell fates in the central nervous system. The nucleic acid and amino acid sequences and antibodies thereto of the invention can be used for the detection and quantitation of Serrate mRNA and protein of human and other species, to study expression thereof, to produce Serrate and fragments and other derivatives and analogs thereof, in the study and manipulation of differentiation and other physiological processes. The present invention also relates to therapeutic and diagnostic methods and compositions based on Serrate proteins and nucleic acids. The invention provides for treatment of disorders of cell fate or differentiation by administration of a therapeutic compound of the invention. Such therapeutic compounds (termed herein "Therapeutics") include: Serrate proteins and analogs and derivatives (including fragments) thereof; antibodies thereto; nucleic acids encoding the Serrate proteins, analogs, or derivatives; and Serrate antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, therapeutics which antagonize, or inhibit, Notch and/or Serrate function (hereinafter "Antagonist Therapeutics") are administered for therapeutic effect. In another embodiment, therapeutics which promote Notch and/or Serrate function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or Serrate protein can be diagnosed by detecting such levels, as described more fully infra.

In a preferred aspect, a therapeutic of the invention is a protein consisting of at least a fragment (termed herein "adhesive fragment") of Serrate which mediates binding to a Notch protein or a fragment thereof.

The invention is illustrated by way of examples infra which disclose, inter alia, the cloning of D. elanogaster Serrate (Section 6); the construction and recombinant expression of a Serrate chimeric/fusion derivative and production of antibodies thereto (Section 7); the recombinant expression of Serrate, a Serrate fragment lacking the EGF-like repeats present in Serrate, and a chimeric Notch-Serrate derivative, and assays for binding to Notch (Section 8); the cloning of a mouse Serrate homolog (Section 9), the cloning of a Xenopus (frog) Serrate homolog (Section 10), the cloning of a chick Serrate homolog (Section 11), and the cloning of the human Serrate homologs Human errate-i (HJ1) and Human Serrate-2 (HJ2) (Section 12).

For clarity of disclosure, and not by way of imitation, the detailed description of the invention is ivided into the sub-sections which follow.

5.1. ISOLATION OF THE SERRATE GENES

The invention relates to the nucleotide sequences of Serrate nucleic acids. In specific embodiments, Drosophila Serrate nucleic acids comprise the cDNA sequences shown in FIG. 9 (SEQ ID NO:5), FIG. 10 (SEQ ID NO:7), FIG. 11 (SEQ ID NO:9) or FIG. 3 (SEQ ID NO:1) or the coding regions thereof, or nucleic acids encoding a Serrate protein (e.g., having the sequence of SEQ ID NO:6, 8, 10, or 2).

The invention provides nucleic acids consisting of at least 8 nucleotides (i.e., a hybridizable portion) of a Serrate sequence; in other embodiments, the nucleic acids consist of at least 10 (continuous) nucleotides, 25 nucleotides, 50 nucleotides, 100 nucleotides, 150 nucleotides, or 200 nucleotides of a Serrate sequence, or a full-length Serrate coding sequence. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of a Serrate gene.

In a specific embodiment, a nucleic acid which is hybridizable to a Serrate nucleic acid (e.g., having sequence SEQ ID NO:5), or to a nucleic acid encoding a Serrate derivative, under conditions of low stringency is provided. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5X SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2X SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

In another specific embodiment, a nucleic acid which is hybridizable to a Serrate nucleic acid under conditions of high stringency is provided. By way of example and not limitation, procedures using such conditions of high stringency are as follows: Prehybridization of filters containing DNA is carried out for 8 h to overnight at 65° C. in buffer composed of 6X SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20 X 10$^6$ cpm of $^{32}$P-labeled probe. Washing of filters is done at 37° C. for 1 h in a solution containing 2X SSC, 0.01% PVP, 0.01% Ficoll, and 0.01% BSA. This is followed by a wash in 0.1X SSC at 50° C. for 45 min before autoradiography. Other conditions of high stringency which may be used are well known in the art.

Nucleic acids encoding fragments and derivatives of Serrate proteins (see Section 5.6), and Serrate antisense nucleic acids (see Section 5.11) are additionally provided. As is readily apparent, as used herein, a "nucleic acid encoding a fragment or portion of a Serrate protein" shall be construed as referring to a nucleic acid encoding only the recited fragment or portion of the Serrate protein and not the other contiguous portions of the Serrate protein as a continuous sequence.

Fragments of Serrate nucleic acids comprising regions of homology to other toporythmic proteins are also provided. For example, the region of homology with Delta spans nucleotides 627–1290 of SEQ ID NO:1. The DSL regions (regions of homology with Drosophila Delta and Serrate) of Serrate proteins of other species are also provided. Nucleic acids encoding conserved regions between Delta and Serrate, such as those represented by Serrate amino acids 63–73, 124–134, 149–158, 195–206, 214–219, and 250–259 of SEQ ID NO:2, or by the DSL domains, or by the sequences of SEQ ID NO:20, 14, or 12, are also provided.

Specific embodiments for the cloning of a Serrate gene, presented as a particular example but not by way of limitation, follows:

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed Serrate product. In one embodiment, anti-Serrate antibodies can be used for selection.

In another preferred aspect, PCR is used to amplify the desired sequence in a genomic or cDNA library, prior to selection. Oligonucleotide primers representing known Serrate sequences can be used as primers in PCR. In a preferred aspect, the oligonucleotide primers encode at least part of the Serrate conserved segments of strong homology between Serrate and Delta. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known Serrate nucleotide sequence and the nucleic acid homolog being isolated. For cross species hybridization, low stringency conditions are preferred. For same species hybridization, moderately stringent conditions are preferred. After successful amplification of a segment of a Serrate homolog, that segment may be cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding Serrate proteins may be identified. Such a procedure is presented by way of example in various examples sections infra.

The above-methods are not meant to limit the following general description of methods by which clones of Serrate may be obtained.

Any eukaryotic cell potentially can serve as the nucleic acid source for the molecular cloning of the Serrate gene. The nucleic acid sequences encoding Serrate can be isolated from human, porcine, bovine, feline, avian, equine, canine, as well as additional primate sources, insects, etc. For example, we have amplified fragments of the appropriate size in Drosophila, mouse, Xenopus, and human, by PCR using cDNA libraries with Drosophila Serrate primers. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if a Serrate (of any species) gene or its specific RNA, or a fragment thereof, e.g., an extracellular domain (see Section 5.6), is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, receptor binding activity, in vitro aggregation activity ("adhesiveness") or antigenic properties as known for Serrate. If an antibody to Serrate is available, the Serrate protein may be identified by binding of labeled antibody to the putatively Serrate synthesizing clones, in an ELISA (enzyme-linked immunosorbent assay)-type procedure.

The Serrate gene can also be identified by mRNA selection by nucleic acid hybridization followed by in vitro translation. In this procedure, fragments are used to isolate complementary mRNAs by hybridization. Such DNA fragments may represent available, purified Serrate DNA of another species (e.g., Drosophila). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Serrate protein. A radiolabeled Serrate cDNA can be synthesized using the selected mRNA (from the adsorbed polysomes) as a template. The radiolabeled mRNA or cDNA may then be used as a probe to identify the Serrate DNA fragments from among other genomic DNA fragments.

Alternatives to isolating the Serrate genomic DNA include, but are not limited to, chemically synthesizing the gene sequence itself from a known sequence or making cDNA to the mRNA which encodes the Serrate protein. For example, RNA for CDNA cloning of the Serrate gene can be isolated from cells which express Serrate. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Serrate gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated Serrate gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The Serrate sequences provided by the instant invention include those nucleotide sequences encoding substantially the same amino acid sequences as found in native Serrate proteins, and those encoded amino acid sequences with functionally equivalent amino acids, all as described in Section 5.6 infra for Serrate derivatives.

5.2. EXPRESSION OF THE SERRATE GENES

The nucleotide sequence coding for a Serrate protein or a functionally active fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native Serrate gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the adhesive portion of the Serrate gene is expressed. In other specific embodiments, a Human Serrate gene or a sequence encoding a functionally active portion of a human Serrate gene, such as Human Serrate-I (HJ2) or Human Serrate-2 (HJ2), is expressed. In yet another embodiment, a fragment of Serrate comprising the extracellular domain, or other derivative, or analog of Serrate is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Serrate protein or peptide fragment may be regulated by a second nucleic acid sequence so that the Serrate protein or peptide Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing Serrate gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted toporythmic gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the Serrate gene is inserted within the marker gene sequence of the vector, recombinants containing the Serrate insert can be identified by the absence of the marker gene function. In the third approach, recombinant expression is expressed in a host transformed with the recombinant DNA molecule. For example, expression of a Serrate protein may be controlled by any promoter/enhancer element known in the art. Promoters which may be used to control toporythmic gene expression include, but are not limited to, the SV40 early promoter region (Bernoist and Chambon, 1981, Nature 290:304–310), the promoter contained in the 31 long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 35 315:115–122), immunoglobulin gene control region which is active in lymphoid cells (Grosschedl et al., 1984, Cell 38:647–658; Adames et al., 1985, Nature 318:533–538; vectors can be identified by assaying the foreign gene product expressed by the recombinant. Such assays can be based, for example, on the physical or functional properties of the Serrate gene product in vitro assay systems, e.g., aggregation (binding) with Notch, binding to a receptor, binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Serrate protein may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous mammalian toporythmic protein. Furthermore, different vector/host expression systems may effect processing reactions such as proteolytic cleavages to different extents.

In other specific embodiments, the Serrate protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.3. IDENTIFICATION AND PURIFICATION OF THE SERRATE GENE PRODUCTS

In particular aspects, the invention provides amino acid sequences of Serrate, preferably a human Serrate homolog, and fragments and derivatives thereof which comprise an antigenic determinant (i.e., can be recognized by an antibody) or which are otherwise functionally active, as well as nucleic acid sequences encoding the foregoing. "Functionally active" material as used herein refers to that material displaying one or more known functional activities associated with a full-length (wild-type) Serrate protein, e.g., binding to Notch or a portion thereof, binding to any other Serrate ligand, antigenicity (binding to an anti-Serrate antibody), etc.

In specific embodiments, the invention provides fragments of a Serrate protein consisting of at least 6 amino acids, 10 amino acids, 25 amino acids, 50 amino acids, or of at least 75 amino acids. In other embodiments, the proteins comprise or consist essentially of an extracellular domain, DSL domain, epidermal growth factor-like repeat (ELR) domain, one or any combination of ELRs, cysteine-rich region, transmembrane domain, or intracellular (cytoplasmic) domain, or a portion which binds to Notch, or any combination of the foregoing, of a Serrate protein. Fragments, or proteins comprising fragments, lacking some or all of the foregoing regions of a Serrate protein are also provided. Nucleic acids encoding the foregoing are provided.

Once a recombinant which expresses the Serrate gene sequence is identified, the gene product can be analyzed. This is achieved by assays based on the physical or functional properties of the product, including radioactive labelling of the product followed by analysis by gel electrophoresis, immunoassay, etc.

Once the Serrate protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once a Serrate protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In a specific embodiment of the present invention, such Serrate proteins, whether produced by recombinant DNA techniques or by chemical synthetic methods, include but are not limited to those containing, as a primary amino acid sequence, all or part of the amino acid sequence substantially as depicted in FIGS. 3, 9, 10, or 12 (SEQ ID NO:2, 6, 8, or 10, respectively), as well as fragments and other derivatives, and analogs thereof.

5.4. STRUCTURE OF THE SERRATE GENE AND PROTEIN

The structure of the Serrate gene and protein can be analyzed by various methods known in the art.

5.4.1. GENETIC ANALYSIS

The cloned DNA or cDNA corresponding to the Serrate gene can be analyzed by methods including but not limited to Southern hybridization (Southern, E. M., 1975, J. Mol. Biol. 98:503–517), northern hybridization (see e.g., Freeman et al., 1983, Proc. Natl. Acad. Sci. U.S.A. 80:4094–4098), restriction endonuclease mapping (Maniatis, T., 1982, Molecular Cloning, A Laboratory, Cold Spring Harbor, N.Y.), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a Serrate-specific probe can allow the detection of the Serrate gene in DNA from various cell types. Methods of amplification other than PCR are commonly known and can also be employed. In one embodiment, Southern hybridization can be used to determine the genetic linkage of Serrate. Northern hybridization analysis can be used to determine the expression of the Serrate gene. Various cell types, at various states of development or activity can be tested for Serrate expression. Examples of such techniques and their results are described in Section 6, infra. The stringency of the hybridization conditions for both Southern and Northern hybridization can be manipulated to ensure detection of nucleic acids with the desired degree of relatedness to the specific Serrate probe used.

Restriction endonuclease mapping can be used to roughly determine the genetic structure of the Serrate gene. In a particular embodiment, cleavage with restriction enzymes can be used to derive the restriction map shown in FIG. 2, infra. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.). The cDNA sequence of a representative Serrate gene comprises the sequence substantially as depicted in FIGS. 9 and 10, and is described in Section 12, infra.

5.4.2. PROTEIN ANALYSIS

The amino acid sequence of the Serrate protein can be derived by deduction from the DNA sequence, or alternatively, by direct sequencing of the protein, e.g., with an automated amino acid sequencer. The amino acid sequence of a representative Serrate protein comprises the sequence substantially as depicted in FIG. 9, and detailed in Section 12, infra, with the representative mature protein that shown by amino acid numbers 30-1218.

The Serrate protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the Serrate protein and the corresponding regions of the gene sequence which encode such regions. A hydrophilicity profile of the Serrate protein described in the examples section infra is depicted in FIG. 4.

Secondary, structural analysis (Chou, P. and Fasman, G., 1974, Biochemistry 13:222) can also be done, to identify regions of Serrate that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. GENERATION OF ANTIBODIES TO SERRATE PROTEINS AND DERIVATIVES THEREOF

According to the invention, Serrate protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, and an Fab expression library. In a specific embodiment, antibodies to human Serrate are produced. In another embodiment, antibodies to the extracellular domain of Serrate are produced. In another embodiment, antibodies to the intracellular domain of Serrate are produced.

Various procedures known in the art may be used for the production of polyclonal antibodies to a Serrate protein 25 or derivative or analog. In a particular embodiment, rabbit polyclonal antibodies to an epitope of the Serrate protein encoded by a sequence depicted in FIG. 9, or a subsequence thereof, can be obtained. For the production of antibody, various host animals can be immunized by injection with the native Serrate protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a Serrate protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 20 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for Serrate together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce Serrate-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for Serrate proteins, derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a Serrate protein, one may assay generated hybridomas for a product which binds to a Serrate fragment containing such domain. For selection of an antibody specific to vertebrate (e.g., human) Serrate, one can select on the basis of positive binding to vertebrate Serrate and a lack of binding to Drosophila Serrate. In another embodiment, one can select for binding to human Serrate and not to Serrate of other species.

The foregoing antibodies can be used in methods known in the art relating to the localization and activity of the protein sequences of the invention (e.g., see Section 5.7, infra), e.g., for imaging these proteins, measuring levels thereof in appropriate physiological samples, in diagnostic methods, etc.

Antibodies specific to a domain of a Serrate protein are also provided. In a specific embodiment, antibodies which bind to a Notch-binding fragment of Serrate are provided.

In another embodiment of the invention (see infra), anti-Serrate antibodies and fragments thereof containing the binding domain are Therapeutics.

5.6. SERRATE PROTEINS, DERIVATIVES AND ANALOGS

The invention further relates to Serrate proteins, and derivatives (including but not limited to fragments) and analogs of Serrate proteins. Nucleic acids encoding Serrate protein derivatives and protein analogs are also provided. In one embodiment, the Serrate proteins are encoded by the Serrate nucleic acids described in Section 5.1 supra. In particular aspects, the proteins, derivatives, or analogs are of fly, frog, mouse, rat, pig, cow, dog, monkey, or human Serrate proteins.

The production and use of derivatives and analogs related to Serrate are within the scope of the present invention. In a specific embodiment, the derivative or analog is functionally active, i.e., capable of exhibiting one or more functional activities associated with a full-length, wild-type Serrate protein. As one example, such derivatives or analogs which have the desired immunogenicity or antigenicity can be used, for example, in immunoassays, for immunization, for inhibition of Serrate activity, etc. Such molecules which retain, or alternatively inhibit, a desired Serrate property, e.g., binding to Notch or other toporythmic proteins, binding to a cell-surface receptor, can be used as inducers, or inhibitors, respectively, of such property and its physiological correlates. A specific embodiment relates to a Serrate fragment that can be bound by an anti-Serrate antibody but cannot bind to a Notch protein or other toporythmic protein. Derivatives or analogs of Serrate can be tested for the desired activity by procedures known in the art, including but not limited to the assays described in Section 5.7.

In particular, Serrate derivatives can be made by altering Serrate sequences by substitutions, additions or deletions that provide for functionally equivalent molecules. Due to the degeneracy of nucleotide coding sequences, other DNA sequences which encode substantially the same amino acid sequence as a Serrate gene may be used in the practice of the present invention. These include but are not limited to nucleotide sequences comprising all or portions of Serrate genes which are altered by the substitution of different codons that encode a functionally equivalent amino acid residue within the sequence, thus producing a silent change. Likewise, the Serrate derivatives of the invention include, but are not limited to, those containing, as a primary amino acid sequence, all or part of the amino acid sequence of a Serrate protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a Serrate protein consisting of at least 10 (continuous) amino acids of the Serrate protein is provided. In other embodiments, the fragment consists of at least 20 or 50 amino acids of the Serrate protein. In specific embodiments, such fragments are not larger than 35, 100 or 200 amino acids. Derivatives or analogs of Serrate include but are not limited to those peptides which are substantially homologous to Serrate or fragments thereof (e.g., at least 30% identity over an amino acid sequence of identical size) or whose encoding nucleic acid is capable of hybridizing to a coding Serrate sequence.

The Serrate derivatives and analogs of the invention can be produced by various methods known in the art. The manipulations which result in their production can occur at the gene or protein level. For example, the cloned Serrate gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of Serrate, care should be taken to ensure that the modified gene remains within the same translational reading frame as Serrate, uninterrupted by translational stop signals, in the gene region where the desired Serrate activity is encoded.

Additionally, the Serrate-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia), etc.

Manipulations of the Serrate sequence may also be made at the protein level. Included within the scope of the invention are Serrate protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Serrate can be chemically synthesized. For example, a peptide corresponding to a portion of a Serrate protein which comprises the desired domain (see Section 5.6.1), or which mediates the desired aggregation activity in vitro, or binding to a receptor, can be synthesized by use of a peptide synthesizer. Furthermore, if desired, nonclassical amino acids or chemical amino acid analogs can be introduced as a substitution or addition into the Serrate sequence. Nonclassical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the Serrate derivative is a chimeric, or fusion, protein comprising a Serrate protein or fragment thereof (preferably consisting of at least a domain or motif of the Serrate protein, or at least 10 amino acids of the Serrate protein) joined at its amino- or carboxy-terminus via a peptide bond to an amino acid sequence of a different protein. In one embodiment, such a chimeric protein is produced by recombinant expression of a nucleic acid encoding the protein (comprising a Serrate-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, a chimeric nucleic acid encoding a mature Serrate protein with a heterologous signal sequence is expressed such that the chimeric protein is expressed and processed by the cell to the mature Serrate protein. As another example, and not by way of limitation, a recombinant molecule can be constructed according to the invention, comprising coding portions of both Serrate and another toporythmic gene, e.g., Delta. The encoded protein of such a recombinant molecule could exhibit properties associated with both Serrate and Delta and portray a novel profile of biological activities, including agonists as well as antagonists. The primary sequence of Serrate and Delta may also be used to predict tertiary structure of the molecules using computer simulation (Hopp and Woods, 1981, Proc. Natl. Acad. Sci. U.S.A. 78:3824–3828); Serrate/Delta chimeric recombinant genes could be designed in light of correlations between tertiary structure and biological function. Likewise, chimeric genes comprising portions of Serrate fused to any heterologous protein-encoding sequences may be constructed. A specific embodiment relates to a chimeric protein comprising a fragment of Serrate of at least ten amino acids. A particular example of the construction and expression of a Notch-Serrate chimera is presented in Section 8 hereof. A particular example of another Serrate fusion protein is presented in Section 7 hereof.

In another specific embodiment, the Serrate derivative is a fragment of Serrate comprising a region of homology with another toporythmic protein. As used herein, a region of a first protein shall be considered "homologous" to a second protein when the amino acid sequence of the region is at least 30% identical or at least 75% either identical or involving conservative changes, when compared to any sequence in the second protein of an equal number of amino acids as the number contained in the region. For example, such a Serrate fragment can comprise one or more regions homologous to Delta, including but not limited to Drosophila Serrate amino acids 63-73, 124-134, 149-158, 195-206, 214-219, 250-259, or 79-282 (or 79-246, excluding the partial EGF-like repeat) (see FIGS. 3, 7), or portions of Serrate of other species most homologous to the foregoing sequences, or DSL domains or portions thereof.

Other specific embodiments of derivatives and analogs are described in the subsections below and examples sections infra.

5.6.1. DERIVATIVES OF SERRATE CONTAINING ONE OR MORE DOMAINS OF THE PROTEIN

In a specific embodiment, the invention relates to Serrate derivatives and analogs, in particular Serrate fragments and derivatives of such fragments, that comprise, or alternatively consist of, one or more domains of the Serrate protein, including but not limited to the extracellular domain, DSL domain, ELR domain, cysteine rich domain, transmembrane domain, intracellular domain, membrane-associated region, and one or more of the EGF-like repeats (ELR) of the Serrate protein, or any combination of the foregoing. In particular examples relating to the human and chick Serrate proteins, such domains are identified in Examples Section 12 and 11, respectively. In particular examples relating to the Drosophila Serrate protein (see example 6), such domains are identified as follows, with reference to FIG. 3: extracellular domain, amino acids numbers (AA) 81–541; transmembrane domain, AA 1221–1245; intracellular domain, AA 1246–1404; membrane-associated region, AA 542–564; ELR (see underscored sequences in FIG. 3).

In a specific embodiment, relating to a Serrate protein of a species other than *D. melanogaster*, the molecules comprising specific fragments of Serrate are those comprising fragments in the respective Serrate protein most homologous to specific fragments of the Drosophila Serrate and/or Delta proteins. In particular embodiments, such a molecule comprises or consists of the amino acid sequences of SEQ ID NO:12, 14 or 20. Alternatively, a fragment comprising a domain of a Serrate homolog can be identified by protein analysis methods as described in Section 5.3.2 or 6.

Serrate derivatives which are Serrate fragments and chimeric/fusion proteins are described by way of example in Sections 7 and 8 infra.

5.6.2. DERIVATIVES OF SERRATE THAT MEDIATE BINDING TO TOPORYTHMIC PROTEIN DOMAINS

The invention also provides for Serrate fragments, and analogs or derivatives of such fragments, which mediate binding to toporythmic proteins (and thus are termed herein "adhesive"), and nucleic acid sequences encoding the foregoing.

In a specific embodiment, the adhesive fragment of Serrate is that comprising the portion of Serrate most homologous to about amino acid numbers 85-283 or 79-282 of the Drosophila Serrate sequence (see FIG. 3).

In a particular embodiment, the adhesive fragment of a Serrate protein comprises the DSL domain, or a portion thereof. Subfragments within the DSL domain that mediate binding to Notch can be identified by analysis of constructs expressing deletion mutants.

The ability to bind to a toporythmic protein (preferably Notch) can be demonstrated by in vitro aggregation assays with cells expressing such a toporythmic protein as well as cells expressing Serrate or a Serrate derivative (See Section 5.7). That is, the ability of a Serrate fragment to bind to a Notch protein can be demonstrated by detecting the ability of the Serrate fragment, when expressed on the surface of a first cell, to bind to a Notch protein expressed on the surface of a second cell.

The nucleic acid sequences encoding toporythmic proteins or adhesive domains thereof, for use in such assays, can be isolated from human, porcine, bovine, feline, avian, equine, canine, or insect, as well as primate sources and any other species in which homologs of known toporythmic genes can be identified.

5.7. ASSAYS OF SERRATE PROTEINS, DERIVATIVES AND ANALOGS

The functional activity of Serrate proteins, derivatives and analogs can be assayed by various methods.

For example, in one embodiment, where one is assaying for the ability to bind or compete with wild-type Serrate for binding to anti-Serrate antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where one is assaying for the ability to mediate binding to a toporythmic protein, e.g., Notch, one can carry out an in vitro aggregation assay such as described infra in Section 8.2.1 (see also Fehon et al., 1990, Cell 61:523–534; Rebay et al., 1991, Cell 67:687–699).

In another embodiment, where a receptor for Serrate is identified, receptor binding can be assayed, e.g., by means well-known in the art. In another embodiment, physiological correlates of Serrate binding to cells expressing a Serrate receptor (signal transduction) can be assayed.

In another embodiment, in insect or other model systems, genetic studies can be done to study the phenotypic effect of a Serrate mutant that is a derivative or analog of wild-type Serrate (see Section 6, infra).

Other methods will be known to the skilled artisan and are within the scope of the invention.

5.8. THERAPEUTIC USES

The invention provides for treatment of disorders of cell fate or differentiation by administration of a therapeutic compound of the invention. Such therapeutic compounds (termed herein "Therapeutics") include: Serrate proteins and analogs and derivatives (including fragments) thereof (e.g., as described hereinabove); antibodies thereto (as described hereinabove); nucleic acids encoding the Serrate proteins, analogs, or derivatives (e.g., as described hereinabove); and Serrate antisense nucleic acids. As stated supra, the Antagonist Therapeutics of the invention are those Therapeutics which antagonize, or inhibit, a Serrate function and/or Notch function (since Serrate is a Notch ligand). Such Antagonist Therapeutics are most preferably identified by use of known convenient in vitro assays, e.g., based on their ability to inhibit binding of Serrate to another protein (e.g., a Notch protein), or inhibit any known Notch or Serrate function as preferably assayed in vitro or in cell culture, although genetic assays (e.g., in Drosophila) may also be employed. In a preferred embodiment, the Antagonist Therapeutic is a protein or derivative thereof comprising a functionally active fragment such as a fragment of Serrate which mediates binding to Notch, or an antibody thereto. In other specific embodiments, such an Antagonist Therapeutic is a nucleic acid capable of expressing a molecule comprising a fragment of Serrate which binds to Notch, or a Serrate antisense nucleic acid (see Section 5.11 herein). It should be noted that preferably, suitable in vitro or in vivo assays, as described infra, should be utilized to determine the effect of a specific Therapeutic and whether its administration is indicated for treatment of the affected tissue, since the developmental history of the tissue may determine whether an Antagonist or Agonist Therapeutic is desired.

In addition, the mode of administration, e.g., whether administered in soluble form or administered via its encoding nucleic acid for intracellular recombinant expression, of the Serrate protein or derivative can affect whether it acts as an agonist or antagonist.

In another embodiment of the invention, a nucleic acid containing a portion of a Serrate gene is used, as an Antagonist Therapeutic, to promote Serrate inactivation by homologous recombination (Koller and Smithies, 1989, Proc. Natl. Acad. Sci. USA 86:8932–8935; Zijlstra et al., 1989, Nature 342:435–438).

The Agonist Therapeutics of the invention, as described supra, promote Serrate function. Such Agonist Therapeutics include but are not limited to proteins and derivatives comprising the portions of Notch that mediate binding to Serrate, and nucleic acids encoding the foregoing (which can be administered to express their encoded products in vivo).

Further descriptions and sources of Therapeutics of the inventions are found in Sections 5.1 through 5.7 herein.

Molecules which retain, or alternatively inhibit, a desired Serrate property, e.g., binding to Notch, binding to an intracellular ligand, can be used therapeutically as inducers, or inhibitors, respectively, of such property and its physiological correlates. In a specific embodiment, a peptide (e.g., in the range of 10–50 or 15–25 amino acids; and particularly of about 10, 15, 20 or 25 amino acids) containing the sequence of a portion of Serrate which binds to Notch is used to antagonize Notch function. In a specific embodiment, such an Antagonist Therapeutic is used to treat or prevent human or other malignancies associated with increased Notch expression (e.g., cervical cancer, colon cancer, breast cancer, squamous adenocarcimas (see infra)). Derivatives or analogs of Serrate can be tested for the desired activity by procedures known in the art, including but not limited to the assays described in the examples infra. For example, molecules comprising Serrate fragments which bind to Notch EGF-repeats (ELR) 11 and 12 and which are smaller than a DSL domain, can be obtained and selected by expressing deletion mutants and assaying for binding of the expressed product to Notch by any of the several methods (e.g., in vitro cell aggregation assays, interaction trap system), some of which are described in the Examples Sections infra. In one specific embodiment, peptide libraries can be screened to select a peptide with the desired activity; such screening can be carried out by assaying, e.g., for binding to Notch or a molecule containing the Notch ELR 11 and 12 repeats.

The Agonist and Antagonist Therapeutics of the invention have therapeutic utility for disorders of cell fate. The Agonist Therapeutics are administered therapeutically (including prophylactically): (1) in diseases or disorders involving an absence or decreased (relative to normal, or desired) levels of Notch or Serrate function, for example, in patients where Notch or Serrate protein is lacking, genetically defective, biologically inactive or underactive, or underexpressed; and (2) in diseases or disorders wherein in vitro (or in vivo) assays (see infra) indicate the utility of Serrate agonist administration. The absence or decreased levels in Notch or Serrate function can be readily detected, e.g., by obtaining a patient tissue sample (e.g., from biopsy tissue) and assaying it in vitro for protein levels, structure and/or activity of the expressed Notch or Serrate protein. Many methods standard in the art can be thus employed, including but not limited to immunoassays to detect and/or visualize Notch or Serrate protein (e.g., western blot, immunoprecipitation followed by sodium dodecyl sulfate polyacrylamide gel electrophoresis, immunocytochemistry, etc.) and/or hybridization assays to detect Notch or Serrate expression by detecting and/or visualizing respectively Notch or Serrate MRNA (e.g., Northern assays, dot blots, in situ hybridization, etc.)

In vitro assays which can be used to determine whether administration of a specific Agonist Therapeutic or Antagonist Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. In a specific aspect, the malignant cell cultures are separately exposed to (1) an Agonist Therapeutic, and (2) an Antagonist Therapeutic; the result of the assay can indicate which type of Therapeutic has therapeutic efficacy.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.8.1 through 5.8.3 infra.

In another specific embodiment, a Therapeutic is indicated for use in treating nerve injury or a nervous system degenerative disorder (see Section 5.8.2) which exhibits in vitro promotion of nerve regeneration/neurite extension from nerve cells of the affected patient type.

In addition, administration of an Antagonist Therapeutic of the invention is also indicated in diseases or disorders determined or known to involve a Notch or Serrate dominant activated phenotype ("gain of function" mutations.) Administration of an Agonist Therapeutic is indicated in diseases or disorders determined or known to involve a Notch or Serrate dominant negative phenotype ("loss of function" mutations). The functions of various structural domains of the Notch protein have been investigated in vivo, by ectopically expressing a series of Drosophila Notch deletion mutants under the hsp70 heat-shock promoter, as well as eye-specific promoters (see Rebay et al., 1993, Cell 74:319–329). Two classes of dominant phenotypes were observed, one suggestive of Notch loss-of function mutations and the other of Notch gain-of-function mutations. Dominant "activated" phenotypes resulted from overexpression of a protein lacking most extracellular sequences, while dominant "negative" phenotypes resulted from overexpression of a protein lacking most intracellular sequences. The results indicated that Notch functions as a receptor whose extracellular domain mediates ligand-binding, resulting in the transmission of developmental signals by the cytoplasmic domain. We have shown that Serrate binds to the Notch ELR 11 and 12 (see Section 8 infra).

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The Antagonist Therapeutics are administered therapeutically (including prophylactically): (1) in diseases or disorders involving increased (relative to normal, or desired) levels of Notch or Serrate function, for example, where the Notch or Serrate protein is overexpressed or overactive; and (2) in diseases or disorders wherein in vitro (or in vivo) assays indicate the utility of Serrate antagonist administration. The increased levels of Notch or Serrate function can be readily detected by methods such as those described above, by quantifying protein and/or RNA. In vitro assays with cells of patient tissue sample or the appropriate cell line or cell type, to determine therapeutic utility, can be carried out as described above.

5.8.1. MALIGNANCIES

Malignant and pre-neoplastic conditions which can be tested as described supra for efficacy of intervention with Antagonist or Agonist Therapeutics, and which can be treated upon thus observing an indication of therapeutic utility, include but are not limited to those described below in Sections 5.8.1 and 5.9.1.

Malignancies and related disorders, cells of which type can be tested in vitro (and/or in vivo), and upon observing the appropriate assay result, treated according to the present invention, include but are not limited to those listed in Table 1 (for a review of such disorders, see Fishman et al., 1985, Medicine, 2d Ed., J.B. Lippincott Co., Philadelphia):

TABLE 1

MALIGNANCIES AND RELATED DISORDERS

Leukemia
    acute leukemia
        acute lymphocytic leukemia
        acute myelocytic leukemia
            myeloblastic TABLE 1-continued

MALIGNANCIES AND RELATED DISORDERS promyelocytic
            myelomonocytic
            monocytic
            erythroleukemia
    chronic leukemia
        chronic myelocytic (granulocytic) leukemia
        chronic lymphocytic leukemia
Polycythemia vera
Lymphoma
    Hodgkin's disease
    non-Hodgkin's disease
Multiple myeloma
Waldenström's macroglobulinemia
Heavy chain disease
Solid tumors
    sarcomas and carcinomas
        fibrosarcoma
        myxosarcoma
        liposarcoma
        chondrosarcoma
        osteogenic sarcoma
        chordoma
        angiosarcoma
        endotheliosarcoma
        lymphangiosarcoma
        lymphangioendotheliosarcoma
        synovioma
        mesothelioma
        Ewing's tumor
        leiomyosarcoma
        rhabdomyosarcoma
        colon carcinoma
        pancreatic cancer
        breast cancer
        ovarian cancer
        prostate cancer
        squamous cell carcinoma
        basal cell carcinoma
        adenocarcinoma
        sweat gland carcinoma
        sebaceous gland carcinoma
        papillary carcinoma
        papillary adenocarcinomas
        cystadenocarcinoma
        medullary carcinoma
        bronchogenic carcinoma
        renal cell carcinoma
        hepatoma
        bile duct carcinoma
        choriocarcinoma
        seminoma
        embryonal carcinoma
        Wilms' tumor
        cervical cancer
        testicular tumor
        lung carcinoma
        small cell lung carcinoma
        bladder carcinoma
        epithelial carcinoma
        glioma
        astrocytoma
        medulloblastoma
        craniopharyngioma
        ependymoma
        pinealoma
        hemangioblastoma
        acoustic neuroma
        oligodendroglioma
        menangioma
        melanoma
        neuroblastoma
        retinoblastoma In specific embodiments, malignancy or dysproliferative changes (such as metaplasias and dysplasias) are treated or prevented in epithelial tissues such as those in the cervix, esophagus, and lung.

Malignancies of the colon and cervix exhibit increased expression of human Notch relative to such non-malignant tissue (see PCT Publication no. WO 94/07474 published Apr. 14, 1994, incorporated by reference herein in its entirety). Thus, in specific embodiments, malignancies or premalignant changes of the colon or cervix are treated or prevented by administering an effective amount of an Antagonist Therapeutic, e.g., a Serrate derivative, that antagonizes Notch function. The presence of increased Notch expression in colon, and cervical cancer suggests that many more cancerous and hyperproliferative conditions exhibit upregulated Notch. Thus, in specific embodiments, various cancers, e.g., breast cancer, squamous adenocarcinoma, seminoma, melanoma, and lung cancer, and premalignant changes therein, as well as other hyperproliferative disorders, can be treated or prevented by administration of an Antagonist Therapeutic that antagonizes Notch function.

5.8.2. NERVOUS SYSTEM DISORDERS

Nervous system disorders, involving cell types which can be tested as described supra for efficacy of intervention with Antagonist or Agonist Therapeutics, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons (see also Section 5.8). For example, and not by way of limitation, Therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo. Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.8.3. TISSUE REPAIR AND REGENERATION

In another embodiment of the invention, a Therapeutic of the invention is used for promotion of tissue regeneration and repair, including but not limited to treatment of benign dysproliferative disorders. Specific embodiments are directed to treatment of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), and baldness (a condition in which terminally differentiated hair follicles (a tissue rich in Notch) fail to function properly). In another embodiment, a Therapeutic of the invention is used to treat degenerative or traumatic disorders of the sensory epithelium of the inner ear.

5.9. PROPHYLACTIC USES

5.9.1. MALIGNANCIES

The Therapeutics of the invention can be administered to prevent progression to a neoplastic or malignant state, including but not limited to those disorders listed in Table 1. Such administration is indicated where the Therapeutic is shown in assays, as described supra, to have utility for treatment or prevention of such disorder. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113) etc.)

In another specific embodiment, an Antagonist Therapeutic of the invention is administered to a human patient to prevent progression to breast, colon, or cervical cancer.

5.9.2. OTHER DISORDERS

In other embodiments, a Therapeutic of the invention can be administered to prevent a nervous system disorder described in Section 5.8.2, or other disorder (e.g., liver cirrhosis, psoriasis, keloids, baldness) described in Section 5.8.3.

5.10. DEMONSTRATION OF THERAPEUTIC OR PROPHYLACTIC UTILITY

The Therapeutics of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.11. ANTISENSE REGULATION OF SERRATE EXPRESSION

The present invention provides the therapeutic or prophylactic use of nucleic acids of at least six or of at least ten nucleotides that are antisense to a gene or cDNA encoding Serrate or a portion thereof. "Antisense" as used herein refers to a nucleic acid capable of hybridizing to a portion of a Serrate RNA (preferably mRNA) by virtue of some sequence complementarity. Such antisense nucleic acids have utility as Antagonist Therapeutics of the invention, and can be used in the treatment or prevention of disorders as described supra in Section 5.8 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the Serrate antisense nucleic acids provided by the instant invention can be used for the treatment of tumors or other disorders, the cells of which tumor type or disorder can be demonstrated (in vitro or in vivo) to express a Serrate gene or a Notch gene. Such demonstration can be by detection of RNA or of protein.

The invention further provides pharmaceutical compositions comprising an effective amount of the Serrate antisense nucleic acids of the invention in a pharmaceutically acceptable carrier, as described infra in Section 5.12. Methods for treatment and prevention of disorders (such as those described in Sections 5.8 and 5.9) comprising administering the pharmaceutical compositions of the invention are also provided.

In another embodiment, the invention is directed to methods for inhibiting the expression of a Serrate nucleic acid sequence in a prokaryotic or eukaryotic cell comprising providing the cell with an effective amount of a composition comprising an antisense Serrate nucleic acid of the invention.

Serrate antisense nucleic acids and their uses are described in detail below.

5.11.1. SERRATE ANTISENSE NUCLEIC ACIDS

The Serrate antisense nucleic acids are of at least six nucleotides and are preferably oligonucleotides (ranging preferably from 10 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a Serrate antisense oligonucleotide is provided, preferably of single-stranded DNA. In a most preferred aspect, such an oligonucleotide comprises a sequence antisense to the sequence encoding an SH3 binding domain or a Notch-binding domain of Serrate, most preferably, of a human Serrate homolog. The oligonucleotide may be modified at any position on its structure with substituents generally known in the art.

The Serrate antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, the Serrate antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the Serrate antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Serrate antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the Serrate antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript specific to a Serrate gene, preferably a human Serrate gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded Serrate antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a Serrate RNA it may contain and still form a stable duplex (or triplex, as the case may be). One skilled in the art can ascertain a tolerable degree of mismatch by use of standard procedures to determine the melting point of the hybridized complex.

5.11.2. THERAPEUTIC UTILITY OF SERRATE ANTISENSE NUCLEIC ACIDS

The Serrate antisense nucleic acids can be used to treat (or prevent) malignancies or other disorders, of a cell type which has been shown to express Serrate or Notch. In specific embodiments, the malignancy is cervical, breast, or colon cancer, or squamous adenocarcinoma. Malignant, eoplastic, and pre-neoplastic cells which can be tested for such expression include but are not limited to those escribed supra in Sections 5.8.1 and 5.9.1. In a preferred embodiment, a single-stranded DNA antisense Serrate oligonucleotide is used.

Malignant (particularly, tumor) cell types which express Serrate or Notch RNA can be identified by various methods known in the art. Such methods include but are not limited to hybridization with a Serrate or Notch-specific nucleic acid (e.g. by Northern hybridization, dot blot hybridization, in situ hybridization), observing the ability of RNA from the cell type to be translated in vitro into Notch or Serrate, immunoassay, etc. In a preferred aspect, primary tumor tissue from a patient can be assayed for Notch or Serrate expression prior to treatment, e.g., by immunocytochemistry or in situ hybridization.

Pharmaceutical compositions of the invention (see Section 5.12), comprising an effective amount of a Serrate antisense nucleic acid in a pharmaceutically acceptable carrier, can be administered to a patient having a malignancy which is of a type that expresses Notch or Serrate RNA or protein.

The amount of Serrate antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Serrate antisense nucleic acids are administered via liposomes, microparticles, or microcapsules. In various embodiments of the invention, it may be useful to use such compositions to achieve sustained release of the Serrate antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

5.12. THERAPEUTIC/PROPHYLACTIC ADMINISTRATION AND COMPOSITIONS

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, chickens, etc., and is preferably a mammal, and most preferably human.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 15 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

In specific embodiments directed to treatment or prevention of particular disorders, preferably the following forms of administration are used:

| Disorder | Preferred Forms of Administration |
| --- | --- |
| Cervical cancer | Topical |
| Gastrointestinal cancer | Oral; intravenous |
| Lung cancer | Inhaled; intravenous |
| Leukemia | Intravenous; extracorporeal |
| Metastatic carcinomas | Intravenous; oral |
| Brain cancer | Targeted; intravenous; intrathecal |
| Liver cirrhosis | Oral; intravenous |
| Psoriasis | Topical |
| Keloids | Topical |
| Baldness | Topical |
| Spinal cord injury | Targeted; intravenous; intrathecal |
| Parkinson's disease | Targeted; intravenous; intrathecal |
| Motor neuron disease | Targeted; intravenous; intrathecal |
| Alzheimer's disease | Targeted; intravenous; intrathecal |

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. optionally associated with such container(s) can be a notice in the form prescribed by a governmental agency regulating the manufacture, use or sale of pharmaceuticals or biological products, which notice reflects approval by the agency of manufacture, use or sale for human administration.

5.13. DIAGNOSTIC UTILITY

Serrate proteins, analogues, derivatives, and subsequences thereof, Serrate nucleic acids (and sequences complementary thereto), anti-Serrate antibodies, have uses in diagnostics. Such molecules can be used in assays, such as immunoassays, to detect, prognose, diagnose, or monitor various conditions, diseases, and disorders affecting Serrate expression, or monitor the treatment thereof. In particular, such an immunoassay is carried out by a method comprising contacting a sample derived from a patient with an anti-Serrate antibody under conditions such that immunospecific binding can occur, and detecting or measuring the amount of any immunospecific binding by the antibody. In a specific aspect, such binding of antibody, in tissue sections, preferably in conjunction with binding of anti-Notch antibody can be used to detect aberrant Notch and/or Serrate localization or aberrant levels of Notch-Serrate colocalization in a disease state. In a specific embodiment, antibody to Serrate can be used to assay in a patient tissue or serum sample for the presence of Serrate where an aberrant level of Serrate is an indication of a diseased condition. Aberrant levels of Serrate binding ability in an endogenous Notch protein, or aberrant levels of binding ability to Notch (or other Serrate ligand) in an endogenous Serrate protein may be indicative of a disorder of cell fate (e.g., cancer, etc.) By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Serrate genes and related nucleic acid sequences and subsequences, including complementary sequences, and other toporythmic gene sequences, can also be used in hybridization assays. Serrate nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in Serrate expression and/or activity as described supra. In particular, such a hybridization assay is carried out by a method comprising contacting a sample containing nucleic acid with a nucleic acid probe capable of hybridizing to Serrate DNA or RNA, under conditions such that hybridization can occur, and detecting or measuring any resulting hybridization.

Additionally, since Serrate binds to Notch, Serrate or a binding portion thereof can be used to assay for the presence and/or amounts of Notch in a sample, e.g., in screening for malignancies which exhibit increased Notch expression such as colon and cervical cancers.

6. THE GENE SERRATE ENCODES A PUTATIVE EGF-LIKE TRANSMEMBRANE PROTEIN ESSENTIAL FOR PROPER ECTODERMAL DEVELOPMENT IN DROSOPHILA MELANOGASTER

As described in the example herein (see Fleming et al., 1990, Genes Dev. 4:2188–2201), mutations in the third chromosome gene Serrate are shown to display genetic interactions with specific alleles of the neurogenic locus Notch, which encodes a transmembrane protein with epidermal growth factor homology. The locus Serrate displays a striking phenotypic interaction with a specific Notch allele known to affect postembryonic development. We present the molecular cloning of Serrate and show that it encodes two coordinately-expressed transcripts from a genomic interval greater than 30 kilobases in length. The deduced protein product of 1404 amino acids contains a single transmembrane domain and 14 epidermal growth factor-like repeats. Whole-mount in situ hybridization analysis revealed complex temporal and spatial patterns of RNA expression consistent with the epidermal and neuronal defects observed in mutant embryos.

We demonstrate that the Serrate locus encodes an essential function, the loss of which results in embryonic lethality brought about by the disruption of both neuronal and epidermal tissues. Serrate is likely to represent an element in a network of interacting molecules operating at the cell surface during the differentiation of certain tissues.

6.1. RESULTS

6.1.1. THE SERRATE AND NOTCH GENES INTERACT PHENOTYPICALLY

In the course of genetic crosses designed to detect interactions between the Notch locus and other genes in Drosophila, a dramatic phenotypic interaction was observed between the Notch allele notchoid (nd) and the third chromosome mutation Serrate (designated $Ser^D$ herein). The recessive nd mutation, which is associated with an amino acid substitution in the intracellular portion of the Notch protein (Xu et al., 1990, Genes Dev. 4:464–475), causes wing notches in the adult (see FIG. 1b; compare to wildtype, FIG. 1a). The $Ser^D$ mutation is dominant and in heterozygous condition produces an adult wing blade very similar to that of nd animals (compare FIGS. 1b and 1c). The phenotypic interaction seen in nd/Y; $Ser^D$/+ males is characterized by loss of anterior and posterior wing margins, as well as loss of distal wing blade tissue. Concomitant with this loss, thickening of the L3 and L5 wing veins is observed (see FIG. 1d).

Even though both the $Ser^D$ and nd mutations affect wing blade development, the interaction appears to be synergistic because a novel phenotype is seen, that is, rather than just additive effects. To explore this question of synergy further, we constructed flies carrying genetic duplications of Notch$^+$. Animals carrying an extra copy of Notch$^+$ normally exhibit a Confluens phenotype characterized by wing vein thickening. Surprisingly, animals bearing $Ser^D$ and an extra copy of Notch$^+$ have essentially wild-type wings (FIG. 1e), that is, both the $Ser^D$ wing nicking and the Confluens phenotypes are suppressed in this combination. This interaction was noted using both Dp(1;2)51b (a large genetic duplication of 3C1-2; 3D6 including N$^+$) and CosP479BE [(N$^+$)(86E5-6), a cosmid construct containing only the N$^+$ gene (Ramos et al., 1989, Genetics 123:337:348)].

Because the $Ser^D$ mutation is neomorphic, the interactions observed between $Ser^D$ and Notch mutations might not be representative of interactions normally occurring between these gene products. We therefore examined the phenotypes of nd males heterozygous for Df(3R) Ser$^{+82/24}$ (nd/Y; Df(3R)Ser$^{+82/24}$/+). These animals exhibit a significantly increased mutant wing phenotype as compared to nd alone (not shown). Thus, it appears that Notch and $Ser^D$ mutually influence each other's phenotypic expression.

6.1.2. GENETIC CHARACTERIZATION OF SERRATE

Figure 1D:
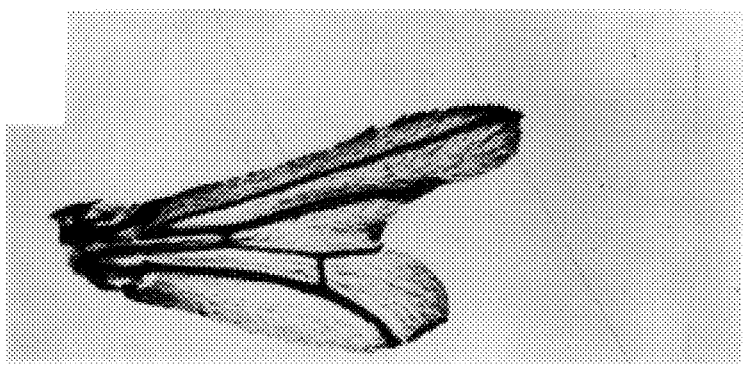
Figure 1E:
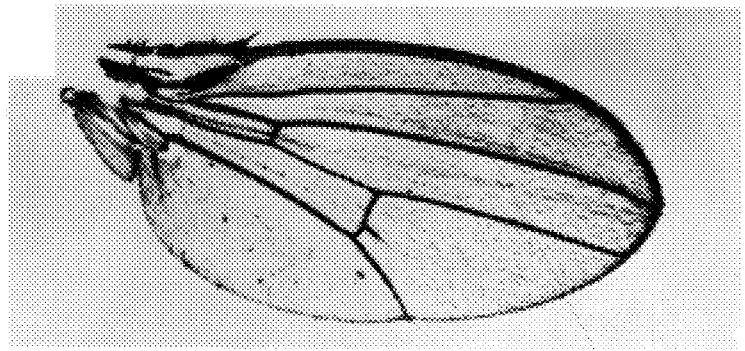
Figure 1F:
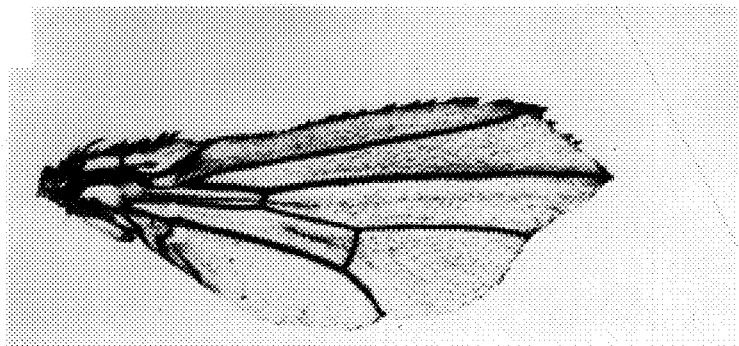

Previous genetic characterizations have demonstrated that the $Ser^D$ mutation maps to the 97F region of the polytene chromosomes and is neomorphic, producing the dominant wing nicking phenotype shown in FIG. 1d (Belt, 1971, Drosophila Inf. Serv. 46:116; P. Lewis, Yale University; unpubl.). The neomorphic nature is demonstrated genetically via the insensitivity of the $Ser^D$ phenotype to the number of wildtype ($Ser^+$) copies present, that is $Ser^D/+/+$ displays a phenotype similar to $Ser^D/+$ and to $Ser^D/$ Deficiency (P. Lewis, pers. comm.). Flies with only one copy of wild-type $Ser^+$ (i.e., individuals heterozygous for a wild-type allele over deficiencies) are phenotypically wild-type, demonstrating that reduction of gene product (i.e., haploinsufficiency) is not causing the dominant phenotype. Finally, when the $Ser^D$ mutation is homozygous, viable adults are produced that display a more severe wing phenotype than heterozygous $Ser^D/+$ animals (FIG. 1f). Thus, the expression of the $Ser^D$ wing phenotype appears to be directly related to the expression of a mutant or novel gene product rather than to $Ser^+$ gene dosage.

In an effort to obtain amorphic alleles of Serrate, we used X-ray mutagenesis to produce phenotypic revertants of the dominant mutation (see Section 6.3 for details). All five of the revertants of the $Ser^D$ mutation are lethal when homozygous and, consistent with the deficiency phenotypes, are phenotypically wild-type when heterozygous with a wild-type chromosome. Complementation tests revealed that the $Ser^{revertants}$ are allelic. Moreover, transheterozygotes of nd with two different $Ser^{revertant}$ alleles (nd/Y; $Ser^{rev2-3}/+$ and nd/Y; $Ser^{rev2-11}/+$) exhibit an enhanced mutant wing phenotype as compared to nd mutants, in agreement with the $Ser^D$-Notch interactions noted previously.

These complementation tests were extended to include another dominant mutation, Beaded of Goldschmidt ($Bd^G$), which also maps to the 97F region. Heterozygous adults bearing the $Bd^G$ mutation display a wing nicking phenotype that is more severe than that observed in $Ser^D$ heterozygotes (data not shown). Moreover, the $Bd^G$ mutation, unlike $Ser^D$, is homozygous lethal. Finally, three alleles ($Bd^{43.5}$, $Bd^{862.5}$, and $pll^{11}$) of a lethal complementation group isolated in K. Anderson's laboratory were shown to be allelic to $Bd^G$ (P. Hecht, unpubl.; a complete listing of the alleles used and their descriptions is provided in Section 6.3). Although transheterozygotes of $Ser^D$ and $Bd^G$ are viable, it is interesting to note that Df(3R)$Ser^{+82f24}$ and most of the $Ser^{revertants}$ fail to complement the $Bd^G$ mutation for viability. The exception is the $Ser^{rev2-3}$ allele, which although homozygous lethal, complements $Bd^G$. Despite the exceptional $Ser^{rev2-3}$ allele, these results suggest that the Serrate and Beaded mutations are alleles of the same gene (see also below). Consistent with this idea is the fact that $Ser^{revertant}$ and Bd alleles have similar phenotypes (see also below).

6.1.3. CHARACTERIZATION OF SERRATE MUTANT PHENOTYPES

Several revertants of $Ser^D$, a dominant allele of Serrate, have been isolated (Thomas et al., 1991, Dev. 111:749–761; Fleming et al., 1990, Genes Dev. 4:2188–2201; Speicher et al., 1994, Develop. 120:535–544). In general, such revertants are lethal, displaying larval lethality. However, the exact timing of lethality has been difficult to determine. A combination of expression data, overexpression studies and genetic analyses, including genetic mosaics, indicate that Serrate function is necessary for imaginal development (Speicher et al., 1994, Develop. 120:535–544). Early phenotypic data suggesting that Serrate affects embryonic development (Fleming et al., 1990, Genes Dev. 4:2188–2201), were shown to be due to interactions between Serrate and the genes in the balancer chromosome TM2 (Gu et al., 1995, Develop. 121, in press).

6.1.4. MOLECULAR CHARACTERIZATION OF SERRATE DNA

In an effort to elucidate the molecular nature of the Serrate gene product, DNA from the 97F region was cloned and characterized. A Drosophila genomic clone, previously isolated on the basis of cross hybridization to the EGF-like domain of the Notch gene (Rothberg et al., 1988, Cell 55:1047–1059), was used as an entry point to initiate a chromosomal walk. From this initial clone, eight recombinant phage spanning ~85 kb of genomic DNA were isolated (see FIG. 2). A BamHI site adjacent to the region of EGF homology was arbitrarily chosen as coordinate position zero.

Genomic Southern blots containing mutant and wild-type DNAs were probed with DNA from the individual phage isolates to detect and localize rearrangement breakpoints that might be associated with the various Serrate alleles. Within the first phage isolate, 010.2, restriction fragment polymorphisms were detected on the original $Ser^D$ chromosome. The polymorphism detected with each of three restriction enzymes (EcoRI, BamHI, and HindIII) was consistent with an insertion of ~5.5 kb of DNA between map coordinates 0 and −3 (FIG. 2). Subsequent Southern analysis using DNA cloned from $Ser^D$ revealed a repeated DNA sequence, suggesting the presence of a mobile insertional element associated with the mutation. In addition to the insertion, the HindIII site at coordinate −2 has been eliminated in the $Ser^D$ chromosome. Because the parental chromosome from which the $Ser^D$ mutation arose is unavailable, we cannot be certain that the noted polymorphisms are causal to the $Ser^D$ phenotype.

Of the five $Ser^{revertant}$ alleles, three ($Ser^{rev2-3}$, $Ser^{rev5-5}$, and $Ser^{rev\ 6-1}$) appeared cytologically normal and did not exhibit DNA polymorphisms detectable by our Southern analyses. The remaining two revertants, $Ser^{rev2-11}$ and $Ser^{rev}$ 3, had polymorphic DNA restriction fragments within the cloned region. $Ser^{rev\ 2-11}$ is an inversion of polytene bands 97F to 98C. The 97F breakpoint was localized between coordinates +1.5 to +4, within the region of strongest detectable EGF homology (FIG. 2). $Ser^{rev\ 3}$ is a reciprocal translocation of chromosomes 3R and 2R, with the 97F breakpoint localized between coordinates +15 and +17 (FIG. 2). In situ hybridization of the cloned wild-type genomic DNAs to polytene chromosomes of $Ser^{rev\ 3}$ and $Ser^{rev\ 2-11}$ confirmed that the observed DNA polymorphisms represent the 97F breakpoints of these chromosomal rearrangements.

As noted earlier, $Ser^{revertant}$ alleles fail to complement $Bd^G$, suggesting that the Serrate and Bd mutations are alleles of the same gene. As with the $Ser^D$ mutation, the parental chromosome for the $Bd^G$ mutation was not available; hence, unambiguous assignment of mutant phenotypes to DNA polymorphisms cannot be made. Cytological observations of the $Bd^G$ chromosome failed to reveal any visible abnormalities; however, two regions of DNA polymorphism were detectable by Southern analysis. These regions lie between coordinates 0 to +1 and +14 to +17. Investigations of the polymorphism at position 0 to +1 were pursued by cloning the mutant DNA sequences. Preliminary results indicate that the polymorphisms do not result from a small inversion between these two regions but, rather, from a more complex event.

Of the three mutant chromosomes, $Bd^{43.5}$, $Bd^{862.5}$, and $pll^{11}$, only $pll^{11}$ was found to have a DNA polymorphism, which was localized between coordinates +17 and +19 (FIG. 2). Genetic and cytological data for the $pll^{11}$ mutation suggest the presence of a very small chromosomal aberration within the 97F region (P. Hecht, pers. comm.), and the molecular data are consistent with this observation. Finally, T(Y:3)R128 is a reciprocal translocation that also breaks within the 97F region (Lindsley et al., 1972, Genetics 71:157–184) and fails to complement $Bd^G$ (P. Hecht, pers. comm.). The DNA breakpoint for this translocation resides at map coordinates +25 to +28 (FIG. 2). Taken together, these findings strengthen the genetic evidence that Serrate and Bd mutations are alleles of the same gene. In summary, of eleven tested chromosomes containing Serrate or Bd mutation, six were shown to have associated DNA rearrangements within a 30 kb region known to contain EGF homologous sequences.

To examine the structure of the Serrate transcription unit, we probed northern blots containing 2- to 14-hour embryonic poly(A)$^+$ RNA with the recombinant phages spanning this region ($\phi$10.1, $\phi$1.3 and $\phi$15 K; FIG. 2). This analysis revealed the presence of two transcripts of ~5.5 kb and 5.6 kb. We isolated two overlapping cDNA clones, denoted C1 and C3, from an early pupal library (see Section 6.3). Sequence analysis of these cDNAs revealed a perfect overlap of 109 bp for a combined length of 5.6 kb, which is in excellent agreement with the larger of the two transcripts as determined by northern analysis. Genomic probes unique to the 5' end of C3 only detected the larger 5.6 kb transcript. Thus, the size difference between the 5.5 and 5.6 kb transcripts may represent an alteration in the potential protein coding capacity or an alteration of 5' untranslated sequence. The composite 5.6 kb cDNA confirms that the Serrate transcription unit spans ~30 kb of genomic DNA, encompasses the EGF homologous region, and is interrupted by at least five of the six DNA rearrangements that affect Serrate function (FIG. 2). From Southern analysis, at least two introns are apparent; additional introns are likely but not detectable at this level of resolution.

6.1.5. SERRATE ENCODES A PUTATIVE TRANSMEMBRANE PROTEIN WITH 14 EGF-LIKE REPEATS

Figure 4A:
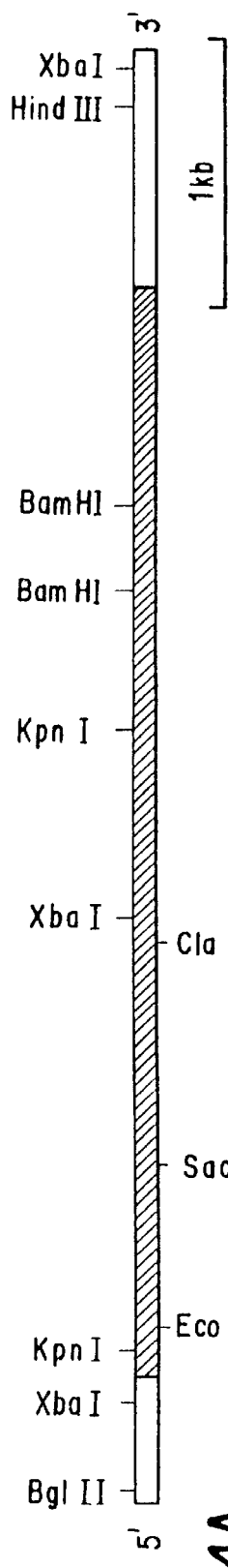

The complete nucleotide sequence compiled from the cDNAs C1 and C3 is 5561 bp (see FIG. 3) and agrees with the transcript sizes determined by northern analysis. Within this sequence there is a single large open reading frame (ORF) of 4329 bp. There are two possible initiator AUG codons at positions 433 and 442. Of these, the second AUG is within a sequence context that agrees with the Drosophila consensus sequence determined for translation initiation [CAAAAUG; (Cavener, 1987, Nucl. Acids Res. 15:1353–1361)]. Predicted codon usage within this ORF is highly consistent with established *Drosophila melanogaster* codon preferences (Beachy et al., 1985, Nature 313:545–550). Assuming that translation starts at the second AUG, the Serrate mRNA contains an untranslated leader sequence of at least 441 base pairs, encodes an expected protein product of 1404 amino acids, and terminates with 908 bp of untranslated 3' sequence (FIG. 4a). However, if translation begins at the first AUG, the protein product is 1443 amino acids.

Figure 4B:
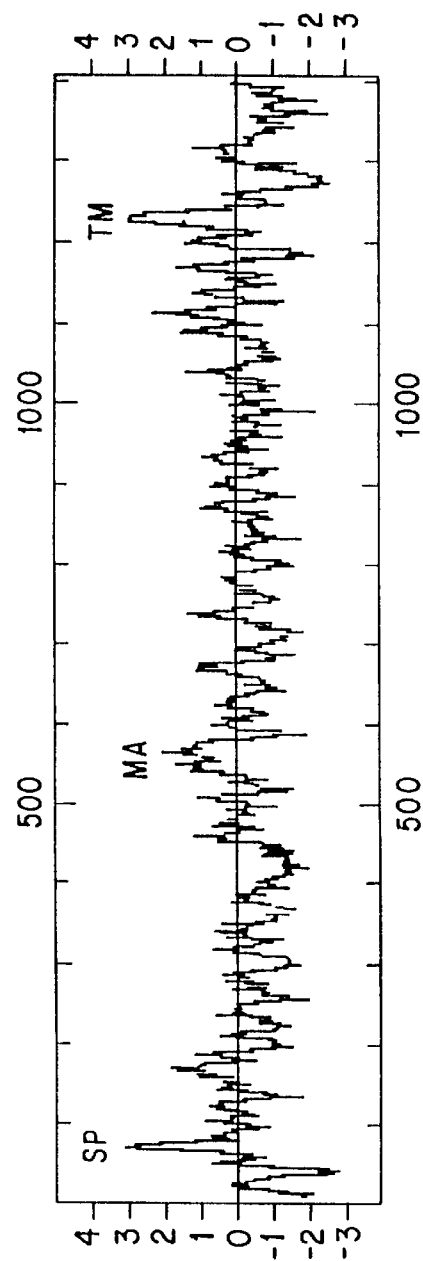

Hydropathy plots revealed three major hydrophobic regions (FIG. 4b; see also Section 6.3). The first, beginning at amino acid 51, is likely to represent a signal peptide sequence; a potential signal cleavage site occurs at amino acid 80. A second hydrophobic domain runs from amino acid 540 to 560. This region does not have a requisite transmembrane structure and is more likely to be a membrane-associated domain. The third hydrophobic domain (amino acids 1220 to 1245) is bounded by hydrophilic residues and is therefore likely to represent a true transmembrane domain.

Figure 4C:
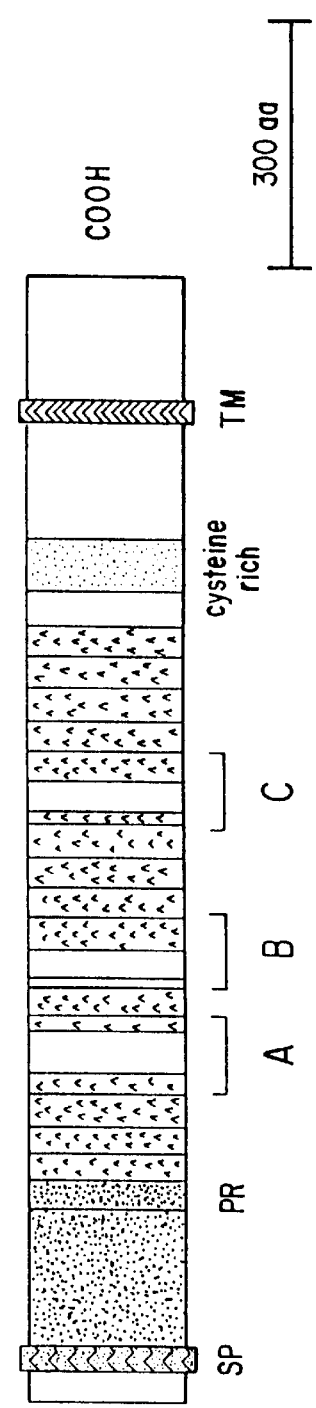

The most striking structural feature of the predicted protein is the series of EGF-like repeats (see FIG. 4c). There are 14 copies of this motif with an additional partial or degenerate repeat occurring toward the amino terminus (see below). In addition, at least three of these repeats are interrupted by stretches of amino acids. The first interruption (labeled A in FIG. 4c), which occurs in the fourth complete EGF-like repeat (repeats are numbered beginning from the amino terminus), is ~64 amino acids in length and is enriched for serine residues. The second interruption (labeled B in FIG. 4c), occurring in the sixth repeat, is ~44 amino acids long and has numerous hydrophobic residues. This region represents the putative membrane-associated domain noted earlier. The final interruption (labeled C in FIG. 4c), which occurs in the tenth repeat and is 29 amino acids in length, has an unusual run of threonines [$Thr_{(9)}$ Ala $Thr_{(3)}$].

Within the amino-terminal region of the Serrate protein, considerable structural homology (darkly-shaded region in FIG. 4c) is observed with the main protein product of the Delta locus (Vässin et al., 1987, EMBO J. 6:3431–3440; Kopczynski et al., 1988, Genes Dev. 2:1723–1735). Near the signal peptides for both of these molecules there lies a stretch of ~210 conserved amino acids. Within the first 165 amino acids, there is ~32% identity, which increases to greater than 50% for the remaining 45 amino acids. The latter region corresponds to the partial EGF-like repeat (designated PR in FIG. 4c), which lacks a cysteine residue but retains the other characteristic cysteines and conserved amino acids typically found in the remaining EGF-like repeats. The homology between Serrate and Delta extends beyond these amino-terminal regions, since both of these proteins contain EGF-like repeats.

In addition to the extracellular EGF-like sequences, the predicted Serrate protein contains a small intracellular domain of ~160 amino acids. The internal domain does not contain any significant known structural homologies, although there are numerous potential sites for phosphorylation (Those identified in the putative intracellular region by the SITES program were at amino acid positions 1283, 1292, 1297, 1349, 1365, 1371, 1389, and 1390).

6.1.6. EXPRESSION OF SERRATE RNA

Northern analysis of developmentally staged RNAs revealed that the majority of Serrate expression is represented by two coordinately regulated transcripts of 5.5 kb and 5.6 kb, which first appear 4 to 8 hours into embryogenesis (FIG. 5). These transcripts show peak expression between 8 and 12 hours of embryogenesis and diminish thereafter; however, they continue to be readily detectable throughout development except for the adult stages (FIG. 5). In addition to these major transcripts, a smaller (3.4 kb) transcript is expressed transiently between 2 and 4 hours of embryogenesis (FIG. 5).

We undertook an analysis of the spatial distribution of RNA transcripts from the Serrate locus in order to identify regions of the embryo that may require Serrate function. Using the whole mount in situ method (Tautz and Pfeifle, 1989, Chromosoma 98:81–85) and employing nonradioactive probes that hybridize to both the 5.5 kb and 5.6 kb transcripts, we found that Serrate mRNA accumulates in a dynamic pattern beginning from mid-embryogenesis (late stage 10) and persisting until the latest stages examined (stage 16); (embryonic stages are those of Campos-Ortega and Hartenstein, 1985, *The Embryonic Development of Drosophila Melanogaster*, Springer-Verlag, Berlin).

Because the tissue distribution of the two transcripts may be independently regulated, we note that the observed RNA localizations may represent a composite for both transcripts. We also note the possibility of a low level of Serrate RNA in the yolk of pre-gastrulation embryos because faint staining of the yolk was observed consistently. Although this staining was never observed with control probes (see Section 6.3), the presence of yolk staining is known to be a common artifact of the whole-mount in situ technique (Ashburner, 1989, *Drosophila—A laboratory manual*, Cold Spring Harbor Laboratory Press, Cold Spring Harbor, N.Y.). However, if this observation is not artifactual, the observed staining may correspond to the expression of the transient 3.4 kb RNA species observed by the Northern analysis of this same developmental stage.

Figure 6A:
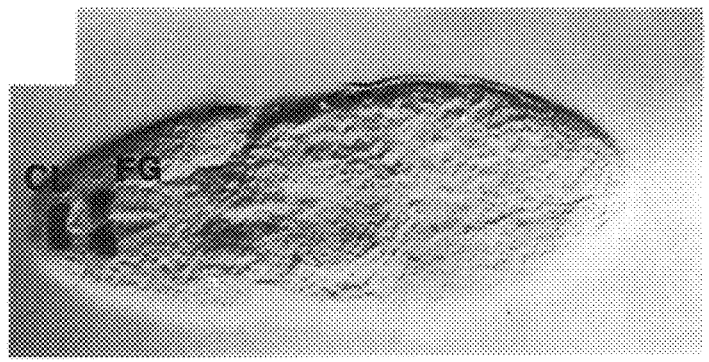
Figure 6B:
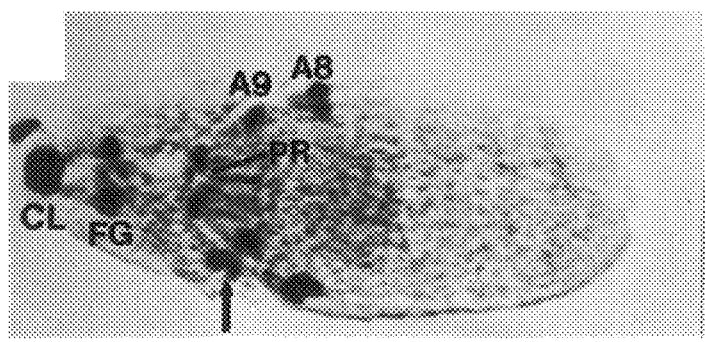
Figure 6C:
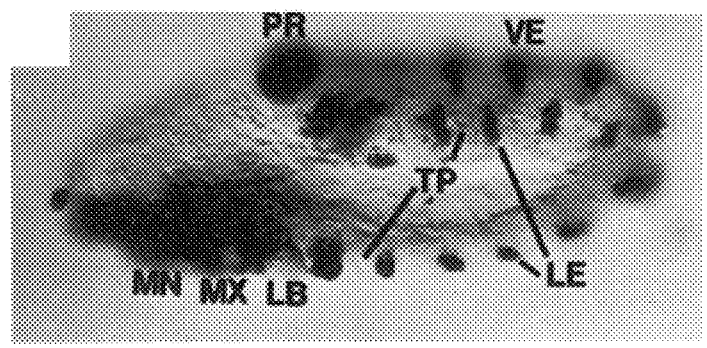

Initial cellular localization was seen in late-stage 10 embryos and consisted of a ring of cells in the foregut. The foregut is formed by the invagination of the stomodeum (the initial event of stage 10); thus, the foregut is actually derived from ectodermal tissue. Shortly thereafter, a bilateral patch of expressing cells appeared in the anterior-most portion of the head, the presumptive clypeolabrum (FIG. 6a). Additional areas of expression appeared abruptly at the end of stage 10 in a group of cells on the lateral edge of abdominal segment 8, followed by cells near the proctodeum and lateral epidermis of abdominal segment 9 (FIG. 6b). Later, during stage 11, expression was detected within cells located at the junction between the labial and maxillary lobes and within cells located near the tracheal pit of the first thoracic segment. The expression pattern progressed to include a group of lateral epidermal cells located between the tracheal pits in each of the thoracic and abdominal segments (FIG. 6c). In addition, each abdominal segment displayed a cluster of cells on either side of the ventral midline.

Figure 6D:
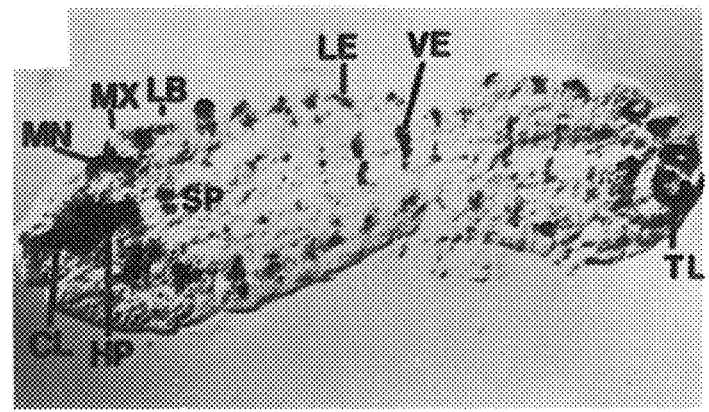
Figure 6E:
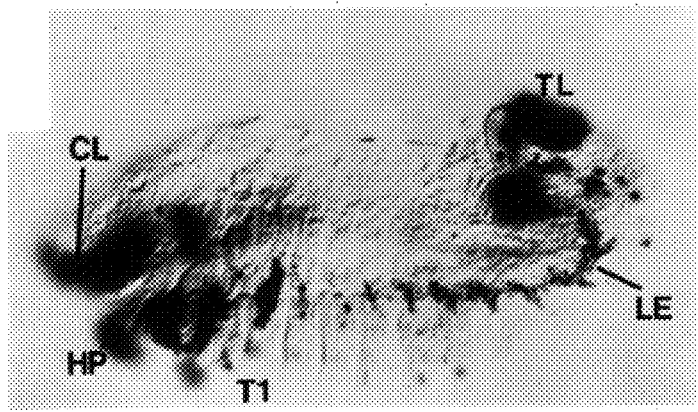
Figure 6F:
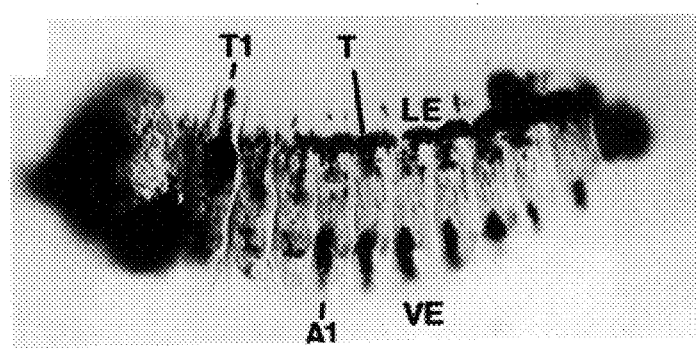
Figure 6G:
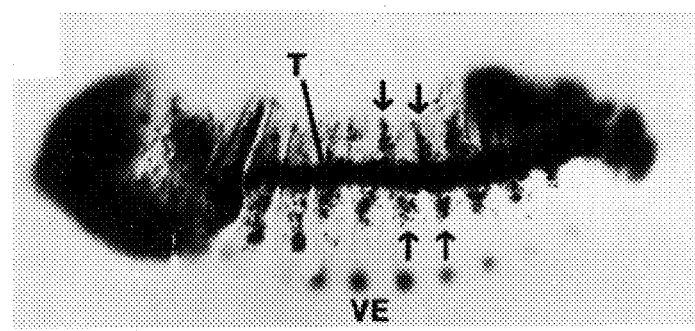
Figure 6H:
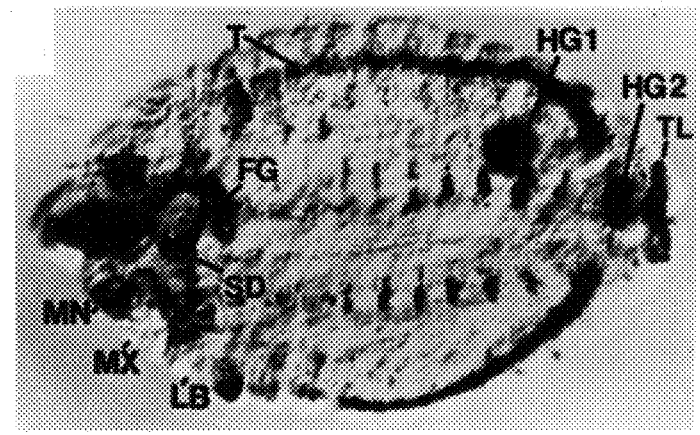
Figure 6I:
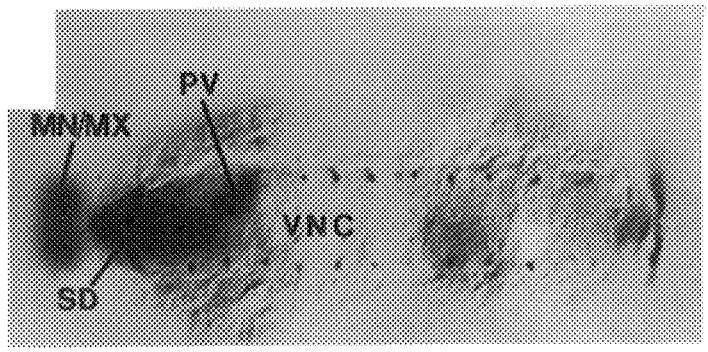
Figure 6J:
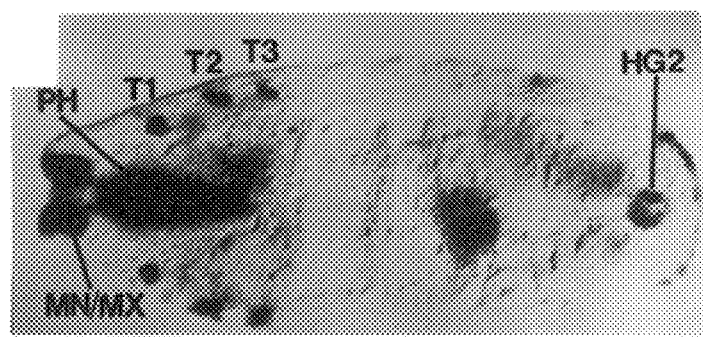
Figure 6K:
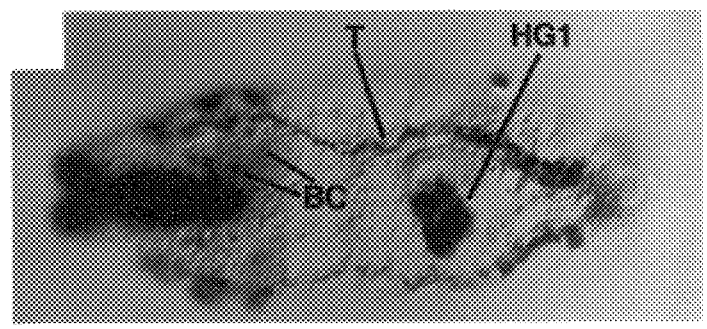
Figure 6L:
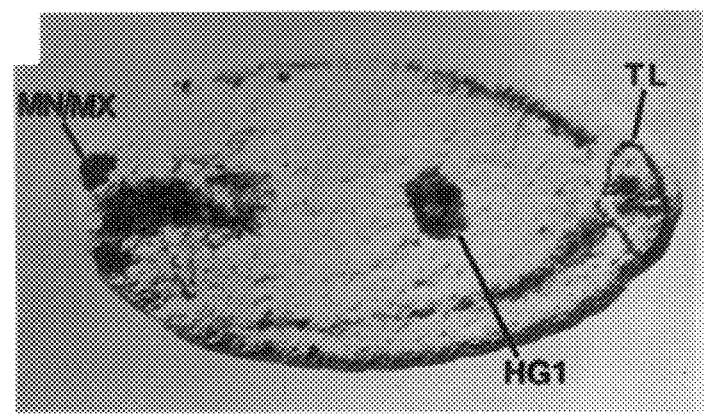

During germ band retraction (stage 12), the lateral epidermal cell patches broadened to form stripes that lie in the middle of each segment. A portion of these cells appeared to coalesce into an internal longitudinal stripe that was coincident with the developing tracheae (see FIG. 6e, f, g, and h). The cells that remained on the surface extended dorsally and ventrally forming a zig-zag shaped pattern (FIG. 6g, arrows). This surface expression in the thoracic segments was wider, more intense, and extended further dorsally and ventrally than in the abdominal segments (FIG. 6g). Later in embryogenesis (stages 14 and 15) the surface epidermal expression, with the exception of the first thoracic segment, diminished relative to the tracheal expression. Later, intense expression was observed in what appeared to be ectodermal invaginations located throughout embryonic development, eventually forming a ring of cells around the presumptive anal pads (FIG. 6l).

Within the head region, Serrate expression was temporally and spatially dynamic. The earliest expression occurred in the presumptive clypeolabrum (stage 10; FIG. 6a) and became broader and more intense as development proceeded. Early expression between the labial and maxillary lobes increased along their borders, and expression was also seen in the anterior of the mandibular lobe during stage 12 (FIG. 6d and e). In addition, expression was now observed in the hypopharyngeal region, just posterior to the stomodeum, and at the base of the labial lobes in an area encompassing the salivary gland duct opening (FIG. 6d). There was also low level expression in the dorsal procephalic epidermal region (not shown). By the end of germ band retraction (stage 13), expression encompassed the entire mandibular lobe. As a consequence of the cellular movements associated with head involution (stages 14–16), the expressing cells of the clypeolabrum, hypopharynx and labial lobes combined to form the pharynx. Prior expression in the area of the salivary gland placodes was now limited to the ducts of the developing salivary gland (FIG. 6i). The maxillary and mandibular lobes, which have moved to the anterior-most region of the embryo, expressed intensely at this time (FIG. 6j).

Serrate expression in the central nervous system (CNS) was apparent during stage 12 as a segmentally-reiterated array of single cells along the lateral edge of the ventral nerve cord and within the supraesophogeal ganglia (brain hemispheres). By the end of germ band retraction (stage 13), there were now two cells that appeared to express in each hemisegment of the ventral nerve cord (not shown). However, by stage 15, ventral nerve cord expression was again limited to a single cell per hemisegment (FIG. 6i) while expression in the brain hemispheres remained unchanged (FIG. 6k).

In summary, there are a wide array of tissues that express Serrate mRNA, and the expression pattern is tightly regulated both temporally and spatially. In addition, it should be stressed that at the present level of resolution, Serrate expression appears to be restricted exclusively to cells of ectodermal origin.

6.2. DISCUSSION

Unlike Notch and Delta, the fourteen EGF repeats of Serrate are not completely contiguous. At least three of these repeats contain sizeable interruptions consisting of insertions of long stretches of amino acids. Similarly, interruptions have been noted in two of the thirty EGF-like repeats of the Drosophila gene crumbs (Tepass et al., 1990, Cell 61:787–799). In Serrate, the interruption that occurs in the sixth repeat is particularly intriguing because it consists largely of hydrophobic amino acids. Although hydropathy plots indicate that this region does not conform to known transmembrane regions, it could represent a membrane-associated domain that serves to "tie" the protein back to the membrane. The interruption in the tenth repeat is also unusual in that it bears a stretch of threonines [$Thr_{(9)}Ala$ $Thr_{(3)}$]. A similar motif of thirteen contiguous threonine residues is found in the glycoprotein glutactin, a basement membrane protein of Drosophila (Olson et al., 1990, EMBO J. 9:1219–1227).

If the observed genetic interactions between Notch and Serrate had been only with the original $Ser^D$ allele, it could have been argued that this neomorphic mutation is allowing two functionally disparate but structurally similar molecules to interact out of their normal contexts. But because we observe genetic interactions with other Serrate alleles, it is likely that we are observing a manifestation of normal Serrate-Notch interactions.

We have shown that phenotypic revertants of $Ser^D$ behave genetically in a similar fashion to known deficiencies for the locus; that is, they are homozygous lethal during embryogenesis and completely recessive as heterozygotes. We also gathered evidence indicating that the mutation $Bd^G$, dorsolaterally on the thoracic segments (FIG. 6j). These pockets of cells may correspond to primordia of imaginal discs; in the first thoracic segment they appeared to be closely associated with opening of the anterior spiracle.

Coincident with the lateral expression, another segmentally reiterated pattern evolved in the ventral epidermis of the trunk. In the extended germ band embryo, this pattern, which consisted of stripes of expressing cells near the anterior border of the abdominal segments, lay out of register with the corresponding lateral expression (FIG. 6c). The pattern in the thorax contrasted with that in the abdomen and consisted of only small clusters of expressing cells in the latero-ventral region (see FIG. 6f and h). The ventral expression was quite intense through stage 13 and dissipated thereafter (FIG. 6l).

Serrate expression was also observed in the ectodermally-derived portions of the gut. The earliest expression was evident in the foregut and persisted throughout embryonic development (FIG. 6a). During germband retraction, a tightly defined, intensely expressing ring of cells lay at the junction with the anterior midgut. The proventriculus develops from this area; however, expression was limited to the ectodermally-derived portion of this composite structure (King, 1988, J. Morph. 196:253–282). Hindgut expression, though appearing later than foregut expression, occurred at an analogous position, that is, where ectoderm meets endoderm. The initial expression in the hindgut was seen at the time of germ band retraction (stage 12) as a wide band of cells where the Malphigian tubules were forming, but never included the tubules themselves. Later still (stage 14), an additional ring of expression appeared in the hindgut approximately mid-way between the insertion point of the Malphigian tubules and the proctodeum (FIG. 6h). Expression at the posterior-most end of the embryo, near the proctodeal opening, initiated early (stage 11) (FIG. 6b). This expression within the telson remained at high levels which was thought to belong to a distinct complementation group, may in fact be an allele of Serrate.

The embryonic lethal phenotypes of $Ser^{rev2-3}$, $Ser^{rev2-11}$, and $Ser^{rev5-5}$, which are essentially indistinguishable from one another, appear unchanged when in homozygous or hemizygous condition. This latter result genetically defines these alleles genetically as amorphic. However, since the $Ser^{rev2-3}$ allele complements the $Bd^G$ mutation, the $Ser^{rev2-3}$ mutation is probably not a protein null allele.

Consistent with the defects observed in the cuticle and nervous system of Ser⁻ embryos, Serrate transcripts are localized in complex patterns within these tissues. The abundant and widespread expression of Serrate transcripts in the segments that make up the embryonic head and thorax correlates well with the lack of embryonic head and thoracic structures commonly seen in Ser⁻ embryos. Likewise, the pattern of Serrate expression in the ventral epidermis of the abdominal segments correlates with the frequently absent or improperly formed denticles. Although Serrate is expressed in a small number of cells within the CNS, the gross morphological defects observed in the CNS of Ser⁻ embryos may reflect contributions from two components. The first is the loss of Serrate CNS expression itself, and the second may be a consequence of mechanical stresses (e.g., lack of germ band retraction) imposed by an improperly differentiating epidermis.

In the course of examining the embryonic phenotypes associated with Serrate lethal mutations, we noticed their similarity to those produced by several alleles of the gene coding for the Drosophila EGF receptor homolog known as DER, faint little ball or torpedo (Livneh et al., 1985, Cell 40:599–607; Price et al., 1989, Cell 56:1085–1092; Schejter and Shilo, 1989, Cell 56:1093–1104).

6.3. MATERIALS AND METHODS

6.3.1. Drosophila Cultures and Strains

Cultures were maintained on standard cornmeal/molasses/agar Drosophila medium supplemented with active dry yeast and were raised at 25° C. The red $Ser^D$, $Df(3R)Ser^{+82f24}$, and $Bd^G$ chromosomes were obtained from Peter Lewis. The red $Ser^D$ chromosome was maintained in homozygous condition. The mutations $p11^{11}$, $Bd^{862.5}$, and $Bd^{43.5}$ were generously provided by Kathryn Anderson. The Notch duplication CosP479 is an ~40 kb P-element cosmid construct inserted into the third chromosome (Ramos et al., 1989, Genetics 123:337–348). Other mutations and chromosomes have been described previously (Lindsley and Grell, 1968, Genetic variations of Drosophila melanogaster, Carnegie Inst. Wash. Publ. 627).

6.3.2. MUTAGENESIS

Males aged 3–7 days and homozygous for the red $Ser^D$ chromosome were irradiated with approximately 4500 R (150 kV, 5 mA, 9.2 min exposure; Torrex 150 Source, Torr X-Ray Corp.) and mated immediately to $C(1)A;y/y^2Y611$ or $C(1)Dx;yf/y^2Y611$ virgin females. The $F_1$ males were scored for the absence of the $Ser^D$ wing phenotype and mated to $Gl^{pl-3}fz$ red e/Tm2, red e virgin females to establish balanced $Ser^{rev}$/Tm2, red e stocks.

Mutations used in this study are shown in Table 1.

TABLE I

| Mutation | Origin | Description |
|---|---|---|
| $Ser^D$ | Spontaneous; information (Lindsley and Grell, 1968, Carnegie Inst. Wash. Publ. 627) | heterozygous dominant wing phenotype, homozygous viable; cytologically normal |
| $Bd^G$ | recovered among heat-treated flies (Gottschewski, 1935, Dros. Inf. Serv. 4:14, 16) | heterozygous dominant wing phenotype homozygous lethal, cytologically normal |
| $Ser^{rev\,3}$ | X-ray (this study) | homozygous lethal; reciprocal translocation of 3R (97F) to 2R (57) |
| $Ser^{rev2-3}$ | X-ray (this study) | Homozygous lethal; cytologically normal |
| $Ser^{rev2-11}$ | X-ray (this study) | homozygous lethal; inversion of 97F to 98C |
| $Ser^{rev5-5}$ | X-ray (this study) | homozygous lethal; cytologically normal |
| $Ser^{rev6-1}$ | X-ray (this study) | homozygous lethal; cytologically normal |
| $Bd^{43.5}$ | EMS (K. Anderson, unpubl.) | homozygous lethal; cytologically normal |
| $Bd^{862.5}$ | EMS (K. Anderson, unpubl.) | homozygous lethal; cytologically normal |
| $p11^{11}$ | EMS (K. Anderson, unpubl.) | homozygous lethal; possible small inversion within the 97F interval |
| T(Y:3)R128 | X-ray (Lindsley et al., 1972, Genetics 71:157–184) | homozygous lethal; reciprocal translocation of 3R (97F) to Y short arm |
| $Df(3R)Ser^{+82f24}$ | X-ray (P. Lewis, unpubl.) | deficiency for chromosome bands 97D to 97F-98A1 |

6.3.3. EMBRYONIC PHENOTYPE ANALYSIS

Cuticle preparations were according to the protocol of Wieschaus and Nüsslein-Volhard (1986, in Drosophila. A Practical Approach, (ed. D. B. Roberts), IRL Press, Oxford, pp. 199–227) on embryos aged for a minimum of 24 hours at 25° C. Anti-horseradish peroxidase antibody staining of the embryonic nervous system (Jan and Jan, 1982, Proc. Natl. Acad. Sci. USA 79:2700–2704) was carried out using fluorescein-conjugated antibody (Cappel) as described in Preiss et al. (1988, EMBO J. 7:3917–3927). CNS preparations of $torpedo^{2C82}$ were used for comparison studies.

6.3.4. ISOLATION OF NUCLEIC ACIDS

Genomic DNA was isolated as described in Pirrotta et al. (1983, EMBO J. 2:927–934). Restriction enzyme cleavage, agarose gel electrophoresis, capillary transfer to nitrocellulose and hybridization conditions were carried out according to standard procedures. DNA probes labeled with $^{32}P$ were prepared by random oligonucleotide priming, as described in Feinberg and Vogelstein (1983, Anal. Biochem. 132:6–13). Stage-specific total RNAs from a Canton-S strain were extracted in guanidinium thiocyanate essentially as described in Chirgwin et al. (1979, Biochem. 18:5294–5299). Pupal and adult RNAs were generously provided by A. Preiss (Preiss et al., 1988, EMBO J. 7:3917–3927). Poly (A)$^+$ RNA was selected by serial passage over oligo(dT)-cellulose (Stratagene) according to Sambrook et al. (1989, *Molecular Cloning: A Laboratory Manual*, 2d Ed., Cold Spring Harbor Laboratory Press, Cold Spring Harbor, N.Y.) and stored in ethanol. RNA was size fractionated in formaldehyde agarose gels and blotted onto Nytran membrane (Schleicher & Schuell) by capillary transfer. RNA was fixed to the membrane via UV crosslinking.

Two Drosophila genomic phage libraries (Preiss et al., 1985, Nature 313:27–32; R. Karess, unpubl.) were screened and recombinant clones were isolated as described in Benton and Davis (1977, Science 196:180–182). cDNAs in $\lambda$gt10 were isolated from the early pupal library of Poole et al. (1985, Cell 40:37–43). We isolated the C1 cDNA using the genomic EGF-like sequences from coordinates +1.5 to +4 (FIG. 2) as probe. Subsequently, we isolated the C3 cDNA using the 5' 700 bp terminal fragment of the C1 cDNA as probe.

6.3.5. SEQUENCING AND ANALYSIS

The EcoRI cDNA inserts from $\lambda$gt10 were subcloned directly into Bluescript KS+ and KS– vectors (Stratagene). Single-stranded DNAs were produced according to the manufacturer's instructions. Both strands of the cDNAs were sequenced using the dideoxynucleotide chain-termination procedure (Sanger, et al., 1977, Proc. Natl. Acad. Sci. USA 74:5463–5467) using the Sequenase kit (U.S. Biochemical). Sequence was obtained using the M13 and reverse primers for these vectors. Additional sequence was obtained by generating internal deletions through the use of restriction sites within the Bluescript polylinker and the cDNA inserts. The remaining cDNA sequences that were not accessible by these methods were obtained by using synthetic primers (Research Genetics) complementary to the end of a previously determined sequence.

Sequences were entered by sonic digitizer and overlapping sequence compilation; manipulation, translation, and secondary structure prediction were accomplished by using the Intelligenetics PC-GENE. Open reading frame prediction and plotting were performed using the University of Wisconsin program CODONPREFERENCE (Gribshov et al., 1984, Nucl. Acids Res. 12:539–549). The SITES program (PCGENE) was used to predict the location of the signal sequence, transmembrane domain, EGF-like repeats, and phosphorylation sites.

6.3.6. WHOLE MOUNT IN SITU PROCEDURE

A modification of the whole-mount in situ procedure of D. Tautz (Procedure 84a in Ashburner, 1989, *Drosophila: A Laboratory Manual*, Cold Spring Harbor Laboratory Press, Cold Spring Harbor, N.Y.) was used. The differences were as follows: Proteinase K (Boehringer-Mannheim) treatment was 10 to 14 minutes; 100 µl (rather than 10 µl) of boiled probe was used; after washing the embryos with 1:4 hybridization buffer to PBT, they were washed twice in PBT for 20 minutes, and then twice in 1×PBS, 0.1% BSA (globin free, Sigma), 0.2% Triton-X100 for 20 minutes; the antibody treatment was done in the same PBS, BSA, Triton solution at 4° C. overnight; the embryos were washed four times in the PBS, BSA, Triton solution at room temperature; after the alkaline phosphatase reaction, embryos were dehydrated twice in 70% and 100% ethanol and then cleared in xylenes; the embryos were mounted in Permount (Sigma). Dissected embryos were rehydrated, dissected in PBT, and mounted in 90% glycerol [10% Tris-HCl at pH 8.0, with 0.5% n-propylgalate (wt/vol; Sigma)].

The probe was made by runoff of a PCR reaction in 50 mM KCl, 10 mM Tris-HCl (pH 8.3), 1.5 mM MgCl$_2$, 0.01% (wt/vol) gelatin, 0.2 mM dATP, 0.2 mM dCTP, 0.2 mM dGTP, 0.15 mM dTTP, and 0.07 mM digoxigenin-11-dUTP (Boehringer Mannheim) using 150 ng of custom synthesized primer and approximately 400 ng of linearized DNA. Probe was synthesized from cDNA coordinates 4826 to 3854; the opposite strand constituted the control probe and was synthesized from coordinates 4458 to 5015 (refer to FIG. 5). The conditions for the PCR thermal cycler were 95° C. for 45 seconds, 55° C. for 30 seconds, and 72° C. for 1 minute, which were run for 30 cycles. The probe was ethanol precipitated twice and resuspended in 300 µl of hybridization solution.

7. EXPRESSION OF A SERRATE FRAGMENT AS A FUSION PROTEIN AND PRODUCTION OF ANTIBODIES THERETO

Mouse anti-Serrate polyclonal antisera were made as follows: A BamHI fragment encoding amino acids 78–425 (FIG. 3) was subcloned into the pGEX-1 expression vector (Smith and Johnson, 1988, Gene 67:31–40). Fusion proteins were purified on glutathione-agarose beads (SIGMA), and injected into mice for antibody production. Mouse antisera were precipitated with 50% (NH$_4$)$_2$SO$_4$ and resuspended in PBS (150 mM NaCl, 14 mM Na$_2$HPO$_4$, 6 mM NaH$_2$PO$_4$) with 0.02% NaN$_3$.

8. EXPRESSION OF SERRATE AND A FRAGMENT AND A CHIMERIC DERIVATIVE THEREOF; IDENTIFICATION OF A NOTCH-BINDING DOMAIN

We describe herein the recombinant expression of Serrate, of a deletion construct (fragment) thereof, and of a chimeric Notch-Serrate fragment, and show that the full-length Serrate and the chimeric derivative are capable of binding to Notch in vitro.

8.1. EXPRESSION OF SERRATE AND OF DERIVATIVES THEREOF

For the Serrate expression construct, a synthetic primer containing an artificial BamHI site immediately 5' to the initiator AUG at position 442 of the Drosophila sequence (all sequence numbers are according to Fleming et al., 1990, Genes & Dev. 4:2188–2201) and homologous through position 464, was used in conjunction with a second primer from position 681–698 to generate a DNA fragment of ~260 base pairs. This fragment was cut with BamHI and KpnI (position 571) and ligated into Bluescript KS+ (Stratagene). This construct, BTSer5'PCR, was checked by sequencing, then cut with KpnI. The Serrate KpnI fragment (571–2981) was inserted and the proper orientation selected, to generate BTSer5'PCR-Kpn. The 5' SacII fragment of BTSer5'PCR-Kpn (SacII sites in Bluescript polylinker and in Serrate (1199)) was isolated and used to replace the 5' SacII fragment of cDNA C1 (Fleming et al., 1990, Genes & Dev.

4:2188–2201), thus regenerating the full length Serrate cDNA minus the 5' untranslated regions. This insert was isolated by a SalI and partial BamHI digestion and shuttled into the BamHI and SalI sites of the metallothionein promoter vector pRmHa-3 (Bunch et al., 1988, Nucl. Acids. Res. 16:1043–1061) to generate the final expression construct, Ser-mtn.

A Serrate deletion expression construct was also made, in which nucleotides 672–1293 (encoding amino acids 77–284) (FIGS. 3, 7, 8) were deleted. This deletion construct was made as follows: The Ser-mtn construct was digested with EcoRV, which cuts at nucleotide 672, and with SfiI, which cuts at nucleotide 4073. The linearized vector, lacking the EcoRV-SfiI (672–4073) fragment, was isolated. Plasmid SerFL was then digested with NdeI, which cuts at nucleotide 1289, and treated with mung bean nuclease resulting in the "trimming back" of four bases. The resulting SerFL fragment was then digested with SfiI which cuts at base 4073, and the resulting 1293–4073 fragment was isolated and ligated into the EcoRV-SfiI vector isolated above.

In addition, a Notch-Serrate chimeric construct was made using a clone consisting of Drosophila Notch cDNA with a deletion of all the Notch EGF-like repeats ("ΔEGF") (see PCT Publication WO 92/19734 published Nov. 12, 1992; Rebay et al., 1991, Cell 67:687–699 (FIG. 12, construct no. 25)). An N-terminal region of Serrate with homology to Delta and including the Serrate EGF-like repeats (Serrate nucleotide numbers 676–1287, encoding amino acids 79–282; FIGS. 7, 8) was placed into the ΔEGF deletion of Notch.

The above constructs were expressed in Drosophila S2 cells. The S2 cell line (Schneider, 1972, J. Embryol. Exp. Morph. 27, 353–365) was grown in M3 medium (prepared by Hazleton Co.) supplemented with 2.5 mg/ml Bacto-Peptone (Difco), 1 mg/ml TC Yeastolate (Difco), 11% heat-inactivated fetal calf serum (FCS) (Hyclone), and 100 U/ml penicillin-100 µg/ml streptomycin-0.25 µg/ml fungizone (Hazleton). Cells growing in log phase at ~2×10$^6$ cells/ml were transfected with 20 µg of DNA-calcium phosphate coprecipitate in 1 ml per 5 ml of culture as previously described (Wigler et al., 1979, Proc. Natl. Acad. Sci. USA 78, 1373–1376), with the exception that BES buffer (SIGMA) was used in place of HEPES buffer (Chen and Okayama, 1987, Mol. Cell. Biol. 7, 2745–2752). After 16–18 hr, cells were transferred to conical centrifuge tubes, pelleted in a clinical centrifuge at full speed for 30 seconds, rinsed once with ¼ volume of fresh complete medium, resuspended in their original volume of complete medium, and returned to the original flask. Transfected cells were then allowed to recover for 24 hr before induction. Expression from the metallothionein constructs was induced by the addition of CuSO$_4$ to 0.7 mM.

8.2. AGGREGATION ASSAYS FOR BINDING TO NOTCH

8.2.1. Methods

Two types of aggregation assays were used. In the first assay, a total of 3 ml of cells (5–10×10$^6$ cells/ml) was placed in a 25 ml Erlenmeyer flask and rotated at 40–50 rpm on a rotary shaker for 24–48 hr at room temperature. For these experiments, cells were mixed 1–4 hr after induction began and induction was continued throughout the aggregation period. In the second assay, ~0.6 ml of cells were placed in a 0.6 ml Eppendorf tube (leaving a small bubble) after an overnight induction (12–16 hr) at room temperature and rocked gently for 1–2 hr at 4° C. Ca$^{2+}$ dependence experiments were performed using the latter assay. For Ca$^{2+}$ dependence experiments, cells were first collected and rinsed in balanced saline solution (BSS) with 11% FCS (BSS-FCS; FCS was dialyzed against 0.9% NaCl, 5 mM Tris [pH 7.5]) or in Ca$^{2+}$ free BSS-FCS containing 10 mM EGTA (Snow et al., 1989, Cell 59: 313–323) and then resuspended in the same medium at the original volume.

For viewing by immunofluorescence, cells were collected by centrifugation (3000 rpm for 20 seconds in an Eppendorf microcentrifuge) and fixed in 0.6 ml Eppendorf tubes with 0.5 ml of freshly made 2% paraformaldehyde in PBS for 10 min at room temperature. After fixing, cells were collected by centrifugation, rinsed twice in PBS, and stained for 1 hr in primary antibody in PBS with 0.1% saponin (SIGMA) and 1% normal goat serum (Pocono Rabbit Farm, Canadensis, Pa.). Sera were appropriately diluted (e.g., 1:1000) for this step. Cells were then rinsed once in PBS and stained for 1 hr in specific secondary antibodies (double-labeling grade goat anti-rabbit and goat anti-mouse), in PBS-saponin-normal goat serum. After this incubation, cells were rinsed twice in PBS and mounted on slides in 90% glycerol, 10% 1 M Tris (pH 8.0), and 0.5% n-propyl gallate. Cells were viewed under epifluorescence on a Leitz Orthoplan 2 microscope.

Confocal micrographs were taken using the Bio-Rad MRC 500 system connected to a Zeiss Axiovert compound microscope. Images were collected using the BHS and GHS filter sets, aligned using the ALIGN program, and merged using MERGE. Fluorescent bleed-through from the green into the red channel was reduced using the BLEED program (all software provided by Bio-Rad). Photographs were obtained directly from the computer monitor using Kodak Ektar 125 film.

Notch-expressing cells for the assays were obtained similarly, using metallothionein promoter-driven plasmid constructions containing D. melanogaster Notch (see PCT Publication Wo 92/19734 published Nov. 12, 1992; Fehon et al., 1990, Cell 61:523–534; Rebay et al., 1991, Cell 67:687–699).

8.2.2. RESULTS

We found that Serrate expressing cells adhere to Notch expressing cells in a calcium dependent manner (see also Rebay et al., 1991, Cell 67:687–699). However, unlike Delta, under the experimental conditions tested, Serrate did not appear to interact homotypically. In addition, we detect no interactions between Serrate and Delta. It is possible that such interactions do occur, but at an affinity such that they are below the level of detection in our assay system.

We have tested a subset of our Notch deletion constructs to map the Serrate-binding domain and have found that Notch EGF-like repeats 11 and 12, in addition to binding to Delta, also mediate interactions with Serrate. In addition, the Serrate-binding function of these repeats also appears to have been conserved in the corresponding two EGF repeats of Xenopus Notch (construct #33ΔCla+XEGF(10–13); see Rebay et al., supra).

We were also able to define the Serrate region which is essential for the Notch/Serrate aggregation. Deleting nucleotides 672–1293 (i.e. amino acids 77–284) eliminated the ability of the Serrate protein to aggregate with Notch. While both cells expressing Notch and cells expressing the Serrate fragments were detected by immunofluorescence with anti-Notch and anti-Serrate antibodies, respectively, these cells did not co-aggregate.

Aggregation assays with cells expressing Notch and cells expressing the chimeric ΔEGF Notch-Serrate construct showed binding between Notch and the chimeric construct. These experiments thus demonstrated that a fragment of Serrate consisting of amino acids 79–282 (see SEQ ID NO:2) is capable of mediating binding to Notch. Similar experiments with Delta from the laboratory of M. Muskavitch (personal communication) have demonstrated that the homologous region of Delta (without the partial EGF-like repeat) was sufficient to mediate Notch-Delta binding. Therefore, it is likely that the partial EGF-like repeat of Serrate is not essential for this binding to occur.

Work in our laboratory has shown that Notch and Delta proteins interact directly at the molecular level (Fehon et al., 1990, Cell 61:523–534; International Publication No. WO 92/19734 published Nov. 12, 1992; collectively incorporated by reference herein in their entireties), as demonstrated by the specific binding of Notch-expressing cells to Delta-expressing cells in vitro. We have also shown that EGF-like repeats repeats 11 and 12 of Notch are required and sufficient for Notch-Delta-mediated aggregation, and that Delta participates in heterotypic (Delta-Notch) and homotypic (Delta-Delta) interactions mediated by its amino-terminus (id.). Thus, it is conceivable that the Serrate and Delta proteins compete for binding with the Notch protein. Such interplay could underlie the genetic interactions observed between Notch and Serrate.

Notch and Serrate appeared to aggregate less efficiently than Notch and Delta, perhaps because the Notch-Serrate interaction is weaker. For example, when scoring Notch-Delta aggregates, we detect ~40% of all Notch expressing cells in clusters with Delta expressing cells and ~40% of all Delta expressing cells in contact with Notch expressing cells. For Notch-Serrate, we find only ~20% of all Notch expressing cells and ~15% of all Serrate expressing cells in aggregates. For the various Notch deletion constructs tested, we consistently detect a reduction in the amount of aggregation between Notch and Serrate as compared to the corresponding Notch-Delta levels, with the possible exception of two constructs which exhibit severely reduced levels of aggregation even with Delta. One trivial explanation for this reduced amount of aggregation could be that our Serrate construct simply does not express as much protein at the cell surface as the Delta construct, thereby diminishing the strength of the interaction. Alternatively, the difference in strength of interaction may indicate a fundamental functional difference between Notch-Delta and Notch-Serrate interactions that may be significant in vivo.

9. ISOLATION AND CHARACTERIZATION OF A MOUSE SERRATE HOMOLOG

A mouse Serrate homolog, termed M-Serrate-1, was isolated as follows:

Mouse Serrate-1 gene
  Tissue origin: 10.5-day mouse embryonic RNA
  Isolation method:
    a) random primed cDNA against above RNA
    b) PCR of above cDNA using
       PCR primer 1: CGI(C/T)TTTGC(C/T)TIAA(A/G)(G/C)AITA(C/T)CA (SEQ ID NO: 11) {encoding RLCCK(H/E)YQ (SEQ ID NO:12)}:
       PCR primer 2: TCIATGCAIGTICCICC(A/G)TT (SEQ ID NO:13) {encoding NGGTCID (SEQ ID NO:14)}
  Amplification conditions: 50 ng cDNA, 1 μg each primer, 0.2 mM dNTP's, 1.8 U Taq (Perkin-Elmer) in 50 μl of supplied buffer, 40 cycles of: 94° C./30 sec, 45° C./2 min, 72° C./1 min extended by 2 sec each cycle.

Yielded a 1.8 kb fragment which was sequenced at both ends and identified as corresponding to C-Serrate-1

Partial DNA sequence of M-Serrate-1:
  From 5' end:

```
GTCCCGCGTCACTGCCGGGGGACCCTGCAGCTTCGGCTCAGGGTCTACGCCTGTCATCGGG    (SEQ ID NO:15)

GGTAACACCTTCAATCTCAAGGCCAGCCGTGGCAACGACCGTAATCGCATCGTACTGCCTT

TCAGTTTCACCTGGCCGAGGTCCTACACTTTGCTGGTGGAG
```

Protein translation of above:

SRVTAGGPCSFGSGSTPVIGGNTFN-
LKASRGNDRNRIVLPFSFTWPRSYTLLVE  (SEQ ID NO:16)

(corresponds to amino-terminal sequence upstream of the DSL domain)
From 3' end (but coding strand)

```
TCTTCTAACGTCTGTGGTCCCCATGGCAAGTGCAAGAGCCAGTCGGCAGGCAAATTCACCT    (SEQ ID NO:17)

GTGACTGTAACAAAGGCTTCACCGGCACCTACTGCCATGAAAATATCAACGACTGCGAGAG

CAACCCCTGTAAA
```

Protein translation of above:

SSNVCGPHGKCKSQSAGKFTCDCNKGFT-
GTYCHENINDCESNPCK  (SEQ ID NO:18)

(within tandemly arranged EGF-like repeats)
Expression pattern: The expression pattern was determined to be the same as that observed for C-Serrate-1 (chicken Serrate) (see Section 11 infra), including expression in the developing central nervous system, peripheral nervous system, limb, kidney, lens, and vascular system.

10. ISOLATION AND CHARACTERIZATION OF A XENOPUS SERRATE HOMOLOG

A Xenopus Serrate homolog, termed Xenopus Serrate-1 was isolated as follows:
Xenopus Serrate-1 gene
  Tissue origin: neurula-stage embryonic RNA
  Isolation method:
    a) random primed cDNA against above RNA
    b) PCR using:
       Primer 1: CGI(C/T)TTTGC(C/T)TIAA(A/G)(G/C)AITA(C/T)CA (SEQ ID NO:11) {encoding RLCCK(H/E)YQ (SEQ ID NO:12)}:

PCR primer 2: TCIATGCAIGTICCICC(A/G)TT (SEQ ID NO:13) {encoding NGGTCID (SEQ ID NO:14)}

Amplification conditions: 50 ng cDNA, 1 μg each primer, 0.2 mM dNTP's, 1.8 U Taq (Perkin-Elmer) in 50 μl of supplied buffer. 40 cycles of: 94° C./30 sec, 45° C./2 min, 72° C./1 min extended by 2 sec each cycle.

Yielded a ~700 bp fragment which was partially sequenced to confirm its relationship to C-Serrate-1.

11. ISOLATION AND CHARACTERIZATION OF A CHICK SERRATE HOMOLOG

In the example herein, we report the cloning and sequence of a chick Serrate homolog, C-Serrate, and of fragments of two chick Notch homologs, C-Notch-1 and C-Notch-2, together with their expression patterns during early embryogenesis. The patterns of transcription of C-Serrate overlaps with that of C-Notch-1 in many regions of the embryo, suggesting that C-Notch-1, like Notch in Drosophila, is a receptor for Serrate. In particular, Notch and Serrate are expressed in the neurogenic regions of the developing central and peripheral nervous system.

Our data show that Serrate, a known ligand of Notch, has been conserved from arthropods to chordates. The overlapping expression patterns suggest conservation of its functional relationship with Notch and imply that development of the chick and in particular of its central nervous system involves the interaction of C-Notch-1 with Serrate at several specific locations.

Materials and Methods

Embryos

White Leghorn chicken eggs were obtained from University Park Farm and incubated at 38° C. Embryos were staged according to Hamburger and Hamilton (1951, J. Exp. Zool. 88:49–92).

Cloning of chicken homologs of Notch

Approximately 1000 base pair PCR fragments of the chicken Notch 1 and Notch 2 genes were amplified from otic explant RNA (see below) using degenerate primers and PCR conditions as outlined in Lardelli and Lendahl (1993, Exp. Cell Res. 204:364–372). The PCR fragment was subcloned into Bluescript KS–, sequenced and used as a template for making a DIG antisense RNA probe (RNA Transcription Kit, Stratagene; DIG RNA labelling mix, Boehringer Mannheim).

Cloning of a chicken homologue of Drosophila Serrate

Otic explants were dissected from embryos of stages 8 to 13. Each otic explant consisted of the two otic cups, a short section of intervening hindbrain and pharynx and the associated head ectoderm and mesenchyme. RNA was extracted using a modification of standard protocols (Sambrook et al., 1989, in Molecular Cloning: A Laboratory Manual, 2nd ed., Cold Spring Harbor Laboratory Press, Cold Spring Harbor, N.Y.) and polyA+ mRNA was isolated from total RNA using the PolyATtract mRNA Isolation System (Promega). First strand cDNA was synthesized using the SuperScript Preamplification System (Gibco).

PCR and degenerate primers were used to amplify a fragment of a chicken gene homologous to the Drosophila gene Serrate from the otic explant cDNA. The primers were designed to recognize peptide motifs found in both the fly Delta and Serrate proteins:

1) primer 1, 5-CGI(T/C)TITGC(T/C)TIAA(G/A)(G/C)AITA(C/T)CA-3' (SEQ ID NO:19), corresponds to the motif RLCLK(E/H)YQ (SEQ ID NO:20) located at the amino-terminus of the fly Delta and Serrate proteins.

2) primer 2, 5'-TCIATGCAIGTICCICC(A/G)TT-3'(SEQ ID NO:13), corresponds to the motif NGGTCID (SEQ ID NO:14) found in several of the EGF-like repeats. The PCR conditions were as follows: 35 cycles of 94° C. for 1 minute, 45° C. for 1.5 minutes and 72° C. for 2 minutes; followed by a final extension step of 72° C. for 10 minutes. A PCR product of approximately 900 base pairs in length was purified, subcloned into Bluescript KS– (Stratagene) and its DNA sequence partially determined to confirm that it was a likely Serrate homolog. It was then used to recover larger cDNA clones by screening two cDNA libraries:

1) a stage 8–13 otic explant random primed cDNA library
2) a stage 17 chick spinal cord oligo dT primed cDNA library Overlapping cDNAs were isolated, and two (termed 9 and 3A.1) that together cover almost the entire coding region of the gene were subcloned into Bluescript KS–. DNA sequence was determined from nested deletion series generated using the double-stranded Nested Deletion Kit (Pharmacia) and Sanger dideoxy chain termination method with the Sequenase enzyme (US Biochemical Corporation). Sequences were aligned and analyzed using Geneworks 2.3 and Intelligenetics. Homology searches were done using the program Sharq.

To obtain the most 5' end of the open reading frame, a number of other PCR based strategies were used including the screening of a number of other libraries (cDNA and genomic) using the method of Lardelli et al. (1994, Mechanisms of Development 46:123–136).

In situ hybridization

Patterns of gene transcription were determined by in situ hybridization using DIG-labeled RNA probes and:

1) a high-stringency wholemount in situ hybridization protocol, and
2) in situ hybridization on cryostat sections based on the protocol of Strähle et al. (1994, Trends in Genet. 10:7).

Results

To obtain insight into the likely role of chick Serrate in the vertebrate embryo, we examined its expression in relation to that of chick Notch, since functional coupling of Notch and Serrate occurs in Drosophila. Two chick Notch homologs were obtained as described below.

C-Notch-1 and C-Notch-2 are apparent counterparts of the rodent Notch-1 and Notch-2 genes, respectively We searched for Notch homologs in the chick by PCR, using cDNA prepared from two-day chick embryos and degenerate primers based on conserved regions common to the known rodent Notch homologs. In this way, we obtained fragments, each approximately 1000 nucleotides long, of two distinct genes, which we have called C-Notch-1 and C-Notch-2. The fragments extend from the third Notch/lin12 repeat up to and including the last five or so EGF-like repeats. EGF-like repeats are present in a large number of proteins, most of which are otherwise unrelated to Notch. The three Notch/lin12 repeats, however, are peculiar to the Notch family of genes and are found in all its known members. C-Notch-1 shows the highest degree of amino-acid identity with rodent Notch1 (Weinmaster et al., 1991, Development 113:199–205), and is expressed in broadly similar domains to rodent Notch1 (see below). Of the rodent Notch genes, C-Notch-2 appears most similar to Notch2 (Weinmaster et al., 1992, Development 116:931–941).

We examined the expression patterns of C-Notch-1 in early embryos by in situ hybridization. C-Notch-1 was expressed in the 1- to 2-day chick embryo in many well-defined domains, including the neural tube, the presomitic mesoderm, the nephrogenic mesoderm (the prospective mesonephros), the nasal placode, the otic placode/vesicle, the lens placode, the epibranchial placodes, the endothelial lining of the vascular system, in the heart, and the apical ectodermal ridges (AER) of the limb buds. These sites match the reported sites of Notch1 expression in rodents at equivalent stages (Table II). Taking the sequence data together with the expression data, we conclude that C-Notch-1 is either the chick ortholog of rodent Notch1, or a very close relative of it.

TABLE II

COMPARISON OF DOMAINS OF RODENT-NOTCH1 AND CHICK NOTCH-1 EXPRESSION THROUGHOUT EMBRYOGENESIS

| Body Region | R-Notch1[a] | C-Notch1 |
|---|---|---|
| primitive streak | + | + |
| Hensen's node | − | − |
| neural tube | + | + |
| retina | + | + |
| lens | + | + |
| otic placode/vesicle | + | + |
| epibranchial placodes | + | + |
| nasal placode | + | + |
| dorsal root ganglia | + | + |
| presomitic mesoderm | + | + |
| somites | + | + |
| notochord | ? | + |
| mesonephric kidney | + | + |
| metanephric kidney | + | + |
| blood vessels | + | + |
| heart | + | + |
| whisker follicles | + | N/A |
| thymus | + | ? |
| toothbuds | + | N/A |
| salivary gland | + | ? |
| limb bud (AER) | ? | + |

[a]from Weinmaster et al., 1991, Development 113:199–205; Franco del Amo et al., 1992, Development 115:737–744; Reaume et al., 1992, Dev. Biol. 154:377–387; Kopan and Weintraub, 1993, J. Cell. Biol. 121:631–641; Lardelli et al., 1994, Mech. of Dev. 46:123–126.

C-Serrate is a homolog of Drosophila Serrate, and codes for a candidate ligand for a receptor belonging to the Notch family In Drosophila, two ligands for Notch are known, encoded by the two related genes Delta and Serrate. The amino-acid sequences corresponding to these genes are homologous at their 5' ends, including a region, the DSL motif, which is necessary and sufficient for in vitro binding to Notch. To isolate a fragment of a chicken homolog of Serrate, we used PCR and degenerate primers designed to recognize sequences on either side of the DSL motif (see Materials and methods). A 900 base pair PCR fragment was recovered and used to screen a library, allowing us to isolate overlapping cDNA clones. The DNA sequence of the cDNA clones revealed an almost complete single open reading frame of 3582 nucleotides, lacking only a few 5' bases. Comparison with the amino acid sequences of Drosophila Delta and Serrate suggests that we are missing only the portion of the coding sequence that encodes part of the signal sequence of the chick Serrate protein.

Translation of the nucleotide sequence (SEQ ID NO:9) (FIG. 11) predicts a protein of 1230 amino acids (SEQ ID NO:10) (FIG. 12). A hydropathy plot reveals a single hydrophobic region characteristic of a transmembrane domain (Kyte and Doolittle, 1982, J. Mol. Biol. 157:105–132). In addition, the protein has sixteen EGF-like repeats organized in a tandem array in its extracellular domain. Comparison of the chick sequence with sequences of D. melanogaster Delta and Serrate suggests that the clones encode a chicken homolog of Serrate (FIG. 13; FIG. 14). Whereas Drosophila Serrate contains 14 EGF-like repeats with large insertions in repeats 4, 6 and 10, the chicken homolog has an extra two EGF-like repeats and only one small insertion of 16 amino acids in the 10th repeat. Both proteins have a second cysteine-rich region between the EGF-like repeats and the transmembrane domain; the spacing of the cysteines in this region is almost identical in the two proteins (compare $CX_2CXCX_6CX_4CX_{15}CX_5CX_7CX_4CX_5C$ in Drosophila Serrate with $CX_2CXCX_6CX_4CX_9CX_5CX_7CX_4CX_5C$ in C-Serrate). The intracellular domain of C-Serrate bears no significant homology to the intracellular domains of either Drosophila Delta or Serrate.

C-Serrate is expressed in the central nervous system, cranial placodes, nephric mesoderm, vascular system, and limb bud mesenchyme In situ hybridization was performed to examine the expression of C-Serrate in whole-mount preparations during early embryogenesis, from stage 4 to stage 21, at intervals of roughly 12 hours. Later stages were studied by in situ hybridization on cryosections.

The main sites of early expression of C-Serrate, as seen in whole mounts, can be grouped under five headings: central nervous system, cranial placodes, nephric mesoderm, vascular system, and limb bud mesenchyme.

Central nervous system

The first detectable expression of C-Serrate was seen in the central nervous system at stage 6 (0 somites/24 hrs), within the posterior portion of the neural plate. By stage 10 (9–11 somites/35.5 hrs), a strong stripe of expression was seen in the prospective diencephalon. Additional faint staining was seen in the hindbrain and in the prospective spinal cord.

At stage 13, there were several patches of expression in the neural tube. In the diencephalon, there was a strong triangular stripe of expression that appeared to correspond to neuromere D2. There were two patches (one on either side of the midline) on the floor of the anterior mesencephalon as well as diffuse staining in the dorsal mesencephalon. In the hindbrain and rostral spinal cord, there were two longitudinal stripes of expression on either side of the midline: one along the dorsal edge of the neural tube and a second more ventral one, adjacent to the floor plate. Both were located within the domain of (rat) Notch 1 expression. The anterior limit of the ventral stripe was at the midbrain/hindbrain boundary. The dorsal stripe was continuous with the expression in the dorsal mesencephalon. In the anterior spinal cord, expression was more spotty, the stripes being replaced by isolated scattered cells expressing C-Serrate.

At stage 17 (58 hrs), expression in the diencephalon and midbrain was unchanged. In the hindbrain and spinal cord, there were an additional two longitudinal stripes: one midway along the dorsoventral axis and a second wider more ventral stripe; the anterior limits of these stripes coincided with the anterior border of rhombomere 2. All four longitudinal stripes in the hindbrain continued into the spinal cord of the embryo; decreasing towards its posterior end. These stripes of expression were maintained at least up to and including stage 31 (E7). By stage 21 (84 hrs), additional expression was seen in the cerebral hemispheres and strong expression in a salt and pepper distribution of cells in the optic tectum.

Cranial placodes

It is striking that C-Serrate is expressed in all the cranial placodes—the lens placode, the nasal placode, the otic placode/vesicle and the epibranchial placodes, as well as a patch of cranial ectoderm anterior to the otic placode that may correspond to the trigeminal placode (which is not well-defined morphologically).

In the lens placode, expression was already seen at stage 11, rapidly became very strong, and persisted at least to stage 21. Expression was weaker in the nasal placode and was only detected from stage 13. Again, expression was maintained at least until stage 21.

Likewise for the otic placode, expression began to be visible at stage 10 and was strong by early stage 11 (12–14 somites, 42.5 hours). Curiously, there was a "hole" in the otic expression domain—an anteroventral region of the placode in which the gene was not expressed. Subsequently, as the placode invaginates to form an otic vesicle, the strongest expression was seen at the anterolateral and posteromedial poles. Later still, as the otic vesicle becomes transformed into the membranous labyrinth of the inner ear, C-Serrate expression became restricted to the sensory patches.

The epibranchial expression was seen at stage 13/14 as strong staining in the ectoderm around the dorsal margins of the first and second branchial clefts. It was accompanied by expression of the gene in the deep part of the lining of the clefts and in the endodermal lining of the branchial pouches, where the two epithelia abut one another.

Lastly, a large and strong but transient patch of expression was seen in the cranial ectoderm just anterior and ventral to the ear rudiment at stage 11. From its location, we suspect this to be, or to include, the region of the trigeminal placode.

Nephric mesoderm

Expression was detectable in the cells of the intermediate mesoderm from stage 10 and in older embryos (stage 17 to 21) in the developing mesonephric tubules.

Limb buds

C-Serrate mRNA was localized to a patch of mesenchyme at the distal end of the developing limb bud. This may suggest a role in limb growth.

Other sites

Expression was also seen in the tail bud, allantoic stalk, and possibly other tissues at late stages.

All major sites of C-Serrate expression lie within domains of C-Notch-1 expression The conservation of the DSL domain and adjacent N-terminal region in C-Serrate suggests that it functions as a ligand for a receptor belonging to the Notch family. We thus expected to find sites where C-Serrate expression is accompanied by expression of a Notch gene. At such sites, overlapping or contiguous expression of the two genes can be taken as an indication that cells are communicating by Serrate-Notch signalling. We have compared the expression pattern of C-Serrate, as shown by in situ hybridization, with that of C-Notch-1, to discover what overlaps in fact occur, over a range of stages up to 8 days of incubation (E8). All the observed sites of C-Serrate expression indeed lay within, or very closely adjacent to, domains of expression of C-Notch-1 (Table III).

TABLE III

COMPARISON OF C-NOTCH-1 AND C-SERRATE EXPRESSION AT STAGE 17a

| Body region | C-Notch-1 | C-Serrate |
|---|---|---|
| brain and spinal cord | ++ (almost everywhere) | ++ (specific regions) |
| retina | ++ | – |
| lens | + | ++ |
| otic placode/vesicle | ++ | ++ |
| epibranchial placodes | ++ | ++ |
| nasal placode | ++ | ++ |
| dorsal root ganglia | + | – |
| branchial mesenchyme | – | – |
| branchial ectoderm | + | ++ (furrows) |
| branchial endoderm | + | ++ (tips of pouches) |
| presomitic mesoderm | ++ | – |
| somites | ++ | – |
| notochord | ++ | – |
| mesonephric kidney | ++ | ++ |
| metanephric kidney | ++ | ++ |
| blood vessels | ++ | ++ |
| heart | + | ++ |
| limb bud (stage 21) | ++ (AER) | ++ (distal mesenchyme) | a Hamburger and Hamilton, 1951, J. Exp. Zool. 88:49–92.

Because of the importance of Notch and its partners in insect neurogenesis, it was of particular interest to us to see whether the homologous genes are involved in the development of the vertebrate CNS. C-Serrate is expressed in the CNS, and its pattern of expression shows a remarkable relationship to that of the Notch homologs.

We analyzed transverse sections through the spinal cord of a six day chicken embryo hybridized with C-Notch-1 and C-Serrate antisense RNA probes. C-Notch-1 was expressed throughout the luminal region as described previously; within this region, there were two small patches in which Serrate was strongly expressed.

Discussion

In Drosophila development, cell-cell signalling via the product of the Notch gene plays a cardinal role in the final cell-fate decisions that specify the detailed pattern of differentiated cell types. This signalling pathway, in which the Notch protein has been identified as a transmembrane receptor, is best known for its role in neurogenesis: loss-of-function mutations in Notch or any of a set of other genes required for signal transmission via Notch alter cell fates in the neuroectoderm, causing cells that should have remained epidermal to become neural instead. Notch-dependent signalling is, however, as important in non-neural as in neural tissues. It regulates choices of mode of differentiation in oogenesis, in myogenesis, in formation of the Malpighian tubules and in the gut, for example, as well as in development of the retina, the peripheral sensilla, and the central nervous system. In most of these cases the signal delivered via Notch appears to mediate lateral inhibition, a type of interaction by which a cell that becomes committed to differentiate in a particular way—for example, as a neuroblast—inhibits its immediate neighbors from doing likewise. This forces adjacent cells to behave in contrasting ways, creating a fine-grained pattern of different cell types.

There are, however, good reasons to believe that this is not the only function of signals delivered via Notch. Two direct ligands of Notch have been identified. These are the products of the Delta and Serrate genes. Both of them, like Notch itself, code for transmembrane proteins with tandem arrays of EGF-like repeats in their extracellular domain. Both the Delta and the Serrate protein have been shown to bind to Notch in a cell adhesion assay, and they share a large region of homology at their amino-termini including a motif that is necessary and sufficient for interaction with Notch in vitro, the so-called EBD or DSL domain. Yet despite these biochemical similarities, they seem to have quite different developmental functions. Although Serrate is expressed in many sites in the fly, it is apparently required only in the humeral, wing and halteres disks. When Serrate function is lost by mutation, these structures fail to grow. Studies on the wing disc have indicated that it is specifically the wing margin that depends on Serrate; when Serrate is lacking, this critical signaling region and growth centre fails to form, and when Serrate is expressed ectopically under a GAL4-UAS promoter in the ventral part of the wing disc, ectopic wing margin tissue is induced, leading to ectopic outgrowths. Notch appears to be the receptor for Serrate at the wing margin, since some mutant alleles of Notch cause similar disturbances of wing margin development and allele-specific interactions are seen in the effects of the two genes.

Here we describe the identification and full length sequence of a homolog of the Drosophila gene Serrate, and identification and partial sequence of chick homologs of rat/mouse Notch1 and Notch2.

Within the chick Serrate cDNA there is a single open reading frame predicted to encode a large transmembrane protein with 16 EGF repeats in its extracellular domain. It has a well conserved DSL motif suggesting that it would interact directly with Notch. The intracellular domain of chick Serrate exhibits no homology to anything in the current databases including the intracellular domains of Drosophila Delta and Serrate. It should he pointed out however that the intracellular domains of chick and human Serrate (see Section 12) are almost identical.

The spatial distributions of C-Notch-1 and C-Serrate were investigated during early embryogenesis by in situ hybridization. C-Notch-1 and C-Serrate exhibit dynamic and complex patterns of expression including several regions in which they are coexpressed (CNS, ear, branchial region, lens, heart, nasal placodes and mesonephros). The overlapping expression together with the finding that C-Serrate has a well conserved Notch binding domain suggests that this receptor/ligand interaction has been conserved from Drosophila through to vertebrates.

In Drosophila, the Notch receptor is quite widely distributed and its ligands are found in overlapping but more restricted domains. In the chick a similar situation is observed.

Fly Notch is necessary for many steps in the development of Drosophila; its role in lateral inhibition especially in the development of the central nervous system and peripheral sense organs being the best studied examples. However, Notch is a multifunctional receptor and can interact with different signalling molecules (including Delta and Serrate) and in developmental processes that do not easily fit within the framework of lateral inhibition. While available evidence implicates Delta as the signalling molecule in lateral inhibition there is no data to suggest that Serrate participates in lateral inhibition. Rather, Serrate appears to be necessary for development of the dorsal imaginal discs of the larva; that is, the humeral, haltere and wing discs. In the latter, the best studied of these processes, Serrate and Notch are important for the development of the dorsoventral wing margin, a structure necessary for the organization of wing development as a whole.

That C-Serrate has a significant function can be inferred from the conservation of its sequence, in particular, of its Notch-binding domain. The expression patterns reported for C-Serrate in this paper provide the following information. First, since the Serrate gene is expressed in or next to sites where C-Notch-1 is expressed (possibly in conjunction with other Notch homologs), it is highly probable that C-Serrate exerts its action by binding to C-Notch-1 (or to another chick Notch homolog with a similar expression pattern). Second, the expression in the developing kidney, the vascular system and the limb buds might reflect an involvement in inductive signalling between mesoderm and ectoderm, which plays an important part in the development of all these organs. In the limb buds, for example, C-Serrate is expressed in the distal mesoderm, and C-Notch-1 is expressed in the overlying apical ectodermal ridge, whose maintenance is known to depend on a signal from the mesoderm below. In the cranial placodes, a similar role is possible, but the evidence for inductive signalling is weaker, and C-Serrate may equally be involved in communications between cells within the placodal epithelium, for example, in regulating the specialized modes of differentiation of the placodal calls.

What might C-Serrate's function be within the curiously restricted domains of its expression in the CNS? One possibility is that it is involved in regulating the production of oligodendrocytes, which have likewise been reported to originate from narrow bands of tissue extending along the cranio-caudal axis of the neural tube.

12. ISOLATION AND CHARACTERIZATION OF HUMAN SERRATE HOMOLOGS

Clones for the human Serrate sequence were obtained as described below.

The polymerase chain reaction (PCR) was used to amplify DNA from a human placenta cDNA library. Degenerate oligonucleotide primers used in this reaction were designed based on amino-terminal regions of high homology between Drosophila Serrate and Drosophila Delta (see FIG. 13); this high homology region includes the 5' "DSL" domain, that is believed to code for the Notch-binding portion of Delta and Serrate. Two PCR products were isolated and used, one a 350 bp fragment, and one a 1.2 kb fragment. These PCR fragments were labeled with $^{32}$P and used to screen a commercial human fetal brain cDNA library made from a 17–18 week old fetus (previously available from Stratagene), in which the cDNAs were inserted into the EcoRI site of a λ-Zap vector.

The 1.2 kb fragment hybridized to a single clone out of the $10^6$ clones screened. We rescued this fragment from the λ DNA by converting the isolated phage λ clone to a plasmid via the manufacturer's instructions, yielding the Serrate-homologous cDNA as an insert in the EcoRI site of the vector Bluescript KS– (Stratagene). This plasmid was named "pBS39" and the gene corresponding to this cDNA clone was called Human Serrate-1 (also known as Human Jagged-1 ("HJ1")). The isolated cDNA was 6464 nucleotides long and contained a complete open reading frame as well as 5' and 3' untranslated regions (FIG. 9). Sequencing was carried out using the Sequenase® sequencing system (U.S. Biochemical Corp.) on 5 and 6% Sequagel acrylamide sequencing gels.

The 350 bp fragment hybridized with two clones, containing cDNA inserts of approximately 1.1 and 3.1 kb in length; the plasmid constructs containing these inserts were named pBS14 and pBS15, respectively. Each clone was isolated, its respective insert rescued from the λ cDNA, and sequenced as above. The nucleotide sequence of the pBS14 insert was identical to a 1.1 kb stretch of sequence contained internally within the pBS15 cDNA insert and therefore, this clone was not characterized further. The sequence of the 3.1 kb pBS15 insert encoded a single open reading frame which spanned all but the 5' 20 nucleotides of the insert. The methionine located at the amino terminal residue of this predicted open reading was homologous to the start methionine encoded by the Human Serrate-1 (HJ1) cDNA clone in pBS39. The gene encoding the cDNA insert of pBS15 was named Human Serrate-2 and is also known as Human Jagged-2 ("HJ2").

The pBS15 (HJ2) 3.1 kb insert was then labeled with $^{32}$P and used to screen another human fetal brain library (from Clontech), in which cDNA generated from a 25–26 week-old fetus was cloned into the EcoRI site of λgt11. This screen identified three potential positive clones. To isolate the cDNAs, λgt11 DNA was prepared from a liquid lysate and purified over a DEAE column. The purified DNA was then cut with EcoRI and the cDNA inserts were isolated and subcloned into the EcoRI site of Bluescript KS–. The bluescript constructs containing these cDNAs were named pBS3-15, pBS3-2, and pBS3-20. Two of these cDNA clones, pBS3-2 and pBS3-20, contained sequences that partially overlapped with pBS15 and were further characterized. pBS3-2 had a 3.2 kb insert extending from nucleotide 1210 of the pBS15 cDNA insert to just after the polyadenylation signal. The 2.6 kb insert of pBS3-20, was restriction mapped and partially sequenced to determine its 3' and 5' ends. This analysis indicated that the PBS3-20 insert had a nucleic acid sequence that was fully contained within the pBS3-2 cDNA insert and therefore, the pBS3-20 insert was not characterized further. The insert of pBS3-15 was determined to be a Bluescript vector fragment contaminant.

Alignment of the deduced amino acid sequence (SEQ ID NO:8) of the "complete" Human Serrate-2 (HJ2) cDNA (SEQ ID NO:7) generated on the computer with the deduced amino acid sequence of Human Serrate-1 (HJ1) from pBS39 (SEQ ID NO:6) revealed a gap of about 120 bases, leading to a frameshift, in the region encoded by the pBS15 (HJ2) insert, between the putative signal sequence and the beginning of the DSL domain. The nucleotides missing in the gap of the pBS15 insert would be located between nucleotides 240 and 241 of SEQ ID NO:7 (FIG. 10). This missing region probably resulted from a cloning artifact in the construction of the Stratagene library.

Attempts to clone the 5' end of HJ2 using anchored PCR, RACE, and Takara extended PCR techniques were unsuccessful. However, three human genomic clones potentially containing the 5' end of HJ2 were obtained from the screening of a human genomic cosmid library in which 30 kb fragments were cloned into a unique XhoI site introduced into the BamHI site of a pWE15 vector (the unmodified vector is available from Stratagene). This cosmid library was screened with a PCR fragment that had been amplified from the 5' end of pBS15 (HJ2) and three positive cosmid clones were isolated. Two different sets of primers were used to amplify DNA corresponding to the 5' end of pBS15 using the cosmid clones as a template, and both sets generated single bands that were subcloned, but which were determined to contain PCR artifacts. Portions of the cosmid clones are being subcloned directly, without PCR, in order to obtain clones that contain the 120 nucleotide stretch of DNA that is missing from pBS15.

The pBS39 cDNA insert, encoding the Human Serrate-1 homolog (HJ1), has been sequenced and contains the complete coding sequence for the gene product. The nucleotide (SEQ ID NO:5) and protein (SEQ ID NO:6) sequences are shown in FIG. 9. The nucleotide sequence of Human Serrate-1 (HJ1) was translated using MacVector software (International Biotechnology Inc., New Haven, Conn.). The coding region consists of nucleotide numbers 371–4024 of SEQ ID NO:5. The Protean protein analysis software program from DNAStar (Madison, Wis.) was used to predict signal peptide and transmembrane regions (based on hydrophobicity). The signal peptide was predicted to consist of amino acids 14–29 of SEQ ID NO:6 (encoded by nucleotide numbers 410–457 of SEQ ID NO:5), whereby the amino terminus of the mature protein was predicted to start with Gly at amino acid number 30. The transmembrane domain was predicted to be amino acid numbers 1068–1089 of SEQ ID NO:6, encoded by nucleotide numbers 3572–3637 of SEQ ID NO:5. The consensus (DSL) domain, the region of homology with Drosophila Delta and Serrate, predicted to mediate binding with Notch (in articular, Notch ELR 11 and 12), spans amino acids 185–229 of SEQ ID NO:6, encoded by nucleotide numbers 923–1057 of SEQ ID NO:5. Epidermal growth factor-like (ELR) repeats in the amino acid sequence were identified by eye; 15 (full-length) ELRs were identified and 3 partial ELRs as follows:

ELR 1: amino acid numbers 234–264
ELR 2: amino acid numbers 265–299
ELR 3: amino acid numbers 300–339
ELR 4: amino acid numbers 340–377
ELR 5: amino acid numbers 378–415
ELR 6: amino acid numbers 416–453
ELR 7: amino acid numbers 454–490
ELR 8: amino acid numbers 491–528
ELR 9: amino acid numbers 529–566
Partial ELR: amino acid numbers 567–598
Partial ELR: amino acid numbers 599–632
ELR 10: amino acid numbers 633–670
ELR 11: amino acid numbers 671–708
ELR 12: amino acid numbers 709–747
ELR 13: amino acid numbers 748–785
ELR 14: amino acid numbers 786–823
ELR 15: amino acid numbers 824–862
Partial ELR: amino acid numbers 863–879
Partial ELR: amino acid numbers 880–896
The total ELR domain is thus amino acid numbers 234–896 (encoded by nucleotide numbers 1070–3058 of SEQ ID NO:5). The extracellular domain is thus predicted to be amino acid numbers 1–1067 of SEQ ID NO:6, encoded by nucleotide numbers 371–3571 of SEQ ID NO:5 (amino acid numbers 30–1067 in the mature protein; encoded by nucleotides number 458–3571 of SEQ ID NO:5). The intracellular (cytoplasmic) domain is thus predicted to be amino acid numbers 1090–1218 of SEQ ID NO:6, encoded by nucleotide numbers 3638–4024 of SEQ ID NO:5.

The expression of HJ1 in certain human tissues was established by probing a Clontech Human Multiple Tissue Northern blot with radio-labeled pBS39. The probe hybridized to a single band of about 6.6 kb, and was expressed in all of the tissue assayed, which included, heart, brain, placenta, lung, skeletal muscle, pancreas, liver and kidney. The observation that HJ1 was expressed in adult skeletal and heart muscle was particularly interesting, because adult muscle fibers are completely surrounded by a lamina of extracellular matrix, and it is unlikely, therefore, that the role of HJ1 in these cells is in direct cell-cell communication.

The "complete" (containing an internal deletion) Human Serrate-2 (HJ2) cDNA nucleotide sequence (SEQ ID NO:7) and amino acid sequence (SEQ ID NO:8) generated on the computer are shown in FIG. 10. The nucleotide sequence translated using MacVector software (International Biotechnology Inc., New Haven, Conn.). The coding region consists of nucleotides number 332–4102 of SEQ ID NO:7. The Protean protein analysis software program from DNAStar (Madison, Wis.) was used to predict signal peptide and transmembrane regions (based on hydrophobicity). The transmembrane domain was predicted to be amino acid numbers 912–933 of SEQ ID NO:8, encoded by nucleotides number 3065–3130 of SEQ ID NO:7. The consensus (DSL) domain, the region of homology with Drosophila Delta and Serrate, predicted to mediate binding with Notch (in particular, Notch ELR 11 and 12), spans amino acids 26–70 of SEQ ID NO:8, encoded by nucleotide numbers 407–541 of SEQ ID NO:7. Epidermal growth factor-like (ELR) repeats in the amino acid sequence were identified by eye; 15 (full-length) ELRs were identified and 3 partial ELRs as follows:
ELR 1: amino acid numbers 75–105
ELR 2: amino acid numbers 106–140
ELR 3: amino acid numbers 141–180
ELR 4: amino acid numbers 181–218
ELR 5: amino acid numbers 219–256
ELR 6: amino acid numbers 257–294
ELR 7: amino acid numbers 295–331
ELR 8: amino acid numbers 332–369
ELR 9: amino acid numbers 370–407
Partial ELR: amino acid numbers 408–435
Partial ELR: amino acid numbers 436–469
ELR 10: amino acid numbers 470–507
ELR 11: amino acid numbers 508–545
ELR 12: amino acid numbers 546–584
ELR 13: amino acid numbers 585–622
ELR 14: amino acid numbers 623–660
ELR 15: amino acid numbers 664–701
Partial ELR: amino acid numbers 702–718
Partial ELR: amino acid numbers 719–735
The total ELR domain is thus amino acid numbers 75–735 (encoded by nucleotides number 554–2536 of SEQ ID NO:7). The extracellular domain is thus predicted to be amino acid numbers 1–912 of SEQ ID NO:8, encoded by nucleotides number 332–3064 of SEQ ID NO:7. The intracellular (cytoplasmic) domain is thus predicted to be amino acid numbers 934–1257 of SEQ ID NO:8, encoded by nucleotide numbers 3131–4102 of SEQ ID NO:7.

Like Human Serrate-1 (HJ1), the "complete" (with an internal deletion) Human Serrate-2 (HJ2) cDNA (SEQ ID NO:7) generated on the computer encodes a protein containing 16 complete and 2 interrupted EGF repeats as well as the diagnostic cryptic EGF repeat known as the DSL domain, which has been found only in putative Notch ligands. The open reading frame of the computer generated "complete" Human Serrate-2 (HJ-2) is about 1400 amino acids long, approximately 182 amino acids longer than the carboxy terminus of HJ1 and the rat Serrate homologue Jagged. While there is significant homology between the complete HJ2 and HJ1 in the amino terminal portion of the protein, this homology is lost just before the putative transmembrane domain at about amino acid number 1029 of HJ1. This result is particularly interesting because the presence of a long COOH-terminal tail implies the possibility of some additional function or regulation of HJ2.

The "complete" (with an internal deletion) Human Serrate-2 (HJ2) cDNA (SEQ ID NO:7) sequence can be constructed by taking advantage of the unique restriction sites for AccI, DraIII, or BamHI present in the sequence overlap of pBS15 and pBS3-2, and which enzymes cleave the pBS15 insert at nucleotides 1431, 2648, and 2802, respectively.

The expression of HJ2 in certain human tissues was established by probing a Clontech Human Multiple Tissue northern blot with radio-labeled clone pBS15. This probe hybridized to a single band of about 5.2 kb and was expressed in heart, brain, placenta, lung, skeletal muscle, and pancreas, but was absent or nearly undetectable in liver and kidney. As in the case of HJ1 expression discussed supra, the observation that the pBS15 insert component of HJ2 was expressed in adult skeletal and heart muscle was particularly interesting, because adult muscle fibers are completely surrounded by a lamina of extracellular matrix, and it is unlikely, therefore, that the role of HJ2 in these cells is in direct cell-cell communication.

Expression constructs are made using the isolated clone (s). The clone is excised from its vector as an EcoRI restriction fragment(s) and subcloned into the EcoRI restriction site of an expression vector. This allows for the expression of the Human Serrate protein product from the subclone in the correct reading frame. Using this methodology, expression constructs in which the HJ1 cDNA insert of pBS39 was cloned into an expression vector for expression under the control of a cytomegalovirus promoter have been generated and HJ1 has been expressed in both 3T3 and HAKAT human keratinocyte cell lines.

13. DEPOSIT OF MICROORGANISMS

Bacteria strain XL1-Blue containing plasmid SerFL, containing an EcoRI fragment encoding a full-length Drosophila Serrate, was deposited on Dec. 11, 1991 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 68876.

Plasmid pBS39, containing an EcoRI fragment encoding a full-length Human Serrate-1 (HJ1), was deposited on Feb. 28, 1995 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 97068.

Plasmid pBS15, containing a 3.1 kb EcoRI fragment encoding the amino terminus of Human Serrate-2 (HJ2), cloned into the EcoRI site of Bluescript KS–, was deposited on Mar. 5, 1996 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 97459.

Plasmid pBS3-2 containing an 3.2 kb EcoRI fragment encoding the carboxy terminus of Human Serrate-2 (HJ2), cloned into the EcoRI site of Bluescript KS–, was deposited on Mar. 5, 1996 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 97460.

The present invention is not to be limited in scope by the microorganisms deposited or the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A purified vertebrate Serrate protein comprising a sequence selected from the group consisting of the mouse Serrate sequence of SEQ ID NO:16, the mouse Serrate sequence of SEQ ID NO:18, amino acids 6 to 1193 of the chick Serrate sequence depicted in FIGS. 12A–12B (SEQ ID NO:10), amino acids 30 to 1218 of the human Serrate sequence depicted in FIGS. 9A–9G (SEQ ID NO:6), and the human Serrate sequence depicted in FIGS. 10A–10G (SEQ ID NO:8).

2. The protein of claim 1 which is a human protein.

3. The protein of claim 2 which comprises the amino acid sequence as set forth in amino acid numbers 30–1218 of SEQ ID NO:6.

4. The protein of claim 2 which comprises the amino acid sequence as set forth in amino acid numbers 1–1257 of SEQ ID NO:8.

5. A purified vertebrate Serrate protein produced according to a method comprising growing a recombinant cell containing a recombinant nucleic acid encoding a vertebrate Serrate protein comprising a sequence selected from the group consisting of the mouse Serrate sequence of SEQ ID NO:16, the mouse Serrate sequence of SEQ ID NO:18, amino acids 6 to 1193 of the chick Serrate sequence depicted in FIGS. 12A–12B (SEQ ID NO:10), amino acids 30 to 1218 of the human Serrate sequence depicted in FIGS. 9A–9G (SEQ ID NO:6), and the human Serrate sequence depicted in FIGS. 10A–10G (SEQ ID NO:8), such that the encoded Serrate protein is expressed by the cell, and purifying the expressed Serrate protein.

6. A purified protein encoded by the complementary strand of a nucleic acid hybridizable to a sequence selected from the group consisting of the mouse Serrate sequence of SEQ ID NO:15, the mouse Serrate sequence of SEQ ID NO:17, the chick Serrate sequence depicted in FIGS. 11A–11B (SEQ ID NO:9), the human Serrate sequence depicted in FIGS. 9A–9G (SEQ ID NO:5), and the human Serrate sequence depicted in FIGS. 10A–10G (SEQ ID NO:7), wherein said hybridization is under high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 µg/ml denatured salmon sperm DNA, for 48 hours at 65° C., and wash in a buffer consisting of 0.1×SSC, for 45 minutes at 50° C., and wherein said protein is capable of being bound by an anti-vertebrate Serrate antibody.

7. A purified protein encoded by the complementary strand of a nucleic acid hybridizable to a sequence selected from the group consisting of the mouse Serrate sequence of SEQ ID NO:15, the mouse Serrate sequence of SEQ ID NO:17, the chick Serrate sequence depicted in FIGS. 11A–11B (SEQ ID NO:9), the human Serrate sequence depicted in FIGS. 9A–9G (SEQ ID NO:5), and the human Serrate sequence depicted in FIGS. 10A–10G (SEQ ID NO:7), wherein said hybridization is under low stringency conditions comprising hybridization in a buffer consisting of 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt/vol) dextran sulfate, for 18–20 hours at 40° C., and wash in a buffer consisting of 2×SSC, 25 mM Tris-HCl (pH 7.4), 5 mM EDTA, and 0.1% SDS, for 1.5 hours at 60° C., and wherein said protein is able to be bound by an anti-vertebrate Serrate antibody.

8. A purified fragment of a vertebrate Serrate protein, said fragment consisting of at least 20 amino acids of a sequence selected from the group consisting of the mouse Serrate sequence of SEQ ID NO:16, the mouse Serrate sequence of SEQ ID NO:18, the chick Serrate sequence depicted in FIGS. 12A–12B (SEQ ID NO:10), the human Serrate sequence depicted in FIGS. 9A–9G (SEQ ID NO:6), and the human Serrate sequence depicted in FIGS. 10A–10G (SEQ ID NO:8), wherein said fragment is capable of being bound by an anti-Serrate antibody.

9. A purified fragment of a vertebrate Serrate protein, said fragment consisting of at least 20 amino acids of a sequence selected from the group consisting of the mouse Serrate sequence of SEQ ID NO:16, the mouse Serrate sequence of SEQ ID NO:18, the chick Serrate sequence depicted in FIGS. 12A–12B (SEQ ID NO:10), the human Serrate sequence depicted in FIGS. 9A–9G (SEQ ID NO:6), and the human Serrate sequence depicted in FIGS. 10A–10G (SEQ ID NO:8), wherein said fragment is capable of being bound by an anti-vertebrate Serrate antibody.

10. The fragment of claim 9, wherein the vertebrate Serrate protein is human.

11. The fragment of claim 9, wherein the fragment is capable of being bound by an anti-human Serrate antibody.

12. A purified molecule comprising the fragment of claim 9.

13. The fragment of claim 9 wherein the fragment is of amino acids 30 to 1218 of the human Serrate sequence depicted in FIG. 9 (SEQ ID NO:6).

14. The fragment of claim 9 wherein the fragment is of the Serrate sequence depicted in FIG. 10 (SEQ ID NO:8).

15. A purified fragment of a vertebrate Serrate protein, said fragment consisting of at least 20 amino acids of a vertebrate Serrate protein sequence selected from the group consisting of the chick Serrate sequence depicted in FIGS. 12A–12B (SEQ ID NO:10), the human Serrate sequence depicted in FIGS. 9A–9G (SEQ ID NO:6), and the human Serrate sequence depicted in FIGS. 10A–10G (SEQ ID NO:8) which fragment is able to bind to a Notch protein.

16. The fragment of claim 15 wherein the Serrate protein is a human Serrate protein.

17. The fragment of claim 8 or 16, which is a fragment consisting of at least 20 amino acids of the human Serrate sequence depicted in FIG. 9 (SEQ ID NO:6).

18. The fragment of claim 16, which is a fragment of SEQ ID NO:8.

19. A purified molecule comprising the fragment of claim 15.

20. The fragment of claim 15, which lacks the epidermal growth factor-like repeats of the Serrate protein.

21. A purified fragment of a vertebrate Serrate protein, which fragment consists of at least 20 amino acids of an epidermal growth factor-like repeat of a sequence selected from the group consisting of the mouse Serrate sequence of SEQ ID NO:18, the chick Serrate sequence depicted in FIGS. 12A–12B (SEQ ID NO:10), the human Serrate sequence depicted in FIGS. 9A–9G (SEQ ID NO:6), and the human Serrate sequence depicted in FIGS. 10A–10G (SEQ ID NO:8).

22. The fragment of claim 21 wherein the fragment is of the human Serrate sequence depicted in FIG. 9 (SEQ ID NO:6).

23. The fragment of claim 21 wherein the fragment is of the human Serrate sequence depicted in FIG. 10 (SEQ ID NO:8).

24. A purified fragment of a vertebrate Serrate protein, said fragment consisting of an at least 20 amino acid portion of a sequence selected from the group consisting of the mouse Serrate sequence of SEQ ID NO:16, the mouse Serrate sequence of SEQ ID NO:18, the chick Serrate sequence depicted in FIGS. 12A–12B (SEQ ID NO:10), the human Serrate sequence depicted in FIGS. 9A–9G (SEQ ID NO:6) and the human Serrate sequence depicted in FIGS. 10A–10G (SEQ ID NO:8), wherein said fragment (a) is capable of being bound by an anti-vertebrate Serrate antibody; and (b) lacks the transmembrane and intracellular domains of the protein.

25. The fragment of claim 24 wherein the Serrate protein is a human Serrate protein.

26. The fragment claim of 25 wherein the fragment is of the human Serrate sequence depicted in FIG. 9 (SEQ ID NO:6).

27. The fragment of claim 25 wherein fragment is of the human Serrate sequence depicted in FIG. 10 (SEQ ID NO:8).

28. A purified fragment of a vertebrate Serrate protein, said fragment consisting of an at least 20 amino acid portion of a sequence selected from the group consisting of the chick Serrate sequence depicted in FIGS. 12A–12B (SEQ ID NO:10), the human Serrate sequence depicted in FIGS. 9A–9G (SEQ ID NO:6) and the human Serrate sequence depicted in FIGS. 10A–10G (SEQ ID NO:8) wherein said fragment (a) is capable of being bound by an anti-vertebrate Serrate antibody; and (b) lacks the extracellular domain of the protein.

29. The fragment of claim 28 wherein the fragment is of the human Serrate sequence depicted in FIG. 9 (SEQ ID NO:6).

30. The fragment of claim 28 wherein the fragment is of the human Serrate sequence depicted in FIG. 10 (SEQ ID NO:8).

31. A purified fragment of a vertebrate Serrate protein produced according to a method comprising growing a recombinant cell containing a recombinant nucleic acid comprising a nucleotide sequence encoding a fragment of a vertebrate Serrate protein, which fragment consists of at least (a) 20 amino acids of a sequence selected from the group consisting of the chick Serrate sequence depicted in FIGS. 12A–12B (SEQ ID NO:10), the human Serrate sequence depicted in FIGS. 9A–9G (SEQ ID NO:6) and the human Serrate sequence depicted in FIGS. 10A–10G (SEQ ID NO:8) and (b) a domain of the protein selected from the group consisting of the extracellular domain, DSL domain, epidermal growth factor-like repeat domain, cysteine-rich domain, transmembrane domain, and intracellular domain, such that the encoded fragment is expressed by the cell, and purifying the expressed fragment.

32. A chimeric protein comprising a fragment of a vertebrate Serrate protein consisting of at least 20 amino acids of a sequence selected from the group consisting of the mouse Serrate sequence of SEQ ID NO:16, the mouse Serrate sequence of SEQ ID NO:18, the chick Serrate sequence depicted in FIGS. 12A–12B (SEQ ID NO:10), the human Serrate sequence depicted in FIGS. 9A–9G (SEQ ID NO:6), and the human Serrate sequence depicted in FIGS. 10A–10G (SEQ ID NO:8), which fragment is fused via a covalent bond to an amino acid sequence of a second protein, wherein the second protein is not a vertebrate Serrate protein.

33. The chimeric protein of claim 32 wherein the fragment of a Serrate protein is a fragment capable of being bound by an anti-vertebrate Serrate antibody.

34. The chimeric protein of claim 33 wherein the Serrate protein is a human protein.

35. The chimeric protein of claim 34, wherein the fragment is of the human Serrate sequence depicted in FIG. 9 (SEQ ID NO:6).

36. The chimeric protein of claim 34, wherein the fragment is of the human Serrate sequence depicted in FIG. 10 (SEQ ID NO:8).

37. The chimeric protein of claim 32 which is able to bind to a Notch protein.

38. A purified human Serrate protein, the amino acid sequence of which consists of amino acids 30 to 1218 of SEQ ID NO:6.

39. A purified vertebrate Serrate protein produced according to a method comprising growing a recombinant cell containing a recombinant nucleic acid comprising nucleotides 371 to 4024 of the human Serrate sequence depicted in FIG. 9 (SEQ ID NO:5), such that the encoded protein is expressed by the cell, and purifying the expressed protein.

40. A purified vertebrate Serrate protein produced according to a method comprising growing a recombinant cell containing a recombinant nucleic acid comprising nucleotides 332 to 4102 of the human Serrate sequence depicted in FIG. 10 (SEQ ID NO:7), such that the encoded protein is expressed by the cell, and purifying the expressed protein.

41. A purified vertebrate Serrate protein produced according to a method comprising growing a recombinant cell containing a recombinant nucleic acid encoding a vertebrate Serrate protein comprising amino acid numbers 30 to 1218 of the human Serrate sequence depicted in FIG. 9 (SEQ ID NO:6), such that the encoded protein is expressed by the cell, and purifying the expressed protein.

42. A purified vertebrate Serrate protein produced according to a method comprising growing a recombinant cell containing a recombinant nucleic acid encoding a vertebrate Serrate protein comprising amino acid numbers 1 to 1257 of the human Serrate sequence depicted in FIG. 10 (SEQ ID NO:8), such that the encoded protein is expressed by the cell, and purifying the expressed protein.

43. A purified human Serrate protein encoded by plasmid pBS39 as deposited with the ATCC and assigned accession number 97068.

44. A purified human Serrate protein encoded by plasmid pBS15 as deposited with the ATCC and assigned accession number 97459.

45. A purified human Serrate protein encoded by plasmid pBS3-2 as deposited with the ATCC and assigned accession number 97460.

46. A purified protein encoded by a nucleic acid hybridizable to plasmid pBS39 or the human Serrate sequence in said plasmid deposited with the ATCC and assigned accession number 97068, wherein said hybridization is under high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 ug/ml denatured salmon sperm DNA, for 48 hours at 65° C., and wash in a buffer consisting of 0.1×SSC, for 45 minutes at 50° C., and wherein said protein is able to be bound by an anti-vertebrate Serrate antibody.

47. The protein of claim 46, wherein said protein is able to bind to a Notch protein.

48. A purified protein produced according to a method comprising growing a recombinant cell containing a recombinant nucleic acid hybridizable to pBS39 or the human Serrate sequence therein as deposited with the ATCC and assigned accession number 97068, wherein said hybridization conditions are under high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 ug/ml denatured salmon sperm DNA, for 48 hours at 65° C., and wash in a buffer consisting of 0.1×SSC, for 45 minutes at 50° C., and wherein said nucleic acid encodes a protein able to be bound by an anti-vertebrate Serrate antibody, such that the encoded protein is expressed by the cell and purifying the expressed protein.

49. A purified protein encoded by a nucleic acid hybridizable to plasmid pBS39 or the Serrate sequence in said plasmid deposited with the ATCC and assigned accession number 97068, wherein said hybridization is under low stringency conditions comprising hybridization in a buffer consisting of 35% formamide, 5×SSC, 50 mM Tris-HCl (pH 7.5), 5 mM EDTA, 0.02% PVP, 0.02% Ficoll, 0.2% BSA, 100 ug/ml denatured salmon sperm DNA, and 10% (wt/vol) dextran sulfate, for 18–20 hours at 40° C., and wash in a buffer consisting of 2×SSC, 25 mM Tris HCl (pH 7.4), 5 mM EDTA, and 0.1% SDS, for 1.5 hours at 60° C., and wherein said protein is able to be bound by an anti-vertebrate Serrate antibody.

50. A purified protein encoded by a nucleic acid hybridizable to plasmid pBS15 or the Serrate sequence in said plasmid deposited with the ATCC and assigned accession number 97459, wherein said hybridization is under high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 ug/ml denatured salmon sperm DNA, for 48 hours at 65° C., and wash in a buffer consisting of 0.1×SSC, for 45 minutes at 50° C., and wherein said protein is able to be bound by an anti-vertebrate Serrate antibody.

51. A purified protein encoded by a nucleic acid hybridizable to plasmid pBS15 or the Serrate sequence in said plasmid deposited with the ATCC and assigned accession number 97459, wherein said hybridization is under low stringency conditions comprising hybridization in a buffer consisting of 35% formamide, 5×SSC, 50 mM Tris-HCl (pH 7.5), 5 mM EDTA, 0.02% PVP, 0.02% Ficoll, 0.2% BSA, 100 ug/ml denatured salmon sperm DNA, and 10% (wt/vol) dextran sulfate, for 18–20 hours at 40° C., and wash in a buffer consisting of 2×SSC, 25 mM Tris HCl (pH 7.4), 5 mM EDTA, and 0.1% SDS, for 1.5 hours at 60° C., and wherein said protein is able to be bound by an anti-vertebrate Serrate antibody.

52. A purified protein encoded by a nucleic acid hybridizable to plasmid pBS3-2 or the Serrate sequence in said plasmid deposited with the ATCC and assigned accession number 97460, wherein said hybridization is under high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 ug/ml denatured salmon sperm DNA, for 48 hours at 65° C., and wash in a buffer consisting of 0.1×SSC, for 45 minutes at 50° C., and wherein said protein is able to be bound by an anti-vertebrate Serrate antibody.

53. The protein of claim 7, 45, 49, 50, 51 or 52 which is a human protein.

54. A purified protein encoded by a nucleic acid hybridizable to plasmid pBS3-2 or the Serrate sequence in said plasmid deposited with the ATCC and assigned accession number 97460, wherein said hybridization is under low stringency conditions comprising hybridization in a buffer consisting of 35% formamide, 5×SSC, 50 mM Tris-HCl (pH 7.5), 5 mM EDTA, 0.02% PVP, 0.02% Ficoll, 0.2% BSA, 100 ug/ml denatured salmon sperm DNA, and 10% (wt/vol) dextran sulfate, for 18–20 hours at 40° C., and wash in a buffer consisting of 2×SSC, 25 mM Tris HCl (pH 7.4), 5 mM EDTA, and 0.1% SDS, for 1.5 hours at 60° C., and wherein said protein is able to be bound by an anti-vertebrate Serrate antibody.

55. A pharmaceutical composition comprising the protein of claim 6; and a pharmaceutically acceptable carrier.

56. A purified fragment of a human Serrate protein, which fragment consists of at least (a) 20 amino acids of the human Serrate sequence depicted in FIG. 9 (SEQ ID NO:6), and (b) a domain of the protein selected from the group consisting of the extracellular domain, DSL domain, epidermal growth factor-like repeat domain, cysteine-rich domain, transmembrane domain, and intracellular domain.

57. The fragment of claim 56 wherein the fragment of the human Serrate protein comprises an amino acid sequence selected from the group consisting of amino acid numbers 1 to 1067, 30 to 1067, 185 to 229, 234 to 896, 1068 to 1089, and 1090 to 1218, as depicted in FIG. 9 (SEQ ID NO:6).

58. A purified fragment of a human Serrate protein consisting of at least 10 amino acids of the human Serrate sequence depicted in FIG. 10 (SEQ ID NO:8), said fragment comprising a domain of the protein selected from the group consisting of the extracellular domain, DSL domain, epidermal growth factor-like repeat domain, cysteine-rich domain, transmembrane domain, and intracellular domain.

59. The fragment of claim 58 wherein the fragment of the human Serrate protein comprises an amino acid sequence selected from the group consisting of amino acid numbers 1 to 912, 26 to 70, 75 to 735, 912 to 933, and 934 to 1257, as depicted in FIG. 10 (SEQ ID NO:8).

60. A purified fragment of a chick Serrate protein consisting of at least 20 amino acids of the chick Serrate sequence depicted in FIG. 12 (SEQ ID NO: 10), said fragment comprising a domain of the protein selected from the group consisting of the extracellular domain, DSL domain, epidermal growth factor-like repeat domain, cysteine-rich domain, transmembrane domain, and intracellular domain.

61. A purified *D. melanogaster* Serrate protein comprising amino acids 81 to 1404 of the sequence depicted in FIG. 3 (SEQ ID NO:2).

62. A purified fragment of a *D. melanogaster* Serrate protein consisting of at least 10 amino acids of the *D. melanogaster* Serrate protein sequence depicted in FIG. 3 (SEQ ID NO:2), said fragment comprising a domain of the protein selected from the group consisting of the extracellular domain, epidermal growth factor-like repeat domain, membrane-associated region, transmembrane domain, and intracellular domain.

63. A purified fragment of a *D. melanogaster* Serrate protein, said fragment consisting of at least 10 amino acids of amino acids 81–1404 of the sequence depicted in FIG. 3 (SEQ ID NO:2).

64. A purified fragment of a *D. melanogaster* Serrate protein, said fragment consisting of at least 10 amino acids of amino acids 81–1404 of the sequence depicted in FIG. 3 (SEQ ID NO:2), wherein said fragment is able to bind to a Notch protein.

65. A pharmaceutical composition comprising a vertebrate Serrate protein comprising a sequence selected from the group consisting of the mouse Serrate sequence of SEQ ID NO:16, the mouse Serrate sequence of SEQ ID NO:18, amino acids 6 to 1193 of the chick Serrate sequence depicted in FIGS. 12A–12B (SEQ ID NO:10), amino acids 30 to 1218 of the human Serrate sequence depicted in FIGS. 9A–9G (SEQ ID NO:6), and the human Serrate sequence depicted in FIGS. 10A–10G (SEQ ID NO:8); and a pharmaceutically acceptable carrier.

66. The pharmaceutical composition of claim 65 wherein the Serrate protein is a human Serrate protein.

67. The pharmaceutical composition of claim 66 wherein the human Serrate protein comprises amino acids 30 to 1218 of the human Serrate sequence depicted in FIG. 9 (SEQ ID NO:6).

68. The pharmaceutical composition of claim 66 wherein the human Serrate protein comprises the human Serrate sequence depicted in FIG. 10 (SEQ ID NO:8).

69. A pharmaceutical composition comprising the fragment of claim 15; and a pharmaceutically acceptable carrier.

70. The pharmaceutical composition of claim 69 wherein the vertebrate Serrate protein is a human Serrate protein.

71. The pharmaceutical composition of claim 70 wherein the human Serrate protein has the human Serrate sequence depicted in FIG. 9 (SEQ ID NO:6).

72. The pharmaceutical composition of claim 70 wherein the human vertebrate protein sequence is the Serrate sequence depicted in FIG. 10 (SEQ ID NO:8).

73. A pharmaceutical composition comprising the protein of claim 46 and a pharmaceutically acceptable carrier.

74. A pharmaceutical composition comprising the fragment of claim 56; and a pharmaceutically acceptable carrier.

75. A pharmaceutical composition comprising the fragment of claim 9 and a pharmaceutically acceptable carrier.

* * * * *